United States Patent [19]

Kaneko et al.

[11] Patent Number: 5,691,319
[45] Date of Patent: Nov. 25, 1997

[54] PYRIMIDINE NUCLEOSIDE DERIVATIVES HAVING ANTI-TUMOR ACTIVITY, THEIR PREPARATION AND USE

[75] Inventors: Masakatsu Kaneko; Hitoshi Hotoda; Tomoyuki Shibata; Tomowo Kobayashi; Yoshihiro Mitsuhashi, all of Tokyo; Akira Matsuda, Sapporo; Takuma Sasaki, Kanazawa, all of Japan

[73] Assignee: Sankyo Company, Limited, Tokyo, Japan

[21] Appl. No.: 465,127

[22] Filed: Jun. 5, 1995

Related U.S. Application Data

[63] Continuation of Ser. No. 954,764, Sep. 30, 1992, abandoned.

[30] Foreign Application Priority Data

Sep. 30, 1991 [JP] Japan ................................. 3-252015

[51] Int. Cl.⁶ .................... A61K 31/505; A61K 31/70; C07H 19/09
[52] U.S. Cl. .................... 514/49; 536/28.51; 536/28.4; 536/28.1; 536/22.1
[58] Field of Search ............................. 536/26.8, 22.1, 536/28.51, 28.4, 28.1; 514/49

[56] References Cited

U.S. PATENT DOCUMENTS

| | | | |
|---|---|---|---|
| 4,211,773 | 7/1980 | Lopez et al. | 424/180 |
| 4,818,750 | 4/1989 | Rideout et al. | 536/26.8 |

FOREIGN PATENT DOCUMENTS

| | | |
|---|---|---|
| 0325537 | 7/1989 | European Pat. Off. . |
| 0346170 | 12/1989 | European Pat. Off. . |
| 0357495 | 3/1990 | European Pat. Off. . |
| WO 91/19713 | 12/1991 | WIPO . |

OTHER PUBLICATIONS

Ho et al, Cancer Res. 37:1640–1643 (1977).
Martin et al, J. Pharm. Sci. 76(2): 180–184 (1987).
Wechter et al., J. Med. Chem. 18(4): 339–344 (1975).
Baker et al, J. Med. Chem. 21(12): 1218–1221 (1978).
Baker et al, J. Med. Chem. 22(3): 273–279 (1979).
Matsuda et al (1991) J. Med. Chem, 34, 2917–2919.
Matsuda et al (1990) Nucleic Acids Symp. Ser. 22, 51–52 (Abstract).
Hibich et al (1988) Synthesis, 12, 943–47.
Greengrass et al (1989) J. Med. Chem, 32, 618–23.
Matsuda et al (1990) Nucleic Acid Research Ser. 22, 51–52.
Camarada et al (1989) J. Med. Chem. 132, 1732–38.

*Primary Examiner*—John W. Rollins
*Assistant Examiner*—Francisco C. Prats
*Attorney, Agent, or Firm*—Frishauf, Holtz, Goodman, Langer & Chick, P.C.

[57] ABSTRACT

Compounds of formula (I):

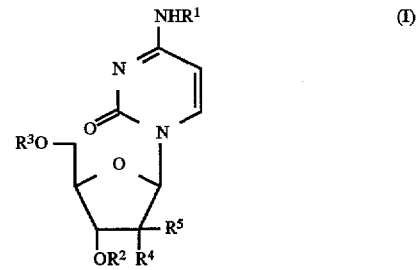

wherein:

$R^1$, $R^2$ and $R^3$ are independently selected from the group consisting of hydrogen atoms, optionally substituted alkanoyl groups and alkenylcarbonyl groups, PROVIDED THAT at least one of $R^1$, $R^2$ and $R^3$ represents an unsubstituted alkanoyl group having from 5 to 24 carbon atoms, said substituted alkanoyl group or said alkenylcarbonyl group; and one of $R^4$ and $R^5$ represents a hydrogen atom and the other represents a cyano group; have valuable anti-tumor activity.

11 Claims, No Drawings

PYRIMIDINE NUCLEOSIDE DERIVATIVES HAVING ANTI-TUMOR ACTIVITY, THEIR PREPARATION AND USE

This application is a Continuation of application Ser. No. 07/954,764, filed Sep. 30, 1992, now abandoned.

BACKGROUND TO THE INVENTION

The present invention relates to a series of new pyrimidine nucleosides, which may be regarded as cytidine derivatives, and which have extremely valuable anti-tumor activity. The invention also provides a process for producing these compounds, as well as methods and compositions using them for the treatment and prophylaxis of tumorous conditions.

The compounds of the present invention are 2'-cyano-2'-deoxy derivatives of 1-β-D-arabinofuranosylcytosine, which have been found to have valuable anti-tumor activity. Compounds of this general type are known and are known to have this type of activity, see, for example Matsuda et al. [Nucleic Acids Research, Symposium Series No. 22, page 51 (1990)] and Matsuda et al. [J. Med. Chem., 34, 2917–2919 (1991), published after the priority date hereof]. However, they have several disadvantages, including low activity, and there is a need for compounds of this type which do not suffer these disadvantages.

Corresponding 3'-cyano-3'-deoxy derivatives are also known [Häbich et al., Synthesis, 12, 943–947 (1988)], but these suffer similar disadvantages.

A number of other compounds of this type is also known. For example, European Patent Specifications No. 357 495, 348 170 and 325 537 all disclose compounds of this general type as anti-viral agents, especially for the treatment, prophylaxis or support of patients suffering from AIDS. However, these prior compounds differ structurally in several respects from the compounds of the present invention and have not been proposed for use for the treatment or prophylaxis of tumorous conditions.

For the avoidance of doubt, the numbering system used on the compounds herein is as shown on the skelatal structure given in the following formula (A):

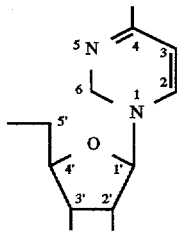

BRIEF SUMMARY OF INVENTION

It is, therefore, an object of the present invention to provide a series of new pyrimidine nucleosides.

It is a further, and more specific, object of the present invention to provide such compounds having anti-tumor activity.

Other objects and advantages of the present invention will become apparent as the description proceeds.

The compounds of the present invention are those compounds of formula (I):

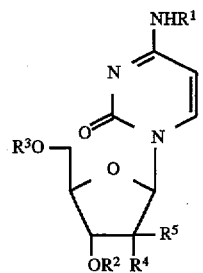

wherein:
$R^1$, $R^2$ and $R^3$ are independently selected from the group consisting of
hydrogen atoms,
alkanoyl groups having from 2 to 24 carbon atoms,
substituted alkanoyl groups which have from 2 to 24 carbon atoms and which are substituted by at least one substituent selected from the group consisting of substituents A and substituents B, defined below, and
alkenylcarbonyl groups having from 3 to 24 carbon atoms;

PROVIDED THAT at least one of $R^1$, $R^2$ and $R^3$ represents an unsubstituted alkanoyl group having from 5 to 24 carbon atoms, said substituted alkanoyl group or said alkenylcarbonyl group;

one of $R^4$ and $R^5$ represents a hydrogen atom and the other represents a cyano group;

said substituents A are selected from the group consisting of
hydroxy groups,
amino groups,
mercapto groups,
carboxy groups,
protected amino groups,
protected mercapto groups,
azido groups,
cyano groups, and
halogen atoms;

said substituents B are selected from the group consisting of
alkoxy groups having from 1 to 10 carbon atoms,
alkoxyalkoxy groups in which each alkoxy part has from 1 to 6 carbon atoms,
alkylthioalkoxy groups in which the alkyl part and the alkoxy part each has from 1 to 6 carbon atoms,
alkoxyalkoxyalkoxy groups in which each alkoxy part has from 1 to 6 carbon atoms,
aryloxy groups where the aryl part is as defined below,
aralkyloxy groups where the alkyl part has from 1 to 4 carbon atoms and the aryl part is as defined below,
aliphatic carboxylic acyloxy groups having from 1 to 30 carbon atoms,
aromatic carboxylic acyloxy groups where the aryl part is as defined below,
alkoxycarbonyloxy groups where the alkoxy part has from 1 to 6 carbon atoms,
aralkyloxycarbonyloxy groups where the alkyl part has from 1 to 4 carbon atoms and the aryl part is as defined below,
haloalkoxycarbonyloxy groups in which the alkoxy part has from 1 to 6 carbon atoms, and which have at least one halogen atom,
aryloxycarbonyloxy groups where the aryl part is as defined below,
tri-substituted silyloxy groups where the substituents are independently selected from the group consisting of alkyl groups having from 1 to 6 carbon atoms and
aryl groups as defined below, alkylthio groups having from 1 to 6 carbon atoms,
arylthio groups where the aryl part is as defined below, aralkylthio groups where the alkyl part has from 1 to 4 carbon atoms and the aryl part is as defined below, alkyldithio groups having from 1 to 6 carbon atoms, aryldithio groups where the aryl part is as defined below, aralkyldithio groups where the alkyl part has from 1 to 4 carbon atoms and the aryl part is as defined below, alkylsulfonyloxy groups where the alkyl part has from 1 to 6 carbon atoms, arylsulfonyloxy groups where the aryl part is as defined below, carbamoyl groups, and carbamoyloxy groups;

said aryl groups are carbocyclic aryl groups having from to 14 ring carbon atoms in at least one aromatic carbocyclic ring and which are unsubstituted or are substituted by at least one substituent selected from the group consisting of substituents C, defined below; and said substituents C are selected from the group consisting of alkyl groups having from 1 to 6 carbon atoms, alkoxy groups having from 1 to 6 carbon atoms, aliphatic carboxylic acyl groups having from 1 to 6 carbon atoms, halogen atoms, nitro groups, cyano groups, and amino groups, and pharmaceutically acceptable salts thereof and, where said substituent A is a carboxy group, pharmaceutically acceptable esters thereof.

The invention also provides a pharmaceutical composition for the treatment or prophylaxis of tumors, which comprises an effective amount of an active compound in admixture with a pharmaceutically acceptable carrier or diluent, wherein said active compound is selected from the group consisting of compounds of formula (I) and salts and esters thereof, as defined above.

The invention also provides a method for the treatment or prophylaxis of tumors, which comprises administering to an animal, e.g. a mammal, which may be human, an effective amount of an active compound, wherein said active compound is selected from the group consisting of compounds of formula (I) and salts and esters thereof, as defined above.

The invention also provides various processes for preparing the compounds of the present invention, which are described in greater detail hereafter.

DETAILED DESCRIPTION OF INVENTION

In the compounds of the present invention, where $R^1$, $R^2$ or $R^3$ represents an alkanoyl group having from 2 to 24 carbon atoms, this may be a straight or branched chain group, and examples include the acetyl, propionyl, butyryl, isobutyryl, valeryl, isovaleryl, pivaloyl, 2-methylbutyryl, hexanoyl, isohexanoyl, 3-methylvaleryl, 4,4-dimethylbutyryl, 2-ethylbutyryl, heptanoyl, 5-methylhexanoyl, 4-methylhexanoyl, 3-methylhexanoyl, 2-methylhexanoyl, 4,4-dimethylvaleryl, 3,3-dimethylvaleryl, 2,2-dimethylvaleryl, 2,3-dimethylvaleryl, 2,4-dimethylvaleryl, 3,4-dimethylvaleryl, 3-ethylvaleryl, octanoyl, 2-methylheptanoyl, 3-methylheptanoyl, 4-methylheptanoyl, 5-methylheptanoyl, 6-methylheptanoyl, 2-propylvaleryl, 5,5-dimethylhexanoyl, nonanoyl, 2-methyloctanoyl, 3-methyloctanoyl, 4-methyloctanoyl, 5-methyloctanoyl, 6-methyloctanoyl, 7-methyloctanoyl, 2-propylhexanoyl, 3-ethylheptanoyl, 6,6-dimethylheptanoyl, decanoyl, 4-methylnonanoyl, 5-methylnonanoyl, 6-methylnonanoyl, 7-methylnonanoyl, 2-propylheptanoyl, 3-ethyloctanoyl, 7,7-dimethyloctanoyl, undecanoyl, 2-methyldecanoyl, 4-methyldecanoyl, 9-methyldecanoyl, 4-ethylnonanoyl, 4,8-dimethylnonanoyl, 8,8-dimethylnonanoyl, lauroyl, 4,8-dimethyldecanoyl, tridecanoyl, myristoyl, pentadecanoyl, palmitoyl, 3,7,11-trimethyltridecanoyl, heptadecanoyl, 4,8,12-trimethylmyristoyl, 1-methylpalmitoyl, 14-methylpalmitoyl, 13,13-dimethylpentadecanoyl, stearoyl, 15-methylheptadecanoyl, nonadecanoyl, 1-methylstearoyl, icosanoyl, henicosanoyl, 3,7,11,15-tetramethylheptadecanoyl, docosanoyl, tricosanoyl and tetracosanoyl groups. In general it is preferred that the unsubstituted alkanoyl groups should have from 5 to 24 carbon atoms, and those groups having from 2 to 4 carbon atoms may only be present in the compounds of the present invention when at least one other of $R^1$, $R^2$ or $R^3$ represents a substituted alkanoyl group, an alkenoyl group or a substituted alkenoyl group. Of these unsubstituted alkanoyl groups, we prefer those alkanoyl groups having from 5 to 22 carbon atoms, and more prefer alkanoyl groups having from 10 to 22 carbon atoms.

Where $R^1$, $R^2$ or $R^3$ represents a substituted alkanoyl group having from 2 to 24 carbon atoms, this may likewise be a straight or branched chain group having from 2 to 24 carbon atoms and substituted by at least one substituent selected from the group consisting of substituents A and B, defined above and exemplified below. Examples of the substituted groups include the same groups as listed above for the unsubstituted groups but substituted by at least one of substituents A and B. Of these, we prefer the alkanoyl groups having from 3 to 20 carbon atoms, and more prefer the alkanoyl groups having from 6 to 16 carbon atoms. There may be one or more substituents selected from the group consisting of substituents A and B, defined above and exemplified below, and there is no limitation on the number of such substituents, except such as may be imposed by the number of substitutable carbon atoms, or, possibly, by steric constraints. In general, however, from 1 to 5, more preferably from 1 to 3, are preferred, subject to the number of substitutable carbon atoms, and one substituent is normally most preferred. Specific examples of preferred substituted alkanoyl groups include the hydroxyacetyl, 3-hydroxypropionyl, 4-hydroxybutyryl, 6-hydroxyhexanoyl, 8-hydroxyoctanoyl, 10-hydroxydecanoyl, 12-hydroxydodecanoyl, 14-hydroxytetradecanoyl, 16-hydroxyhexadecanoyl, 18-hydroxyoctadecanoyl, 20-hydroxyicosanoyl, 6-methoxymethoxyhexanoyl, 8-methoxymethoxyoctanoyl, 10-methoxymethoxydecanoyl, 12-methoxymethoxydodecanoyl, 14-methoxymethoxytetradecanoyl, 16-methoxymethoxyhexadecanoyl, 18-methoxymethoxyoctadecanoyl, 20-methoxymethoxyicosanoyl, 6-[(2-methoxyethoxy)methoxy]hexanoyl, 10-[(2-methoxyethoxy)methoxy]decanoyl, 12-[(2-methoxyethoxy)methoxy]dodecanoyl, 14-[(2-methoxyethoxy)methoxy]tetradecanoyl, 16-[(2-methoxyethoxy)methoxy]hexadecanoyl, 20-[(2-methoxyethoxy)methoxy]icosanoyl, 12-acetoxydodecanoyl, 14-acetoxytetradecanoyl, 16-acetoxyhexadecanoyl, 18-acetoxyoctadecanoyl, 16-(methylthiomethoxy)

hexadecanoyl, 12-(methylthiomethoxy)dodecanoyl, 16-(methanesulfonyloxy)hexadecanoyl, 12-(methanesulfonyloxy)dodecanoyl, 16-(p-toluenesulfonyloxy)hexadecanoyl, 18-(p-toluenesulfonyloxy)octadecanoyl, 16-carbamoyloxyhexadecanoyl, 12-carbamoyloxydodecanoyl, 11-methoxycarbonylundecanoyl, 13-methoxycarbonyltridecanoyl, 15-methoxycarbonylpentadecanoyl, 16-methoxycarbonylhexadecanoyl, 11-carbamoylundecanoyl, 15-carbamoylpentadecanoyl, 16-carbamoylhexadecanoyl, 11-cyanoundecanoyl, 15-cyanopentadecanoyl, 16-cyanohexadecanoyl, 19-cyanononadecanoyl, 21-cyanohenicosanoyl, 12-acetylthiododecanoyl, 16-acetylthiohexadecanoyl, 18-acetylthiooctadecanoyl, 3-(benzyldithio)propionyl, 6-(benzyldithio)hexadecanoyl, 10-aminodecanoyl, 12-aminododecanoyl, 14-aminotetradecanoyl, 16-aminohexadecanoyl, 17-aminoheptadecanoyl, 18-aminooctadecanoyl, 19-aminononadecanoyl, 20-aminoicosanoyl, 10-(benzyloxycarbonylamino)decanoyl, 12-(butoxycarbonylamino)dodecanoyl, 14-acetamidotetradecanoyl, 16-(allyloxycarbonylamino)hexadecanoyl, 12-benzylaminododecanoyl, 20-benzamidoicosanoyl, 16-azidohexadecanoyl, 12-azidododecanoyl, 10-fluorodecanoyl, 16-fluorohexadecanoyl, 12-chlorododecanoyl, 14-chlorotetradecanoyl, 16-chlorohexadecanoyl, 6-bromohexanoyl and 8-bromooctanoyl groups, preferably the 12-hydroxydodecanoyl, 14-hydroxytetradecanoyl, 16-hydroxyhexadecanoyl, 12-methoxymethoxydodecanoyl, 14-methoxymethoxytetradecanoyl, 16-methoxymethoxyhexadecanoyl, 12-[(2-methoxyethoxy)methoxy]dodecanoyl, 14-[(2-methoxyethoxy)methoxy]tetradecanoyl, 16-[(2-methoxyethoxy)methoxy]hexadecanoyl, 11-cyanoundecanoyl and 15-cyanopentadecanoyl groups.

Where $R^1$, $R^2$ or $R^3$ represents an alkenoyl group, this may be a straight or branched chain group which has from 3 to 24 carbon atoms, and which has at least one carbon-carbon double bond. Examples include the acryloyl, methacryloyl, 3-butenoyl, crotonoyl, isocrotonoyl, oleoyl, elaidoyl, 2-pentenoyl, 3-pentenoyl, 4-pentenoyl, 2-methyl-2-butenoyl, 3-methyl-2-butenoyl, 2,2-dimethylpropenoyl, 1,2-dimethylpropenoyl, 2-hexenoyl, 3-hexenoyl, 4-hexenoyl, 5-hexenoyl, 2-heptenoyl, 3-heptenoyl, 4-heptenoyl, 5-heptenoyl, 6-heptenoyl, 2-octenoyl, 3-octenoyl, 4-octenoyl, 5-octenoyl, 6-octenoyl, 7-octenoyl, 3-nonenoyl, 4-decenoyl, 4-undecenoyl, 5-dodecenoyl, 6-tridecenoyl, 7-tetradecenoyl, 8-pentadecenoyl, 9-hexadecenoyl (e.g. palmitoleoyl), 10-heptadecenoyl, 9-octadecenoyl (e.g. oleoyl), 12-octadecenoyl, octadecadienoyl (e.g. 9,12-octadecadienoyl, i.e. linoleoyl), octadecatrienoyl (e.g. 9,12,15-octadecatrienoyl, i.e. linolenoyl), 15-nonadecenoyl, 11-icosenoyl, icosatetraenoyl (e.g. 5,8,11,14-icosatetraenoyl, i.e. arachidonyl), 16-henicosenoyl, 18-tricosenoyl and 20-tetracosenoyl groups, of which those groups having from 12 to 20 carbon atoms are preferred, and those having from 18 to 20 carbon atoms are most preferred, especially the oleoyl, linoleoyl, linolenoyl and arachidonyl groups.

Substituents A include the following groups and atoms:
hydroxy groups,
amino groups,
mercapto groups,
carboxy groups,
protected amino and mercapto groups, as exemplified below
azido groups,
cyano groups, and
halogen atoms, such as the fluorine, chlorine, bromine and iodine atoms, especially the fluorine, chlorine and bromine atoms.

There is no particular restriction on the nature of the protecting group used for the protected amino or mercapto groups, unless the resulting compound is to be used for pharmaceutical purposes, in which case it should, as is well known in the art, not adversely affect the activity or the toxicity of the compound. However, where the protected compound is to be used for other purposes, for example as an intermediate in the preparation of other, and perhaps more active, compounds, this restriction does not apply and the protecting group may be chosen, in the usual way, having regard only to its use in any reaction process. Examples of suitable mercapto-protecting groups include:

aliphatic acyl groups, preferably: alkanoyl groups having from 1 to 25 carbon atoms, more preferably from 1 to 20 carbon atoms, still more preferably from 1 to 6 carbon atoms, and most preferably from 1 to 4 carbon atoms (such as those exemplified above in relation to $R^1$, $R^2$ and $R^3$, especially the formyl, acetyl, propionyl, butyryl, isobutyryl, pivaloyl, valeryl, isovaleryl, hexanoyl, heptanoyl, octanoyl, lauroyl, myristoyl, tridecanoyl, palmitoyl and stearoyl groups, of which the acetyl group is most preferred); halogenated alkanoyl groups having from 2 to 6 carbon atoms, especially halogenated acetyl groups (such as the chloroacetyl, dichloroacetyl, trichloroacetyl and trifluoroacetyl groups); lower alkoxyalkanoyl groups in which the alkoxy part has from 1 to 5, preferably from 1 to 3, carbon atoms and the alkanoyl part has from 2 to 6 carbon atoms and is preferably an acetyl group (such as the methoxyacetyl group); and unsaturated analogs of such groups, especially alkenoyl or alkynoyl groups having from 3 to 6 carbon atoms [such as the acryloyl, methacryloyl, propioloyl, crotonoyl, isocrotonoyl and (E)-2-methyl-2-butenoyl groups];

aromatic acyl groups, preferably arylcarbonyl groups, in which the aryl part has from 6 to 14, more preferably from 6 to 10, still more preferably 6 or 10, and most preferably 6, ring carbon atoms and is a carbocyclic group, which is unsubstituted or has from 1 to 5, preferably from 1 to 3 substituents, preferably selected from the group consisting of substituents C, defined above and exemplified below, preferably: unsubstituted groups (such as the benzoyl, α-naphthoyl, β-naphthoyl, 1-phenanthrylcarbonyl, 2-phenanthrylcarbonyl, 1-anthrylcarbonyl and 2-anthrylcarbonyl groups, especially the benzoyl, α-naphthoyl and β-naphthoyl groups, and most especially the benzoyl group); halogenated arylcarbonyl groups (such as the 2-bromobenzoyl and 4-chlorobenzoyl groups); lower alkyl-substituted arylcarbonyl groups, in which the or each alkyl substituent has from 1 to 5, preferably from 1 to 4, carbon atoms (such as the 2,4,6-trimethylbenzoyl and 4-toluoyl groups); lower alkoxy-substituted arylcarbonyl groups, in which the or each alkoxy substituent preferably has from 1 to 5, preferably from 1 to 4, carbon atoms (such as the 4-anisoyl group); nitro-substituted arylcarbonyl groups (such as the 4-nitrobenzoyl and 2-nitrobenzoyl groups); lower alkoxycarbonylsubstituted arylcarbonyl groups, in which the or each alkoxycarbonyl substituent preferably has from 2 to 6 carbon atoms [such as the 2-(methoxycarbonyl)benzoyl group]; and arylsubstituted arylcarbonyl groups, in which the aryl substituent is as defined above, except that, if it is substituted by a further aryl group, that aryl group is not itself substituted by an aryl group (such as the 4-phenylbenzoyl group);

heterocyclic groups having 5 or 6 ring atoms, of which 1 or 2 are hetero-atoms selected from the group consisting of oxygen, sulfur and nitrogen atoms, preferably oxygen or sulfur atoms, which groups may be unsubstituted or may have at least one substituent selected from the group consisting of substituents C, defined and exemplified above, and oxygen atoms; examples include: the tetrahydropyranyl groups, which may be substituted or unsubstituted, such as the tetrahydropyran-2-yl, 3-bromotetrahydropyran-2-yl and 4-methoxytetrahydropyran-4-yl groups; tetrahydrothiopyranyl groups, which may be substituted or unsubstituted, such as the tetrahydrothiopyran-2-yl and 4-methoxytetrahydrothiopyran-4-yl groups; tetrahydrofuranyl groups, which may be substituted or unsubstituted, such as the tetrahydrofuran-2-yl group; and tetrahydrothienyl groups, which may be substituted or unsubstituted, such as the tetrahydrothien-2-yl group;

tri-substituted silyl groups, in which all three or two or one of the substituents are alkyl groups having from 1 to 8, preferably from 1 to 5 and more preferably from 1 to 4, carbon atoms, and none, one or two of the substituents are aryl groups, as defined above, but preferably phenyl or substituted phenyl groups; examples of such aryl groups are given above and examples of the alkyl groups include the methyl, ethyl, butyl, isobutyl, sec-butyl, t-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, heptyl, 1-methylhexyl, 2-methylhexyl, 3-methylhexyl, 4-methylhexyl, 5-methylhexyl, 1-propylbutyl, 4,4-dimethylpentyl, octyl, 1-methylheptyl, 2-methylheptyl, 3-methylheptyl, 4-methylheptyl, 5-methylheptyl, 6-methylheptyl, 1-propylpentyl, 2-ethylhexyl and 5,5-dimethylhexyl groups; preferred examples of the trisilyl groups are: tri(lower alkyl)silyl groups (such as the trimethylsilyl, triethylsilyl, isopropyldimethylsilyl, t-butyldimethylsilyl, methyldiisopropylsilyl, methyldi-t-butylsilyl and triisopropylsilyl groups); and tri(lower alkyl)silyl groups in which one or two of the alkyl groups have been replaced by aryl groups (such as the diphenylmethylsilyl, diphenylbutylsilyl, diphenyl-t-butylsilyl, diphenylisopropylsilyl and phenyldiisopropylsilyl groups);

alkoxyalkyl groups, in which the alkoxy and alkyl parts each have from 1 to 5, preferably from 1 to 4, carbon atoms, especially alkoxymethyl groups, and such groups which have at least one, preferably from 1 to 5, more preferably from 1 to 3, and most preferably 1, substituents, preferably: lower alkoxymethyl groups and other alkoxyalkyl groups (such as the methoxymethyl, 1,1-dimethyl-1-methoxymethyl, ethoxymethyl, propoxymethyl, isopropoxymethyl, butoxymethyl and t-butoxymethyl groups); lower alkoxy-substituted lower alkoxymethyl groups (such as the 2-methoxyethoxymethyl group); halogenated lower alkoxymethyl groups [such as the 2,2,2-trichloroethoxymethyl and bis(2-chloroethoxy)methyl groups] and lower alkoxy-substituted ethyl groups (such as the 1-ethoxyethyl, 1-methyl-1-methoxyethyl and 1-isopropoxyethyl groups);

other substituted ethyl groups, preferably: halogenated ethyl groups (such as the 2,2,2-trichloroethyl group); and arylselenyl-substituted ethyl groups, in which the aryl part is as defined above [such as the 2-(phenylselenyl)ethyl group];

alkoxycarbonyl groups, especially such groups having from 2 to 21, more preferably from 2 to 11 and most preferably from 2 to 5, carbon atoms; examples of such alkoxycarbonyl groups include the methoxycarbonyl, ethoxycarbonyl, butoxycarbonyl, isobutoxycarbonyl, sec-butoxycarbonyl, t-butoxycarbonyl, pentyloxycarbonyl, isopentyloxycarbonyl, 2-methylbutoxycarbonyl, neopentyloxycarbonyl, 1-ethylpropoxycarbonyl, hexyloxycarbonyl, 4-methylpentyloxycarbonyl, 3-methylpentyloxycarbonyl, 2-methylpentyloxycarbonyl, 1-methylpentyloxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl, 2,3-dimethylbutoxycarbonyl, 2-ethylbutoxycarbonyl, heptyloxycarbonyl, 1-methylhexyloxycarbonyl, 2-methylhexyloxycarbonyl, 3-methylhexyloxycarbonyl, 4-methylhexyloxycarbonyl, 5-methylhexyloxycarbonyl, 1-propylbutoxycarbonyl, 4,4-dimethylpentyloxycarbonyl, octyloxycarbonyl, 1-methylheptyloxycarbonyl, 2-methylheptyloxycarbonyl, 3-methylheptyloxycarbonyl, 4-methylheptyloxycarbonyl, 5-methylheptyloxycarbonyl, 6-methylheptyloxycarbonyl, 1-propylpentyloxycarbonyl, 2-ethylhexyloxycarbonyl, 5,5-dimethylhexyloxycarbonyl, nonyloxycarbonyl, 3-methyloctyloxycarbonyl, 4-methyloctyloxycarbonyl, 5-methyloctyloxycarbonyl, 6-methyloctyloxycarbonyl, 1-propylhexyloxycarbonyl, 2-ethylheptyloxycarbonyl, 6,6-dimethylheptyloxycarbonyl, decyloxycarbonyl, 1-methylnonyloxycarbonyl, 3-methylnonyloxycarbonyl, 8-methylnonyloxycarbonyl, 3-ethyloctyloxycarbonyl, 3,7-dimethyloctyloxycarbonyl, 7,7-dimethyloctyloxycarbonyl, undecyloxycarbonyl, 4,8-dimethylnonyloxycarbonyl, dodecyloxycarbonyl, tridecyloxycarbonyl, tetradecyloxycarbonyl, pentadecyloxycarbonyl, 3,7,11-trimethyldodecyloxycarbonyl, hexadecyloxycarbonyl, 4,8,12-trimethyltridecyloxycarbonyl, 1-methylpentadecyloxycarbonyl, 14-methylpentadecyloxycarbonyl, 13,13-dimethyltetradecyloxycarbonyl, heptadecyloxycarbonyl, 15-methylhexadecyloxycarbonyl, octadecyloxycarbonyl, 1-methylheptadecyloxycarbonyl, nonadecyloxycarbonyl, icosyloxycarbonyl and 3,7,11,15-tetramethylhexadecyloxycarbonyl groups; such alkoxycarbonyl groups may be unsubstituted (such as the methoxycarbonyl, ethoxycarbonyl, t-butoxycarbonyl and isobutoxycarbonyl groups) or substituted with a halogen atom or a tri-substituted silyl group, e.g. a tri(lower alkylsilyl) group (such as the 2,2,2-trichloroethoxycarbonyl and 2-trimethylsilylethoxycarbonyl groups);

alkenyloxycarbonyl groups in which the alkenyl part has from 2 to 6, preferably from 2 to 4, carbon atoms (such as the vinyloxycarbonyl and allyloxycarbonyl groups);

sulfo groups; and aralkyloxycarbonyl groups, in which the alkyl part has from 1 to 4 carbon atoms and the aryl part is as defined and exemplified above, and in which the aryl ring, if substituted, preferably has one or two lower alkoxy or nitro substituents (such as the benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups).

In the case of the protected amino groups, there may be one or two protecting groups, preferably one protecting group. Examples of such protected amino groups are as follows:

Amino groups protected by one or two alkyl groups, each of which has from 1 to 10, preferably from 1 to 4, carbon atoms and substituted alkyl groups which have from 1 to 4 carbon atoms and which are substituted by at least one substituent, as exemplified below. Examples of the unsubstituted alkyl groups include the methyl, ethyl, butyl, isobutyl, sec-butyl, t-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, heptyl, 1-methylhexyl, 2-methylhexyl, 3-methylhexyl, 4-methylhexyl, 5-methylhexyl, 1-propylbutyl, 4,4-dimethylpentyl, octyl, 1-methylheptyl, 2-methylheptyl, 3-methylheptyl, 4-methylheptyl, 5-methylheptyl, 6-methylheptyl, 1-propylpentyl, 2-ethylhexyl, 5,5-dimethylhexyl, nonyl, 3-methyloctyl, 4-methyloctyl, 5-methyloctyl, 6-methyloctyl, 1-propylhexyl, 2-ethylheptyl, 6,6-dimethylheptyl, decyl, 1-methylnonyl, 3-methylnonyl, 8-methylnonyl, 3-ethyloctyl, 3,7-dimethyloctyl and 7,7-dimethyloctyl groups. Examples of the substituted alkyl groups which may be used as protecting groups include the methoxymethyl, ethoxymethyl, propoxymethyl, butoxymethyl, 2-methoxyethyl, 2-ethoxyethyl, formyloxymethyl, acetoxymethyl, propionyloxymethyl, 2-formyloxyethyl, 2-acetoxyethyl, 2-propionyloxyethyl, 3-acetoxypropyl, 4-acetoxybutyl, valeryloxymethyl, pivaloyloxymethyl, benzoyloxymethyl, naphthoyloxymethyl, p-toluoyloxymethyl, p-chlorobenzoyloxymethyl, 2-benzoyloxyethyl, 3-benzoyloxypropyl and 4-benzoyloxybutyl groups. Specific examples of these protected amino groups include the amino, methylamino, ethylamino, propylamino, isopropylamino, butylamino, isobutylamino, sec-butylamino, t-butylamino, dimethylamino, diethylamino, dipropylamino, diisopropylamino, dibutylamino, methylethylamino, methylpropylamino, N-(methoxymethyl)amino, N-(2-methoxyethyl)amino, N-(acetoxymethyl)amino, N-(pivaloyloxymethyl) amino, N-(benzoylmethyl)amino, N-(2-acetoxyethyl) amino, N-(2-pivaloyloxyethyl)amino and N-(2-benzoylethyl)amino groups.

Monoarylamino groups and diarylamino groups in which the aryl part, which may be substituted or unsubstituted, is as defined and exemplified above, preferably the phenyl, 1-naphthyl, 2-naphthyl, 1-phenanthryl, 2-phenanthryl, 1-anthryl and 2-anthryl groups, more preferably the phenyl group. Preferred examples of such arylamino groups include the phenylamino, diphenylamino and 1-naphthylamino groups.

Monoaralkylamino groups and diaralkylamino groups, in which the alkyl part is an alkyl group having from 1 to 17, preferably from 1 to 10 and more preferably from 1 to 4, carbon atoms, such as the methyl, ethyl, butyl, isobutyl, sec-butyl, t-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, heptyl, 1-methylhexyl, 2-methylhexyl, 3-methylhexyl, 4-methylhexyl, 5-methylhexyl, 1-propylbutyl, 4,4-dimethylpentyl, octyl, 1-methylheptyl, 2-methylheptyl, 3-methylheptyl, 4-methylheptyl, 5-methylheptyl, 6-methylheptyl, 1-propylpentyl, 2-ethylhexyl, 5,5-dimethylhexyl, nonyl, 3-methyloctyl, 4-methyloctyl, 5-methyloctyl, 6-methyloctyl, 1-propylhexyl, 2-ethylheptyl, 6,6-dimethylheptyl, decyl, 1-methylnonyl, 3-methylnonyl, 8-methylnonyl, 3-ethyloctyl, 3,7-dimethyloctyl, 7,7-dimethyloctyl, undecyl, 4,8-dimethylnonyl, dodecyl, tridecyl, tetradecyl, pentadecyl, 3,7-11-trimethyldodecyl, hexadecyl, 4,8,12-trimethyltridecyl, 1-methylpentadecyl, 4-methylpentadecyl, 13,13-dimethyltetradecyl, heptadecyl and 15-methylhexadecyl groups. The aryl part may be any of the aryl groups defined and exemplified above, and may be substituted or unsubstituted. Examples include the phenyl, 1-naphthyl, 2-naphthyl, 1-phenanthryl, 2-phenanthryl, 1-anthryl and 2-anthryl groups, preferably the phenyl group. The alkyl part may be substituted by one or more aryl groups, the maximum being dictated only by the number of substitutable positions and possibly also by steric constraints; however, from 1 to 3 aryl groups are normally preferred, 1 or 2 being more preferred and 1 being most preferred. Specific examples of the aralkylamino groups include the benzylamino, N-(1-naphthylmethyl)amino, N-(2-naphthylmethyl)amino, phenethylamino, N-(α-methylbenzyl)amino, N-(3-phenylpropyl)amino, N-(2-phenylpropyl)amino, N-(1-phenylpropyl)amino, N-(4-phenylbutyl)amino, benzhydrylamino and tritylamino groups (of these, the benzylamino group is preferred), the diaralkylamino analogs of such groups and such groups which are substituted by one or more of substituents C.

Monoalkanoylamino groups and dialkanoylamino groups, where the or each alkanoyl part may be a straight or branched chain group which has from 1 to 21 carbon atoms. Examples of such alkanoyl groups include the formyl group and those groups having from 2 to 21 carbon atoms and previously exemplified in relation to the alkanoyl groups which may be represented by $R^1$, $R^2$ and $R^3$. Specific examples of the alkanoylamino groups include the formamido, acetamido, propionamido, butyramido, isobutyramido, valerylamino, isovalerylamino, pivaloylamino, hexanoylamino, heptanoylamino, octanoylamino, nonanoylamino, decanoylamino, lauroylamino, myristoylamino, palmitoylamino and stearoylamino groups, of which those groups having from 1 to 12 carbon atoms are preferred, those having from 2 to 10 carbon atoms are more preferred, and those having from 2 to 5 carbon atoms are most preferred, especially the acetamido, propionamido, butyramido, pivaloylamino, nonanoylamino and decanoylamino groups, of which the acetamido, propionamido, butyramido and pivaloylamino groups are most preferred.

Alkenoylamino groups, in which the alkenoyl part may be a straight or branched chain group having from 3 to 6 carbon atoms. Examples of such groups include the acryloylamino, methacryloylamino, 2-butenoylamino, 2-pentenoylamino and 2-hexenoylamino groups, of which the acryloylamino and methacryloylamino groups are preferred.

Cycloalkylcarbonylamino groups, which have from 4 to 8 carbon atoms, that is the cycloalkyl group itself has from 3 to 7 ring carbon atoms. Examples of such groups include the cyclopropylcarbonylamino, cyclobutylcarbonylamino, cyclopentylcarbonylamino, cyclohexylcarbonylamino and cycloheptylcarbonylamino groups, of which the cyclopropylcarbonylamino and cyclobutylcarbonylamino groups are particularly preferred.

Monoarylcarbonylamino groups and diarylcarbonylamino groups, in which the aryl part is as defined above, and examples of such groups include the benzamido, 1-naphthoylamino, 2-naphthoylamino, o-, m- and p-toluoylamino, o-, m- and p-chlorobenzamido, o-, m- and p-fluorobenzamido, o-, m- and p-methoxybenzamido, 2,4-dichlorobenzamido, 2,4-difluorobenzamido and 2,4,6-trifluorobenzamido groups, preferably the benzamido group, and diarylcarbonylamino analogs thereof.

Alkoxycarbonylamino groups, in which the alkoxy part may be a straight or branched chain group, and the alkoxycarbonylamino group has from 2 to 21, preferably from 2 to 11 and more preferably from 2 to 5, carbon atoms, that is the alkoxy part has from 1 to 20, preferably from 1 to 10 and more preferably from 1 to 4, carbon atoms. Examples of such alkoxycarbonyl groups are as given above in relation to mercapto-protecting groups, and specific examples of such alkoxycarbonylamino groups include the methoxycarbonylamino, ethoxycarbonylamino, propoxycarbonylamino, isopropoxycarbonylamino, butoxycarbonylamino, isobutoxycarbonylamino, sec-butoxycarbonylamino and t-butoxycarbonylamino groups. Of these, we prefer those alkoxycarbonylamino groups having from 1 to 3 carbon atoms in the alkoxy part and the t-butoxycarbonylamino group, more preferably the methoxycarbonylamino, ethoxycarbonylamino and t-butoxycarbonylamino groups.

Haloalkoxycarbonylamino groups, in which the alkoxy part may be a straight or branched chain group, and the haloalkoxycarbonylamino group has from 2 to 17, preferably from 2 to 11 and more preferably from 2 to 5, carbon atoms, that is the alkoxy part has from 1 to 16, preferably from 1 to 10 and more preferably from 1 to 4, carbon atoms. This is substituted by at least one halogen atom, for example a fluorine, chlorine, bromine or iodine atom. There is no limitation on the number of halogen substituents, except such as may be imposed by the number of substitutable carbon atoms, or possibly by steric constraints. However, generally from one to three halogen substituents is preferred. Examples of such haloalkoxycarbonyl groups are as given above in relation to mercapto-protecting groups but with one or more halogen substituents, and specific examples of such haloalkoxycarbonylamino groups include the fluoromethoxycarbonylamino, 2-fluoroethoxycarbonylamino, 3-fluoropropoxycarbonylamino, 2-fluoro-1-methylethoxycarbonylamino, 4-fluorobutoxycarbonylamino, 3-fluoro-2-propoxycarbonylamino, 2-fluoro-1,1-dimethylethoxycarbonylamino, chloromethoxycarbonylamino, 2-chloroethoxycarbonylamino, 3-chloropropoxycarbonylamino, 2-chloro-1-methylethoxycarbonylamino, 4-chlorobutoxycarbonylamino, 3-chloro-2-propoxycarbonylamino, 2-chloro-1,1-dimethylethoxycarbonylamino, bromomethoxycarbonylamino, 2-bromoethoxycarbonylamino, 3-bromopropoxycarbonylamino, 2-bromo-1-methylethoxycarbonylamino, 4-bromobutoxycarbonylamino, 3-bromo-2-propoxycarbonylamino, 2-bromo-1,1-dimethylethoxycarbonylamino, iodomethoxycarbonylamino, 2-iodoethoxycarbonylamino, 3-iodopropoxycarbonylamino, 2-iodo-1-methylethoxycarbonylamino, 4-iodobutoxycarbonylamino, 3-iodo-2-propoxycarbonylamino, 2-iodo-1,1-dimethylethoxycarbonylamino, trifluoromethoxycarbonylamino, 2,2,2-trifluoroethoxycarbonylamino and 2,2,2-trichloroethoxycarbonylamino groups, preferably the 2,2,2-trichloroethoxycarbonylamino group.

Aralkyloxycarbonylamino groups, in which the aralkyl part may be as defined and exemplified in relation to the aralkylamino groups above. Specific examples of the aralkyloxycarbonylamino groups include the benzyloxycarbonylamino, N-(1-naphthylmethoxycarbonyl)amino, N-(2-naphthylmethoxycarbonyl)amino, phenethyloxycarbonylamino, N-(α-methylbenzyloxycarbonyl)amino, N-(3-phenylpropoxycarbonyl)amino, N-(2-phenylpropoxycarbonyl)amino, N-(1-phenylpropoxycarbonyl)amino, N-(4-phenylbutoxycarbonyl)amino, benzhydryloxycarbonylamino and trityloxycarbonylamino groups (of these, the benzyloxycarbonylamino group is preferred), and such groups which are substituted by one or more of substituents C; and Tri-substituted silylamino groups, in which the silyl part is as defined and exemplified in relation to the mercapto-protecting groups. We prefer trialkylsilylamino groups. Specific examples of such tri-substituted silylamino groups include the trimethylsilylamino, triethylsilylamino, isopropyldimethylsilylamino, t-butyldimethylsilylamino, methyldiisopropylsilylamino, methyldi-t-butylsilylamino, triisopropylsilylamino, diphenylmethylsilylamino, diphenylbutylsilylamino, diphenyl-t-butylsilylamino, diphenylisopropylsilylamino and phenyldiisopropylsilylamino groups.

Substituents B are selected from the group consisting of:
Alkoxy groups having from 1 to 10, preferably from 1 to 6 and more preferably from 1 to 4, carbon atoms, such as the methoxy, ethoxy, butoxy, isobutoxy, sec-butoxy, t-butoxy, pentyloxy, isopentyloxy, 2-methylbutoxy, neopentyloxy, 1-ethylpropoxy, hexyloxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy, 2-ethylbutoxy, heptyloxy, 1-methylhexyloxy, 2-methylhexyloxy, 3-methylhexyloxy, 4-methylhexyloxy, 5-methylhexyloxy, 1-propylbutoxy, 4,4- dimethylpentyloxy, octyloxy, 1-methylheptyloxy, 2-methylheptyloxy, 3-methylheptyloxy, 4-methylheptyloxy, 5-methylheptyloxy, 6-methylheptyloxy, 1-propylpentyloxy, 2-ethylhexyloxy, 5,5-dimethylhexyloxy, nonyloxy, 3-methyloctyloxy, 4-methyloctyloxy, 5-methyloctyloxy, 6-methyloctyloxy, 1-propylhexyloxy, 2-ethylheptyloxy, 6,6-dimethylheptyloxy, decyloxy, 1-methylnonyloxy, 3-methylnonyloxy, 8-methylnonyloxy, 3-ethyloctyloxy, 3,7-dimethyloctyloxy and 7,7-dimethyloctyloxy groups.

Alkoxyalkoxy groups in which each alkoxy part has from 1 to 6, preferably from 1 to 4, carbon atoms, such as the methoxymethoxy, ethoxymethoxy, propoxymethoxy, butoxymethoxy, isobutoxymethoxy, t-butoxymethoxy, pentyloxymethoxy, hexyloxymethoxy, 2-methoxyethoxy, 2-ethoxyethoxy, 2-propoxyethoxy, 2-butoxyethoxy, 2-isobutoxyethoxy, 2-t-butoxyethoxy, 2-pentyloxyethoxy, 2-hexyloxyethoxy, 3-methoxypropoxy, 3-ethoxypropoxy, 3-propoxypropoxy, 3-butoxypropoxy, 3-isobutoxypropoxy, 3-t-butoxypropoxy, 4-methoxybutoxy, 4-ethoxybutoxy, 4-propoxybutoxy, 4-butoxybutoxy, 4-isobutoxybutoxy, 4-t-butoxybutoxy, 5-methoxypentyloxy, 5-ethoxypentyloxy, 5-propoxypentyloxy, 5-butoxypentyloxy, 5-isobutoxypentyloxy, 5-t-butoxypentyloxy, 6-methoxyhexyloxy, 6-ethoxyhexyloxy, 6-propoxyhexyloxy, 6-butoxyhexyloxy, 6-isobutoxyhexyloxy, 6-t-butoxyhexyloxy, 6-pentyloxyhexyloxy and 6-hexyloxyhexyloxy groups, most preferably the methoxymethoxy group.

Alkylthioalkoxy groups in which the alkyl part and the alkoxy part each has from 1 to 6, preferably from 1 to 4, carbon atoms, such as the methylthiomethoxy, ethylthiomethoxy, propylthiomethoxy, butylthiomethoxy, isobutylthiomethoxy, t-butylthiomethoxy, pentylthiomethoxy, hexylthiomethoxy, 2-methylthioethoxy, 2-ethylthioethoxy, 2-propylthioethoxy, 2-butylthioethoxy, 2-isobutylthioethoxy, 2-t-butylthioethoxy, 2-pentylthioethoxy, 2-hexylthioethoxy, 3-methylthiopropoxy, 3-ethylthiopropoxy, 3-propylthiopropoxy, 3-butylthiopropoxy, 3-isobutylthiopropoxy, 3-t-butylthiopropoxy, 4-methylthiobutoxy, 4-ethylthiobutoxy, 4-propylthiobutoxy, 4-butylthiobutoxy, 4-isobutylthiobutoxy, 4-t-butylthiobutoxy, 5-methylthiopentyloxy, 5-ethylthiopentyloxy, 5-propylthiopentyloxy, 5-butylthiopentyloxy, 5-isobutylthiopentyloxy, 5-t-butylthiopentyloxy, 6-methylthiohexyloxy, 6-ethylthiohexyloxy, 6-propylthiohexyloxy, 6-butylthiohexyloxy, 6-isobutylthiohexyloxy, 6-t-butylthiohexyloxy, 6-pentylthiohexyloxy and 6-hexylthiohexyloxy groups, most preferably the methylthiomethoxy group.

Alkoxyalkoxyalkoxy groups in which each alkoxy part has from 1 to 6, preferably from 1 to 4, carbon atoms, such as the methoxymethoxymethoxy, ethoxymethoxymethoxy, 2-propoxymethoxyethoxy, 3-butoxymethoxypropoxy, isobutoxymethoxymethoxy, t-butoxymethoxymethoxy, pentyloxymethoxymethoxy, hexyloxymethoxymethoxy, (2-methoxyethoxy)methoxy, (2-ethoxyethoxy)methoxy, 2-(2-propoxyethoxy)ethoxy, (2-butoxyethoxy)methoxy, (2-isobutoxyethoxy)methoxy, 4-(2-t-butoxyethoxy)butoxy, (2-pentyloxyethoxy)methoxy, 6-(2-hexyloxyethoxy) hexyloxy, (3-methoxypropoxy)methoxy, (3-ethoxypropoxy) methoxy, 5-(3-propoxypropoxy)pentyloxy, (3-butoxypropoxy)methoxy, (3-isobutoxypropoxy)methoxy, (3-t-butoxypropoxy)methoxy, (4-methoxybutoxy)methoxy, (4-ethoxybutoxy)methoxy, (4-propoxybutoxy)methoxy, (4-butoxybutoxy)methoxy, (4-isobutoxybutoxy)methoxy, (4-t-butoxybutoxy)methoxy, (5-methoxypentyloxy) methoxy, (5-ethoxypentyloxy)methoxy, (5-propoxypentyloxy)methoxy, (5-butoxypentyloxy) methoxy, (5-isobutoxypentyloxy)methoxy, (5-t-butoxypentyloxy)methoxy, (6-methoxyhexyloxy)methoxy, (6-ethoxyhexyloxy)methoxy, (6-propoxyhexyloxy) methoxy, (6-butoxyhexyloxy)methoxy, (6-isobutoxyhexyloxy)methoxy, (6-t-butoxyhexyloxy) methoxy, (6-pentyloxyhexyloxy)methoxy and (6-hexyloxyhexyloxy)methoxy groups, most preferably the methoxymethoxymethoxy and (2-methoxyethoxy)methoxy groups.

Aryloxy groups where the aryl part is as defined above, for example the phenoxy, α-naphthyloxy, β-naphthyoxyl, 1-phenanthryloxy, 2-phenanthryloxy, 1-anthryloxy and 2-anthryloxy groups, especially the phenoxy, α-naphthyloxy and β-naphthyloxy groups, and most especially the phenoxy group.

Aralkyloxy groups where the aralkyl part is as defined and exemplified in relation to the aralkylamino groups, and preferably the alkyl part has from 1 to 4 carbon atoms and the aryl part is as defined above. Specific examples of the aralkyloxy groups include the benzyloxy, 1-naphthylmethoxy, 2-naphthylmethoxy, phenethyloxy, α-methylbenzyloxy, 3-phenylpropoxy, 2-phenylpropoxy, 1-phenylpropoxy, 4-phenylbutoxy, benzhydryloxy and trityloxy groups, of which the benzyloxy group is preferred.

Aliphatic carboxylic acyloxy groups having from 1 to 30 carbon atoms, such as the formyloxy, acetoxy, propionyloxy, butyryloxy, isobutyryloxy, valeryloxy, isovaleryloxy, pivaloyloxy, 2-methylbutyryloxy, hexanoyloxy, isohexanoyloxy, 3-methylvaleryloxy, 4,4-dimethylbunyryloxy, 2-ethylbutyryloxy, heptanoyloxy, 5-methylhexanoyloxy, 4-methylhexanoyloxy, 3-methylhexanoyloxy, 2-methylhexanoyloxy, 4,4-dimethylvaleryloxy, 3,3-dimethylvaleryloxy, 2,2-dimethylvaleryloxy, 2,3-dimethylvaleryloxy, 2,4-dimethylvaleryloxy, 3,4-dimethylvaleryloxy, 3-ethylvaleryloxy, octanoyloxy, 2-methylheptanoyloxy, 3-methylheptanoyloxy, 4-methylheptanoyloxy, 5-methylheptanoyloxy, 6-methylheptanoyloxy, 2-propylvaleryloxy, 5,5-dimethylhexanoyloxy, nonanoyloxy, 2-methyloctanoyloxy, 3-methyloctanoyloxy, 4-methyloctanoyloxy, 5-methyloctanoyloxy, 6-methyloctanoyloxy, 7-methyloctanoyloxy, 2-propylhexanoyloxy, 3-ethylheptanoyloxy, 6,6-dimethylheptanoyloxy, decanoyloxy, 4-methylnonanoyloxy, 5-methylnonanoyloxy, 6-methylnonanoyloxy, 7-methylnonanoyloxy, 2-propylheptanoyloxy, 3-ethyloctanoyloxy, 7,7-dimethyloctanoyloxy, undecanoyloxy, 2-methyldecanoyloxy, 4-methyldecanoyloxy, 9-methyldecanoyloxy, 4-ethylnonanoyloxy, 4,8-dimethylnonanoyloxy, 8,8-dimethylnonanoyloxy, lauroyloxy, 4,8-dimethyldecanoyloxy, tridecanoyloxy, myristoyloxy, pentadecanoyloxy, palmitoyloxy, 3,7,11-trimethyltridecanoyloxy, heptadecanoyloxy, 4,8,12-trimethylmyristoyloxy, 1-methylpalmitoyloxy, 14-methylpalmitoyloxy, 13,13-dimethylpentadecanoyloxy, stearoyloxy, 15-methylheptadecanoyloxy, nonadecanoyloxy, 1-methylstearoyloxy, icosanoyloxy, henicosanoyloxy, 3,7,11,15-tetramethylheptadecanoyloxy, docosanoyloxy, tricosanoyloxy, tetracosanoyloxy and triacontanoyloxy groups.

Aromatic carboxylic acyloxy groups where the aryl part is as defined above, preferably: unsubstituted groups (such as the benzoyl, α-naphthoyl, β-naphthoyl, 1-phenanthrylcarbonyl, 2-phenanthrylcarbonyl, 1-anthrylcarbonyl and 2-anthrylcarbonyl groups, especially the benzoyl, α-naphthoyl and β-naphthoyl groups, and most especially the benzoyl group); halogenated arylcarbonyl groups (such as the 2-bromobenzoyl and 4-chlorobenzoyl groups); lower alkyl-substituted arylcarbonyl groups, in which the or each alkyl substituent has from 1 to 5, preferably from 1 to 4, carbon atoms (such as the 2,4,6-trimethylbenzoyl and 4-toluoyl groups); lower alkoxy-substituted arylcarbonyl groups, in which the or each alkoxy substituent preferably has from 1 to 5, preferably from 1 to 4, carbon atoms (such as the 4-anisoyl group); nitro-substituted arylcarbonyl groups (such as the 4-nitrobenzoyl and 2-nitrobenzoyl groups); lower alkoxycarbonyl substituted arylcarbonyl groups, in which the or each alkoxycarbonyl substituent preferably has from 2 to 6 carbon atoms [such as the 2-(methoxycarbonyl)benzoyl group]; and aryl-substituted arylcarbonyl groups, in which the aryl substituent is as defined above, except that, if it is substituted by a further aryl group, that aryl group is not itself substituted by an aryl group (such as the 4-phenylbenzoyl group).

Aralkyloxycarbonyloxy groups where the aralkyl part is as defined and exemplified in relation to the aralkylamino groups, and preferably the alkyl part has from 1 to 4 carbon atoms and the aryl part is as defined above. Specific examples of the aralkyloxycarbonyloxy groups include the benzyloxycarbonyloxy, 1-naphthylmethoxycarbonyloxy, 2-naphthylmethoxycarbonyloxy, phenethyloxycarbonyloxy, α-methylbenzyloxycarbonyloxy, 3-phenylpropoxycarbonyloxy, 2-phenylpropoxycarbonyloxy, 1-phenylpropoxycarbonyloxy, 4-phenylbutoxycarbonyloxy, benzhydryloxycarbonyloxy and trityloxycarbonyloxy groups, of which the benzyloxycarbonyloxy group is preferred.

Haloalkoxycarbonyloxy groups, in which the alkoxy part may be a straight or branched chain group, and the haloalkoxycarbonyloxy group has from 2 to 17, preferably from 2 to 11 and more preferably from 2 to 5, carbon atoms, that is the alkoxy part has from 1 to 16, preferably from 1 to 10 and more preferably from 1 to 4, carbon atoms. This is substituted by at least one halogen atom, for example a fluorine, chlorine, bromine or iodine atom. There is no limitation on the number of halogen substituents, except such as may be imposed by the number of substitutable carbon atoms, or possibly by steric constraints. However, generally from one to three halogen substituents is preferred. Examples of such haloalkoxycarbonyl groups are as given above in relation to mercapto-protecting groups but with one or more halogen substituents, and specific examples of such alkoxycarbonyloxy groups include the fluoromethoxycarbonyloxy, 2-fluoroethoxycarbonyloxy, 3-fluoropropoxycarbonyloxy, 2-fluoro-1-methylethoxycarbonyloxy, 4-fluorobutoxycarbonyloxy, 3-fluoro-2-propoxycarbonyloxy, 2-fluoro-1,1-dimethylethoxycarbonyloxy, chloromethoxycarbonyloxy, 2-chloroethoxycarbonyloxy, 3-chloropropoxycarbonyloxy, 2-chloro-1-methylethoxycarbonyloxy, 4-chlorobutoxycarbonyloxy, 3-chloro-2-propoxycarbonyloxy, 2-chloro-1,1-dimethylethoxycarbonyloxy, bromomethoxycarbonyloxy, 2-bromoethoxycarbonyloxy, 3-bromopropoxycarbonyloxy, 2-bromo-1-methylethoxycarbonyloxy, 4-bromobutoxycarbonyloxy, 3-bromo-2-propoxycarbonyloxy, 2-bromo-1,1-dimethylethoxycarbonyloxy, iodomethoxycarbonyloxy, 2-iodoethoxycarbonyloxy, 3-iodopropoxycarbonyloxy, 2-iodo-1-methylethoxycarbonyloxy, 4-iodobutoxycarbonyloxy, 3-iodo-2-propoxycarbonyloxy, 2-iodo-1,1-dimethylethoxycarbonyloxy, trifluoromethoxycarbonyloxy, 2,2,2-trifluoroethoxycarbonyloxy and 2,2,2-trichloroethoxycarbonyloxy groups.

Aryloxycarbonyloxy groups where the aryl part is as defined above, for example the phenoxycarbonyloxy, α-naphthyloxycarbonyloxy, β-naphthyloxycarbonyloxy, 1-phenanthryloxycarbonyloxy, 2-phenanthryloxycarbonyloxy, 1-anthryloxycarbonyloxy and 2-anthryloxycarbonyloxy groups, especially the phenoxycarbonyloxy, α-naphthyloxycarbonyloxy and β-naphthyloxycarbonyloxy groups, and most especially the phenoxycarbonyloxy group.

Tri-substituted silyloxy groups, in which all three or two or one of the substituents are alkyl groups having from 1 to 8, preferably from 1 to 5 and more preferably from 1 to 4, carbon atoms, and none, one or two of the substituents are aryl groups, as defined above, but preferably phenyl or substituted phenyl groups; examples of such aryl groups and alkyl groups are given above in relation to tri-substituted silyl groups which may be used as mercapto-protecting groups. Preferred examples of the trisilyloxy groups are: tri(lower alkyl)silyloxy groups (such as the trimethylsilyloxy, triethylsilyloxy, isopropyldimethylsilyloxy, t-butyl-dimethylsilyloxy, methyldiisopropylsilyloxy, methyldi-t-butylsilyloxy and tri-isopropylsilyloxy groups); and tri(lower alkyl)silyloxy groups in which one or two of the alkyl groups have been replaced by aryl groups (such as the diphenylmethylsilyloxy, diphenylbutylsilyloxy, diphenyl-t-butylsilyloxy, diphenylisopropylsilyloxy and phenyldiisopropylsilyloxy groups).

Alkylthio groups having from 1 to 10, preferably from 1 to 6 and more preferably from 1 to 4, carbon atoms, such as the methylthio, ethylthio, butylthio, isobutylthio, sec-butylthio, t-butylthio, pentylthio, isopentylthio, 2-methylbutylthio, neopentylthio, 1-ethylpropylthio, hexylthio, 4-methylpentylthio, 3-methylpentylthio, 2-methylpentylthio, 1-methylpentylthio, 3,3-dimethylbutylthio, 2,2-dimethylbutylthio, 1,1-dimethylbutylthio, 1,2-dimethylbutylthio, 1,3-dimethylbutylthio, 2,3-dimethylbutylthio, 2-ethylbutylthio, heptylthio, 1-methylhexylthio, 2-methylhexylthio, 3-methylhexylthio, 4-methylhexylthio, 5-methylhexylthio, 1-propylbutylthio, 4,4-dimethylpentylthio, octylthio, 1-methylheptylthio, 2-methylheptylthio, 3-methylheptylthio, 4-methylheptylthio, 5-methylheptylthio, 6-methylheptylthio, 1-propylpentylthio, 2-ethylhexylthio, 5,5-dimethylhexylthio, nonylthio, 3-methyloctylthio, 4-methyloctylthio, 5-methyloctylthio, 6-methyloctylthio, 1-propylhexylthio, 2-ethylheptylthio, 6,6-dimethylheptylthio, decylthio, 1-methylnonylthio, 3-methylnonylthio, 8-methylnonylthio, 3-ethyloctylthio, 3,7-dimethyloctylthio and 7,7-dimethyloctylthio groups.

Arylthio groups, in which the aryl part, which may be substituted or unsubstituted, is as defined and exemplified above, for example the phenylthio, 1-naphthylthio, 2-naphthylthio, 1-phenanthrylthio, 2-phenanthrylthio, 1-anthrylthio and 2-anthrylthio groups, more preferably the phenylthio group.

Aralkylthio groups where the aralkyl part is as defined and exemplified in relation to the aralkylamino groups, and preferably the alkyl part has from 1 to 4 carbon atoms and the aryl part is as defined above. Specific examples of the aralkylthio groups include the benzylthio, 1-naphthylmethylthio, 2-naphthylmethylthio, phenethylthio, α-methylbenzylthio, 3-phenylpropylthio, 2-phenylpropylthio, 1-phenylpropylthio, 4-phenylbutylthio, benzhydrylthio and tritylthio groups, of which the benzylthio group is preferred.

Alkyldithio groups having from 1 to 10, preferably from 1 to 6 and more preferably from 1 to 4, carbon atoms, such as the methyldithio, ethyldithio, butyldithio, isobutyldithio, sec-butyldithio, t-butyldithio, pentyldithio, isopentyldithio, 2-methylbutyldithio, neopentyldithio, 1-ethylpropyldithio, hexyldithio, 4-methylpentyldithio, 3-methylpentyldithio, 2-methylpentyldithio, 1-methylpentyldithio, 3,3-dimethylbutyldithio, 2,2-dimethylbutyldithio, 1,1-dimethylbutyldithio, 1,2-dimethylbutyldithio, 1,3-dimethylbutyldithio, 2,3-dimethylbutyldithio, 2-ethylbutyldithio, heptyldithio, 1-methylhexyldithio, 2-methylhexyldithio, 3-methylhexyldithio, 4-methylhexyldithio, 5-methylhexyldithio, 1-propylbutyldithio, 4,4-dimethylpentyldithio, octyldithio, 1-methylheptyldithio, 2-methylheptyldithio, 3-methylheptyldithio, 4-methylheptyldithio, 5-methylheptyldithio, 6-methylheptyldithio, 1-propylpentyldithio, 2-ethylhexyldithio, 5,5-dimethylhexyldithio, nonyldithio, 3-methyloctyldithio, 4-methyloctyldithio, 5-methyloctyldithio, 6-methyloctyldithio, 1-propylhexyldithio, 2-ethylheptyldithio, 6,6-dimethylheptyldithio, decyldithio, 1-methylnonyldithio, 3-methylnonyldithio, 8-methylnonyldithio, 3-ethyloctyldithio, 3,7-dimethyloctyldithio and 7,7-dimethyloctyldithio groups.

Aryldithio groups, in which the aryl part, which may be substituted or unsubstituted, is as defined and exemplified above, for example the phenyldithio, 1-naphthyldithio, 2-naphthyldithio, 1-phenanthryldithio, 2-phenanthryldithio, 1-anthryldithio and 2-anthryldithio groups, more preferably the phenyldithio group.

Aralkyldithio groups where the aralkyl part is as defined and exemplified in relation to the aralkylamino groups, and preferably the alkyl part has from 1 to 4 carbon atoms and the aryl part is as defined above. Specific examples of the aralkyldithio groups include the benzyldithio, 1-naphthylmethyldithio, 2-naphthylmethyldithio, phenethyldithio, α-methylbenzyldithio, 3-phenylpropyldithio, 2-phenylpropyldithio, 1-phenylpropyldithio, 4-phenylbutyldithio, benzhydryldithio and trityldithio groups, of which the benzyldithio group is preferred.

Alkylsulfonyloxy groups having from 1 to 10, preferably from 1 to 6 and more preferably from 1 to 4, carbon atoms, such as the methylsulfonyloxy, ethylsulfonyloxy, butylsulfonyloxy, isobutylsulfonyloxy, sec-butylsulfonyloxy, t-butylsulfonyloxy, pentylsulfonyloxy, isopentylsulfonyloxy, 2-methylbutylsulfonyloxy, neopentylsulfonyloxy, 1-ethylpropylsulfonyloxy, hexylsulfonyloxy, 4-methylpentylsulfonyloxy, 3-methylpentylsulfonyloxy, 2-methylpentylsulfonyloxy, 1-methylpentylsulfonyloxy, 3,3-dimethylbutylsulfonyloxy, 2,2-dimethylbutylsulfonyloxy, 1,1-dimethylbutylsulfonyloxy, 1,2-dimethylbutylsulfonyloxy, 1,3-dimethylbutylsulfonyloxy, 2,3-dimethylbutylsulfonyloxy, 2-ethylbutylsulfonyloxy, heptylsulfonyloxy, 1-methylhexylsulfonyloxy, 2-methylhexylsulfonyloxy, 3-methylhexylsulfonyloxy, 4-methylhexylsulfonyloxy, 5-methylhexylsulfonyloxy, 1-propylbutylsulfonyloxy, 4,4-dimethylpentylsulfonyloxy, octylsulfonyloxy, 1-methylheptylsulfonyloxy, 2-methylheptylsulfonyloxy, 3-methylheptylsulfonyloxy, 4-methylheptylsulfonyloxy, 5-methylheptylsulfonyloxy, 6-methylheptylsulfonyloxy, 1-propylpentylsulfonyloxy, 2-ethylhexylsulfonyloxy, 5,5-dimethylhexylsulfonyloxy, nonylsulfonyloxy, 3-methyloctylsulfonyloxy, 4-methyloctylsulfonyloxy, 5-methyloctylsulfonyloxy, 6-methyloctylsulfonyloxy, 1-propylhexylsulfonyloxy, 2-ethylheptylsulfonyloxy, 6,6-dimethylheptylsulfonyloxy, decylsulfonyloxy, 1-methylnonylsulfonyloxy, 3-methylnonylsulfonyloxy, 8-methylnonylsulfonyloxy, 3-ethyloctylsulfonyloxy, 3,7-dimethyloctylsulfonyloxy and 7,7-dimethyloctylsulfonyloxy groups.

Arylsulfonyloxy groups, in which the aryl part, which may be substituted or unsubstituted, is as defined and exemplified above, for example the phenylsulfonyloxy, 1-naphthylsulfonyloxy, 2-naphthylsulfonyloxy, 1-phenanthrylsulfonyloxy, 2-phenanthrylsulfonyloxy, 1-anthrylsulfonyloxy and 2-anthrylsulfonyloxy groups, more preferably the phenylsulfonyloxy group.

Carbamoyl groups.

Carbamoyloxy groups.

Substituents C are selected from the group consisting of:

alkyl groups having from 1 to 6 carbon atoms, such as the methyl, ethyl, propyl, butyl, isobutyl, sec-butyl, t-butyl, pentyl, isopentyl, neopentyl, hexyl and isohexyl groups, preferably the methyl or ethyl groups;

alkoxy groups having from 1 to 6 carbon atoms, such as the methoxy, ethoxy, propoxy, butoxy, isobutoxy, sec-butoxy, t-butoxy, pentyloxy, isopentyloxy, neopentyloxy, hexyloxy and isohexyloxy groups, preferably the methoxy or ethoxy groups;

aliphatic carboxylic acyl groups having from 1 to 6 carbon atoms, preferably: alkanoyl groups having from 1 to 6 carbon atoms, and most preferably from 1 to 4 carbon atoms (such as those exemplified above in relation to $R^1$, $R^2$ and $R^3$, especially the formyl, acetyl, propionyl, butyryl, isobutyryl, pivaloyl, valeryl, isovaleryl and hexanoyl groups, of which the acetyl group is most preferred); halogenated alkanoyl groups having from 2 to 6 carbon atoms, especially halogenated acetyl groups (such as the chloroacetyl, dichloroacetyl, trichloroacetyl and trifluoroacetyl groups); lower alkoxyalkanoyl groups in which the alkoxy part has from 1 to 5, preferably from 1 to 3, carbon atoms and the alkanoyl part has from 2 to 6 carbon atoms and is preferably an acetyl group (such as the methoxyacetyl group); and unsaturated analogs of such groups, especially alkenoyl or alkynoyl groups having from 3 to 6 carbon atoms [such as the acryloyl, methacryloyl, propioloyl, crotonoyl, isocrotonoyl and (E)-2-methyl-2-butenoyl groups];

halogen atoms, such as the fluorine, chlorine, bromine and iodine atoms;

nitro groups, cyano groups, and amino groups.

Where substituent A represents a carboxy group, the resulting compound is a carboxylic acid and can thus form esters in the usual way well understood by those skilled in the art. There is no particular limitation on the nature of the esters thus obtained, provided that, where they are to be used for pharmaceutical purposes, they are pharmaceutically acceptable, that is the ester does not have an increased toxicity, or an unacceptably increased toxicity, and does not have a reduced activity, or an unacceptably reduced activity, as compared to the free acid. Where the compound is to be used for non-pharmaceutical purposes, even this limitation does not apply. Examples of ester groups include:

$C_1$–$C_{20}$ alkyl groups, more preferably $C_1$–$C_6$ alkyl groups, such as those exemplified in relation to substituents C and higher alkyl groups as are well known in the art, such as the heptyl, octyl, nonyl, decyl, dodecyl, tridecyl, pentadecyl, octadecyl, nonadecyl and icosyl groups, but most preferably the methyl, ethyl and t-butyl groups;

$C_3$–$C_7$ cycloalkyl groups, for example the cyclopropyl, cyclobutyl, cyclopentyl, cyclohexyl and cycloheptyl groups;

aralkyl groups, in which the alkyl part is a $C_1$–$C_3$ alkyl group and the aryl part is a $C_6$–$C_{14}$ carbocyclic aromatic group which may be substituted or unsubstituted and, if substituted, has at least one substituent selected from substituents C defined and exemplified below, although the unsubstituted groups are preferred; examples of such aralkyl groups include the benzyl, phenethyl, 1-phenylethyl, 3-phenylpropyl, 2-phenylpropyl, 1-naphthylmethyl, 2-naphthylmethyl, 2-(1-naphthyl)ethyl, 2-(2-naphthyl)ethyl, benzhydryl (i.e. diphenylmethyl), triphenylmethyl, bis(o-nitrophenyl)methyl, 9-anthrylmethyl, 2,4,6-trimethylbenzyl, 4-bromobenzyl, 2-nitrobenzyl, 4-nitrobenzyl, 3-nitrobenzyl, 4-methoxybenzyl and piperonyl groups;

alkenyl groups having from 2 to 6 carbon atoms, such as the the vinyl, allyl, 2-methylallyl, 1-propenyl, isopropenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl and 5-hexenyl groups, of which the vinyl, allyl, 2-methylallyl, 1-propenyl, isopropenyl and butenyl groups are preferred, the allyl and 2-methylallyl groups being most preferred.

halogenated $C_1$–$C_6$, preferably $C_1$–$C_4$, alkyl groups in which the alkyl part is as defined and exemplified in relation to the alkyl groups above, and the halogen atom is chlorine, fluorine, bromine or iodine, such as the 2,2,2-trichloroethyl, 2-haloethyl (e.g. 2-chloroethyl, 2-fluoroethyl, 2-bromoethyl or 2-iodoethyl), 2,2-dibromoethyl and 2,2,2-tribromoethyl group;

substituted silylalkyl groups, in which the alkyl part is as defined and exemplified above, and the silyl group has up to 3 substituents selected from $C_1$14 $C_6$ alkyl groups and phenyl groups which are unsubstituted or have an least one substituent selected from substituents C defined and exemplified below, for example a 2-trimethylsilylethyl group;

phenyl groups, in which the phenyl group is unsubstituted or substituted, preferably with at least one $C_1$–$C_4$ alkyl or acylamino group, for example the phenyl, tolyl and benzamidophenyl groups;

phenacyl groups, which may be unsubstituted or have at least one substituent selected from substituents C defined and exemplified above, for example the phenacyl group itself or the p-bromophenacyl group;

cyclic and acyclic terpenyl groups, for example the geranyl, neryl, linalyl, phytyl, menthyl (especially m- and p-menthyl), thujyl, caryl, pinanyl, bornyl, notcaryl, norpinanyl, norbornyl, menthenyl, camphenyl and norbornenyl groups;

alkoxymethyl groups, in which the alkoxy part is $C_1$–$C_6$, preferably $C_1$–$C_4$, and may itself be substituted by a single unsubstituted alkoxy group, such as the methoxymethyl, ethoxymethyl, propoxymethyl, isopropoxymethyl, butoxymethyl and methoxyethoxymethyl groups;

aliphatic acyloxyalkyl groups, in which the acyl group is preferably an alkanoyl group and is more preferably a $C_2$–$C_6$ alkanoyl group, and the alkyl part is a $C_2$–$C_6$, and preferably $C_2$–$C_4$, alkyl group, such as the acetoxymethyl, propionyloxymethyl, butyryloxymethyl, isobutyryloxymethyl, pivaloyloxymethyl, 1-pivaloyloxyethyl, 1-acetoxyethyl, 1-isobutyryloxyethyl, 1-pivaloyloxypropyl, 2-methyl-1-pivaloyloxypropyl, 2-pivaloyloxypropyl, 1-isobutyryloxyethyl, 1-isobutyryloxypropyl, 1-acetoxypropyl, 1-acetoxy-2-methylpropyl, 1-propionyloxyethyl, 1-propionyloxypropyl, 2-acetoxypropyl and 1-butyryloxyethyl groups;

cycloalkyl-substituted aliphatic acyloxyalkyl groups, in which the acyl group is preferably an alkanoyl group and is more preferably a $C_2$–$C_6$ alkanoyl group, the cycloalkyl substituent is $C_3$–$C_7$, and the alkyl part is a $C_1$–$C_6$ alkyl group, preferably a $C_1$–$C_4$ alkyl group, such as the (cyclohexylacetoxy)methyl, 1-(cyclohexylacetoxy)ethyl, 1-(cyclohexylacetoxy)propyl, 2-methyl-1-(cyclohexylacetoxy)propyl, (cyclopentylacetoxy)methyl, 1-(cyclopentylacetoxy)ethyl, 1-(cyclopentylacetoxy)propyl and 2-methyl-1-(cyclopentylacetoxy)propyl, groups;

alkoxycarbonyloxyalkyl groups, especially 1-(alkoxycarbonyloxy)ethyl groups, in which the alkoxy part is $C_1$–$C_{10}$, preferably $C_1$–$C_6$, and more preferably $C_1$–$C_4$, and the alkyl part is $C_1$–$C_6$, preferably $C_1$–$C_4$, such as the 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl, 1-isobutoxycarbonyloxyethyl, 1-sec-butoxycarbonyloxyethyl, 1-t-butoxycarbonyloxyethyl, 1-(1-ethylpropoxycarbonyloxy)ethyl and 1-(1,1-dipropylbutoxycarbonyloxy)ethyl groups, and other alkoxycarbonylalkyl groups, in which both the alkoxy and alkyl groups are $C_1$–$C_6$, preferably $C_1$–$C_4$, such as the 2-methyl-1-(isopropoxycarbonyloxy)propyl, 2-(isopropoxycarbonyloxy)propyl, isopropoxycarbonyloxymethyl, t-butoxycarbonyloxymethyl, methoxycarbonyloxymethyl and ethoxycarbonyloxymethyl groups;

cycloalkylcarbonyloxyalkyl and cycloalkyloxycarbonyloxyalkyl groups, in which the cycloalkyl group is $C_3$–$C_{10}$, preferably $C_3$–$C_7$, is mono- or poly-cyclic and is optionally substituted by at least one (and preferably only one) $C_1$–$C_4$ alkyl group (e.g. selected from those alkyl groups exemplified above) and the alkyl group is a $C_1$–$C_6$, more preferably $C_1$–$C_4$, alkyl group (e.g. selected from those alkyl groups exemplified above) and is most preferably methyl, ethyl or propyl, for example the 1-methylcyclohexylcarbonyloxymethyl, 1-methylcyclohexyloxycarbonyloxymethyl, cyclopentyloxycarbonyloxymethyl, cyclopentyloxycarbonyloxymethyl, cyclopentylcarbonyloxymethyl, 1-cyclohexyloxycarbonyloxyethyl, 1-cyclohexylcarbonyloxyethyl, 1-cyclopentyloxycarbonyloxyethyl, 1-cyclopentylcarbonyloxyethyl, 1-cycloheptyloxycarbonyloxyethyl,
1-cycloheptylcarbonyloxyethyl,
1-methylcyclopentylcarbonyloxymethyl,
1-methylcyclopentyloxycarbonyloxymethyl, 2-methyl-1-(1-methylcyclohexylcarbonyloxy)propyl, 1-(1-methylcyclohexylcarbonyloxy)propyl, 2-(1-methylcyclohexylcarbonyloxy)propyl, 1-(cyclohexylcarbonyloxy)propyl, 2-(cyclohexylcarbonyloxy)propyl, 2-methyl-1-(1-methylcyclopentylcarbonyloxy)propyl, 1-(1-methylcyclopentylcarbonyloxy)propyl, 2-(1-methylcyclopentylcarbonyloxy)propyl, 1-(cyclopentylcarbonyloxy)propyl, 2-(cyclopentylcarbonyloxy)propyl, 1-(1-methylcyclopentylcarbonyloxy)ethyl, 1-(1-methylcyclopentylcarbonyloxy)propyl, adamantyloxycarbonyloxymethyl, adamantylcarbonyloxymethyl, 1-adamantyloxycarbonyloxyethyl and 1-adamantylcarbonyloxyethyl groups;

cycloalkylalkoxycarbonyloxyalkyl groups in which the alkoxy group has a single cycloalkyl substituent, the cycloalkyl substituent being $C_3$–$C_{10}$, preferably $C_3$–$C_7$, and mono- or poly-cyclic, for example the cyclopropylmethoxycarbonyloxymethyl, cyclobutylmethoxycarbonyloxymethyl, cyclopentylmethoxycarbonyloxymethyl, cyclohexylmethoxycarbonyloxymethyl, 1-(cyclopropylmethoxycarbonyloxy)ethyl, 1-(cyclobutylmethoxycarbonyloxy)ethyl, 1-(cyclopentylmethoxycarbonyloxy)ethyl and 1-(cyclohexylmethoxycarbonyloxy)ethyl groups;

terpenylcarbonyloxyalkyl and terpenyloxycarbonyloxyalkyl groups, in which the terpenyl group is as exemplified above, and is preferably a cyclic terpenyl group, for example the 1-(menthyloxycarbonyloxy)ethyl, 1-(menthylcarbonyloxy)ethyl, menthyloxycarbonyloxymethyl, menthylcarbonyloxymethyl, 1-(3-pinanyloxycarbonyloxy)ethyl, 1-(3-pinanylcarbonyloxy)ethyl, 3-pinanyloxycarbonyloxymethyl and 3-pinanylcarbonyloxymethyl groups;

5-alkyl or 5-phenyl [which may be substituted by at least one substituent selected from substituents C, defined and exemplified above] (2-oxo-1,3-dioxolen-4-yl)alkyl groups in which each alkyl group (which may be the same or different) is $C_1$–$C_6$, preferably $C_1$–$C_4$, for example the (5-methyl-2-oxo-1,3-dioxolen-4-yl)methyl, (5-phenyl-2-oxo-1,3-dioxolen-4-yl)methyl, (5-isopropyl-2-oxo-1,3-dioxolen-4-yl)methyl, (5-t-butyl-2-oxo-1,3-dioxolen-4-yl)methyl and 1-(5-methyl-2-oxo-1,3-dioxolen-4-yl)ethyl groups; and other groups, especially groups which are easily removed in vivo such as the phthalidyl, indanyl and 2-oxo-4,5,6,7-tetrahydro-1,3-benzodioxolen-4-yl groups.

Of the above groups, we especially prefer those groups which can be removed easily in vivo, and most preferably the aliphatic acyloxyalkyl groups, alkoxycarbonyloxyalkyl groups, cycloalkylcarbonyloxyalkyl groups, phthalidyl groups and (5-substituted 2-oxo-1,3-dioxolen-4-yl)methyl groups.

The compounds of the present invention can also form salts. Examples of such salts include, when the compound contains a carboxy group: salts with an alkali metal, such as sodium, potassium or lithium; salts with an alkaline earth metal, such as barium or calcium; salts with another metal, such as magnesium or aluminum; organic base salts, such as a salt with triethylamine, diisopropylamine, cyclohexylamine or dicyclohexylamine; and salts with a basic amino acid, such as lysine or arginine. Also, the compound of the present invention contains a basic group in its molecule, and can thus form acid addition salts. Examples of such acid addition salts include: salts with mineral acids, especially hydrohalic acids (such as hydrofluoric acid, hydrobromic acid, hydroiodic acid or hydrochloric acid), nitric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; and salts with organic carboxylic acids, such as acetic acid, fumaric acid, tartaric acid, oxalic acid, maleic acid, malic acid, succinic acid, benzoic acid, mandelic acid, ascorbic acid, lactic acid, gluconic acid, citric, propionic and hexanoic acid. Of these, we particularly prefer the salts with mineral acids, especially the hydrochloride, and salts with aliphatic carboxylic acids, especially acetic acid.

Depending on the nature of the substituents represented by $R^1$, $R^2$ and $R^3$, the compounds of the present invention may contain one or more asymmetric carbon atoms in their molecules, and can thus form optical isomers. Although these are all represented herein by a single molecular formula, the present invention includes both the individual, isolated isomers and mixtures, including racemates thereof. Where stereospecific synthesis techniques are employed or optically active compounds are employed as starting materials, individual isomers may be prepared directly; on the other hand, if a mixture of isomers is prepared, the individual isomers may be obtained by conventional resolution techniques.

Of the compounds of the present invention, we particularly prefer compounds of formula (I) and pharmaceutically acceptable salts thereof and, where said substituent A is a carboxy group, pharmaceutically acceptable esters thereof wherein:

$R^1$, $R^2$ and $R^3$ are independently selected from the group consisting of
hydrogen atoms,
alkanoyl groups having from 5 to 24 carbon atoms,
substituted alkanoyl groups which have from 2 to 24 carbon atoms and which are substituted by at least one substituent selected from the group consisting of substituents A and substituents B, defined above, and
alkenylcarbonyl groups having from 3 to 24 carbon atoms;

PROVIDED THAT at least one of $R^1$, $R^2$ and $R^3$ represents said unsubstituted alkanoyl group, said substituted alkanoyl group or said alkenylcarbonyl group.

More preferred compounds of the present invention are those compounds of formula (I) and pharmaceutically acceptable salts thereof and, where said substituent A is a carboxy group, pharmaceutically acceptable esters thereof wherein:

$R^1$, $R^2$ and $R^3$ are independently selected from the group consisting of
hydrogen atoms,
alkanoyl groups having from 8 to 20 carbon atoms,
substituted alkanoyl groups which have from 6 to 20 carbon atoms and which are substituted by at least one substituent selected from the group consisting of substituents A and substituents B, defined above, and
alkenylcarbonyl groups having from 8 to 20 carbon atoms;

PROVIDED THAT at least one of $R^1$, $R^2$ and $R^3$ represents said unsubstituted alkanoyl group, said substituted alkanoyl group or said alkenylcarbonyl group.

Still more preferred compounds of the present invention are those compounds of formula (I) and pharmaceutically acceptable salts thereof wherein:

$R^1$, $R^2$ and $R^3$ are independently selected from the group consisting of
  hydrogen atoms,
  alkanoyl groups having from 8 to 20 carbon atoms,
  substituted alkanoyl groups which have from 6 to 20 carbon atoms and which are substituted by at least one substituent selected from the group consisting of substituents A' and substituents B', defined below, and
  alkenylcarbonyl groups having from 8 to 20 carbon atoms;

PROVIDED THAT at least one of $R^1$, $R^2$ and $R^3$ represents said unsubstituted alkanoyl group, said substituted alkanoyl group or said alkenylcarbonyl group.

said substituents A' are selected from the group consisting of
  hydroxy groups,
  amino groups,
  mercapto groups,
  protected amino groups,
  protected mercapto groups,
  azido groups, and
  cyano groups;

said substituents B' are selected from the group consisting of
  alkoxy groups having from 1 to 10 carbon atoms,
  alkoxyalkoxy groups in which each alkoxy part has from 1 to 3 carbon atoms,
  alkoxyalkoxyalkoxy groups in which each alkoxy part has from 1 to 3 carbon atoms,
  aliphatic carboxylic acyloxy groups having from 1 to 20 carbon atoms, and
  tri-substituted silyloxy groups where the substituents are independently selected from the group consisting of alkyl groups having from 1 to 6 carbon atoms and aryl groups as defined above.

Still more preferred compounds of the present invention are those compounds of formula (I) and pharmaceutically acceptable salts thereof wherein:

$R^1$, $R^2$ and $R^3$ are independently selected from the group consisting of
  hydrogen atoms,
  alkanoyl groups having from 8 to 20 carbon atoms,
  substituted alkanoyl groups which have from 6 to 20 carbon atoms and which are substituted by at least one substituent selected from the group consisting of substituents A" and substituents B", defined below, and
  alkenylcarbonyl groups having from 8 to 20 carbon atoms;

PROVIDED THAT at least one of $R^1$, $R^2$ and $R^3$ represents said unsubstituted alkanoyl group, said substituted alkanoyl group or said alkenylcarbonyl group.

said substituents A' are selected from the group consisting of
  hydroxy groups,
  amino groups,
  protected amino groups,
  azido groups, and
  cyano groups;

said substituents B' are selected from the group consisting of
  alkoxy groups having from 1 to 10 carbon atoms,
  alkoxymethoxy groups in which the alkoxy part has from 1 to 3 carbon atoms,
  alkoxyalkoxymethoxy groups in which each alkoxy part has from 1 to 3 carbon atoms, and
  aliphatic carboxylic acyloxy groups having from 1 to 20 carbon atoms.

Particularly preferred compounds of the present invention are those compounds of formula (I) and pharmaceutically acceptable salts thereof wherein:

one of $R^1$ and $R^2$ represents a hydrogen atom, and the other of $R^1$ and $R^2$ represents an alkanoyl group having from 12 to 18 carbon atoms or a substituted alkanoyl group which has from 12 to 18 carbon atoms and which is substituted by at least one substituent selected from the group consisting of hydroxy groups, cyano groups, methoxymethoxy groups and methoxyethoxymethoxy groups; and $R^3$ represents a hydrogen atom.

The most preferred compounds of the present invention are those compounds of formula (I) and pharmaceutically acceptable salts thereof wherein:

$R^1$ represents an alkanoyl group having from 12 to 18 carbon atoms or a substituted alkanoyl group which has from 12 to 18 carbon atoms and which is substituted by at least one substituent selected from the group consisting of cyano groups, methoxymethoxy groups and methoxyethoxymethoxy groups; and $R^2$ and $R^3$ both represent hydrogen atoms.

Specific examples of preferred compounds of the present invention are those compounds of formula (I-1) and (I-2), in which $R^1$, $R^2$ and $R^3$ are as defined in the following Tables 1 and 2 [Table 1 relates to formula (I-1) and Table 2 relates to formula (I-2)]:

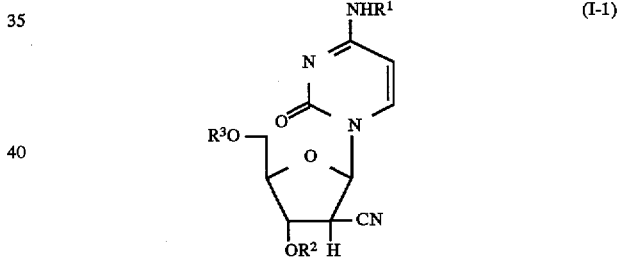

(I-1)

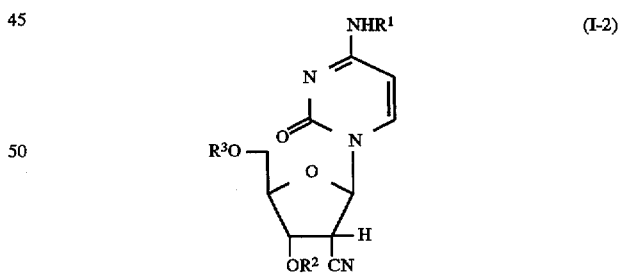

(I-2)

In the Table, the following abbreviations are used to refer to certain substituent groups:

| | |
|---|---|
| Ac | acetyl |
| Aoc | allyloxycarbonyl |
| Boc | butoxcarbonyl |
| Boz | benzoyl |
| Bz | benzyl |
| Bzc | benzyloxycarbonyl |
| Mec | methoxycarbonyl |
| Mem | methoxyethoxymethyl |
| Mes | methanesulfonyl |

-continued

| | | |
|---|---|---|
| Mom | methoxymethyl | |
| Mtm | methylthiomethyl | |
| Tos | p-toluenesulfonyl | |

TABLE 1

| Cpd. No. | $R^1$ | $R^2$ | $R^3$ |
|---|---|---|---|
| 1-1 | $CH_3(CH_2)_4CO$ | H | H |
| 1-2 | $CH_3(CH_2)_5CO$ | H | H |
| 1-3 | $CH_3(CH_2)_6CO$ | H | H |
| 1-4 | $CH_3(CH_2)_7CO$ | H | H |
| 1-5 | $CH_3(CH_2)_8CO$ | H | H |
| 1-6 | $CH_3(CH_2)_9CO$ | H | H |
| 1-7 | $CH_3(CH_2)_{10}CO$ | H | H |
| 1-8 | $CH_3(CH_2)_{11}CO$ | H | H |
| 1-9 | $CH_3(CH_2)_{12}CO$ | H | H |
| 1-10 | $CH_3(CH_2)_{13}CO$ | H | H |
| 1-11 | $CH_3(CH_2)_{14}CO$ | H | H |
| 1-12 | $CH_3(CH_2)_{15}CO$ | H | H |
| 1-13 | $CH_3(CH_2)_{16}CO$ | H | H |
| 1-14 | $CH_3(CH_2)_{17}CO$ | H | H |
| 1-15 | $CH_3(CH_2)_{18}CO$ | H | H |
| 1-16 | $CH_3(CH_2)_{19}CO$ | H | H |
| 1-17 | $CH_3(CH_2)_{20}CO$ | H | H |
| 1-18 | $HOCH_2CO$ | H | H |
| 1-19 | $HO(CH_2)_2CO$ | H | H |
| 1-20 | $HO(CH_2)_3CO$ | H | H |
| 1-21 | $HO(CH_2)_5CO$ | H | H |
| 1-22 | $HO(CH_2)_7CO$ | H | H |
| 1-23 | $HO(CH_2)_9CO$ | H | H |
| 1-24 | $HO(CH_2)_{11}CO$ | H | H |
| 1-25 | $HO(CH_2)_{13}CO$ | H | H |
| 1-26 | $HO(CH_2)_{15}CO$ | H | H |
| 1-27 | $HO(CH_2)_{17}CO$ | H | H |
| 1-28 | $HO(CH_2)_{19}CO$ | H | H |
| 1-29 | $MomO(CH_2)_5CO$ | H | H |
| 1-30 | $MomO(CH_2)_7CO$ | H | H |
| 1-31 | $MomO(CH_2)_9CO$ | H | H |
| 1-32 | $MomO(CH_2)_{11}CO$ | H | H |
| 1-33 | $MomO(CH_2)_{13}CO$ | H | H |
| 1-34 | $MomO(CH_2)_{15}CO$ | H | H |
| 1-35 | $MomO(CH_2)_{17}CO$ | H | H |
| 1-36 | $MomO(CH_2)_{19}CO$ | H | H |
| 1-37 | $MemO(CH_2)_5CO$ | H | H |
| 1-38 | $MemO(CH_2)_9CO$ | H | H |
| 1-39 | $MemO(CH_2)_{11}CO$ | H | H |
| 1-40 | $MemO(CH_2)_{13}CO$ | H | H |
| 1-41 | $MemO(CH_2)_{15}CO$ | H | H |
| 1-42 | $MemO(CH_2)_{19}SC$ | H | H |
| 1-43 | $AcO(CH_2)_{11}CO$ | H | H |
| 1-44 | $AcO(CH_2)_{13}CO$ | H | H |
| 1-45 | $AcO(CH_2)_{15}CO$ | H | H |
| 1-46 | $AcO(CH_2)_{17}CO$ | H | H |
| 1-47 | $MtmO(CH_2)_{15}CO$ | H | H |
| 1-48 | $MtmO(CH_2)_{11}CO$ | H | H |
| 1-49 | $MesO(CH_2)_{15}CO$ | H | H |
| 1-50 | $MesO(CH_2)_{11}CO$ | H | H |
| 1-51 | $TosO(CH_2)_{15}CO$ | H | H |
| 1-52 | $TosO(CH_2)_{17}CO$ | H | H |
| 1-53 | $NH_2COO(CH_2)_{15}CO$ | H | H |
| 1-54 | $NH_2COO(CH_2)_{11}CO$ | H | H |
| 1-55 | $Mec(CH_2)_{10}CO$ | H | H |
| 1-56 | $Mec(CH_2)_{12}CO$ | H | H |
| 1-57 | $Mec(CH_2)_{14}CO$ | H | H |
| 1-58 | $Mec(CH_2)_{15}CO$ | H | H |
| 1-59 | $NH_2CO(CH_2)_{10}CO$ | H | H |
| 1-60 | $NH_2CO(CH_2)_{14}CO$ | H | H |
| 1-61 | $NH_2CO(CH_2)_{15}CO$ | H | H |
| 1-62 | $NC(CH_2)_{10}CO$ | H | H |
| 1-63 | $NC(CH_2)_{14}CO$ | H | H |
| 1-64 | $NC(CH_2)_{15}CO$ | H | H |
| 1-65 | $NC(CH_2)_{18}CO$ | H | H |
| 1-66 | $NC(CH_2)_{20}CO$ | H | H |
| 1-67 | $AcS(CH_2)_{11}CO$ | H | H |
| 1-68 | $AcS(CH_2)_{15}CO$ | H | H |

TABLE 1-continued

| Cpd. No. | R¹ | R² | R³ |
|---|---|---|---|
| 1-69 | AcS(CH$_2$)$_{17}$CO | H | H |
| 1-70 | BzSS(CH$_2$)$_2$CO | H | H |
| 1-71 | BzSS(CH$_2$)$_{15}$CO | H | H |
| 1-72 | NH$_2$(CH$_2$)$_9$CO | H | H |
| 1-73 | NH$_2$(CH$_2$)$_{11}$CO | H | H |
| 1-74 | NH$_2$(CH$_2$)$_{13}$CO | H | H |
| 1-75 | NH$_2$(CH$_2$)$_{15}$CO | H | H |
| 1-76 | NH$_2$(CH$_2$)$_{16}$CO | H | H |
| 1-77 | NH$_2$(CH$_2$)$_{17}$CO | H | H |
| 1-78 | NH$_2$(CH$_2$)$_{18}$CO | H | H |
| 1-79 | NH$_2$(CH$_2$)$_{19}$CO | H | H |
| 1-80 | BzcNH(CH$_2$)$_{15}$CO | H | H |
| 1-81 | BocNH(CH$_2$)$_{11}$CO | H | H |
| 1-82 | AcNH(CH$_2$)$_{13}$CO | H | H |
| 1-83 | AocNH(CH$_2$)$_{15}$CO | H | H |
| 1-84 | BzNH(CH$_2$)$_{11}$CO | H | H |
| 1-85 | BozNH(CH$_2$)$_{19}$CO | H | H |
| 1-86 | N$_3$(CH$_2$)$_{15}$CO | H | H |
| 1-87 | N$_3$(CH$_2$)$_{11}$CO | H | H |
| 1-88 | F(CH$_2$)$_9$CO | H | H |
| 1-89 | F(CH$_2$)$_{15}$CO | H | H |
| 1-90 | Cl(CH$_2$)$_{11}$CO | H | H |
| 1-91 | Cl(CH$_2$)$_{13}$CO | H | H |
| 1-92 | Cl(CH$_2$)$_{15}$CO | H | H |
| 1-93 | Br(CH$_2$)$_5$CO | H | H |
| 1-94 | Br(CH$_2$)$_7$CO | H | H |
| 1-95 | 9-palmitoleoyl | H | H |
| 1-96 | 9,12,15-octadecatrienoyl | H | H |
| 1-97 | linoleyl | H | H |
| 1-98 | linolenyl | H | H |
| 1-99 | oleoyl | H | H |
| 1-100 | arachidonyl | H | H |
| 1-101 | H | H | CH$_3$(CH$_2$)$_4$CO |
| 1-102 | H | H | CH$_3$(CH$_2$)$_5$CO |
| 1-103 | H | H | CH$_3$(CH$_2$)$_6$CO |
| 1-104 | H | H | CH$_3$(CH$_2$)$_7$CO |
| 1-105 | H | H | CH$_3$(CH$_2$)$_8$CO |
| 1-106 | H | H | CH$_3$(CH$_2$)$_9$CO |
| 1-107 | H | H | CH$_3$(CH$_2$)$_{10}$CO |
| 1-108 | H | H | CH$_3$(CH$_2$)$_{11}$CO |
| 1-109 | H | H | CH$_3$(CH$_2$)$_{12}$CO |
| 1-110 | H | H | CH$_3$(CH$_2$)$_{13}$CO |
| 1-111 | H | H | CH$_3$(CH$_2$)$_{14}$CO |
| 1-112 | H | H | CH$_3$(CH$_2$)$_{15}$CO |
| 1-113 | H | H | CH$_3$(CH$_2$)$_{16}$CO |
| 1-114 | H | H | CH$_3$(CH$_2$)$_{17}$CO |
| 1-115 | H | H | CH$_3$(CH$_2$)$_{18}$CO |
| 1-116 | H | H | CH$_3$(CH$_2$)$_{19}$CO |
| 1-117 | H | H | CH$_3$(CH$_2$)$_{20}$CO |
| 1-118 | H | H | HOCH$_2$CO |
| 1-119 | H | H | HO(CH$_2$)$_2$CO |
| 1-120 | H | H | HO(CH$_2$)$_3$CO |
| 1-121 | H | H | HO(CH$_2$)$_5$CO |
| 1-122 | H | H | HO(CH$_2$)$_7$CO |
| 1-123 | H | H | HO(CH$_2$)$_9$CO |
| 1-124 | H | H | HO(CH$_2$)$_{11}$CO |
| 1-125 | H | H | HO(CH$_2$)$_{13}$CO |
| 1-126 | H | H | HO(CH$_2$)$_{15}$CO |
| 1-127 | H | H | HO(CH$_2$)$_{17}$CO |
| 1-128 | H | H | HO(CH$_2$)$_{19}$CO |
| 1-129 | H | H | MomO(CH$_2$)$_5$CO |
| 1-130 | H | H | MomO(CH$_2$)$_7$CO |
| 1-131 | H | H | MomO(CH$_2$)$_9$CO |
| 1-132 | H | H | MomO(CH$_2$)$_{11}$CO |
| 1-133 | H | H | MomO(CH$_2$)$_{13}$CO |
| 1-134 | H | H | MomO(CH$_2$)$_{15}$CO |
| 1-135 | H | H | MomO(CH$_2$)$_{17}$CO |
| 1-136 | H | H | MomO(CH$_2$)$_{19}$CO |
| 1-137 | H | H | MemO(CH$_2$)$_5$CO |
| 1-138 | H | H | MemO(CH$_2$)$_9$CO |
| 1-139 | H | H | MemO(CH$_2$)$_{11}$CO |
| 1-140 | H | H | MemO(CH$_2$)$_{13}$CO |
| 1-141 | H | H | MemO(CH$_2$)$_{15}$CO |
| 1-142 | H | H | MemO(CH$_2$)$_{19}$CO |
| 1-143 | H | H | AcO(CH$_2$)$_{11}$CO |
| 1-144 | H | H | AcO(CH$_2$)$_{13}$CO |
| 1-145 | H | H | AcO(CH$_2$)$_{15}$CO |

TABLE 1-continued

| Cpd. No. | R¹ | R² | R³ |
|---|---|---|---|
| 1-146 | H | H | AcO(CH₂)₁₇CO |
| 1-147 | H | H | MtmO(CH₂)₁₅CO |
| 1-148 | H | H | MtmO(CH₂)₁₁CO |
| 1-149 | H | H | MesO(CH₂)₁₄CO |
| 1-150 | H | H | MesO(CH₂)₁₅CO |
| 1-151 | H | H | TosO(CH₂)₁₅CO |
| 1-152 | H | H | TosO(CH₂)₁₇CO |
| 1-153 | H | H | NH₂COO(CH₂)₁₅CO |
| 1-154 | H | H | NH₂COO(CH₂)₁₇CO |
| 1-155 | H | H | Mec(CH₂)₁₀CO |
| 1-156 | H | H | Mec(CH₂)₁₄CO |
| 1-157 | H | H | Mec(CH₂)₁₆CO |
| 1-158 | H | H | Mec(CH₂)₁₈CO |
| 1-159 | H | H | NH₂CO(CH₂)₁₂CO |
| 1-160 | H | H | NH₂CO(CH₂)₁₄CO |
| 1-161 | H | H | NH₂CO(CH₂)₁₀CO |
| 1-162 | H | H | NC(CH₂)₁₂CO |
| 1-163 | H | H | NC(CH₂)₁₄CO |
| 1-164 | H | H | NC(CH₂)₁₆CO |
| 1-165 | H | H | NC(CH₂)₁₈CO |
| 1-166 | H | H | NC(CH₂)₁₀CO |
| 1-167 | H | H | AcS(CH₂)₁₃CO |
| 1-168 | H | H | AcS(CH₂)₁₅CO |
| 1-169 | H | H | AcS(CH₂)₁₁CO |
| 1-170 | H | H | BzSS(CH₂)₉CO |
| 1-171 | H | H | BzSS(CH₂)₁₅CO |
| 1-172 | H | H | NH₂(CH₂)₉CO |
| 1-173 | H | H | NH₂(CH₂)₁₁CO |
| 1-174 | H | H | NH₂(CH₂)₁₃CO |
| 1-175 | H | H | NH₂(CH₂)₁₅CO |
| 1-176 | H | H | NH₂(CH₂)₁₆CO |
| 1-177 | H | H | NH₂(CH₂)₁₇CO |
| 1-178 | H | H | NH₂(CH₂)₁₈CO |
| 1-179 | H | H | NH₂(CH₂)₁₉CO |
| 1-180 | H | H | BzcNH(CH₂)₉CO |
| 1-181 | H | H | BocNH(CH₂)₁₁CO |
| 1-182 | H | H | AcNH(CH₂)₁₃CO |
| 1-183 | H | H | AocNH(CH₂)₁₅CO |
| 1-184 | H | H | BzNH(CH₂)₁₇CO |
| 1-185 | H | H | BozNH(CH₂)₁₉CO |
| 1-186 | H | H | N₃(CH₂)₁₅CO |
| 1-187 | H | H | N₃(CH₂)₁₁CO |
| 1-188 | H | H | F(CH₂)₉CO |
| 1-189 | H | H | F(CH₂)₁₅CO |
| 1-190 | H | H | Cl(CH₂)₁₁CO |
| 1-191 | H | H | Cl(CH₂)₁₃CO |
| 1-192 | H | H | Cl(CH₂)₁₅CO |
| 1-193 | H | H | Br(CH₂)₁₅CO |
| 1-194 | H | H | Br(CH₂)₁₇CO |
| 1-195 | H | H | 9-palmitolenoyl |
| 1-196 | H | H | 9,12,15-octadecatrienoyl |
| 1-197 | H | H | linoeyl |
| 1-198 | H | H | linolenyl |
| 1-199 | H | H | oleoyl |
| 1-200 | H | H | arachidonyl |
| 1-201 | CH₃(CH₂)₄CO | H | CH₃(CH₂)₄CO |
| 1-202 | CH₃(CH₂)₅CO | H | CH₃(CH₂)₅CO |
| 1-203 | CH₃(CH₂)₆CO | H | CH₃(CH₂)₆CO |
| 1-204 | CH₃(CH₂)₇CO | H | CH₃(CH₂)₇CO |
| 1-205 | CH₃(CH₂)₈CO | H | CH₃(CH₂)₈CO |
| 1-206 | CH₃(CH₂)₉CO | H | CH₃(CH₂)₉CO |
| 1-207 | CH₃(CH₂)₁₀CO | H | CH₃(CH₂)₁₀CO |
| 1-208 | CH₃(CH₂)₁₂CO | H | CH₃(CH₂)₁₂CO |
| 1-209 | CH₃(CH₂)₁₄CO | H | CH₃(CH₂)₁₀CO |
| 1-210 | CH₃(CH₂)₁₄CO | H | CH₃(CH₂)₁₂CO |
| 1-211 | CH₃(CH₂)₁₄CO | H | CH₃(CH₂)₁₄CO |
| 1-212 | CH₃(CH₂)₁₄CO | H | CH₃(CH₂)₁₆CO |
| 1-213 | CH₃(CH₂)₁₄CO | H | CH₃(CH₂)₁₈CO |
| 1-214 | CH₃(CH₂)₁₆CO | H | CH₃(CH₂)₁₆CO |
| 1-215 | CH₃(CH₂)₁₈CO | H | CH₃(CH₂)₁₈CO |
| 1-216 | CH₃(CH₂)₁₉CO | H | CH₃(CH₂)₁₉CO |
| 1-217 | CH₃(CH₂)₁₄CO | H | CH₃(CH₂)₁₄CO |
| 1-218 | HOCH₂CO | H | HO(CH₂)₂CO |
| 1-219 | HO(CH₂)₇CO | H | HO(CH₂)₇CO |
| 1-220 | HO(CH₂)₉CO | H | HO(CH₂)₉CO |
| 1-221 | HO(CH₂)₁₁CO | H | HO(CH₂)₁₁CO |
| 1-222 | HO(CH₂)₁₅CO | H | HO(CH₂)₇CO |

TABLE 1-continued

| Cpd. No. | R$^1$ | R$^2$ | R$^3$ |
|---|---|---|---|
| 1-223 | HO(CH$_2$)$_{15}$CO | H | HO(CH$_2$)$_9$CO |
| 1-224 | HO(CH$_2$)$_{15}$CO | H | HO(CH$_2$)$_{11}$CO |
| 1-225 | HO(CH$_2$)$_{15}$CO | H | CH$_3$(CH$_2$)$_{14}$CO |
| 1-226 | HO(CH$_2$)$_{17}$CO | H | CH$_3$(CH$_2$)$_{14}$CO |
| 1-227 | HO(CH$_2$)$_{19}$CO | H | CH$_3$(CH$_2$)$_{14}$CO |
| 1-228 | HO(CH$_2$)$_{19}$CO | H | CH$_3$(CH$_2$)$_{14}$CO |
| 1-229 | MomO(CH$_2$)$_5$CO | H | MomO(CH$_2$)$_5$CO |
| 1-230 | MomO(CH$_2$)$_7$CO | H | MomO(CH$_2$)$_7$CO |
| 1-231 | MomO(CH$_2$)$_9$CO | H | MomO(CH$_2$)$_9$CO |
| 1-232 | MomO(CH$_2$)$_{11}$CO | H | MomO(CH$_2$)$_{11}$CO |
| 1-233 | MomO(CH$_2$)$_{13}$CO | H | MomO(CH$_2$)$_{13}$CO |
| 1-234 | MomO(CH$_2$)$_{15}$CO | H | MomO(CH$_2$)$_{15}$CO |
| 1-235 | MomO(CH$_2$)$_{17}$CO | H | MomO(CH$_2$)$_{17}$CO |
| 1-236 | MomO(CH$_2$)$_{19}$CO | H | MomO(CH$_2$)$_{19}$CO |
| 1-237 | MemO(CH$_2$)$_5$CO | H | MemO(CH$_2$)$_5$CO |
| 1-238 | MemO(CH$_2$)$_9$CO | H | MemO(CH$_2$)$_9$CO |
| 1-239 | MemO(CH$_2$)$_{11}$CO | H | MemO(CH$_2$)$_{11}$CO |
| 1-240 | MemO(CH$_2$)$_{13}$CO | H | MemO(CH$_2$)$_{13}$CO |
| 1-241 | MemO(CH$_2$)$_{15}$CO | H | MemO(CH$_2$)$_{15}$CO |
| 1-242 | MemO(CH$_2$)$_{19}$CO | H | MemO(CH$_2$)$_{19}$CO |
| 1-243 | AcO(CH$_2$)$_{11}$CO | H | AcO(CH$_2$)$_{11}$CO |
| 1-244 | AcO(CH$_2$)$_{13}$CO | H | AcO(CH$_2$)$_{13}$CO |
| 1-245 | AcO(CH$_2$)$_{15}$CO | H | AcO(CH$_2$)$_{15}$CO |
| 1-246 | AcO(CH$_2$)$_{17}$CO | H | AcO(CH$_2$)$_{17}$CO |
| 1-247 | MtmO(CH$_2$)$_{15}$CO | H | MtmO(CH$_2$)$_{15}$CO |
| 1-248 | MtmO(CH$_2$)$_{17}$CO | H | MtmO(CH$_2$)$_{17}$CO |
| 1-249 | MesO(CH$_2$)$_{14}$CO | H | MesO(CH$_2$)$_{14}$CO |
| 1-250 | MesO(CH$_2$)$_{15}$CO | H | MesO(CH$_2$)$_{15}$CO |
| 1-251 | H | CH$_3$(CH$_2$)$_4$CO | H |
| 1-252 | H | CH$_3$(CH$_2$)$_5$CO | H |
| 1-253 | H | CH$_3$(CH$_2$)$_6$CO | H |
| 1-254 | H | CH$_3$(CH$_2$)$_7$CO | H |
| 1-255 | H | CH$_3$(CH$_2$)$_8$CO | H |
| 1-256 | H | CH$_3$(CH$_2$)$_9$CO | H |
| 1-257 | H | CH$_3$(CH$_2$)$_{10}$CO | H |
| 1-258 | H | CH$_3$(CH$_2$)$_{11}$CO | H |
| 1-259 | H | CH$_3$(CH$_2$)$_{12}$CO | H |
| 1-260 | H | CH$_3$(CH$_2$)$_{13}$CO | H |
| 1-261 | H | CH$_3$(CH$_2$)$_{14}$CO | H |
| 1-262 | H | CH$_3$(CH$_2$)$_{15}$CO | H |
| 1-263 | H | CH$_3$(CH$_2$)$_{16}$CO | H |
| 1-264 | H | CH$_3$(CH$_2$)$_{17}$CO | H |
| 1-265 | H | CH$_3$(CH$_2$)$_{18}$CO | H |
| 1-266 | H | CH$_3$(CH$_2$)$_{19}$CO | H |
| 1-267 | H | CH$_3$(CH$_2$)$_{20}$CO | H |
| 1-268 | H | HOCH$_2$CO | H |
| 1-269 | H | HO(CH$_2$)$_2$CO | H |
| 1-270 | H | HO(CH$_2$)$_3$CO | H |
| 1-271 | H | HO(CH$_2$)$_5$CO | H |
| 1-272 | H | HO(CH$_2$)$_7$CO | H |
| 1-273 | H | HO(CH$_2$)$_9$CO | H |
| 1-274 | H | HO(CH$_2$)$_{11}$CO | H |
| 1-275 | H | HO(CH$_2$)$_{13}$CO | H |
| 1-276 | H | HO(CH$_2$)$_{15}$CO | H |
| 1-277 | H | HO(CH$_2$)$_{17}$CO | H |
| 1-278 | H | HO(CH$_2$)$_{19}$CO | H |
| 1-279 | H | MomO(CH$_2$)$_5$CO | H |
| 1-280 | H | MomO(CH$_2$)$_7$CO | H |
| 1-281 | H | MomO(CH$_2$)$_9$CO | H |
| 1-282 | H | MomO(CH$_2$)$_{11}$CO | H |
| 1-283 | H | MomO(CH$_2$)$_{13}$CO | H |
| 1-284 | H | MomO(CH$_2$)$_{15}$CO | H |
| 1-285 | H | MomO(CH$_2$)$_{17}$CO | H |
| 1-286 | H | MomO(CH$_2$)$_{19}$CO | H |
| 1-287 | H | MemO(CH$_2$)$_5$CO | H |
| 1-288 | H | MemO(CH$_2$)$_9$CO | H |
| 1-289 | H | MemO(CH$_2$)$_{11}$CO | H |
| 1-290 | H | MemO(CH$_2$)$_{13}$CO | H |
| 1-291 | H | MemO(CH$_2$)$_{15}$CO | H |
| 1-292 | H | MemO(CH$_2$)$_{19}$CO | H |
| 1-293 | H | AcO(CH$_2$)$_{11}$CO | H |
| 1-294 | H | AcO(CH$_2$)$_{13}$CO | H |
| 1-295 | H | AcO(CH$_2$)$_{15}$CO | H |
| 1-296 | H | AcO(CH$_2$)$_{17}$CO | H |
| 1-297 | H | MtmO(CH$_2$)$_{15}$CO | H |
| 1-298 | H | MtmO(CH$_2$)$_{11}$CO | H |
| 1-299 | H | MesO(CH$_2$)$_{11}$CO | H |

TABLE 1-continued

| Cpd. No. | R$^1$ | R$^2$ | R$^3$ |
|---|---|---|---|
| 1-300 | H | MesO(CH$_2$)$_{15}$CO | H |
| 1-301 | H | TosO(CH$_2$)$_{15}$CO | H |
| 1-302 | H | TosO(CH$_2$)$_{17}$CO | H |
| 1-303 | H | NH$_2$COO(CH$_2$)$_{15}$CO | H |
| 1-304 | H | NH$_2$COO(CH$_2$)$_{17}$CO | H |
| 1-305 | H | Mec(CH$_2$)$_{12}$CO | H |
| 1-306 | H | Mec(CH$_2$)$_{14}$CO | H |
| 1-307 | H | Mec(CH$_2$)$_{16}$CO | H |
| 1-308 | H | Mec(CH$_2$)$_{10}$CO | H |
| 1-309 | H | NH$_2$CO(CH$_2$)$_{10}$CO | H |
| 1-310 | H | NH$_2$CO(CH$_2$)$_{14}$CO | H |
| 1-311 | CH$_3$(CH$_2$)$_4$CO | CH$_3$(CH$_2$)$_4$CO | H |
| 1-312 | CH$_3$(CH$_2$)$_5$CO | CH$_3$(CH$_2$)$_5$CO | H |
| 1-313 | CH$_3$(CH$_2$)$_6$CO | CH$_3$(CH$_2$)$_6$CO | H |
| 1-314 | CH$_3$(CH$_2$)$_7$CO | CH$_3$(CH$_2$)$_7$CO | H |
| 1-315 | CH$_3$(CH$_2$)$_8$CO | CH$_3$(CH$_2$)$_8$CO | H |
| 1-316 | CH$_3$(CH$_2$)$_9$CO | CH$_3$(CH$_2$)$_9$CO | H |
| 1-317 | CH$_3$(CH$_2$)$_{10}$CO | CH$_3$(CH$_2$)$_{10}$CO | H |
| 1-318 | CH$_3$(CH$_2$)$_{11}$CO | CH$_3$(CH$_2$)$_{11}$CO | H |
| 1-319 | CH$_3$(CH$_2$)$_{12}$CO | CH$_3$(CH$_2$)$_{12}$CO | H |
| 1-320 | CH$_3$(CH$_2$)$_{13}$CO | CH$_3$(CH$_2$)$_{13}$CO | H |
| 1-321 | CH$_3$(CH$_2$)$_{14}$CO | CH$_3$(CH$_2$)$_{10}$CO | H |
| 1-322 | CH$_3$(CH$_2$)$_{14}$CO | CH$_3$(CH$_2$)$_{12}$CO | H |
| 1-323 | CH$_3$(CH$_2$)$_{14}$CO | CH$_3$(CH$_2$)$_{14}$CO | H |
| 1-324 | CH$_3$(CH$_2$)$_{14}$CO | CH$_3$(CH$_2$)$_{16}$CO | H |
| 1-325 | CH$_3$(CH$_2$)$_{16}$CO | CH$_3$(CH$_2$)$_{14}$CO | H |
| 1-326 | CH$_3$(CH$_2$)$_{18}$CO | CH$_3$(CH$_2$)$_{18}$CO | H |
| 1-327 | CH$_3$(CH$_2$)$_{20}$CO | CH$_3$(CH$_2$)$_{20}$CO | H |
| 1-328 | HOCH$_2$CO | CH$_3$(CH$_2$)$_{14}$CO | H |
| 1-329 | HO(CH$_2$)$_2$CO | CH$_3$(CH$_2$)$_{14}$CO | H |
| 1-330 | HO(CH$_2$)$_3$CO | CH$_3$(CH$_2$)$_{14}$CO | H |
| 1-331 | H | CH$_3$(CH$_2$)$_4$CO | CH$_3$(CH$_2$)$_4$CO |
| 1-332 | H | CH$_3$(CH$_2$)$_5$CO | CH$_3$(CH$_2$)$_5$CO |
| 1-333 | H | CH$_3$(CH$_2$)$_6$CO | CH$_3$(CH$_2$)$_6$CO |
| 1-334 | H | CH$_3$(CH$_2$)$_7$CO | CH$_3$(CH$_2$)$_7$CO |
| 1-335 | H | CH$_3$(CH$_2$)$_8$CO | CH$_3$(CH$_2$)$_8$CO |
| 1-336 | H | CH$_3$(CH$_2$)$_9$CO | CH$_3$(CH$_2$)$_9$CO |
| 1-337 | H | CH$_3$(CH$_2$)$_{10}$CO | CH$_3$(CH$_2$)$_{10}$CO |
| 1-338 | H | CH$_3$(CH$_2$)$_{11}$CO | CH$_3$(CH$_2$)$_{11}$CO |
| 1-339 | H | CH$_3$(CH$_2$)$_{12}$CO | CH$_3$(CH$_2$)$_{12}$CO |
| 1-340 | H | CH$_3$(CH$_2$)$_{14}$CO | CH$_3$(CH$_2$)$_{10}$CO |
| 1-341 | H | CH$_3$(CH$_2$)$_{14}$CO | CH$_3$(CH$_2$)$_{12}$CO |
| 1-342 | H | CH$_3$(CH$_2$)$_{14}$CO | CH$_3$(CH$_2$)$_{14}$CO |
| 1-343 | H | CH$_3$(CH$_2$)$_{14}$CO | CH$_3$(CH$_2$)$_{16}$CO |
| 1-344 | H | CH$_3$(CH$_2$)$_{16}$CO | CH$_3$(CH$_2$)$_{16}$CO |
| 1-345 | H | CH$_3$(CH$_2$)$_{18}$CO | CH$_3$(CH$_2$)$_{18}$CO |
| 1-346 | H | CH$_3$(CH$_2$)$_{19}$CO | CH$_3$(CH$_2$)$_{19}$CO |
| 1-347 | H | CH$_3$(CH$_2$)$_{20}$CO | CH$_3$(CH$_2$)$_{20}$CO |
| 1-348 | H | HOCH$_2$CO | CH$_3$(CH$_2$)$_{14}$CO |
| 1-349 | H | HO(CH$_2$)$_2$CO | CH$_3$(CH$_2$)$_{14}$CO |
| 1-350 | H | HO(CH$_2$)$_3$CO | CH$_3$(CH$_2$)$_{14}$CO |
| 1-351 | CH$_3$(CH$_2$)$_4$CO | CH$_3$(CH$_2$)$_4$CO | CH$_3$(CH$_2$)$_4$CO |
| 1-352 | CH$_3$(CH$_2$)$_5$CO | CH$_3$(CH$_2$)$_5$CO | CH$_3$(CH$_2$)$_5$CO |
| 1-353 | CH$_3$(CH$_2$)$_6$CO | CH$_3$(CH$_2$)$_6$CO | CH$_3$(CH$_2$)$_6$CO |
| 1-354 | CH$_3$(CH$_2$)$_7$CO | CH$_3$(CH$_2$)$_7$CO | CH$_3$(CH$_2$)$_7$CO |
| 1-355 | CH$_3$(CH$_2$)$_8$CO | CH$_3$(CH$_2$)$_8$CO | CH$_3$(CH$_2$)$_8$CO |
| 1-356 | CH$_3$(CH$_2$)$_9$CO | CH$_3$(CH$_2$)$_9$CO | CH$_3$(CH$_2$)$_9$CO |
| 1-357 | CH$_3$(CH$_2$)$_{10}$CO | CH$_3$(CH$_2$)$_{10}$CO | CH$_3$(CH$_2$)$_{10}$CO |
| 1-358 | CH$_3$(CH$_2$)$_{11}$CO | CH$_3$(CH$_2$)$_{11}$CO | CH$_3$(CH$_2$)$_{11}$CO |
| 1-359 | CH$_3$(CH$_2$)$_{12}$CO | CH$_3$(CH$_2$)$_{12}$CO | CH$_3$(CH$_2$)$_{12}$CO |
| 1-360 | CH$_3$(CH$_2$)$_{13}$CO | CH$_3$(CH$_2$)$_{13}$CO | CH$_3$(CH$_2$)$_{13}$CO |
| 1-361 | CH$_3$(CH$_2$)$_{14}$CO | CH$_3$(CH$_2$)$_{14}$CO | CH$_3$(CH$_2$)$_{14}$CO |
| 1-362 | CH$_3$(CH$_2$)$_{14}$CO | CH$_3$(CH$_2$)$_{16}$CO | CH$_3$(CH$_2$)$_{14}$CO |
| 1-363 | CH$_3$(CH$_2$)$_{14}$CO | CH$_3$(CH$_2$)$_{12}$CO | CH$_3$(CH$_2$)$_{14}$CO |
| 1-364 | CH$_3$(CH$_2$)$_{16}$CO | CH$_3$(CH$_2$)$_{12}$CO | CH3 (CH$_2$)$_{16}$CO |
| 1-365 | HO(CH$_2$)$_4$CO | HO(CH$_2$)$_4$CO | HO(CH$_2$)$_4$CO |
| 1-366 | HO(CH$_2$)$_5$CO | HO(CH$_2$)$_5$CO | HO(CH$_2$)$_5$CO |
| 1-367 | HO(CH$_2$)$_6$CO | HO(CH$_2$)$_6$CO | HO(CH$_2$)$_6$CO |
| 1-368 | HO(CH$_2$)$_7$CO | HO(CH$_2$)$_7$CO | HO(CH$_2$)$_7$CO |
| 1-369 | HO(CH$_2$)$_8$CO | HO(CH$_2$)$_8$CO | H9(CH$_2$)$_8$CO |
| 1-370 | HO(CH$_2$)$_9$CO | HO(CH$_2$)$_9$CO | HO(CH$_2$)$_9$CO |
| 1-371 | HO(CH$_2$)$_{10}$CO | HO(CH$_2$)$_{10}$CO | HO(CH$_2$)$_{10}$CO |
| 1-372 | HO(CH$_2$)$_{11}$CO | HO(CH$_2$)$_{11}$CO | HO(CH$_2$)$_{11}$CO |
| 1-373 | HO(CH$_2$)$_{12}$CO | HO(CH$_2$)$_{12}$CO | HO(CH$_2$)$_{12}$CO |
| 1-374 | HO(CH$_2$)$_{13}$CO | HO(CH$_2$)$_{13}$CO | HO(CH$_2$)$_{13}$CO |
| 1-375 | HO(CH$_2$)$_{15}$CO | HO(CH$_2$)$_{13}$CO | HO(CH$_2$)$_{15}$CO |
| 1-376 | HO(CH$_2$)$_{15}$CO | HO(CH$_2$)$_{14}$CO | HO(CH$_2$)$_{15}$CO |

TABLE 1-continued

| Cpd. No. | $R^1$ | $R^2$ | $R^3$ |
|---|---|---|---|
| 1-377 | $HO(CH_2)_{15}CO$ | $HO(CH_2)_{17}CO$ | $HO(CH_2)_{15}CO$ |
| 1-378 | $HO(CH_2)_{17}CO$ | $HO(CH_2)_{17}CO$ | $HO(CH_2)_{17}CO$ |
| 1-379 | $CH_3(CH_2)_8CO$ | $HO(CH_2)_8CO$ | $CH_3(CH_2)_8CO$ |
| 1-380 | $CH_3(CH_2)_9CO$ | $CH_3(CH_2)_9CO$ | $HO(CH_2)_9CO$ |
| 1-381 | $HO(CH_2)_{10}CO$ | $CH_3(CH_2)_{10}CO$ | $CH_3(CH_2)_{10}CO$ |
| 1-382 | $HO(CH_2)_{11}CO$ | $CH_3(CH_2)_{11}CO$ | $HO(CH_2)_{11}CO$ |
| 1-383 | $CH_3(CH_2)_{12}CO$ | $HO(CH_2)_{12}CO$ | $HO(CH_2)_{12}CO$ |
| 1-384 | $HO(CH_2)_{13}CO$ | $HO(CH_2)_{13}CO$ | $CH_3(CH_2)_{13}CO$ |
| 1-385 | $HO(CH_2)_{15}CO$ | $CH_3(CH_2)_{16}CO$ | $CH_3(CH_2)_{14}CO$ |
| 1-386 | $CH_3(CH_2)_{16}CO$ | $HO(CH_2)_{15}CO$ | $HO(CH_2)_{15}CO$ |
| 1-387 | $CH_3(CH_2)_{16}CO$ | $CH_3(CH_2)_{16}CO$ | $HO(CH_2)_{15}CO$ |
| 1-388 | $HO(CH_2)_{15}CO$ | $CH_3(CH_2)_{16}CO$ | $CH_3(CH_2)_{16}CO$ |
| 1-389 | $AcO(CH_2)_8CO$ | $AcO(CH_2)_8CO$ | $AcO(CH_2)_8CO$ |
| 1-390 | $AcO(CH_2)_9CO$ | $AcO(CH_2)_9CO$ | $CH_3(CH_2)_9CO$ |
| 1-391 | $AcO(CH_2)_{10}CO$ | $CH_3(CH_2)_{10}CO$ | $AcO(CH_2)_{10}CO$ |
| 1-392 | $MomC(CH_2)_{11}CO$ | $MomC(CH_2)_{11}CO$ | $MomC(CH_2)_{11}CO$ |
| 1-393 | $MomC(CH_2)_{12}CO$ | $CH_3(CH_2)_{12}CO$ | $MomC(CH_2)_{12}CO$ |
| 1-394 | $CH_3(CH_2)_{13}CO$ | $MomC(CH_2)_{13}CO$ | $MomC(CH_2)_{13}CO$ |
| 1-395 | $MomO(CH_2)_{15}CO$ | $MomC(CH_2)_{15}CO$ | $CH_3(CH_2)_{14}CO$ |
| 1-396 | $CH_3(CH_2)_{14}CO$ | $MomC(CH_2)_{15}CO$ | $CH_3(CH_2)_{14}CO$ |
| 1-397 | $CH_3(CH_2)_{14}CO$ | $CH_3(CH_2)_{14}CO$ | $MomC(CH_2)_{14}CO$ |
| 1-398 | $MomC(CH_2)_{16}CO$ | $CH_3(CH_2)_{16}CO$ | $CH_3(CH_2)_{16}CO$ |
| 1-399 | $MemO(CH_2)_8CO$ | $CH_3(CH_2)_8CO$ | $CH_3(CH_2)_8CO$ |
| 1-400 | $CH_3(CH_2)_9CO$ | $MemO(CH_2)_9CO$ | $CH_3(CH_2)_9CO$ |
| 1-401 | Ac | H | $CH_3(CH_2)_{14}CO$ |
| 1-402 | $CH_3(CH_2)_{14}CO$ | H | Ac |
| 1-403 | $CH_3(CH_2)_{14}CO$ | Ac | H |
| 1-404 | Ac | H | $CH_3(CH_2)_{10}CO$ |
| 1-405 | $CH_3(CH_2)_{10}CO$ | H | Ac |
| 1-406 | $CH_3(CH_2)_{10}CO$ | Ac | H |
| 1-407 | Ac | H | $HO(CH_2)_{15}CO$ |
| 1-408 | $HO(CH_2)_{15}CO$ | H | Ac |
| 1-409 | $HO(CH_2)_{15}CO$ | Ac | H |
| 1-410 | Ac | H | $HO(CH_2)_{11}CO$ |
| 1-411 | $HO(CH_2)_{11}CO$ | H | Ac |
| 1-412 | $HO(CH_2)_{11}CO$ | Ac | H |

TABLE 2

| Cpd. No. | $R^1$ | $R^2$ | $R^3$ |
|---|---|---|---|
| 2-1 | $CH_3(CH_2)_4CO$ | H | H |
| 2-2 | $CH_3(CH_2)_5CO$ | H | H |
| 2-3 | $CH_3(CH_2)_6CO$ | H | H |
| 2-4 | $CH_3(CH_2)_7CO$ | H | H |
| 2-5 | $CH_3(CH_2)_8CO$ | H | H |
| 2-6 | $CH_3(CH_2)_9CO$ | H | H |
| 2-7 | $CH_3(CH_2)_{10}CO$ | H | H |
| 2-8 | $CH_3(CH_2)_{11}CO$ | H | H |
| 2-9 | $CH_3(CH_2)_{12}CO$ | H | H |
| 2-10 | $CH_3(CH_2)_{13}CO$ | H | H |
| 2-11 | $CH_3(CH_2)_{14}CO$ | H | H |
| 2-12 | $CH_3(CH_2)_{15}CO$ | H | H |
| 2-13 | $CH_3(CH_2)_{16}CO$ | H | H |
| 2-14 | $CH_3(CH_2)_{17}CO$ | H | H |
| 2-15 | $CH_3(CH_2)_{18}CO$ | H | H |
| 2-16 | $CH_3(CH_2)_{19}CO$ | H | H |
| 2-17 | $CH_3(CH_2)_{20}CO$ | H | H |

Of the compounds listed above, the following are preferred, that is to say Compounds No. 1-5, 1-6, 1-7, 1-8, 1-9, 1-10, 1-11, 1-12, 1-13, 1-14, 1-15, 1-24, 1-25, 1-26, 1-27, 1-32, 1-33, 1-34, 1-35, 1-36, 1-39, 1-40, 1-41, 1-62, 1-63, 1-64, 1-65, 1-73, 1-75, 1-81, 1-83, 1-86, 1-87, 1-106, 1-107, 1-108, 1-109, 1-110, 1-111, 1-112, 1-113, 1-114, 1-124, 1-125, 1-126, 1-127, 1-132, 1-133, 1-134, 1-135, 1-139, 1-140, 1-141, 1-142, 1-162, 1-163, 2-7, 2-8, 2-9, 2-10, 2-11, 2-12 and 2-13, of which Compounds No. 1-7, 1-8, 1-9, 1-10, 1-11, 1-12, 1-13, 1-24, 1-25, 1-26, 1-32, 1-33, 1-34, 1-35, 1-39, 1-40, 1-41, 1-62, 1-63, 1-64, 1-107, 1-108, 1-109, 1-110, 1-111, 1-112, 1-113, 1-124, 1-125, 1-126, 1-132, 1-133, 1-134, 1-139, 1-140, 1-141, 1-162, 1-163, 2-7, 2-8, 2-9, 2-10, 2-11, 2-12 and 2-13, are more preferred.

The most preferred compounds are Compounds No.:

1-7. 2'-Cyano-2'-deoxy-$N^4$-lauroyl-1-β-D-arabinofuranosylcytosine;

1-9. 2'-Cyano-2'-deoxy-$N^4$-tetradecanoyl-1-β-D-arabinofuranosylcytosine;

1-10. 2'-Cyano-2'-deoxy-$N^4$-pentadecanoyl-1-β-D-arabinofuranosylcytosine;

1-11. 2'-Cyano-2'-deoxy-$N^4$-palmitoyl-1-β-D-arabinofuranosylcytosine;

1-12. 2'-Cyano-2'-deoxy-$N^4$-heptadecanoyl-1-β-D-arabinofuranosylcytosine;

1-32. 2'-Cyano-2'-deoxy-$N^4$-(12-methoxymethoxydodecanoyl)-1-β-D-arabinofuranosylcytosine;

1-33. 2'-Cyano-2'-deoxy-$N^4$-(14-methoxymethoxytetradecanoyl)-1-β-D-arabinofuranosylcytosine;

1-39. 2'-Cyano-2'-deoxy-$N^4$-(16-methoxymethoxyhexadecanoyl)-1-β-D-arabinofuranosylcytosine;

1-40. 2'-Cyano-2'-deoxy-$N^4$-(14-methoxyethoxymethoxytetradecanoyl)-1-β-D-arabinofuranosylcytosine;

1-41. 2'-Cyano-2'-deoxy-$N^4$-(16-methoxyethoxymethoxyhexadecanoyl)-1-β-D-arabinofuranosylcytosine;

1-62. 2'-Cyano-$N^4$-(11-cyanoundecanoyl)-2'-deoxy-1-β-D-arabinofuranosylcytosine;

1-63. 2'-Cyano-$N^4$-(15-cyanopentadecanoyl)-2'-deoxy-1-β-D-arabinofuranosylcytosine;

1-64. 2'-Cyano-$N^4$-(16-cyanohexadecanoyl)-2'-deoxy-1-β-D-arabinofuranosylcytosine;

1-111. 2'-Cyano-2'-deoxy-5'-O-palmitoyl-1-β-D-arabinofuranosylcytosine;

2-7. 2'-Cyano-2'-deoxy-$N^4$-lauroylcytidine;

2-9. 2'-Cyano-2'-deoxy-$N^4$-tetradecanoylcytidine;

2-10. 2'-Cyano-2'-deoxy-$N^4$-pentadecanoylcytidine;

2-11. 2'-Cyano-2'-deoxy-$N^4$-palmitoylcytidine; and 2-12. 2'-Cyano-2'-deoxy-$N^4$-heptadecanoylcytidine;

and pharmaceutically acceptable salts thereof.

The compounds of the present invention can be prepared by a variety of methods, whose general techniques are known in the art for the preparation of compounds of this type. For example, they may be prepared by acylating a compound of formula (II):

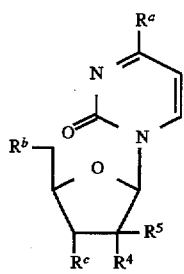

(II)

wherein:

$R^a$ represents an amino group or a protected amino group;

$R^b$ represents an hydroxy group or a protected hydroxy group; and $R^c$ represents an hydroxy group or a protected hydroxy group;

PROVIDED THAT at least one of $R^a$, $R^b$ and $R^c$ represents an unprotected group;

and, if required, the following steps, in any order:

(a) removing any protecting group, to give a compound of formula (I), and, (b) if required, converting any group represented by $R^1$, $R^2$ or $R^3$ to any other group so represented and, (c) if required, converting a compound where $R^4$ represents a hydrogen atom and $R^5$ represents a cyano group to a compound where $R^4$ represents a cyano group and $R^5$ represents a hydrogen atom, or vice versa.

Examples of protected amino groups which may be represented by $R^a$ are as given above in relation to the protected amino groups which may be included in substituents A, and examples of protected hydroxy groups which may be represented by $R^b$ and $R^c$ are given hereafter in relation to the groups which may be represented by $A^2$.

In more detail, the compounds of the present invention may be prepared as illustrated in the following reaction schemes:

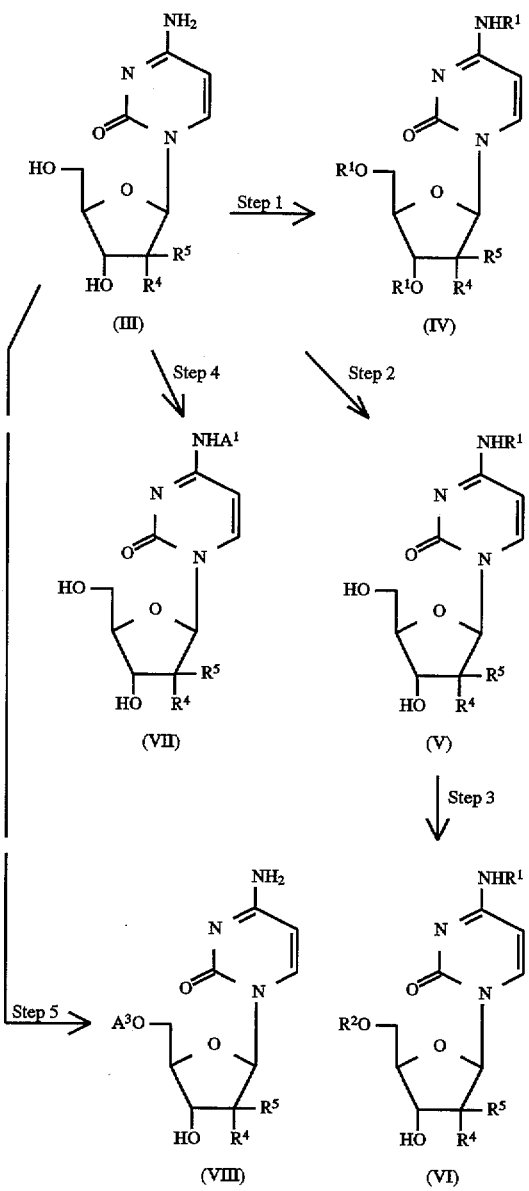

-continued
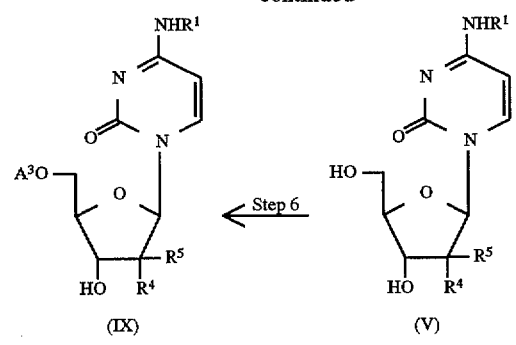
(IX) ← Step 6 — (V)
Step 7 ↓ ↘ Step 8
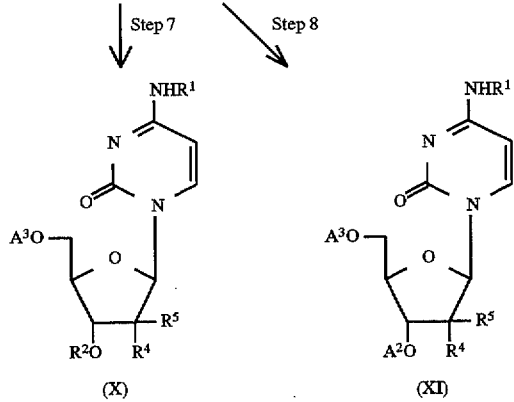
(X)  (XI)
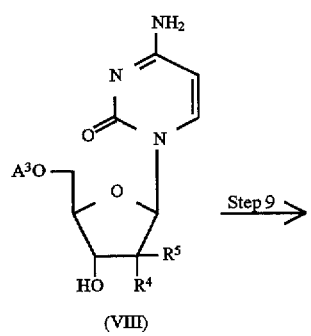
(VIII) — Step 9 →
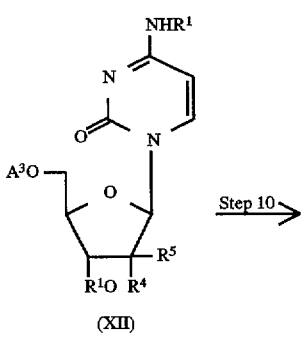
(XII) — Step 10 →
-continued
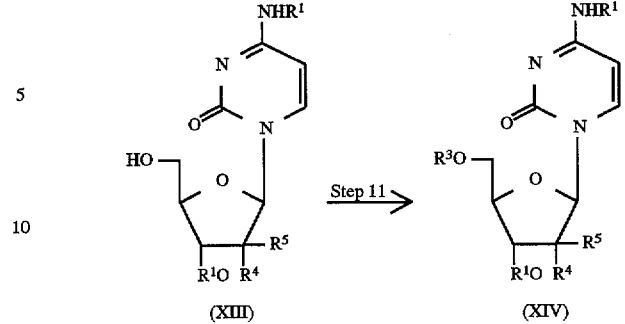
(XIII) — Step 11 → (XIV)
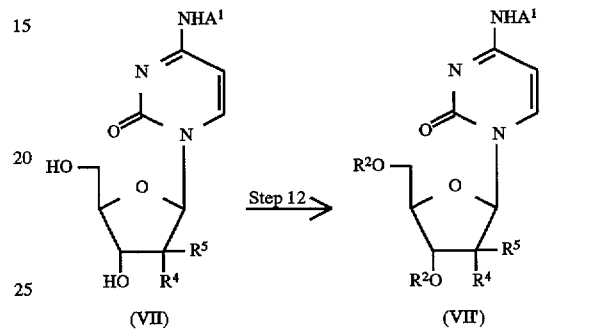
(VII) — Step 12 → (VII')
Step 15 ↙   ↘ Step 13
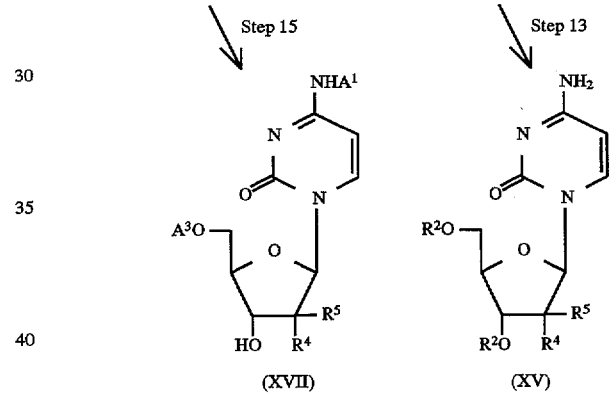
(XVII)  (XV)
Step 16 ↓   ↓ Step 14
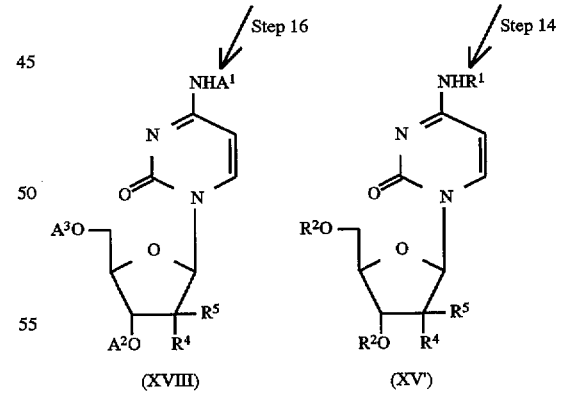
(XVIII)  (XV')

41
-continued
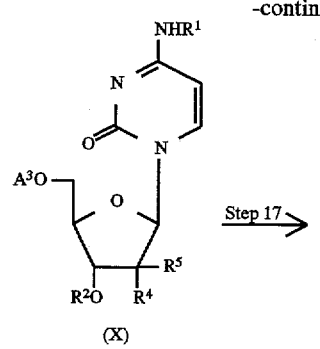
(X) —Step 17→
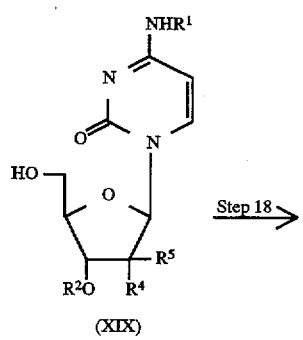
(XIX) —Step 18→
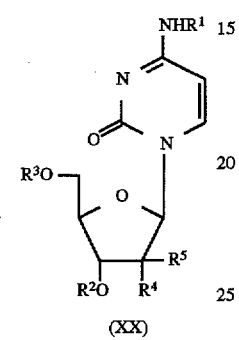
(XX)
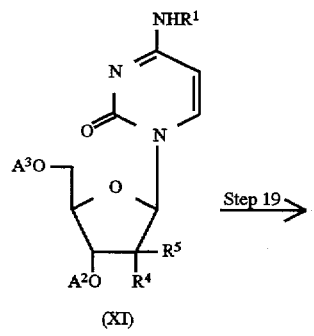
(XI) —Step 19→
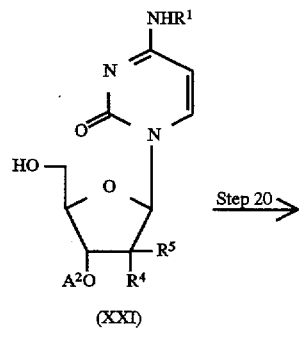
(XXI) —Step 20→
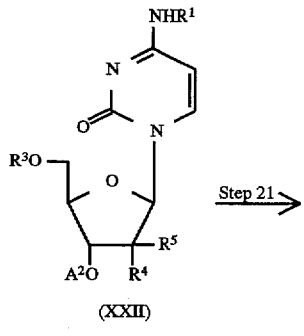
(XXII) —Step 21→
42
-continued
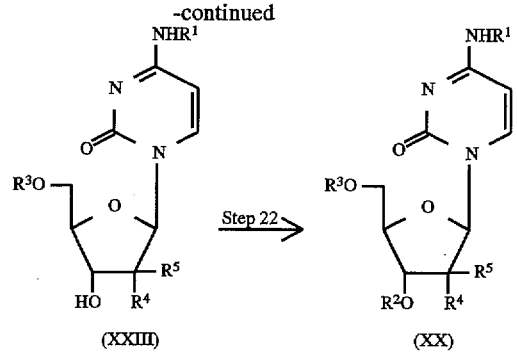
(XXIII) —Step 22→ (XX)
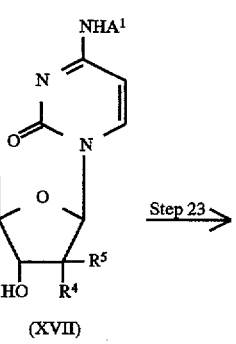
(XVII) —Step 23→
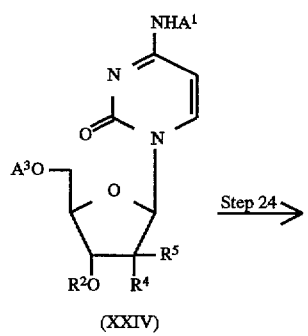
(XXIV) —Step 24→
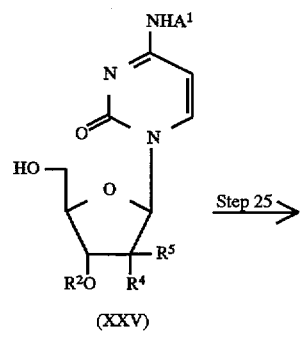
(XXV) —Step 25→
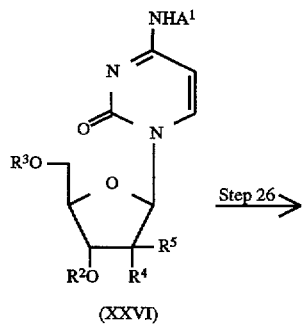
(XXVI) —Step 26→

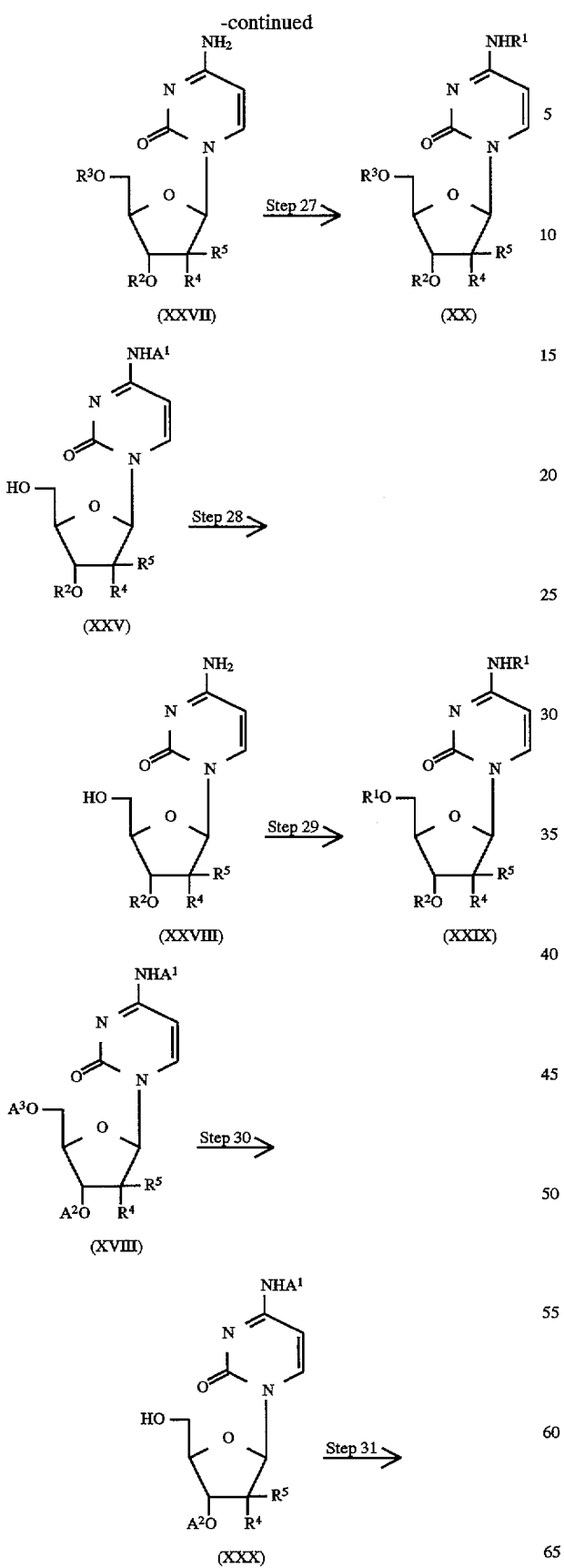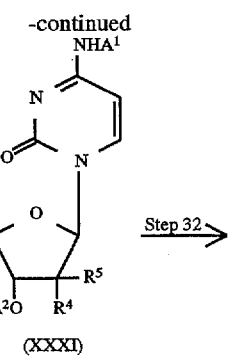

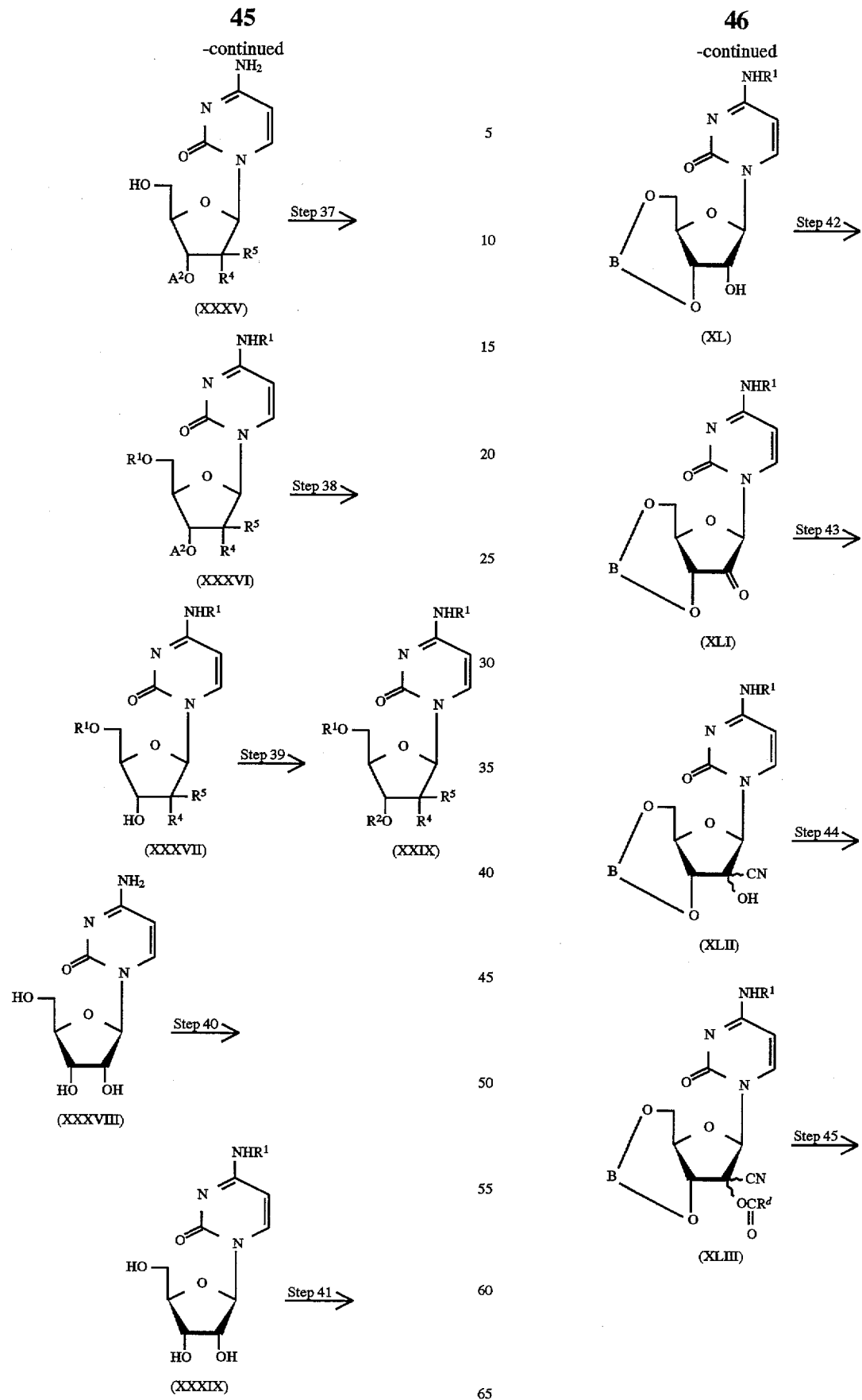

47
-continued
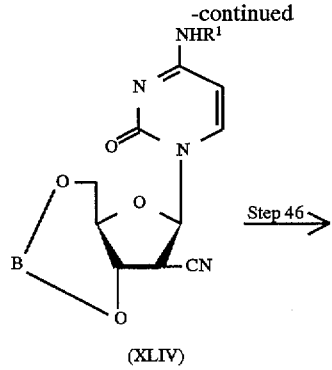
(XLIV)
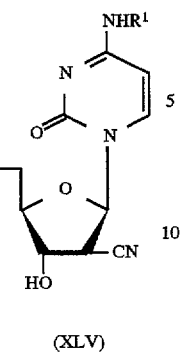
(XLV)
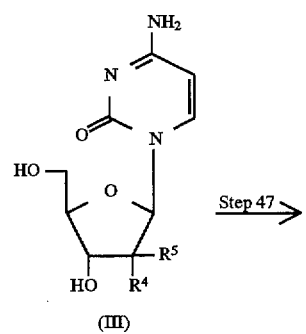
(III)
Step 47→
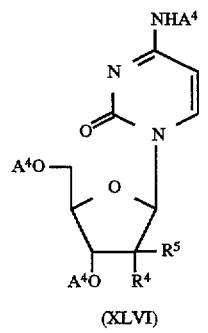
(XLVI)
Step 48→
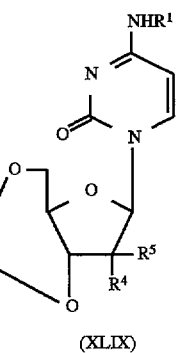
(XLVII)
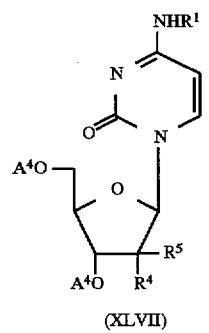
(III)
Step 50→
48
-continued
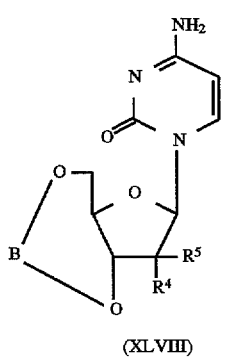
(XLVIII)
Step 51→
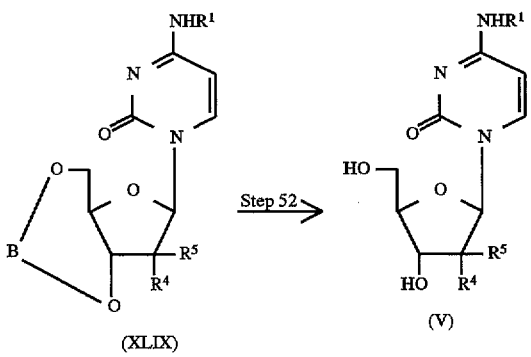
(XLIX) → (V)
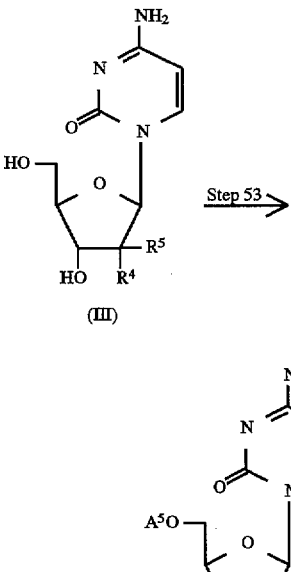
(III)
Step 53→
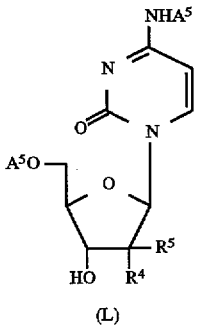
(L)
Step 54→

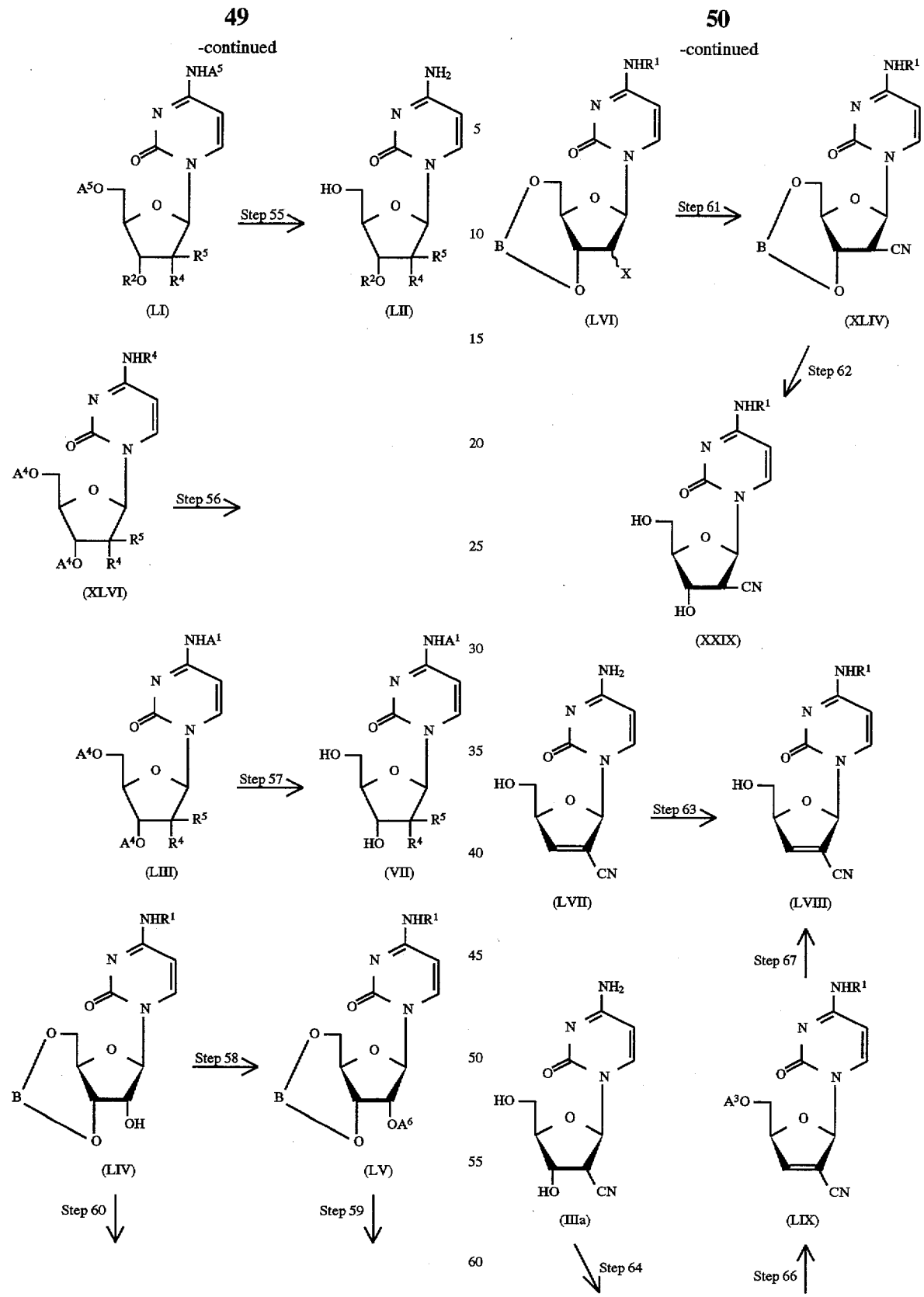

51

-continued

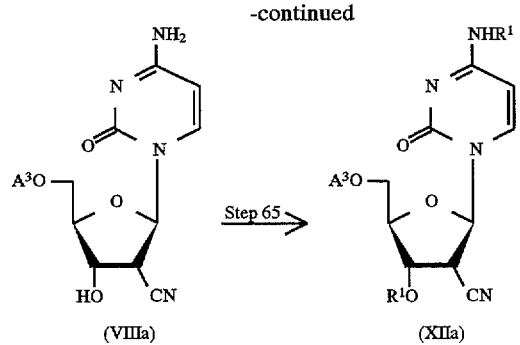

(VIIIa) → Step 65 → (XIIa)

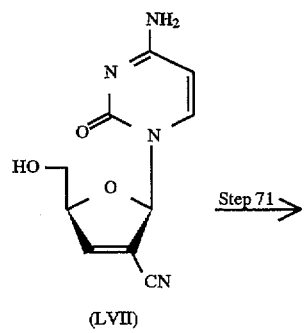

(LVII) → Step 71 →

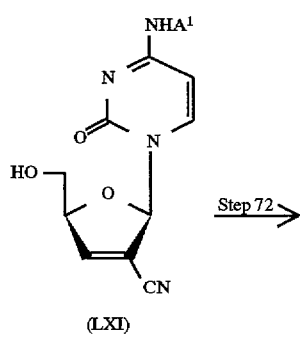

(LXI) → Step 72 →

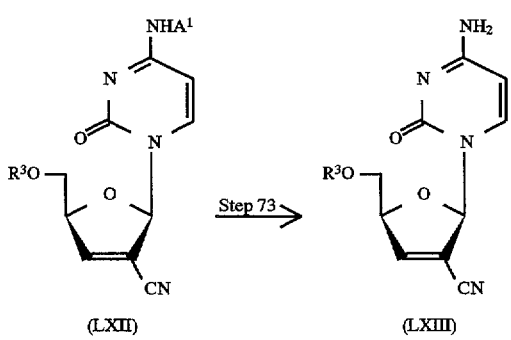

(LXII) → Step 73 → (LXIII)

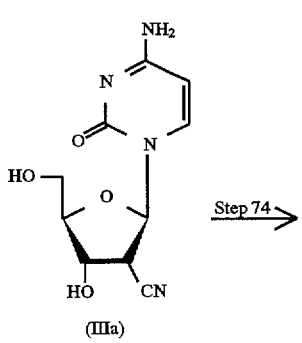

(IIIa) → Step 74 →

52

-continued

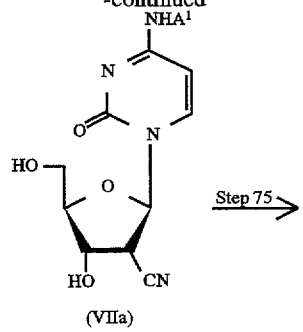

(VIIa) → Step 75 →

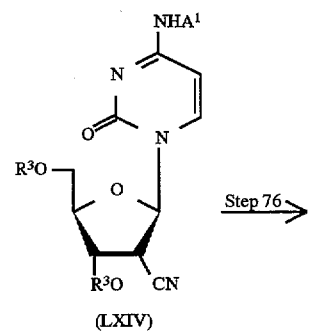

(LXIV) → Step 76 →

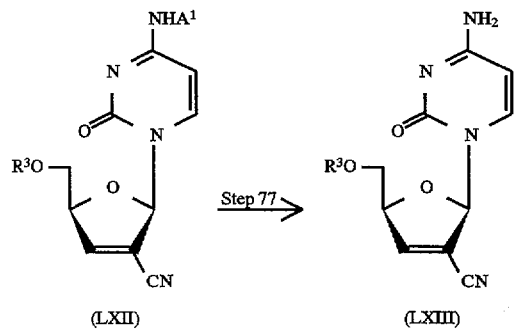

(LXII) → Step 77 → (LXIII)

In the formulae given in these reaction schemes, $R^1$, $R^2$ and $R^3$ are as defined as above.

$A^1$ represents an amino-protecting group, such as those exemplified above in relation to substituents A, for example, a substituted oxycarbonyl group such as a benzyloxycarbonyl or trichloroethoxycarbonyl group.

$A^2$ represents a hydroxy-protecting group, for example, a tri-substituted silyl group, such as those corresponding to the silyloxy groups exemplified above in relation to substituents B, for example, a trimethylsilyl, t-butyldimethylsilyl or t-butyldiphenylsilyl group.

$A^3$ represents a triphenylmethyl group which may optionally have one or more substituents on one or more of the phenyl groups, for example, a triphenylmethyl, 4-methoxytriphenylmethyl or 4,4'-dimethoxytriphenylmethyl group.

$A^4$ represents a tri-substituted silyl group, such as those corresponding to the silyloxy groups exemplified above in relation to substituents B, for example, a trimethylsilyl, triphenylsilyl, t-butyldimethylsilyl or t-butyldiphenylsilyl group.

$A^5$ represents a haloalkyloxycarbonyl group, for example, a trichloroethoxycarbonyl group.

B represents a group of formula:

$$-(R^6)(R^7)Si-O-Si(R^8)(R^9)-,$$

in which $R^6$, $R^7$, $R^8$ and $R^9$ are independently selected from the group consisting of alkyl groups having from 1 to 8, preferably from 1 to 5 and more preferably from 1 to 4, carbon atoms, and aryl groups, as defined above, but preferably phenyl or substituted phenyl groups; examples of such alkyl and aryl groups are as given above in relation to the substituted silyl groups which may be used as hydroxy-protecting groups.

The reactions involved in these reaction schemes are as follows:

Step 1

In this step, a compound of formula (IV) is prepared by reacting a compound of formula (III) with a carboxylic acid compound of formula $R^1OH$ or with a reactive derivative thereof, such as an acid halide of formula $R^1X$ (where $R^1$ is as defined above and X represents a halogen atom), an acid anhydride of formula $R^1OR^1$ (where $R^1$ is as defined above) or a mixed acid anhydride, for example, a compound of formula $R^1OCOOMe$ (where $R^1$ is as defined above and Me represents a methyl group) or $R^1OCOOEt$ (where $R^1$ is as defined above and Et represents an ethyl group).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, which may be aliphatic, aromatic or cycloaliphatic, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; ethers, such as dioxane, dimethoxyethane or diethylene glycol dimethyl ether; ketones, such as acetone, methyl ethyl ketone, methyl isobutyl ketone, isophorone or cyclohexanone; nitro compounds, such as nitroethane or nitrobenzene; nitriles, such as acetonitrile or isobutyronitrile; amides, such as formamide, dimethylformamide, dimethylacetamide or hexamethylphosphoric triamide; and sulfoxides, such as dimethyl sulfoxide or sulfolane. Of these, we prefer the aromatic hydrocarbons, halogenated hydrocarbons, nitriles or amides, and more prefer the halogenated hydrocarbons (particularly methylene chloride) or amides (particularly dimethylformamide).

Where a carboxylic acid compound is employed in the reaction, in general, we prefer to carry out the reaction in the additional presence of a condensing agent. Examples of condensing agents which may be employed include: N-hydroxy compounds, such as N-hydroxysuccinimide, 1-hydroxybenzotriazole or N-hydroxy-5-norbornene-2,3-dicarboximide; diimidazole compounds such as 1,1'-oxazolyldiimidazole or N,N'-carbonyldiimidazole; disulfide compounds, such as 2,2'-dipyridyldisulfide; succinic acid compounds, such as N,N'-disuccinimidyl carbonate; phosphinic chloride compounds, such as N,N'-bis(2-oxo-3-oxazolydinyl)phosphinic chloride; oxalate compounds, such as N,N'-disuccinimidyl oxalate (DSO), N,N'-diphthalimidyl oxalate (DPO), N,N'-bis(norbornenylsuccinimidyl)oxalate (BNO), 1,1'-bis(benzotriazolyl)oxalate (BBTO), 1,1'-bis(6-chlorobenzotriazolyl)oxalate (BCTO) or 1,1'-bis(6-trifluoromethylbenzotriazolyl)oxalate (BTBO); and carbodiimide compounds, such as dicyclohexylcarbodiimide (DCC). Of these, we prefer the diimidazole compounds or the carbodiimide compounds (particularly dicyclohexylcarbodiimide).

Where the reagent is an acid halide, the nature of the acid part will, of course, depend on the nature of the acyl group which it is desired to introduce. The halogen moiety of the acid halide is preferably a chlorine, bromine or iodine atom.

Where an acid halide or acid anhydride compound is employed in the reaction, the efficacy of the reaction can be promoted by the simultaneous addition of a base. There is no particular limitation upon the nature of the base employed, and any base used in conventional reactions of this type can equally be used here. Examples of preferred bases include inorganic bases, such as: alkali metal carbonates, for example sodium carbonate, potassium carbonate or lithium carbonate; alkali metal hydrogencarbonates, for example sodium hydrogencarbonate, potassium hydrogencarbonate or lithium hydrogencarbonate; alkali metal hydrides, for example lithium hydride, sodium hydride or potassium hydride; and alkali metal hydroxides, for example sodium hydroxide, potassium hydroxide, barium hydroxide or lithium hydroxide. Other bases which may be used include: alkali metal alkoxides, such as sodium methoxide, sodium ethoxide, potassium t-butoxide or lithium methoxide; alkali metal salts of mercaptans, such as sodium methylmercaptan or sodium ethylmercaptan; organic bases, such as triethylamine, tributylamine, diisopropylethylamine, N-methylmorpholine, pyridine, 4-(N,N-dimethylamino) pyridine, N,N-dimethylaniline, N,N-diethylaniline, 1,5-diazabicyclo[4.3.0]non-5 -ene, 1,4-diazabicyclo[2.2.2] octane (DABCO) or 1,8-diazabicyclo[5.4.0]undec-7-ene (DBU); and organic metal bases, such as butyllithium or lithium diisopropylamide. Of these, we prefer the organic bases, particularly pyridine, N-methylmorpholine or 1,8-diazabicyclo[5.4.0]undec-7-ene.

The reaction can take place over a wide range of temperatures, and the precise reaction temperature is not critical to the invention. In general, we find it convenient to carry out the reaction at a temperature of from −20° C. to 100° C., more preferably from −10° C. to 50° C. The time required for the reaction may also vary widely, depending on many factors, notably the reaction temperature and the nature of the reagents and solvent employed. However, provided that the reaction is effected under the preferred conditions outlined above, a period of from 1 to 100 hours, more preferably from 1 to 24 hours will usually suffice.

After completion of the reaction, the product can be recovered from the reaction mixture by conventional means. For example, one suitable recovery procedure comprises: filtering off insolubles; distilling off the solvent; pouring the remaining reaction mixture into water; acidifying the resulting mixture with an inorganic acid, such as hydrochloric acid or sulfuric acid; extracting the mixture with a water-immiscible solvent such as benzene, diethyl ether or ethyl acetate; and then distilling off the solvent from the extract. In general, the product can be used as a starting material for the next step without any further purification. However, if desired, the product can be further purified by a wide variety of chromatographic techniques or by recrystallization.

The compound of formula (III), used as a starting material in this step, is known when $R^5$ represents a cyano group, i.e. the β-cyano compound of formula (IIIa), from Matsuda et al. [Nucleic Acids Research, Symposium Series No. 22, page 51 (1990)]. The corresponding α-cyano compounds of formula (IIIb), where $R^4$ represents a cyano group, may be prepared as illustrated hereafter in the following Step 2.

Step 2

In this step, a compound of formula (V) is prepared by reacting the compound of formula (III) with a reactive derivative of a carboxylic acid, such as an acid halide of formula $R^1X$ (where $R^1$ and X are as defined above), an acid anhydride of formula $R^1OR^1$ (where $R^1$ is as defined above) or a mixed acid anhydride, for example, $R^1OCOOMe$ (where $R^1$ and Me are as defined above) or $R^1OCOOEt$ (where $R^1$ and Et are as defined above).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; ketones, such as acetone, methyl ethyl ketone, methyl isobutyl ketone, isophorone or cyclohexanone; nitro compounds, such as nitroethane or nitrobenzene; nitriles, such as acetonitrile or isobutyronitrile; amides, such as formamide, dimethylformamide (DMF), dimethylacetamide, hexamethylphosphoric triamide; and sulfoxides, such as dimethyl sulfoxide or sulfolane. Of these, we prefer the halogenated hydrocarbons (particularly methylene chloride) and the amides (particularly dimethylformamide).

The reaction can take place over a wide range of temperatures, and the precise reaction temperature is not critical to the invention. In general, we find it convenient to carry out the reaction at a temperature of from −20° C. to 150° C. and more preferably from 0° C. to 100° C. The time required for the reaction may also vary widely, depending on many factors, notably the reaction temperature and the nature of the reagents and solvent employed. However, provided that the reaction is effected under the preferred conditions outlined above, a period of from 1 to 100 hours and preferably from 1 to 24 hours will usually suffice.

In order to prevent acylation of the hydroxy groups, it is preferred to restrict the amount of acylating agent employed to about 1 equivalent per mole of the compound of formula (III).

After completion of the reaction, the product can be recovered from the reaction mixture by conventional means. For example, one suitable recovery procedure comprises: distilling off the solvent; pouring the reaction mixture into water; acidifying the resulting mixture with an inorganic acid, such as hydrochloric acid or sulfuric acid; extracting the mixture with a water-immiscible solvent, such as benzene, diethyl ether or ethyl acetate; and then distilling off the solvent from the extract. In general, the product can be used as a starting material for the next step without any further purification. However, if desired, the product can be further purified by a wide variety of chromatographic techniques or by recrystallization.

Step 3

In this step, a compound of formula (VI) can be prepared by reacting a compound of formula (V), which may have been prepared as described in step 2, with a carboxylic acid compound of formula $R^2OH$ (where $R^2$ is as defined above) or with a reactive derivative thereof, such as an acid halide of formula $R^2X$ (where $R^2$ and X are as defined above), an acid anhydride of formula $R^2OR^2$ (where $R^2$ is as defined above) or a mixed acid anhydride, for example, a compound of formula $R^2OCOOMe$ (where $R^2$ and Me are as defined above) or a compound of formula $R^2OCOOEt$ (where $R^2$ and Et are as defined above), normally and preferably in an inert solvent. The reaction in this step is essentially the same as, and can be carried out in a similar manner to, that described in Step 1.

Step 4

In this step, a compound of formula (VII) is prepared by reacting a compound of formula (III) with an amino-protecting reagent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; alcohols, such as methanol, ethanol, propanol, isopropanol, butanol, isobutanol, t-butanol, isoamyl alcohol, diethylene glycol, glycerin, octanol, cyclohexanol or ethylene glycol monomethyl ether; ketones, such as acetone, methyl ethyl ketone, methyl isobutyl ketone, isophorone or cyclohexanone; nitro compounds, such as nitroethane or nitrobenzene; nitriles, such as acetonitrile or isobutyronitrile; amides, such as formamide, dimethylformamide, dimethylacetamide or hexamethylphosphoric triamide; and sulfoxides, such as dimethyl sulfoxide or sulfolane. Of these, we prefer the halogenated hydrocarbons (particularly methylene chloride), the aromatic hydrocarbons (particularly toluene) and the amides (particularly dimethylformamide).

There is no particular limitation upon the nature of the reagent employed to introduce the amino-protecting group, and the nature of the reagent will depend on the nature of the group which it is desired to introduce. There is also no restriction on this group, provided that it can be removed under acidic or neutral conditions. Preferred reagents include: haloalkoxycarbonyl halides, such as trichloroethoxycarbonyl chloride; and aralkyloxycarbonyl halides, such as benzyloxycarbonyl chloride.

Where the protecting reagent employed is a haloalkoxycarbonyl halide or aralkyloxycarbonyl halide, the reaction is normally carried out in the presence of a base. There is no particular restriction on the nature of the bases which may be employed, and preferred examples include organic bases, particularly triethylamine, pyridine, N-methylmorpholine and 1,8-diazabicyclo[5.4.0]undec-7-ene.

The reaction can take place over a wide range of temperatures, and the precise reaction temperature is not critical to the invention. In general, we find it convenient to carry out the reaction at a temperature of from −10° C. to 100° C., more preferably from −10° C. to 50° C. The time required for the reaction may also vary widely, depending on many factors, notably the reaction temperature and the nature of the reagents and solvent employed. However, provided that the reaction is effected under the preferred conditions outlined above, a period of from 1 to 50 hours, more preferably from 1 to 24 hours will usually suffice.

After completion of the reaction, the product can be recovered from the reaction mixture by conventional means. For example, one suitable recovery procedure comprises: distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and then distilling off the solvent from the extract. In general, the product can be used as a starting material for the next step without any further purification. However, if desired, the product can be further purified by a wide variety of chromatographic techniques or by recrystallization.

Step 5

In this step, a compound of formula (III) is reacted with a reagent to introduce a hydroxy-protecting group, to afford a compound of formula (VIII) in which the hydroxy group at the 5'-position alone is selectively protected.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; ketones, such as acetone, methyl ethyl ketone, methyl isobutyl ketone, isophorone or cyclohexanone; nitro compounds, such as nitroethane or nitrobenzene; nitriles, such as acetonitrile or isobutyronitrile; amides, such as formamide, dimethylformamide, dimethylacetamide or hexamethylphosphoric triamide; and sulfoxides, such as dimethyl sulfoxide or sulfolane. Of these, we prefer the halogenated hydrocarbons (particularly methylene chloride) and the amides (particularly dimethylformamide).

There is no particular limitation upon the nature of the reagent employed to introduce the protecting group, provided that the protecting group can selectively protect a hydroxy group at the 5'-position alone and that it can be removed under acidic or neutral conditions. Examples of preferred protecting reagents include triarylmethyl halides, such as trityl chloride, monomethoxytrityl chloride and dimethoxytrityl chloride.

Where the protecting reagent is a triarylmethyl halide, the reaction is normally carried out in the presence of a base. There is no particular restriction on the nature of base employed, and preferred bases include organic bases, particularly triethylamine, pyridine, N-methylmorpholine and 1,8-diazabicyclo[5.4.0]undec-7-ene.

The reaction can take place over a wide range of temperatures, and the precise reaction temperature is not critical to the invention. In general, we find it convenient to carry out the reaction at a temperature of from 0° C. to 150° C., more preferably from 20° C. to 100° C. The time required for the reaction may also vary widely, depending on many factors, notably the reaction temperature and the nature of the reagents and solvent employed. However, provided that the reaction is effected under the preferred conditions outlined above, a period of from 1 to 100 hours, more preferably from 2 to 24 hours will usually suffice.

After completion of the reaction, the product can be recovered from the reaction mixture by conventional means. For example, one suitable recovery procedure comprises: by distilling off the solvent; pouring the reaction mixture into water; acidifying the mixture with an inorganic acid, such as hydrochloric acid or sulfuric acid; extracting the mixture with a water-immiscible solvent such as benzene, diethyl ether or ethyl acetate; and then distilling off the solvent from the extract. In general, the product can be used as a starting material for the next step without any further purification. If desired, the product can be further purified by a wide variety of chromatographic techniques or by recrystallization.

Step 6

In this step, a compound of formula (V) is reacted with a reagent to introduce a hydroxy-protecting group, to afford a compound of formula (IX) in which the hydroxy group at the 5'-position alone is selectively protected. This step is essentially the same as that of, and may be carried out in the same manner as described in, Step 5.

Step 7

In this step, a compound of formula (X) is prepared by reacting a compound of formula (IX) with a carboxylic acid compound of formula $R^2OH$ (where $R^2$ is as defined above) or with a reactive derivative thereof; such as an acid halide of formula $R^2X$ (where $R^2$ and X are as defined above), an acid anhydride of formula $R^2OR^2$ (where $R^2$ is as defined above) or a mixed acid anhydride, for example, a compound of formula $R^2OCOOMe$ (where $R^2$ and Me are as defined above) or a compound of formula $R^2OCOOEt$ (where $R^2$ and Et are as defined above), preferably in the presence of an inert solvent. The reaction is essentially the same as, and may be carried out in a similar manner to that described in, Step 1.

Step 8

In this step, a compound of formula (XI) is prepared by reacting a compound of formula (IX) with a reagent to introduce a hydroxy-protecting group.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; ketones, such as acetone, methyl ethyl ketone, methyl isobutyl ketone, isophorone or cyclohexanone; nitro compounds, such as nitroethane or nitrobenzene; nitriles, such as acetonitrile or isobutyronitrile; amides, such as formamide, dimethylformamide, dimethylacetamide or hexamethylphosphoric triamide; and sulfoxides, such as dimethyl sulfoxide or sulfolane. Of these, we prefer methylene chloride, toluene or dimethylformamide.

There is no particular limitation on the nature of the reagent employed to introduce the protecting group, provided that the protected group produced can be normally deprotected independently of the protecting group at the 5'-position. Examples of preferred protecting agents include: silyl halides, such as t-butyldimethylsilyl chloride; haloalkoxycarbonyl halides, such as trichloroethoxycarbonyl chloride; and aralkyloxycarbonyl halides, such as benzyloxycarbonyl chloride.

Where a silyl halide, a haloalkoxycarbonyl halide or an aralkyloxycarbonyl halide is used as the protecting reagent, the reaction is normally carried out in the presence of a base. There is no particular restriction on the nature of the base used, and examples of preferred bases include organic bases, particularly triethylamine, pyridine, N-methylmorpholine or 1,8-diazabicyclo[5.4.0]undec-7-ene.

The reaction can take place over a wide range of temperatures, and the precise reaction temperature is not critical to the invention. In general, we find it convenient to carry out the reaction at a temperature of from −20° C. to 150° C., more preferably from −10° C. to 50° C. The time required for the reaction may also vary widely, depending on many factors, notably the reaction temperature and the nature of the reagents and solvent employed. However, provided that the reaction is effected under the preferred conditions outlined above, a period of from 1 to 100 hours, more preferably from 1 to 24 hours, will usually suffice.

After completion of the reaction, the product can be recovered from the reaction mixture by conventional means. For example, one suitable recovery procedure comprises: distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product can be further purified by a wide variety of chromatographic techniques or recrystallization.

Step 9

In this step, a compound of formula (VIII) is reacted with a carboxylic acid compound of formula $R^1OH$ (where $R^1$ is as defined above) or with a reactive derivative thereof, such as an acid halide of formula $R^1X$ (where $R^1$ and X are as defined above), an acid anhydride of formula $R^1OR^1$ (where $R^1$ is as defined above) or a mixed acid anhydride, for example, a compound of formula $R^1OCOOMe$ (where $R^1$ and Me are as defined above) or $R^1OCOOEt$ (where $R^1$ and Et are as defined above), preferably in the presence of an inert solvent to give a $N^4$,3'-diacyl compound. The reaction is essentially the same as that of, and may be carried out in a similar manner to that described in, Step 1.

Step 10

In this step, a compound of formula (XIII) is prepared by reacting a compound of formula (XII), which may have been obtained as described in Step 9, with a deprotecting reagent for a hydroxy-protecting group, preferably in the presence of an inert solvent.

Where the protecting group is a triarylmethyl halide, examples of the solvents employed include: aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; alcohols, such as methanol, ethanol, propanol, isopropanol, butanol, isobutanol, t-butanol, isoamyl alcohol, diethylene glycol, glycerine, octanol, cyclohexanol or ethylene glycol monomethyl ether; ketones, such as acetone, methyl ethyl ketone, methyl isobutyl ketone, isophorone or cyclohexanone; nitriles, such as acetonitrile or isobutyronitrile; amides, such as formamide, dimethylformamide, dimethylacetamide or hexamethylphosphoric triamide; and sulfoxides, such as dimethyl sulfoxide or sulfolane; water. Of these, we prefer water or the alcohols.

There is no particular limitation upon the nature of the deprotecting reagent employed, and any such reagent commonly used in conventional reactions may equally be employed here. For example, where a triarylmethyl halide is used as the protecting group, examples of preferred deprotecting reagents include organic acids, such as formic acid or acetic acid, preferably acetic acid.

The reaction can take place over a wide range of temperatures, and the precise reaction temperature is not critical to the invention. In general, we find it convenient to carry out the reaction at a temperature of from 0° C. to 100° C., more preferably from 5° C. to 50° C. The time required for the reaction may also vary widely, depending on many factors, notably the reaction temperature and the nature of the reagents and solvent employed. However, provided that the reaction is effected under the preferred conditions outlined above, a period of from 1 to 50 hours, more preferably from 1 to 24 hours, will usually suffice.

After completion of the reaction, the product can be recovered from the reaction mixture by conventional means. For example, one suitable recovery procedure comprises: distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product can be purified by a wide variety of chromatographic techniques or by recrystallization.

Step 11

In this step, a compound of formula (XIV) is prepared by reacting a compound of formula (XIII), which may have been prepared as described in step 10, with a carboxylic acid compound of formula $R^3OH$ (where $R^3$ is as defined above) or with a reactive derivative thereof, such as an acid halide of formula $R^3X$ (where $R^3$ and X are as defined above), an acid anhydride of formula $R^3OR^3$ where $R^3$ is as defined above) or a mixed acid anhydride, for example, a compound of formula $R^3OCOOMe$ (where $R^3$ and Me are as defined above) or $R^3OCOOEt$ (where $R^3$ and Et are as defined above), preferably in the presence of an inert solvent. The reaction is essentially the same as that of, and can be carried out in a similar manner to that described in, Step 1.

Step 12

This step involves the reaction of a compound of formula (VII) with a carboxylic acid compound of formula $R^2OH$ (where $R^2$ is as defined above) or with a reactive derivative thereof, such as an acid halide of formula $R^2X$ (where $R^2$ and X are as defined above), an acid anhydride of formula $R^2OR^2$ (where $R^2$ is as defined above) or a mixed acid anhydride, for example, a compound of formula $R^2OCOOMe$ (where $R^2$ and Me are as defined above) or $R^2OCOOEt$ (where $R^2$ and Et are as defined above), preferably in the presence of an inert solvent, to give a compound of formula (VII'). The reaction is essentially the same as that of, and may be carried out in the same manner as described in, Step 1.

Step 13

In this step, a compound of formula (XV) is prepared by reacting the compound of formula (VII'), which may have been prepared as described in Step 12, with a deprotecting reagent for an amino-protecting group.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; alcohols, such as methanol, ethanol, propanol, isopropanol, butanol, isobutanol, t-butanol, isoamyl alcohol, diethylene glycol, glycerine, octanol, cyclohexanol or ethylene glycol monomethyl ether; ketones, such as acetone, methyl ethyl ketone, methyl isobutyl ketone, isophorone or cyclohexanone; nitro compounds, such as nitroethane or nitrobenzene; nitriles, such as acetonitrile or isobutyronitrile; amides, such as formamide, dimethylformamide, dimethylacetamide or hexamethylphosphoric triamide; sulfoxides, such as dimethyl sulfoxide or sulfolane; and mixtures of water with an organic acid, such as formic acid, acetic acid or propionic acid. Of these, we prefer methanol, ethanol or 80% by volume aqueous acetic acid.

There is no particular limitation on the nature of the deprotecting reagent employed, and any such reagent normally used in a deprotecting reaction can equally be employed here. For example, when the protecting group is an aralkyloxycarbonyl group, the reaction may be carried out by catalytic reduction. Alternatively, when the protecting group is a haloalkoxycarbonyl group, it may be removed by contacting the compound with zinc in 80% aqueous acetic acid.

The reaction can take place over a wide range of temperatures, and the precise reaction temperature is not critical to the invention. In general, we find it convenient to carry out the reaction at a temperature of from −10° C. to 100° C., more preferably from 0° C. to 50° C. The time required for the reaction may also vary widely, depending on many factors, notably the reaction temperature and the nature of the reagents and solvent employed. However, provided that the reaction is effected under the preferred conditions outlined above, a period of from 1 to 100 hours, more preferably from 1 to 24 hours, will usually suffice.

After completion of the reaction, the product can be recovered from the reaction mixture by conventional means. For example, one suitable recovery procedure comprises: distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product can be purified by a wide variety of chromatographic techniques or recrystallization.

Step 14

In this step, a compound of formula (XV), which may have been prepared as described in step 13, is reacted with a carboxylic acid compound of formula $R^1OH$ (where $R^1$ is as defined above) or with a reactive derivative thereof, such as an acid halide $R^1X$ (where $R^1$ and X are as defined above), an acid anhydride $R^1OR^1$ (where $R^1$ is as defined above) or a mixed acid anhydride, for example, a compound of formula $R^1OCOOMe$ (where $R^1$ and Me are as defined above) or $R^1OCOOEt$ (where $R^1$ and Et are as defined above), preferably in the presence of an inert solvent, to afford a compound of formula (XV'), having a protected amino group. This step is essentially the same as that of, and may be carried out in the same manner as described in, Step 1.

Step 15

In this step, a compound of formula (XVII) in which the hydroxy group at the 5'-position is selectively protected is prepared by reacting a compound of formula (VII) with a hydroxy-protecting reagent in the presence of an inert solvent. The reaction is essentially the same as that of, and may be carried out in the same manner as described in, Step 5.

Step 16

In this step, a compound of formula (XVIII) is prepared by reacting a compound of formula (XVII) with a hydroxy-protecting reagent in the presence of an inert solvent. The reaction is essentially the same as that of, and may be carried out in the same manner as described in, Step 8.

Step 17

In this step, the hydroxy-protecting group at the 5'-position of a compound of formula (X) is removed by reaction with a deprotecting reagent, preferably in the presence of an inert solvent, to afford a compound of formula (XIX).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; alcohols, such as methanol, ethanol, propanol, isopropanol, butanol, isobutanol, t-butanol, isoamyl alcohol, diethylene glycol, glycerine, octanol, cyclohexanol or ethylene glycol monomethyl ether; ketones, such as acetone, methyl ethyl ketone, methyl isobutyl ketone, isophorone or cyclohexanone; nitro compounds, such as nitroethane or nitrobenzene; nitriles, such as acetonitrile or isobutyronitrile; amides, such as formamide, dimethylformamide, dimethylacetamide or hexamethylphosphoric triamide; and sulfoxides, such as dimethyl sulfoxide or sulfolane. Of these, we prefer the alcohols, especially methanol or ethanol.

There is no particular limitation on the nature of the deprotecting reagent employed, and any such agent normally used in deprotecting reactions may equally be used here, for example, acetic acid, trifluoroacetic acid or hydrogen chloride in methanol, preferably acetic acid or trifluoroacetic acid.

The reaction can take place over a wide range of temperatures, and the precise reaction temperature is not critical to the invention. In general, we find it convenient to carry out the reaction at a temperature of from −10° C. to 100° C., more preferably from 0° C. to 50° C. The time required for the reaction may also vary widely, depending on many factors, notably the reaction temperature and the nature of the reagents and solvent employed. However, provided that the reaction is effected under the preferred conditions outlined above, a period of from 1 to 50 hours, more preferably from 1 to 24 hours, will usually suffice.

After completion of the reaction, the product can be recovered from the reaction mixture by conventional means. For example, one suitable recovery procedure comprises: distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product can be purified by a wide variety of chromatographic techniques or by recrystallization.

Step 18

This step involves the reaction of a compound of formula (XIX), which may have been prepared as described in Step 17, with a carboxylic acid compound of formula $R^3OH$ (where $R^3$ is as defined above) or with a reactive derivative thereof, such as an acid halide of formula $R^3X$ (where $R^3$ and X are as defined above), an acid anhydride of formula $R^3OR^3$ (where $R^3$ is as defined above) or a mixed acid anhydride, for example, a compound of formula $R^3OCOOMe$ (where $R^3$ and Me are as defined above) or $R^3OCOOEt$ (where $R^3$ and Et are as defined above), preferably in the presence of an inert solvent.

The reaction is essentially the same as that of, and may be carried out in the same manner as described in, Step 11.

Step 19

In this step, a compound of formula (XI) is reacted with a deprotecting reagent, preferably in the presence of an inert solvent, to remove the hydroxy-protecting group at the 5'-position, and thus to afford a compound of formula (XXI). The reaction is essentially the same as that of, and may be carried out in the same manner as described in, Step 17.

Step 20

This step involves the reaction of a compound of formula (XXI), which may have been prepared as described in Step 19, with a carboxylic acid compound of formula $R^3OH$ (where $R^3$ is as defined above) or with a reactive derivative thereof, such as an acid halide of formula $R^3X$ (where $R^3$ and X are as defined above), an acid anhydride $R^3OR^3$ (where $R^3$ is as defined above) or a mixed acid anhydride, for example, a compound of formula $R^3OCOOMe$ (where $R^3$ and Me are as defined above) or $R^3OCOOEt$ (where $R^3$ and Et are as defined above), preferably in the presence of an inert solvent. This step is essentially the same as that of, and may be carried out in the same manner as described in, Step 11.

Step 21

In this step, a compound of formula (XXII), which may have been prepared as described in Step 20, is reacted with a deprotecting reagent, preferably in the presence of an inert solvent, to remove selectively the hydroxy-protecting group at the 3'-position, and thus to give the compound of formula (XXIII). Examples of the reagents which may be employed include tetrabutylammonium fluoride, potassium fluoride and tetraethylammonium bromide.

The reaction can take place over a wide range of temperatures, and the precise reaction temperature is not critical to the invention. In general, we find it convenient to carry out the reaction at a temperature of from $-10°$ C. to $50°$ C., more preferably from $-5°$ C. to $30°$ C. The time required for the reaction may also vary widely, depending on many factors, notably the reaction temperature and the nature of the reagents and solvent employed. However, provided that the reaction is effected under the preferred conditions outlined above, a period of from 1 to 100 hours, more preferably from 1 to 24 hours, will usually suffice.

After completion of the reaction, the product can be recovered from the reaction mixture by conventional means. For example, one suitable recovery procedure comprises: distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product can be purified by a wide variety of chromatographic techniques or recrystallization.

Step 22

In this step, a compound of formula (XX) is prepared by reacting a compound of formula (XXIII), which may have been prepared as described in Step 21, with a carboxylic acid compound of formula $R^2OH$ (where $R^2$ is as defined above) or with a reactive derivative thereof, such as an acid halide of formula $R^2X$ (where $R^2$ and X are as defined above), an acid anhydride of formula $R^2OR^2$ (where $R^2$ is as defined above) or a mixed acid anhydride, for example, a compound of formula $R^2OCOOMe$ (where $R^2$ and Me are as defined above) or $R^2OCOOEt$ (where $R^2$ and Et are as defined above), preferably in the presence of an inert solvent. The reaction is essentially the same as that of, and may be carried out in the same manner as described in, Step 1.

Step 23

In this step, a protected intermediate of formula (XXIV) is prepared by reacting a compound of formula (XVII) with a carboxylic acid compound of formula $R^2OH$ (where $R^2$ is as defined above) or with a reactive derivative thereof, such as an acid halide of formula $R^2X$ (where $R^2$ and X are as defined above), an acid anhydride of formula $R^2OR^2$ (where $R^2$ is as defined above) or a mixed acid anhydride, for example, a compound of formula $R^2OCOOMe$ (where $R^2$ and Me are as defined above) or $R^2OCOOEt$ (where $R^2$ and Et are as defined above), preferably in the presence of an inert solvent. The reaction is essentially the same as that of, and may be carried out in the same manner as described in, Step 1.

Step 24

In this step, a compound of formula (XXIV), which may have been prepared as described in Step 23, is reacted with a deprotecting reagent, preferably in the presence of an inert solvent, to remove selectively the hydroxy-protecting group at the 5'-position, and thus to give a compound of formula (XXV). The reaction is essentially the same as that of, and may be carried out in the same manner as described in, Step 17.

Step 25

This step involves the reaction of a compound of formula (XXV), which may have been prepared as described in Step 24, with a carboxylic acid compound of formula $R^3OH$ (where $R^3$ is as defined above) or with a reactive derivative thereof, such as an acid halide of formula $R^3X$ (where $R^3$ and X are as defined above), an acid anhydride of formula $R^3OR^3$ (where $R^3$ is as defined above) or a mixed acid anhydride, for example, a compound of formula $R^3OCOOMe$ (where $R^3$ and Me are as defined above) or $R^3OCOOEt$ (where $R^3$ and Et are as defined above), preferably in the presence of an inert solvent. The reaction is essentially the same as that of, and may be carried out in the same manner as described in, Step 1.

Step 26

In this step, a compound of formula (XXVII) is prepared by reacting a compound of formula (XXVI), which may have been prepared as described in Step 25, with a deprotecting reagent for an amino group. The reaction is essentially the same as that of, and may be carried out in the same manner as described in, Step 13.

Step 27

In this step, a compound of formula (XX) is prepared by reacting a compound of formula (XXVII), which may have been prepared as described in Step 26, with a carboxylic acid compound of formula $R^2OH$ (where $R^2$ is as defined above) or with a reactive derivative thereof, such as an acid halide of formula $R^2X$ (where $R^2$ and X are as defined above), an acid anhydride of formula $R^2OR^2$ (where $R^2$ is as defined above) or a mixed acid anhydride, for example, a compound of formula $R^2OCOOMe$ (where $R^2$ and Me are as defined above) or $R^2OCOOEt$ (where $R^2$ and Et are as defined above), preferably in the presence of an inert solvent. The reaction is essentially the same as that of, and may be carried out in the same manner as described in, Step 1.

Step 28

In this step, a compound of formula (XXVIII) is prepared by reacting a compound of formula (XXV) with a deprotecting reagent for an amino-protecting group, preferably in the presence of an inert solvent. The reaction is essentially the same as that of, and may be carried out in the same manner as described in, Step 13.

Step 29

In this step, a compound of formula (XXIX) is prepared by reacting a compound of formula (XXVIII), which may have been prepared as described in Step 28, with a carboxylic acid compound of formula $R^1OH$ (where $R^1$ is as defined above) or with a reactive derivative thereof, such as an acid halide of formula $R^1X$ (where $R^1$ and X are as defined above), an acid anhydride of formula $R^1OR^1$ (where $R^1$ is as defined above) or a mixed acid anhydride, for example, a compound of formula $R^1OCOOMe$ (where $R^1$ and Me are as defined above) or $R^1OCOOEt$ (where $R^1$ and Et are as defined above), preferably in the presence of an inert solvent. The reaction is essentially the same as that of, and may be carried out in the same manner as described in, Step 1.

Step 30

In this step, a compound of formula (XVIII) is reacted with a deprotecting reagent, preferably in the presence of an inert solvent in order to remove selectively a hydroxy-protecting group at the 5'-position, and thus to afford a compound of formula (XXX). The reaction is essentially the same as that of, and may be carried out in the same manner as described in, Step 17.

Step 31

This step involves the reaction of a compound of formula (XXX), which may have been prepared as described in Step 30, with a carboxylic acid compound of formula $R^3OH$ (where $R^3$ is as defined above) or with a reactive derivative thereof, such as an acid halide of formula $R^3X$ (where $R^3$ and X are as defined above), an acid anhydride of formula $R^3OR^3$ (where $R^3$ is as defined above) or a mixed acid anhydride, for example, a compound of formula $R^3OCOOMe$ (where $R^3$ and Me are as defined above) or $R^3OCOOEt$ (where $R^3$ and Et are as defined above), preferably in the presence of an inert solvent. The reaction is essentially the same as that of, and may be carried out in the same manner as described in, Step 1.

Step 32

This step involves the reaction of a compound of formula (XXXI), which may have been prepared as described in Step 31, with a deprotecting reagent for an amino-protecting group, preferably in the presence of an inert solvent. The reaction is essentially the same as that of, and may be carried out in the same manner as described in, Step 13.

Step 33

In this step, a compound of formula (XXXII), which may have been prepared as described in Step 32, is reacted with a deprotecting reagent, preferably in the presence of an inert solvent, in order to remove selectively a hydroxy-protecting group at the 3'-position, and thus to afford a compound of formula (XXXIII). The reaction is essentially the same as that of, and may be carried out in the same manner as described in, Step 21.

Moreover, the order of Step 32 and Step 33 can be reversed, if desired.

Step 34

In this step, a compound of formula (XIV) is prepared by reacting a compound of formula (XXXIII), which may have been prepared as described in Step 33, with a carboxylic acid compound of formula $R^1OH$ (where $R^1$ is as defined above) or with a reactive derivative thereof, such as an acid halide of formula $R^1X$ (where $R^1$ and X are as defined above), an acid anhydride of formula $R^1OR^1$ (where $R^1$ is as defined above) or a mixed acid anhydride, for example, a compound of formula $R^1OCOOMe$ (where $R^1$ and Me are as defined above) or $R^1OCOOEt$ (where $R^1$ and Et are as defined above), preferably in the presence of an inert solvent. The reaction is essentially the same as that of, and may be carried out in the same manner as described in, Step 1.

Step 35

In this step, a compound of formula (XVIII) is reacted with a deprotecting reagent for an amino-protecting group, preferably in the presence of an inert solvent, to afford a compound of formula (XXXIV) having a free amino group. The reaction is essentially the same as that of, and may be carried out in the same manner as described in, Step 13.

Step 36

In this step, a compound of formula (XXXIV), which may have been prepared as described in Step 35, is reacted with a deprotecting reagent, preferably in the presence of an inert solvent, in order to remove selectively a hydroxy-protecting group at the 5'-position, and thus to afford a compound of formula (XXXV). The reaction is essentially the same as that of, and may be carried out in the same manner as described in, Step 19.

Moreover, the order of Step 35 and Step 36 can be reversed, if desired.

Step 37

This step involves the reaction of a compound of formula (XXXV), which may have been prepared as described in Step 36, with a carboxylic acid compound of formula $R^1OH$ (where $R^1$ is as defined above) or with a reactive derivative thereof, such as an acid halide of formula $R^1X$ (where $R^1$ and X are as defined above), an acid anhydride of formula $R^1OR^1$ (where $R^1$ is as defined above) or a mixed acid anhydride, for example, a compound of formula $R^1OCOOMe$ (where $R^1$ and Me are as defined above) or $R^1OCOOEt$ (where $R^1$ and Et are as defined above), preferably in the presence of an inert solvent. The reaction is essentially the same as that of, and may be carried out in the same manner as described in, Step 1.

Step 38

In this step, a compound of formula (XXXVII) is prepared by reacting a compound of formula (XXXVI), which may have been prepared as described in Step 37, with a deprotecting reagent, preferably in the presence of an inert solvent. The reaction is essentially the same as that of, and may be carried out in the same manner as described in, Step 21.

Step 39

In this step, a compound of formula (XXIX) is prepared by reacting a compound of formula (XXXVII), which may have been prepared as described in Step 38, with a carboxylic acid compound of formula $R^2OH$ (where $R^2$ is as defined above) or with a reactive derivative thereof, such as an acid halide of formula $R^2X$ (where $R^2$ and X are as defined above), an acid anhydride of formula $R^2OR^2$ (where $R^2$ is as defined above) or a mixed acid anhydride, for example, a compound of formula $R^2OCOOMe$ (where $R^2$ and Me are as defined above) or $R^2OCOOEt$ (where $R^2$ and Et are as defined above), preferably in the presence of an inert solvent. The reaction is essentially the same as that of, and may be carried out in the same manner as described in, Step 1.

Step 40

In this step, a compound of formula (XXXIX) is prepared by reacting a compound of formula (XXXVIII) with a reactive derivative of a carboxylic acid, such as an acid halide of formula $R^1X$ (where $R^1$ and X are as defined above), an acid anhydride of formula $R^1OR^1$ (where $R^1$ is as defined above) or a mixed acid anhydride, for example, a compound of formula $R^1OCOOMe$ (where $R^1$ and Me are as defined above) or $R^1OCOOEt$ (where $R^1$ and Et are as defined above), preferably in an inert solvent in the absence of a base. The reaction is essentially the same as that of, and may be carried out in the same manner as described in, Step 2.

Step 41

This step involves the preparation of a compound of formula (XL) by simultaneously protecting the hydroxy groups at the 3'- and 5'-positions of a compound of formula (XXXIX), which may have been prepared as described in Step 40, using a compound of formula:

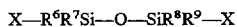

where $R^6$, $R^7$, $R^8$, $R^9$ and X are as defined above. The conditions employed for this step are well known [M. J. Robins, J. S. Wilson, L. Sawyer and M. N. G. James, Can. J. Chem., 61, 1911 (1983)].

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include basic solvents, such as pyridine.

The reaction can take place over a wide range of temperatures, and the precise reaction temperature is not critical to the invention. In general, we find it convenient to carry out the reaction at a temperature of from $-10°$ C. to $100°$ C., more preferably from $0°$ C. to $50°$ C. The time required for the reaction may also vary widely, depending on many factors, notably the reaction temperature and the nature of the reagents and solvent employed. However, provided that the reaction is effected under the preferred conditions outlined above, a period of from 1 to 30 hours, more preferably from 1 to 30 hours, will usually suffice.

After completion of the reaction, the product is recovered from the reaction mixture by conventional means. For example, one suitable recovery procedure comprises: distilling off the solvent; pouring the reaction mixture into water; extracting the mixture with a water-immiscible solvent, such as benzene, diethyl ether or ethyl acetate; and distilling off the solvent from the extract. In general, the product may be used as a starting material for the next step without any further purification. However, if desired, the product may be further purified by a wide variety of chromatographic techniques or by recrystallization.

Step 42

In this step, a compound of formula (XLI) is prepared by oxidizing the hydroxy group at the 2'-position of a compound of formula (XL), which may have been prepared as described in Step 41, according to a well-known method [F. Hansske et al., Tetrahedron, 40, 125 (1984)].

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride or chloroform; ethers, such as diethyl ether, tetrahydrofuran, dioxane or dimethoxyethane; amides, such as dimethylformamide, dimethylacetamide or hexamethylphosphoric triamide; sulfoxides, such as dimethyl sulfoxide; kenones, such as acetone or methyl ethyl kenone; and nitriles, such as acetonitrile. Of these, we prefer the halogenated hydrocarbons, such as methylene chloride or chloroform.

The reaction can take place over a wide range of temperatures, and the precise reaction temperature is not critical to the invention. In general, we find it convenient to carry out the reaction at a temperature of from $0°$ C. to $100°$ C., more preferably from $10°$ C. to $40°$ C. The time required for the reaction may also vary widely, depending on many factors, notably the reaction temperature and the nature of the reagents and solvent employed. However, provided that the reaction is effected under the preferred conditions outlined above, a period of from 10 minutes to 12 hours, more preferably from 30 minutes to 10 hours, will usually suffice.

This oxidation reaction may be accelerated by adding a phase-transfer catalyst such as triethylbenzylammonium chloride or tributylbenzylammoniumbromide to the reaction mixture.

The reaction can take place over a wide range of temperatures, and the precise reaction temperature is not critical to the invention. In general, we find it convenient to carry out the reaction at a temperature of from $0°$ C. to $100°$ C., more preferably from $10°$ C. to $40°$ C. The time required for the reaction may also vary widely, depending on many factors, notably the reaction temperature and the nature of the reagents and solvent employed. However, provided that the reaction is effected under the preferred conditions outlined above, a period of from 10 minutes to 12 hours, more preferably from 30 minutes to 6 hours, will usually suffice.

The compound of formula (XLI) prepared in this step may be recovered, separated and purified by a combination of various conventional means. For example, one suitable recovery procedure comprises: pouring the reaction mixture into water; extracting the mixture with a water-immiscible solvent, such as benzene, diethyl ether or ethyl acetate; and distilling off the solvent from the extract. If necessary, the compound thus obtained may be purified by absorption chromatography using a variety of absorbents, such as active charcoal or silica gel, ion-exchange chromatography, gel filtration using a Sephadex (trade name) column, or recrystallization from organic solvents, such as diethyl ether, ethyl acetate or chloroform.

Step 43

This step involves the preparation of a compound of formula (XLII), which is amongst the compounds of the present invention, by reacting a compound of formula (XLI), which may have been prepared as described in Step 42, with a cyanide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: a mixture of water and an aliphatic hydrocarbon, such as hexane, heptane, ligroin or petroleum ether; a mixture of water and an aromatic hydrocarbon, such as benzene, toluene or xylene; a mixture of water and an ether, such as diethyl ether, diisopropyl ether, tetrahydrofuran, dioxane, dimethoxyethane or diethylene glycol dimethyl ether; and a mixture of water and an ester, such as ethyl acetate or ethyl propionate. Of these, we prefer the mixture of water with an ether or with an ester.

The reaction is normally effected in the presence of a base in order to accelerate the reaction. There is no particular limitation upon the nature of the base, which may be organic or inorganic, employed as the material capable of accelerating the reaction. Examples of suitable bases include: alkali metal hydroxides, such as sodium hydroxide or potassium hydroxide; alkali metal carbonates, such as sodium carbonate or potassium carbonate; and alkali metal phosphates, such as sodium dihydrogenphosphate or sodium hydrogenphosphate.

There is likewise no particular limitation upon the nature of the cyanide employed, provided that it can dissolve in water and can produce a cyano ion. Preferred cyanides include alkali metal cyanides, such as sodium cyanide or potassium cyanide.

The reaction can take place over a wide range of temperatures, and the precise reaction temperature is not critical to the invention. In general, we find it convenient to carry out the reaction at a temperature of from −10° C. to 100° C., more preferably from 0° C. to 40° C. The time required for the reaction may also vary widely, depending on many factors, notably the reaction temperature and the nature of the reagents and solvent employed. However, provided that the reaction is effected under the preferred conditions outlined above, a period of from 30 minutes to 96 hours, more preferably from about 5 to 24 hours, will usually suffice.

The compound of formula (XLII) prepared in this step may be recovered, separated and purified by a combination of various conventional means. For example, one suitable recovery procedure comprises: pouring the reaction mixture into water; extracting the mixture with a water-immiscible solvent, such as benzene, diethyl ether or ethyl acetate; and distilling off the solvent from the extract. If necessary, the compound thus obtained may be purified by absorption chromatography using a variety of absorbents, such as active charcoal or silica gel, ion-exchange chromatography, gel filtration using a Sephadex (trade name) column, or recrystallization from organic solvents, such as diethyl ether, ethyl acetate or chloroform.

In this step, the compound of formula (XLII) obtained from the reaction exists in the form of a mixture of stereoisomers depending upon the α- and β-configurations of the nitrile group, and these isomers may be used in admixture in a subsequent step.

Step 44

This step involves the thiocarbonylation of the hydroxy group at the 2'-position of a compound of formula (XLII), which may have been prepared as described in Step 43, to produce an useful intermediate of formula (XLIII). This reaction is conducted using a substituted thiocarbonylating reagent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: amides, such as dimethylformamide or dimethylacetamide; sulfoxides, such as dimethyl sulfoxide; and nitriles, such as acetonitrile. Of these, we prefer acetonitrile.

There is likewise no particular limitation upon the nature of the thiocarbonylating reagent employed, provided that it can thiocarbonylate a hydroxy group and any such agent conventionally used in reactions of this type may equally be used here. Suitable reagents include: (lower alkoxy) thiocarbonyl halides, such as methoxythiocarbonyl chloride or ethoxythiocarbonyl chloride; and arylthiocarbonyl halides, such as phenoxythiocarbonyl chloride or naphthoxythiocarbonyl chloride.

The reaction can take place over a wide range of temperatures, and the precise reaction temperature is not critical to the invention. In general, we find it convenient to carry out the reaction at a temperature of from −20° C. to 50° C., more preferably from −10° C. to 30° C. The time required for the reaction may also vary widely, depending on many factors, notably the reaction temperature and the nature of the reagents and solvent employed. However, provided that the reaction is effected under the preferred conditions outlined above, a period of from 1 to 30 hours, more preferably from 2 to 5 hours, will usually suffice.

The reaction may, if desired, be accelerated by adding an organic base, such as 4,4-dimethylaminopyridine or triethylamine.

After completion of the reaction, the product may be recovered from the reaction mixture by conventional means. For example, one suitable recovery procedure comprises: pouring the reaction mixture into water; extracting the mixture with a water-immiscible solvent, such as diethyl ether, benzene or ethyl acetate; and distilling off the solvent from the extract. In general, the product may be used as a starting material for the next step without any further purification. However, if desired, the product may be further purified by a variety of chromatographic techniques or by recrystallization.

Step 45

In this step, a compound of formula (XLIV) is prepared by catalytically removing the thiocarbonyloxy group at the 2'-position from the compound of formula (XLIII), which may have been prepared as described in Step 44,. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin or petroleum ether; aromatic hydrocarbons, such as benzene, toluene or xylene; and ethers, such as diethyl ether, diisopropyl ether, tetrahydrofuran, dioxane, dimethoxyethane or diethylene glycol dimethyl ether. Of these, we prefer the aromatic hydrocarbons, such as benzene or toluene. Reagents employed include, as is well known, trialkyltin hydrides, such as tributyltin hydride.

The reaction can take place over a wide range of temperatures, and the precise reaction temperature is not critical to the invention. In general, we find it convenient to carry out the reaction at a temperature of from 50° C. to 250° C., more preferably at the boiling point of the solvent employed. The time required for the reaction may also vary widely, depending on many factors, notably the reaction temperature and the nature of the reagents and solvent employed. However, provided that the reaction is effected under the preferred conditions outlined above, a period of from 30 minutes to 10 hours, more preferably from 30 minutes to 3 hours, will usually suffice.

In order to promote the efficacy of the reaction, a radical initiator, such as azobisisobutyronitrile, may be used as a catalyst.

The desired compound thus obtained can be recovered, separated and purified by a combination of various conventional means. For example, one suitable recovery procedure comprises: pouring the reaction mixture into water; extracting the mixture with a water-immiscible solvent, such as benzene, diethyl ether or ethyl acetate; and distilling off the solvent from the extract. If necessary, the product can be further purified by absorption chromatography using various absorbents, such as active charcoal or silica gel, ion-exchange chromatography, gel filtration through a Sephadex (trade name) column or recrystallization from an organic solvent such as diethyl ether, ethyl acetate or chloroform.

Step 46

In this step, a compound of formula (XLV), which is amongst the compounds of the present invention, is prepared by treating a compound of formula (XLIV), which may have been prepared as described in Step 45, with a deprotecting reagent for a hydroxy-protecting group, preferably in the presence of an inert solvent.

Methods for deprotecting the protected moiety vary depending on the nature of the protecting group, but the deprotection reaction may be carried out using methods well known in the art. Where the protecting group is triarylmethyl or tetraalkylsiloxane group, the deprotection may be conducted in a similar manner to that described in Step 21, and examples of the reagents which may be employed then include tetrabutylammonium fluoride, potassium fluoride and tetraethylammonium bromide. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; ethers, such as tetrahydrofuran or dioxane; and mixtures of water with one or more of these organic solvents.

Preferably, the catalyst employed is an acid. There is no particular limitation upon the nature of the acid, and any compound normally used as a Bronsted acid may equally be used here. Preferred acids include: inorganic acids, such as hydrochloric acid or sulfuric acid; organic acids, such as p-toluenesulfonic acid; and strongly acidic cation ion-exchange resin such as Dowex (trade name) 50W.

The reaction can take place over a wide range of temperatures, and the precise reaction temperature is not critical to the invention. In general, we find it convenient to carry out the reaction at a temperature of from 0° C. to 50° C., more preferably at room temperature. The time required for the reaction may also vary widely, depending on many factors, notably the reaction temperature and the nature of the reagents and solvent employed. However, provided that the reaction is effected under the preferred conditions outlined above, a period of from 10 minutes to 18 hours, more preferably from 30 minutes to 5 hours, will usually suffice.

The desired compound thus obtained can be recovered, separated and purified by a combination of various conventional means. For example, one suitable recovery procedure comprises: pouring the reaction mixture into water; extracting the mixture with a water-immiscible solvent, such as benzene, diethyl ether or ethyl acetate; and distilling off the solvent from the extract. If necessary, the product can be further purified by absorption chromatography using various absorbents, such as active charcoal or silica gel, ion-exchange chromatography, gel filtration through a Sephadex (trade name) column or recrystallization from an organic solvent, such as methanol, ethanol, diethyl ether, ethyl acetate or chloroform.

Step 47

In this step, a compound of formula (XLVI) is prepared by reacting a compound of formula (III) with a tri-substituted silyl halide, preferably in the presence of an inert solvent and preferably of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin or petroleum ether; aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; ketones, such as acetone, methyl ethyl ketone, methyl isobutyl ketone, isophorone or cyclohexanone; nitro compounds, such as nitroethane or nitrobenzene; nitriles, such as acetonitrile or isobutyronitrile; amides, such as formamide, dimethylformamide, dimethylacetamide or hexamethylphosphoric triamide; and sulfoxides, such as dimethyl sulfoxide or sulfolane. Of these, we prefer the aromatic hydrocarbons or halogenated hydrocarbons.

There is likewise no particular limitation upon the nature of the base employed, and any compound used as a base in conventional reactions of this type may equally be used here. Preferred bases include: inorganic bases, such as alkali metal carbonates, for example sodium carbonate, potassium carbonate or lithium carbonate; alkali metal hydrogencarbonates, for example sodium hydrogencarbonate, potassium hydrogencarbonate or lithium hydrogencarbonate; and alkali metal hydrides, for example sodium hydride, potassium hydride, barium hydride or lithium hydride. Other preferred bases include: alkali metal alkoxides, such as sodium methoxide, sodium ethoxide, potassium t-butoxide or lithium methoxide; alkali metal salts of mercaptans, such as sodium methylmercaptan or sodium ethylmercaptan; organic bases, such as triethylamine, tributylamine, diisopropylethylamine, N-methylmorpholine, pyridine, 4-(N,N-dimethylamino) pyridine, N,N-dimethylaniline, N,N-diethylaniline, 1,5-diazabicyclo[4.3.0]non-5-ene, 1,4-diazabicyclo[2.2.2] octane or 1,8-diazabicyclo[5.4.0]undec-7-ene; and organic metal bases, such as butyllithium or lithium isopropylamide. Of these, we prefer triethylamine or pyridine.

Reagents which may be employed include, as is well known: trimethylsilyl chloride, triphenylsilyl bromide, t-butyldimethylsilyl chloride, t-butyldiphenylsilyl bromide and the like. Of these, we prefer trimethylsilyl chloride.

The reaction can take place over a wide range of temperatures, and the precise reaction temperature is not critical to the invention. In general, we find it convenient to carry out the reaction at a temperature of from −20° C. to 100° C., more preferably from −10° C. to 50° C. The time required for the reaction may also vary widely, depending on many factors, notably the reaction temperature and the nature of the reagents and solvent employed. However, provided that the reaction is effected under the preferred conditions outlined above, a period of from 1 to 100 hours, more preferably from 5 to 24 hours, will usually suffice.

After completion of the reaction, the product may be recovered from the reaction mixture by conventional means. For example, one suitable recovery procedure comprises: distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification.

However, if desired, the product may be further purified by a variety of chromatographic techniques or by recrystallization.

Step 48

In this step, a compound of formula (XLVII) can be prepared by reacting a compound of formula (XLVI), which may have been prepared as described in Step 47, with an acid halide of formula $R^1X$ (where $R^1$ and X are as defined above), preferably in the presence of an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin or petroleum ether; aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; alcohols, such as methanol, ethanol, propanol, isopropanol, butanol, isobutanol, t-butanol, isoamyl alcohol, diethylene glycol, glycerine, octanol, cyclohexanol or ethylene glycol monomethyl ether; ketones, such as acetone, methyl ethyl ketone, methyl isobutyl ketone, isophorone or cyclohexanone; nitro compounds, such as nitroethane or nitrobenzene; nitriles, such as acetonitrile or isobutyronitrile; amides, such as formamide, dimethylformamide, dimethylacetamide or hexamethylphosphoric triamide; and sulfoxides, such as dimethyl sulfoxide or sulfolane. Of these, we prefer the aromatic hydrocarbons or the halogenated hydrocarbons.

The halide moiety, X, of the acid halide of formula $R^1X$ employed may be, for example, a chlorine, bromine or iodine atom.

The reaction can take place over a wide range of temperatures, and the precise reaction temperature is not critical to the invention. In general, we find it convenient to carry out the reaction at a temperature of from −20° C. to 100° C., more preferably from −10° C. to 50° C. The time required for the reaction may also vary widely, depending on many factors, notably the reaction temperature and the nature of the reagents and solvent employed. However, provided that the reaction is effected under the preferred conditions outlined above, a period of from 1 to 100 hours, more preferably from 2 to 24 hours, will usually suffice.

After completion of the reaction, the product may be recovered from the reaction mixture by conventional means. For example, one suitable recovery procedure comprises: distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product may be further purified by a wide variety of chromatographic techniques or by recrystallization.

Step 49

In this step, a compound of formula (V) can be prepared by reacting a compound of formula (XLVII), which may have been prepared as described in Step 48, with a deprotecting agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin or petroleum ether; aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; alcohols, such as methanol, ethanol, propanol, isopropanol, butanol, isobutanol, t-butanol, isoamyl alcohol, diethylene glycol, glycerine, octanol, cyclohexanol or ethylene glycol monomethyl ether; ketones, such as acetone, methyl ethyl ketone, methyl isobutyl ketone, isophorone or cyclohexanone; nitro compounds, such as nitroethane or nitrobenzene; nitriles, such as acetonitrile or isobutyronitrile; amides, such as formamide, dimethylformamide, dimethylacetamide or hexamethylphosphoric triamide; and sulfoxides, such as dimethyl sulfoxide or sulfolane. Of these, we prefer the aromatic hydrocarbons or the halogenated hydrocarbons.

The protecting group employed is normally eliminated by stirring the compound of formula (XLVII) in the presence of water or by treating it with a compound capable of producing a fluorine anion, such as tetrabutylammonium fluoride. We prefer that the deprotection should be carried out by stirring in the presence of water.

The reaction can take place over a wide range of temperatures, and the precise reaction temperature is not critical to the invention. In general, we find it convenient to carry out the reaction at a temperature of from −10° C. to 100° C., more preferably from −5° C. to 50° C. The time required for the reaction may also vary widely, depending on many factors, notably the reaction temperature and the nature of the reagents and solvent employed. However, provided that the reaction is effected under the preferred conditions outlined above, a period of from from 1 to 100 hours, more preferably from 2 to 20 hours, will usually suffice.

After completion of the reaction, the product may be recovered from the reaction mixture by conventional means. For example, one suitable recovery procedure comprises: distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product may be further purified by a wide variety of chromatographic techniques or by recrystallization.

Step 50

In this step, a compound of formula (XLVIII) is prepared by simultaneously protecting the hydroxy groups at the 3'- and 5'-positions of a compound of formula (III) with a compound of formula:

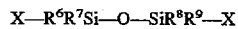

$$X-R^6R^7Si-O-SiR^8R^9-X$$

in which $R^6$, $R^7$, $R^8$, $R^9$ and X are as defined above. The reaction is essentially the same as that of, and may be carried out in the same manner as described in, Step 41.

Step 51

In this step, a compound of formula (XLIX) is prepared by reacting a compound of formula (XLVIII), which may have been prepared as described in Step 50, with a carboxylic acid compound of formula $R^1OH$ (where $R^1$ is as defined above) or with a reactive derivative thereof, such as an acid halide of formula $R^1X$ (where $R^1$ and X are as defined above), an acid anhydride of formula $R^1OR^1$ (where $R^1$ is as defined above) or a mixed acid anhydride, for example, a compound of formula $R^1OCOOMe$ (where $R^1$ and Me are as defined above) or $R^1OCOOEt$ (where $R^1$ and Et are as defined above), preferably in the presence of an inert solvent. The reaction is essentially the same as that of, and may be carried out in the same manner as described in, Step 1.

Step 52

In this step, a compound of formula (V), which is amongst the compounds of the invention, can be prepared by reacting a compound of formula (XLIX), which may have been prepared as described in Step 51, with a deprotecting agent for a hydroxy-protecting group, preferably in the presence of an inert solvent. The reaction is essentially the same as that of, and may be carried out in the same manner as described in, Step 46.

Step 53

In this step, a compound of formula (L) is prepared by reacting a compound of formula (III) with a reagent capable of selectively protecting an amino group at the 4-position and a hydroxy group at the 5'-position, preferably in the presence of an inert solvent, and in the presence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin or petroleum ether; aromatic hydrocarbons, such as benzene, toluene or xylene; halogenated hydrocarbons, such as methylene chloride, chloroform, carbon tetrachloride, dichlorethane, chlorobenzene or dichlorobenzene; esters, such as ethyl formate, ethyl acetate, propyl acetate, butyl acetate or diethyl carbonate; ethers, such as diethyl ether, diisopropyl ether, tetrahydrofuran, dioxane, dimethyoxyethane or diethylene glycol dimethyl ether; ketones, such as acetone, methyl ethyl ketone, methyl isobutyl ketone, isophorone or cyclohexanone; nitro compounds, such as nitroethane or nitrobenzene; nitriles, such as acetonitrile or isobutyronitrile; amides, such as formamide, dimethylformamide, dimethylacetamide or hexamethylphosphoric triamide; and sulfoxides, such as dimethyl sulfoxide or sulfolane. Of these, we prefer the aromatic hydrocarbons or the halogenated hydrocarbons.

Suitable protecting agents which may be employed in this reaction include: triphenylmethyl chloride, 4-methoxytriphenylmethyl chloride and 4,4'-dimethoxytriphenylmethyl chloride. Of these, we prefer 4,4'-dimethoxytriphenylmethyl chloride.

There is likewise no particular limitation upon the nature of the base employed, and any compound used as a base in conventional reactions of this type may equally be used here. Preferred bases include: inorganic bases, such as alkali metal carbonates, for example sodium carbonate, potassium carbonate or lithium carbonate; alkali metal hydrogencarbonates, for example sodium hydrogencarbonate, potassium hydrogencarbonate or lithium hydrogencarbonate; and alkali metal hydrides, for example sodium hydride, potassium hydride, barium hydride or lithium hydride. Other preferred bases include: alkali metal alkoxides, such as sodium methoxide, sodium ethoxide, potassium t-butoxide or lithium methoxide; alkali metal salts of mercaptans, such as sodium methylmercaptan or sodium ethylmercaptan; organic bases, such as triethylamine, tributylamine, diisopropylethylamine, N-methylmorpholine, pyridine, 4-(N,N-dimethylamino) pyridine, N,N-dimethylaniline, N,N-diethylaniline, 1,5-diazabicyclo[4.3.0]non-5-ene, 1,4-diazabicyclo[2.2.2] octane or 1,8-diazabicyclo[5.4.0]undec-7-ene; and organic metal bases, such as butyllithium or lithium isopropylamide. Of these, we prefer triethylamine or pyridine.

The reaction can take place over a wide range of temperatures, and the precise reaction temperature is not critical to the invention. In general, we find it convenient to carry out the reaction at a temperature of from 10° C. to 100° C., more preferably from 20° C. to 80° C. The time required for the reaction may also vary widely, depending on many factors, notably the reaction temperature and the nature of the reagents and solvent employed. However, provided that the reaction is effected under the preferred conditions outlined above, a period of from 1 to 100 hours, more preferably from 1 to 20 hours, will usually suffice.

After completion of the reaction, the product may be recovered from the reaction mixture by conventional means. For example, one suitable recovery procedure comprises: distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product may be further purified by a wide variety of chromatographic techniques or by recrystallization.

Step 54

In this step, a compound of formula (LI) is prepared by reacting a compound of formula (L), which may have been prepared as described in Step 53, with a carboxylic acid compound of formula $R^2OH$ (where $R^2$ is as defined above) or with a reactive derivative thereof, such as an acid halide of formula $R^2X$ (where $R^2$ and X are as defined above), an acid anhydride of formula $R^2OR^2$ (where $R^2$ is as defined above) or a mixed acid anhydride, for example, a compound of formula $R^2OCOOMe$ (where $R^2$ and Me are as defined above) or $R^2OCOOEt$ (where $R^2$ and Et are as defined above), preferably in the presence of an inert solvent. The reaction is essentially the same as that of, and may be carried out in the same manner as described in, Step 1.

Step 55

In this step, a compound of formula (LI), which may have been prepared as described in Step 54, is treated with a deprotecting agent, normally and preferably in the presence of an inert solvent in order to deprotect the hydroxy-protecting group at the 5'-position, and thus to afford a compound of formula (LII). The reaction is essentially the same as that of, and may be carried out in the same manner as described in, Step 17.

Step 56

In this step, a compound of formula (XLVI) is reacted with an amino-protecting agent, preferably in the presence of an inert solvent, to interconvert the amino-protecting group at the 4-position, and thus to afford a compound of formula (LIII).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin or petroleum ether; aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; ketones, such as acetone, methyl ethyl ketone, methyl isobutyl ketone, isophorone or cyclohexanone; nitro compounds, such as nitroethane or nitrobenzene; nitriles, such as acetonitrile or isobutyronitrile; amides, such as formamide, dimethylformamide, dimethylacetamide or hexamethylphosphoric triamide; and sulfoxides, such as dimethyl sulfoxide or sulfolane. Of these, we prefer the aromatic hydrocarbons or the halogenated hydrocarbons.

Suitable protecting agents which may be employed in this reaction include: trichloroethoxycarbonyl chloride or tribromoethoxycarbonyl chloride. Of these, we prefer trichloroethoxycarbonyl chloride.

The reaction can take place over a wide range of temperatures, and the precise reaction temperature is not critical to the invention. In general, we find it convenient to carry out the reaction at a temperature of from −10° C. to 100° C., more preferably from 5° C. to 50° C. The time required for the reaction may also vary widely, depending on many factors, notably the reaction temperature and the nature of the reagents and solvent employed. However, provided that the reaction is effected under the preferred conditions outlined above, a period of from 1 to 100 hours, more preferably from 2 to 24 hours, will usually suffice.

After completion of the reaction, the product may be recovered from the reaction mixture by conventional means. For example, one suitable recovery procedure comprises: distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product may be further purified by a wide variety of chromatographic techniques or by recrystallization.

Step 57

In this step, a compound of formula (VII) can be prepared by reacting a compound of formula (LIII), which may have been prepared as described in Step 56, with a deprotecting agent, preferably in the presence of an inert solvent. The reaction is essentially the same as that of, and may be carried out in the same manner as described in, Step 49.

Step 58

In this step, a compound of formula (LV) can be prepared by reacting a compound of formula (LIV) with a sulfonyl halide, preferably in the presence of an inert solvent, and preferably in the presence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin or petroleum ether; aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; ketones, such as acetone, methyl ethyl ketone, methyl isobutyl ketone, isophorone or cyclohexanone; nitro compounds, such as nitroethane or nitrobenzene; nitriles such as acetonitrile or isobutyronitrile; amides, such as formamide, dimethylformamide, dimethylacetamide or hexamethylphosphoric triamide; and sulfoxides, such as dimethyl sulfoxide or sulfolane. Of these, we prefer the aromatic hydrocarbons or the halogenated hydrocarbons.

Examples of sulfonyl halides which may be employed in this reaction include: trifluoromethanesulfonyl chloride, trifluoromethanesulfonyl bromide and p-toluenesulfonyl chloride. Of these, we prefer trifluoromethanesulfonyl chloride.

There is likewise no particular limitation upon the nature of the base employed, and any compound used as a base in conventional reactions of this type may equally be used here. Preferred bases include: inorganic bases, such as alkali metal carbonates, for example sodium carbonate, potassium carbonate or lithium carbonate; alkali metal hydrogencarbonates, for example sodium hydrogencarbonate, potassium hydrogencarbonate or lithium hydrogencarbonate; and alkali metal hydrides, for example sodium hydride, potassium hydride, barium hydride or lithium hydride. Other preferred bases include: alkali metal alkoxides, such as sodium methoxide, sodium ethoxide, potassium t-butoxide or lithium methoxide; alkali metal salts of mercaptans, such as sodium methylmercaptan or sodium ethylmercaptan; organic bases, such as triethylamine, tributylamine, diisopropylethylamine, N-methylmorpholine, pyridine, 4-(N,N-dimethylamino) pyridine, N,N-dimethylaniline, N,N-diethylaniline, 1,5-diazabicyclo[4.3.0]non-5-ene, 1,4-diazabicyclo[2.2.2] octane or 1,8-diazabicyclo[5.4.0]undec-7-ene; and organic metal bases, such as butyllithium or lithium isopropylamide. Of these, we prefer triethylamine or pyridine.

The reaction can take place over a wide range of temperatures, and the precise reaction temperature is not critical to the invention. In general, we find it convenient to carry out the reaction at a temperature of from −20° C. to 100° C., more preferably from −10° C. to 50° C. The time required for the reaction may also vary widely, depending on many factors, notably the reaction temperature and the nature of the reagents and solvent employed. However, provided that the reaction is effected under the preferred conditions outlined above, a period of from 1 to 50 hours, more preferably from 5 to 24 hours, will usually suffice.

After completion of the reaction, the product may be recovered by conventional means. For example, one suitable recovery procedure comprises: distilling off the solvent; pouring the residual reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material in the next step without any further purification. However, if desired, the product may be further purified by a wide variety of chromatographic techniques or by recrystallization.

Step 59

In this step, a compound of formula (XLIV) is prepared by reacting a compound of formula (LV), which may have been prepared as described in Step 58, with a cyanating agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin or petroleum ether; aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; alcohols, such as methanol, ethanol, propanol, isopropanol, butanol, isobutanol, t-butanol, isoamyl alcohol, diethylene glycol, glycerine, octanol, cyclohexanol or ethylene glycol monomethyl ether; ketones, such as acetone, methyl ethyl ketone, methyl isobutyl ketone, isophorone or cyclohexanone; nitro compounds, such as nitroethane or nitrobenzene; nitriles, such as acetonitrile or isobutyronitrile; amides, such as formamide, dimethylformamide, dimethylacetamide or hexamethylphosphoric triamide; and sulfoxides, such as dimethyl sulfoxide or sulfolane. Of these, we prefer the amides.

Examples of cyanating agents which may be employed in this reaction include: sodium cyanide, potassium cyanide, triethylamine cyanide, and preferably potassium cyanide.

The reaction can take place over a wide range of temperatures, and the precise reaction temperature is not critical to the invention. In general, we find it convenient to carry out the reaction at a temperature of from 5° C. to 100° C., more preferably from 10° C. to 50° C. The time required for the reaction may also vary widely, depending on many factors, notably the reaction temperature and the nature of the reagents and solvent employed. However, provided that the reaction is effected under the preferred conditions outlined above, a period of from 1 to 100 hours, more preferably from 5 to 24 hours, will usually suffice.

After completion of the reaction, the product may be recovered from the reaction mixture by conventional means. For example, one suitable recovery procedure comprises: distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product may be further purified by a wide variety of chromatographic techniques or by recrystallization.

Step 60

In this step, a compound of formula (LVI) is prepared by reacting a compound of formula (LIV) with a halogenating agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin or petroleum ether; aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; ketones, such as acetone, methyl ethyl ketone, methyl isobutyl ketone, isophorone or cyclohexanone; nitro compounds, such as nitroethane or nitrobenzene; nitriles, such as acetonitrile or isobutyronitrile; amides, such as formamide, dimethylformamide, dimethylacetamide or hexamethylphosphoric triamide; and sulfoxides, such as dimethyl sulfoxide or sulfolane.

Examples of halogenating agents which may be employed in this reaction include: phosphorus oxyhalides, such as phosphorus oxychloride or phosphorus oxybromide; thionyl halides, such as thionyl bromide, thionyl chloride or thionyl iodide. Of these, we prefer the thionyl iodide.

The reaction can take place over a wide range of temperatures, and the precise reaction temperature is not critical to the invention. In general, we find it convenient to carry out the reaction at a temperature of from −20° C. to 100° C., more preferably from 10° C. to 50° C. The time required for the reaction may also vary widely, depending on many factors, notably the reaction temperature and the nature of the reagents and solvent employed. However, provided that the reaction is effected under the preferred conditions outlined above, a period of from 1 to 50 hours, more preferably from 5 to 24 hours, will usually suffice.

After completion of the reaction, the product may be recovered from the reaction mixture by conventional means. For example, one suitable recovery procedure comprises: distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product may be further purified by a variety of chromatographic techniques or by recrystallization.

Step 61

In this step, a compound of formula (XLIV) is prepared by reacting a compound of formula (LVI), which may have been prepared as described in Step 60, with a cyanating agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin or petroleum ether; aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; alcohols, such as methanol, ethanol, propanol, isopropanol, butanol, isobutanol, t-butanol, isoamyl alcohol, diethylene glycol, glycerine, octanol, cyclohexanol or ethylene glycol monomethyl ether;

ketones, such as acetone, methyl ethyl ketone, methyl isobutyl ketone, isophorone or cyclohexanone; nitro compounds, such as nitroethane or nitrobenzene; nitriles, such as acetonitrile or isobutyronitrile; amides, especially fatty acid amides, such as formamide, dimethylformamide, or dimethylacetamide and hexaalkylphosphoric triamides, such as hexamethylphosphoric triamide; and sulfoxides, such as dimethyl sulfoxide or sulfolane. Of these, we prefer the fatty acid amides or the hexaalkylphosphoric triamides.

Examples of the cyanating agents which may be employed in this reaction include: sodium cyanide, potassium cyanide or triethylamine cyanide. Of these, we prefer potassium cyanide.

The reaction can take place over a wide range of temperatures, and the precise reaction temperature is not critical to the invention. In general, we find it convenient to carry out the reaction at a temperature of from −10° C. to 200° C., more preferably from 10° C. to 100° C. The time required for the reaction may also vary widely, depending on many factors, notably the reaction temperature and the nature of the reagents and solvent employed. However, provided that the reaction is effected under the preferred conditions outlined above, a period of from 1 to 100 hours, more preferably from 5 to 24 hours, will usually suffice.

After completion of the reaction, the product may be recovered from the reaction mixture by conventional means. For example, one suitable recovery procedure comprises: distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product may be further purified by a variety of chromatographic techniques or by recrystallization.

Step 62

In this step, a desired compound of formula (XXIX), which is amongst the compounds of the present invention, is prepared by treating a compound of formula (XLIV), which may have been prepared as described in Step 61, with a deprotecting agent for a hydroxy-protecting group, preferably in the presence of an inert solvent. The reaction is essentially the same as that of, and may be carried out in the same manner as described in, Step 46.

Step 63

In this step, a compound of formula (LVIII) is prepared by reacting a compound of formula (LVII) with a reactive derivative of a carboxylic acid, such as an acid halide of formula $R^1X$ (where $R^1$ and X are as defined above), an acid anhydride of formula $R^1OR^1$ (where $R^1$ is as defined above) or a mixed acid anhydride, for example, a compound of formula $R^1OCOOMe$ (where $R^1$ and Me are as defined above) or $R^1OCOOEt$ (where $R^1$ and Et are as defined above), preferably in an inert solvent in the absence of a base. The reaction is essentially the same as that of, and may be carried out in the same manner as described in, Step 2.

Step 64

In this step, a compound of formula (IIIa) is reacted with a hydroxy-protecting agent to protect the hydroxy group at the 5'-position alone, and thus to afford a compound of formula (VIIIa). The reaction is essentially the same as that of, and may be carried out in the same manner as described in, Step 5.

Step 65

In this step, a compound of formula (XIIa) is prepared by reacting a compound of formula (VIIIa), which may have been prepared as described in Step 64, with a carboxylic acid compound of formula $R^1OH$ (where $R^1$ is as defined above) or with a reactive derivative thereof, such as an acid halide of formula $R^1X$ (where $R^1$ and X are as defined above), an acid anhydride of formula $R^1OR^1$ (where $R^1$ is as defined above) or a mixed acid anhydride, for example, a compound of formula $R^1OCOOMe$ (where $R^1$ and Me are as defined above) or $R^1OCOOEt$ (where $R^1$ and Et are as defined above), preferably in the presence of an inert solvent. The reaction is essentially the same as that of, and may be carried out in the same manner as described in, Step 1.

Step 66

In this step, a compound of formula (LIX) is prepared by removing an acyloxy group from the compound of formula (XIIa), which may have been prepared as described in Step 65, in the presence or absence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; ethers, such as diethyl ether, diisopropyl ether, tetrahydrofuran, dioxane, dimethoxyethane, diethylene glycol dimethyl ether; ketones, such as acetone, methyl ethyl ketone, methyl isobutyl ketone, isophorone or cyclohexanone; nitro compounds, such as nitroethane or nitrobenzene; nitriles, such as acetonitrile or isobutyronitrile; amide such as formamide, dimethylformamide, dimethylacetamide or hexamethylphosphoric triamide; and sulfoxides, such as dimethyl sulfoxide or sulfolane. Of these, we prefer the alcohols.

There is no particular limitation upon the nature of the base employed, and any base commonly used in conventional reactions of this type may equally be used here. Suitable bases include, for example, organic bases, such as triethylamine, diethylamine or monomethylamine. Of these, triethylamine is preferred.

The reaction can take place over a wide range of temperatures, and the precise reaction temperature is not critical to the invention. In general, we find it convenient to carry out the reaction at a temperature of from −10° C. to 100° C., more preferably from 0° C. to 50° C. The time required for the reaction my also vary widely, depending on many factors, notably the reaction temperature and the nature of the reagents and solvent employed. However, provided that the reaction is effected under the preferred conditions outlined above, a period of from 1 to 100 hours, more preferably from 1 to 24 hours, will usually suffice.

After completion of the reaction, the product may be recovered from the reaction mixture by conventional means. For example, one suitable recovery procedure comprises: distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for a subsequent reaction without any further purification. However, if desired, the product may be further purified by a wide variety of chromatographic techniques or by recrystallization.

Step 67

In this step, a compound of formula (LIX) is treated with a deprotecting agent for a hydroxy-protecting group, preferably in the presence of an inert solvent, to afford the compound of formula (LVIII), which is amongst the compounds of the present invention. The reaction is essentially the same as that of, and may be carried out in the same manner as described in, Step 10.

Step 68

In this step, a compound of formula (LVII) is reacted with a carboxylic acid compound of formula $R^1OH$ (where $R^1$ is as defined above) or with a reactive derivative thereof, such as an acid halide of formula $R^1X$ (where $R^1$ and X are as defined above), an acid anhydride of formula $R^1OR^1$ (where $R^1$ is as defined above) or a mixed acid anhydride, for example, a compound of formula $R^1OCOOMe$ (where $R^1$ and Me are as defined above) or $R^1OCOOEt$ (where $R^1$ and Et are as defined above), preferably in the presence of an inert solvent to afford the compound of formula (LX). The reaction is essentially the same as that of, and may be carried out in the same manner as described in, Step 1.

Step 69

In this step, a compound of formula (IIIa) is reacted with a carboxylic acid compound of formula $R^1OH$ (where $R^1$ is as defined above) or with a reactive derivative thereof, such as an acid halide of formula $R^1X$ (where $R^1$ and X are as defined above), an acid anhydride of formula $R^1OR^1$ (where $R^1$ is as defined above) or a mixed acid anhydride, for example, a compound of formula $R^1OCOOMe$ (where $R^1$ and Me are as defined above) or $R^1OCOOEt$ (where $R^1$ and Et are as defined above), preferably in the presence of an inert solvent to afford the compound of formula (IVa). The reaction is essentially the same as that of, and may be carried out in the same manner as described in, Step 1.

Step 70

In this step, a compound of formula (LX), which is amongst the compounds of the invention, is prepared by removing the acyloxy group from the compound of formula (IVa), which may have been prepared as described in Step 69, preferably in an inert solvent and in the presence or absence of a base. The reaction is essentially the same as that of, and may be carried out in the same manner as described in, Step 65.

Step 71

In this step, a compound of formula (LVII) is reacted with an amino-protecting agent, preferably in the presence of an inert solvent, to afford a compound of formula (LXI). The reaction is essentially the same as that of, and may be carried out in the same manner as described in, Step 4.

Step 72

In this step, a compound of formula (LXI) is reacted with a carboxylic acid compound of formula $R^1OH$ (where $R^1$ is as defined above) or with a reactive derivative thereof, such as an acid halide of formula $R^1X$ (where $R^1$ and X are as defined above), an acid anhydride of formula $R^1OR^1$ (where $R^1$ is as defined above) or a mixed acid anhydride, for example, a compound of formula $R^1OCOOMe$ (where $R^1$ and Me are as defined above) or $R^1OCOOEt$ (where $R^1$ and Et are as defined above), preferably in the presence of an inert solvent to afford a compound of formula (LXII). The reaction is essentially the same as that of, and may be carried out in the same manner as described in, Step 1.

Step 73

In this step, a compound of formula (LXIII), which is amongst the compounds of the invention, is prepared by reacting a compound of formula (LXII), which may have been prepared as described in Step 72, with a deprotecting agent for an amino-protecting group, preferably in the presence of an inert solvent. The reaction is essentially the same as that of, and may be carried out in the same manner as described in, Step 13.

Step 74

In this step, a compound of formula (LXII) is prepared by reacting a compound of formula (IIIa) with an amino-protecting agent, preferably in the presence of an inert solvent. The reaction is essentially the same as that of, and may be carried out in the same manner as described in, Step 4.

Step 75

In this step, a compound of formula (VIIa), which may have been prepared as described in Step 74, is reacted with a carboxylic acid compound of formula $R^1OH$ (where $R^1$ is as defined above) or with a reactive derivative thereof, such as an acid halide of formula $R^1X$ (where $R^1$ and X are as defined above), an acid anhydride of formula $R^1OR^1$ (where $R^1$ is as defined above) or a mixed acid anhydride, for example, a compound of formula $R^1OCOOMe$ (where $R^1$ and Me are as defined above) or $R^1OCOOEt$ (where $R^1$ and Et are as defined above), preferably in the presence of an inert solvent, to afford a compound of formula (LXIV). The reaction is essentially the same as that of, and may be carried out in the same manner as described in, Step 1.

Step 76

In this step, a compound of formula (LXII), which is amongst the compounds of the invention, is prepared by removing the acetoxy group from the compound of formula (LXIV), which may have been prepared as described in Step 75, preferably in an inert solvent and in the presence or absence of a base. The reaction is essentially the same as that of, and may be carried out in the same manner as described in, Step 66.

Step 77

In this step, a compound of formula (LXIII), which is amongst the compounds of the invention, is prepared by reacting a compound of formula (LXII), which may have been prepared as described in Step 76, with a deprotecting agent for an amino-protecting group in the presence of an inert solvent. The reaction is essentially the same as that of, and may be carried out in the same manner as described in, Step 13.

Where the compound prepared by any of Steps 1, 3, 6, 11, 14, 18, 22, 27, 29, 34, 39, 46, 52, 55, 62, 63, 67, 68, 70, 73 and 77 contains a protecting group for a hydroxy, amino, mercapto or carboxy group, each of the steps may also include a protecting step, and may be followed by a deprotecting step.

The method of eliminating a protecting group will vary, depending on the nature of the group, as is well-known in the art. However, by way of example, certain protecting groups may be removed as follows.

Where the hydroxy-protecting group is a silyl group, the protecting group may normally be eliminated by treating the protected compound with a compound capable of producing an fluoride anion, such as tetrabutylammonium fluoride. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include ethers, such as tetrahydrofuran or dioxane.

The reaction can take place over a wide range of temperatures, and the precise reaction temperature is not critical to the invention. In general, we find it convenient to carry out the reaction at a temperature of about room temperature. The time required for the reaction may also vary widely, depending on many factors, notably the reaction temperature and the nature of the reagents and solvent employed. However, provided that the reaction is effected under the preferred conditions outlined above, a period of from 10 minutes to 18 hours will usually suffice.

Where the hydroxy-protecting group is an aralkyl or aralkyloxycarbonyl group, in general, it is preferably eliminated by contacting the protected compound with a reducing agent (preferably by catalytic reduction at room temperature in the presence of a catalyst and of hydrogen gas) or by using an oxidizing agent in the presence of an inert solvent.

In the deprotection reaction by means of catalytic reduction, the reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol, ethanol or isopropanol; ethers, such as diethyl ether, tetrahydrofuran or dioxane; aromatic hydrocarbons, such as toluene, benzene or xylene; aliphatic hydrocarbons, such as hexane or cyclohexane; esters, such as ethyl acetate or propyl acetate; fatty acids, such as acetic acid; and mixtures of water with one or more of these organic solvents.

There is likewise no particular limitation upon the nature of the catalyst employed, and any catalyst commonly used in conventional catalytic reduction reactions may equally be employed here. Preferred catalysts include: palladium on charcoal, Raney nickel, platinum oxide, platinum black, rhodium on a alumina, or a combination of triphenylphosphine and rhodium chloride and palladium on barium sulfate.

The pressure within the reaction vessel is not critical to the reaction, but the reaction is normally and preferably carried out under from 1 to 10 atmospheres pressure.

The reaction can take place over a wide range of temperatures, and the precise reaction temperature is not critical to the invention. In general, we find it convenient to carry out the reaction at a temperature of from 0° C. to 100° C. The time required for the reaction may also vary widely, depending on many factors, notably the reaction temperature and the nature of the reagents and solvent employed. However, provided that the reaction is effected under the preferred conditions outlined above, a period of from 5 minutes to 24 hours will usually suffice.

When oxidation is employed for the deprotection reaction, the reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aqueous organic solvents. Examples of preferred organic solvents include: ketones, such as acetone; halogenated hydrocarbons, such as methylene chloride, chloroform or carbon tetrachloride; nitriles, such as acetonitrile; ethers, such as diethyl ether, tetrahydrofuran or dioxane; amides, such as dimethylformamide, dimethylacetamide or hexamethylphosphoric triamide; and sulfoxides, such as dimethyl sulfoxide.

There is likewise no particular limitation upon the nature of the oxidizing agent employed, and any oxidizing agent commonly employed in oxidation reactions of this type may equally be employed here. Preferred oxidizing agents include: potassium persulfate, sodium persulfate, cerium ammonium nitrate and 2,3-dichloro-5,6-dicyano-p-benzoquinone.

The reaction can take place over a wide range of temperatures, and the precise reaction temperature is not critical to the invention. In general, although the precise temperature employed will depend on several reaction criteria, notably the nature of the catalyst, we find it convenient to carry out the reaction at a temperature of from 0° C. to 150° C. The time required for the reaction may also vary widely, depending on many factors, notably the reaction temperature and the nature of the reagents, catalyst and solvent employed. However, provided that the reaction is effected under the preferred conditions outlined above, a period of from 10 minutes to 24 hours will usually suffice.

Alternatively, where the hydroxy-protecting group is an aralkyl or aralkyloxycarbonyl group, protecting groups can be eliminated by treating the protected compound with an alkali metal, such as lithium metal or sodium metal, in liquid ammonia or in an alcohol, such as methanol or ethanol, at a suitable temperature, for example a temperature of from −78° C. to −20° C.

Another method of eliminating protecting groups, where the hydroxy-protecting group is an aralkyl or aralkyloxycarbonyl group, is by using a combination of aluminum chloride and sodium iodide, or by using an alkylsilyl halide, such as trimethylsilyl iodide, in the presence of a solvent.

There is no particular restriction on the nature of the solvent to be employed, provided that it has no adverse effect on the reaction or on the reagents involved and that it can dissolve the reagents, at least to some extent. Examples of suitable solvents include: nitriles, such as acetonitrile; halogenated hydrocarbons, especially halogenated aliphatic hydrocarbons, such as methylene chloride or chloroform; and mixtures of any two or more of these solvents.

The reaction can take place over a wide range of temperatures, and the precise reaction temperature is not critical to the invention. In general, we find it convenient to carry out the reaction at a temperature of from 0° C. to 50° C. The time required for the reaction may also vary widely, depending on many factors, notably the reaction temperature and the nature of the reagents and solvent employed. However, provided that the reaction is effected under the preferred conditions outlined above, a period of from 5 minutes to 3 days will usually suffice.

Where the substrate includes a group containing a sulfur atom, preferred reagents are a combination of aluminum chloride and sodium iodide.

Where the hydroxy-protecting group is an alkoxymethyl, tetrahydroxpyranyl, tetrahydrothiopyranyl, tetrahydrofuranyl, tetrahydrothiofuranyl or substituted ethyl group, it is normally and preferably eliminated by treating the protected compound with an acid.

There is no particular limitation upon the nature of the acid employed, and any a Bronsted acid commonly used in reactions of this type may equally be used here. Preferred acids include: inorganic acids, such as hydrochloric acid or sulfuric acid; organic acids, such as acetic acid or p-toluenesulfonic acid; and strongly acidic cationic ion-exchange resins, such as Dowex (trade mark) 50W.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; ethers, such as tetrahydrofuran or dioxane; and mixtures of water and one or more of these organic solvents.

The reaction can take place over a wide range of temperatures, and the precise reaction temperature is not critical to the invention. In general, we find it convenient to carry out the reaction at a temperature of from 0° C. to 50° C. The time required for the reaction may also vary widely, depending on many factors, notably the reaction temperature and the nature of the reagents, acid and solvent employed. However, provided that the reaction is effected under the preferred conditions outlined above, a period of from 10 minutes to 18 hours will usually suffice.

Where the protecting group is an allyoxycarbonyl group, deprotection may be carried out simply, using a combination of palladium and triphenylphosphine or nickel tetracarbonyl, and this reaction has the advantage that side reactions can be reduced.

Where the mercapto-protecting group is a silyl group, it is normally and preferably eliminated by treating the protected compound with a compound capable of producing fluoride anions, such as tetrabutylammonium fluoride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include ethers, such as tetrahydrofuran or dioxane.

The reaction can take place over a wide range of temperatures, and the precise reaction temperature is not critical to the invention. In general, we find it convenient to carry out the reaction at a temperature of about room temperature. The time required for the reaction may also vary widely, depending on many factors, notably the reaction temperature and the nature of the reagents and solvent employed. However, provided that the reaction is effected under the preferred conditions outlined above, a period of from 10 to 18 hours will usually suffice.

Where the mercapto-protecting group is an aralkyl or aralkyloxycarbonyl group, it is preferably eliminated by contacting the protected compound with a reducing agent (preferably by catalytic reduction in the presence of a catalyst and of hydrogen) or by using an oxidizing agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol, ethanol or isopropanol; ethers, such as diethyl ether, tetrahydrofuran or dioxane; aromatic hydrocarbons, such as benzene, toluene or xylene; aliphatic hydrocarbons, such as hexane or cyclohexane; esters, such as ethyl acetate or propyl acetate; fatty acids, such as acetic acid; and mixtures of water with any one or more of these organic solvents.

In the case of catalytic reduction, there is no particular limitation upon the nature of the catalyst employed, and any catalyst commonly used for the catalytic reduction of compounds of this type may equally be used here. Preferred catalysts include: palladium on charcoal, Raney nickel, platinum oxide, platinum black, rhodium on alumina, a combination of triphenylphosphine and rhodium chloride or palladium on barium sulfate.

The pressure within the reaction vessel is not critical to the process, but the reaction is normally and preferably carried out under from 1 to 10 atmospheres pressure.

The reaction can take place over a wide range of temperatures, and the precise reaction temperature is not critical to the invention, although, as is well known in the art, the precise preferred temperature will vary depending upon many factors, notably the nature of the catalyst, as well as the nature of the reagents and the solvent. In general, we find it convenient to carry out the reaction at a temperature of from 0° C. to 100° C. The time required for the reaction may also vary widely, depending on many factors, notably the reaction temperature and the nature of the reagents and solvent employed. However, provided that the reaction is effected under the preferred conditions outlined above, a period of from 5 minutes to 24 hours will usually suffice.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Aqueous organic solvents are preferred. Examples of suitable organic solvents which may form part of such a solvent system include: ketones, such as acetone; halogenated hydrocarbons, such as methylene chloride, chloroform or carbon tetrachloride; nitriles, such as acetonitrile; ethers, such as diethyl ether, tetrahydrofuran or dioxane; amides, such as dimethylformamide, dimethylacetamide or hexamethylphosphoric triamide; and sulfoxides, such as dimethyl sulfoxide.

There is likewise no particular limitation upon the oxidizing agent employed, and any oxidizing agent commonly employed for the oxidation of compounds of this type may equally be used here. Preferred oxidizing agents include: potassium persulfate, sodium persulfate, cerium ammonium nitrate and 2,3-dichloro-5,6-dicyano-p-benzoquinone.

The reaction can take place over a wide range of temperatures, and the precise reaction temperature is not critical to the invention, although, as is well known in the art, the precise preferred temperature will vary depending upon many factors, notably the nature of the oxidizing agent, as well as the nature of the reagents and the solvent. In general, we find it convenient to carry out the reaction at a temperature of from 0° C. to 150° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours will usually suffice.

Where the mercapto-protecting group is an aralkyl or aralkyloxycarbonyl group, it can also be eliminated by reacting the protected compound with an alkali metal, such as lithium metal or sodium metal, in liquid ammonia or in an alcohol, such as methanol or ethanol, at a suitable temperature, for example a temperature of from −78° C. to −20° C.

The mercapto-protecting group, where it is an aralkyl or aralkyloxycarbonyl group, can also be eliminated by reacting the protected compound with a combination of aluminum chloride and sodium iodide, or with an alkylsilyl halide, such as trimethylsilyl iodide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: nitriles, such as acetonitrile; halogenated hydrocarbons, such as methylene chloride or chloroform; and mixtures of any two or more of these organic solvents.

The reaction can take place over a wide range of temperatures, and the precise reaction temperature is not critical to the invention. In general, we find it convenient to carry out the reaction at a temperature of from 0° C. to 50° C. The time required for the reaction may also vary widely, depending on many factors, notably the reaction temperature and the nature of the reagents and solvent employed. However, provided that the reaction is effected under the preferred conditions outlined above, a period of from 5 minutes to 3 days will usually suffice.

In particular, a preferred deprotecting agent is a combination of aluminum chloride and sodium iodide.

Where the mercapto-protecting group is an alkoxymethyl, tetrahydropyranyl, tetrahydrothiopyranyl, tetrahydrofuranyl, tetrahydrothiofuranyl or substituted ethyl group, it is normally and preferably eliminated by treating the protected compound with an acid, preferably in the presence of a solvent.

There is no particular limitation upon the nature of the acid employed, and any Bronsted acid commonly used in reactions of this type may equally be employed here. Preferred acids include: inorganic acids, such as hydrochloric acid or sulfuric acid; organic acids, such as acetic acid or p-toluenesulfonic acid; and strongly acidic cationic ion-exchange resins, such as Dowex (trade name) 50W.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol, ethers, such as tetrahydrofuran or dioxane; and mixtures of water with any one or more of these organic solvents.

The reaction can take place over a wide range of temperatures, and the precise reaction temperature is not critical to the invention, although, as is well known in the art, the precise preferred temperature will vary depending upon many factors, notably the nature of the acid used, as well as the nature of the reagents and the solvent. In general, we find it convenient to carry out the reaction at a temperature of from 0° C. to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 18 hours will usually suffice.

Where the mercapto-protecting group is an alkenyloxycarbonyl group, deprotection is normally and preferably carried out by treating the protected compound with a base under the same reaction conditions as those used where the hydroxy-protecting group is the aforementioned aliphatic acyl, aromatic acyl or alkoxycarbonyl group.

Where the mercapto-protecting group is an allyloxycarbonyl group, deprotection may be carried out simply by using a combination of palladium and triphenylphosphine or nickel tetracarbonyl, which has the advantage that side reactions can be reduced.

Where the amino-protecting group is a silyl group, it is normally and preferably eliminated by treating the protected compound with a compound capable of producing an fluoride anion, such as tetrabutylammonium fluoride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include ethers, such as tetrahydrofuran or dioxane.

The reaction can take place over a wide range of temperatures, and the precise reaction temperature is not critical to the invention. In general, we find it convenient to carry out the reaction at a temperature of about room temperature. The time required for the reaction may also vary widely, depending on many factors, notably the reaction temperature and the nature of the reagents and solvent employed. However, provided that the reaction is effected under the preferred conditions outlined above, a period of from 10 to 18 hours will usually suffice.

Where the amino-protecting group is an aralkyl or aralkyloxycarbonyl group, it is preferably eliminated by contacting the protected compound with a reducing agent (preferably by catalytic reduction in the presence of a catalyst) or by using an oxidizing agent in the presence of a solvent.

There is no particular limitation on the nature of the solvent employed in the catalytic reduction, provided that it has no adverse effect on the reaction. Examples of preferred solvents include: alcohols, such as methanol, ethanol or isopropanol; ethers, such as diethyl ether, tetrahydrofuran or dioxane; aromatic hydrocarbons, such as toluene, benzene or xylene; aliphatic hydrocarbons, such as hexane or cyclohexane; esters, such as ethyl acetate or propyl acetate; fatty acids, such as acetic acid; and mixtures of water with any one or more of these organic solvents.

There is no particular limitation upon the nature of the catalyst employed, and any catalyst commonly used in catalytic reduction reactions of this type may equally be used here. Preferred catalysts include: palladium on charcoal, Raney nickel, platinum oxide, platinum black, rhodium on alumina, a combination of triphenylphosphine and rhodium chloride, or rhodium on barium sulfate.

The pressure within the reaction vessel is not critical to the process, but the reaction is normally and preferably carried out under from 1 to 10 atmospheres pressure.

The reaction can take place over a wide range of temperatures, and the precise reaction temperature is not critical to the invention, although, as is well known in the art, the precise preferred temperature will vary depending upon many factors, notably the nature of the catalyst, as well as the nature of the reagents and the solvent. In general, we find it convenient to carry out the reaction at a temperature of from 0° C. to 100° C. The time required for the reaction may also vary widely, depending on many factors, notably the reaction temperature and the nature of the reagents and solvent employed. However, provided that the reaction is effected under the preferred conditions outlined above, a period of from 5 minutes to 24 hours will usually suffice.

In the case of the oxidation reaction, this is normally and preferably effected in the presence of a solvent. There is no particular restriction on the nature of the solvent to be employed, provided that it has no adverse effect on the reaction or on the reagents involved and that it can dissolve the reagents, at least to some extent. Aqueous organic solvents are preferred. Examples of suitable organic solvents which may form part of such a solvent system include: ketones, such as acetone; halogenated hydrocarbons, such as methylene chloride, chloroform or carbon tetrachloride; nitriles, such as acetonitrile; ethers, such as diethyl ether, tetrahydrofuran or dioxane; amides, such as dimethylformamide, dimethylacetamide or hexamethylphosphoric triamide; and sulfoxides, such as dimethyl sulfoxide.

There is likewise no particular limitation upon the oxidizing agent employed, and any oxidizing agent commonly employed for oxidation of this type of compound may equally be used here. Preferred oxidizing agents include: potassium persulfate, sodium persulfate, cerium ammonium nitrate and 2,3-dichloro-5,6-dicyano-p-benzoquinone.

The reaction can take place over a wide range of temperatures, and the precise reaction temperature is not critical to the invention, although, as is well known in the art, the precise preferred temperature will vary depending upon many factors, notably the nature of the oxidizing agent, as well as the nature of the reagents and the solvent. In general, we find it convenient to carry out the reaction at a temperature of from 0° C. to 150° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours will usually suffice.

Where the amino-protecting group is an allyloxycarbonyl group, in particular, it may be eliminated simply, by using a combination of palladium and triphenylphosphine or nickel tetracarbonyl, which has the advantage that side reactions can be reduced.

Where the carboxy-protecting group is a lower alkyl group or an allyl group, it may be eliminated by treating the protected compound with an acid or a base.

Suitable acids include hydrochloric acid, sulfuric acid, phosphoric acid and hydrobromic acid. The nature of a base is not critical, provided that it has no adverse effect on other parts of the compound. Preferred bases include: alkali metal carbonates, such as sodium carbonate or potassium carbonate; alkali metal hydroxides, such as sodium hydroxide or potassium hydroxide; and a concentrated solution of ammonia in methanol.

However, hydrolysis using a base is sometimes accompanied by isomerization.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water; or a mixture of water with one or more organic solvents, such as an alcohol (for example methanol, ethanol or propanol) or an ether (for example tetrahydrofuran or dioxane).

The reaction can take place over a wide range of temperatures, and the precise reaction temperature is not critical to the invention. In general, we find it convenient to carry out the reaction at a temperature of from 0° C. to 150° C. The time required for the reaction may also vary widely, depending on many factors, notably the reaction temperature and the nature of the reagents and solvent employed. However, provided that the reaction is effected under the preferred conditions outlined above, a period of from 1 to 10 hours will usually suffice.

Where the carboxy-protecting group is a diarylmethyl group, such as a diphenylmethyl group, it is normally and preferably eliminated by treating the protected compound with an acid, preferably in the presence of a solvent.

Preferred solvents which may be employed in this reaction include aromatic hydrocarbons, such as anisole; and preferred acids include organic fluorides, such as trifluoroacetic acid.

The reaction can take place over a wide range of temperatures, and the precise reaction temperature is not critical to the invention, although, as is well known in the art, the precise preferred temperature will vary depending upon many factors, notably the nature of the acid used, as well as the nature of the reagents and the solvent. In general, we find it convenient to carry out the reaction at a temperature of about room temperature. The time required for the reaction may also vary widely, depending on many factors, notably the reaction temperature and the nature of the reagents, acid and solvent employed. However, provided that the reaction is effected under the preferred conditions outlined above, a period of from 30 minutes to 10 hours will usually suffice.

Where the carboxy-protecting group is an aralkyl group or a lower haloalkyl group, it is normally and preferably eliminated by reduction, preferably in the presence of a solvent.

In reductive deprotection, where the carboxy-protecting group is a lower haloalkyl group, it is preferably eliminated by chemical reduction using a combination of zinc and acetic acid; and where the carboxy-protecting group is an aralkyl group, it is preferably eliminated by catalytic reduction using a catalyst such as palladium on charcoal or platinum in the presence of hydrogen, or by chemical reduction using an alkali metal sulfide, such as potassium sulfide or sodium sulfide.

Both of these reduction reactions are normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; ethers, such as tetrahydrofuran or dioxane; fatty acids, such as acetic acid; and mixtures of water and any one or more of these organic solvents.

The reaction can take place over a wide range of temperatures, and the precise reaction temperature is not critical to the invention. In general, we find it convenient to carry out the reaction at a temperature of from 0° C. to about room temperature. The time required for the reaction may also vary widely, depending on many factors, notably the reaction temperature and the nature of the reagents and solvent employed. However, provided that the reaction is effected under the preferred conditions outlined above, a period of from 5 minutes to 12 hours will usually suffice.

Where the carboxy-protecting group is an alkoxymethyl group, it is normally and preferably removed by treating the protected compound with an acid, preferably in the presence of a solvent.

There is no particular limitation upon the nature of the acid employed, and any Bronsted acid commonly used in reactions of this type may equally be employed here. Preferred acids include: inorganic acids, such as hydrochloric acid or sulfuric acid; and organic acids, such as acetic acid or p-toluenesulfonic acid.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; ethers, such as tetrahydrofuran or dioxane: and mixtures of water and any one or more of these organic solvents.

The reaction can take place over a wide range of temperatures, and the precise reaction temperature is not critical to the invention. In general, we find it convenient to carry out the reaction at a temperature of from 0° C. to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 18 hours will usually suffice.

The carboxy-protecting group may also be carried out using ammonia by conventional means, but, in this case, it is sometimes accompanied by amidation.

If desired, alkali metal salts of the carboxylic acid compounds prepared as described above can be prepared, by conventional means, by dissolving the free carboxylic acid in a mixture of water and a water-immiscible solvent, such as ethyl acetate, adding an aqueous solution of an alkali metal carbonate or alkali metal hydrogencarbonate, such as potassium carbonate or sodium hydrogencarbonate, at a suitable temperature, for example a temperature of from 0° C. to room temperature, adjusting the pH to a value of about 7, and then collecting the precipitate which separates from the mixture, for example by filtration.

Furthermore, if desired, an ester compound having an ester group which is easily hydrolyzable in vivo can be prepared by reacting a salt or a free carboxylic acid compound with, for example, about 2 equivalents of a base (preferably an organic base, such as triethylamine or dicyclohexylamine, an alkali metal hydride, such as sodium hydride, or an alkali metal carbonate or hydrogencarbonate, such as sodium hydrogencarbonate, sodium carbonate or potassium carbonate); and subsequently reacting the product with an appropriate acylating agent (chosen, as is well known, to introduce the desired ester group), for example: an aliphatic acyloxymethyl halide, such as acetoxymethyl chloride or propionyloxymethyl bromide; a 1-(lower alkoxy)carbonyloxyethyl halide, such as 1-methoxycarbonyloxyethyl chloride or 1-ethoxycarbonyloxyethyl iodide; a phthalidyl halide; or a (2-oxo-5-methyl-1,3-dioxolen-4-yl)methyl halide. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as tetrahydrofuran; and polar solvents, such as N,N-dimethylformamide, dimethyl sulfoxide, hexamethylphosphoric triamide or triethyl phosphate.

The reaction can take place over a wide range of temperatures, and the precise reaction temperature is not critical to the invention. In general, we find it convenient to carry out the reaction at a temperature of from 0° C. to 100° C. The time required for the reaction may also vary widely, depending on many factors, notably the reaction temperature and the nature of the reagents and solvent employed. However, provided that the reaction is effected under the preferred conditions outlined above, a period of from 0.5 to 10 hours will usually suffice.

The carboxylic acid compounds used for preparing the compounds of the present invention are commercially available or can be prepared by any suitable method, for example those described in Step 78 through Step 99 of the following reaction schemes.

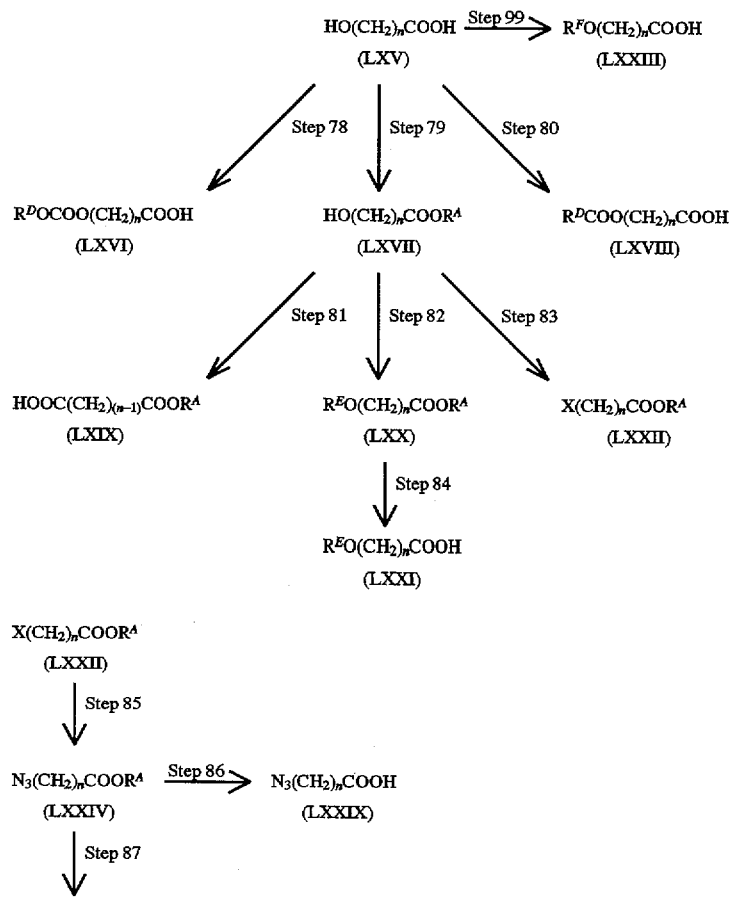

-continued
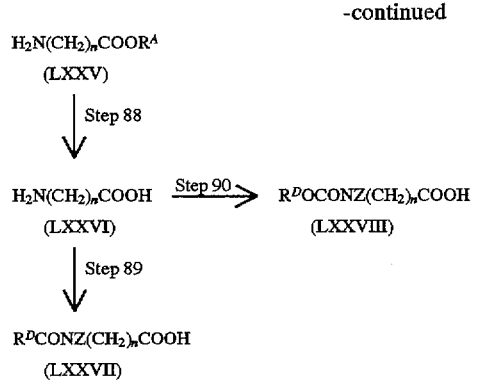
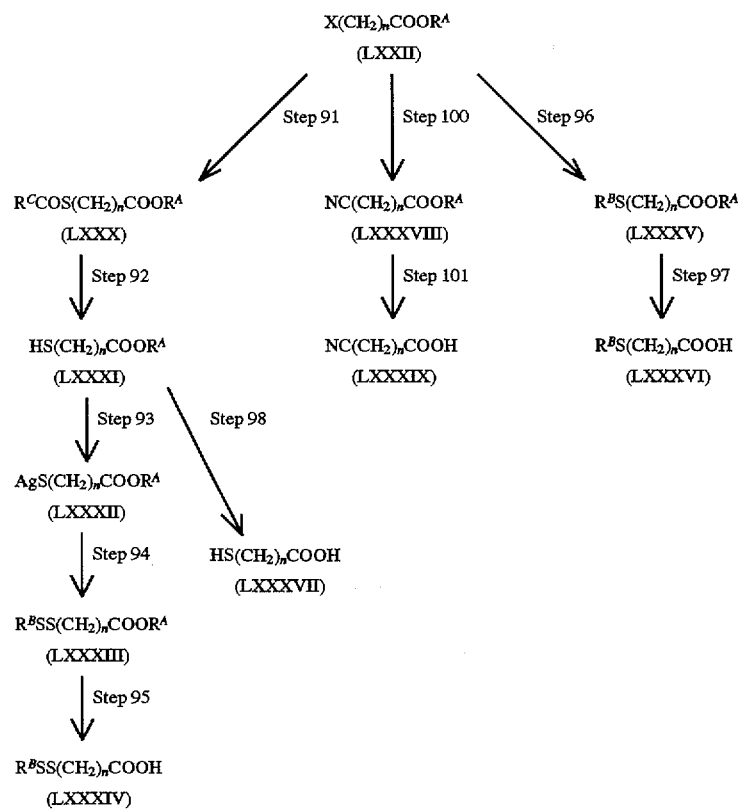
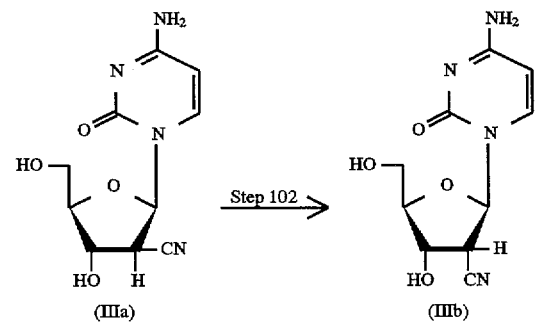

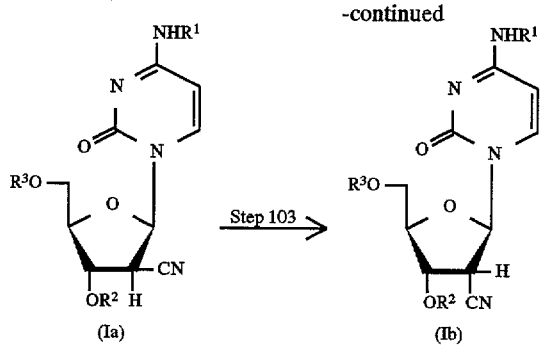

-continued (Ia) Step 103 → (Ib)

In the above formulae:

$R^A$ represents an alkyl group containing from 1 to 4 carbon atoms;

$R^B$ and $R^C$ represent an alkyl, aryl or aralkyl group;

$R^D$ represents an alkyl, aryl or aralkyl group;

$R^{D'}$ represents an alkyl, aryl, aralkyl or halogen-substituted alkyl group;

$R^E$ represents an alkyl, aryl or aralkyl group;

$R^F$ represents a trialkylsilyl group.

X represents a halogen atom; and

Z represents a hydrogen atom or $R^D CO$ (wherein $R^D$ is as defined above).

Examples of the alkyl, aryl, aralkyl and halogen-substituted alkyl groups and halogen atoms referred to above are as previously given in relation to the similar groups and atoms which may be included in substituents A, B and C.

Step 78

In this step, a compound of formula (LXVI) can be prepared by reacting a compound of formula (LXV) with a substituted oxycarbonyl halide of formula $R^D OCOX$ (in which $R^D$ and X are as defined above), preferably in an inert solvent, and in the presence of a base.

Suitable solvents which may be employed in this reaction include mixtures of water with one or more ethers, such as diethyl ether, tetrahydrofuran or dioxane.

There is no particular limitation upon the nature of the base employed, and any base commonly used in conventional reactions of this type may equally be used here. Examples of preferred inorganic bases include: alkali metal carbonates, for example sodium carbonate, potassium carbonate or lithium carbonate; and alkali metal hydroxides, for example sodium hydroxide, potassium hydroxide, barium hydroxide or lithium hydroxide. Examples of preferred organic bases include: triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane and 1,8-diazabicyclo[5.4.0]undec-7-ene. Of these, we prefer the alkali metal hydroxides and the organic bases (particularly, pyridine, N-methylmorpholine and 1,8-diazabicyclo[5.4.0]undec-7-ene).

After completion of the reaction, the product may be recovered from the reaction mixture by conventional means. For example, one suitable recovery procedure comprises: filtering off insoluble materials; distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product may be further purified by a variety of chromatographic techniques or by recrystallization.

Step 79

In this step, a compound of formula (LXVII) is prepared by reacting a compound of formula (LXV) with an alcohol of formula $R^A OH$ (in which $R^A$ is as defined above), preferably in an inert solvent, and in the presence of an acid.

Preferred solvents which may be employed in this reaction include alcohols, such as methanol and ethanol.

There is no particular limitation upon the nature of the acid employed, and any acid capable of being used in conventional reaction of this type as an acid catalyst may equally be used here. Examples of preferred Bronsted acids include: inorganic acids, such as hydrochloric acid, hydrobromic acid, sulfuric acid, perchloric acid or phosphoric acid; and organic acids, such as acetic acid, formic acid, oxalic acid, methanesulfonic acid, p-toluenesulfonic acid, trifluoroacetic acid and trifluoromethanesulfonic acid. Examples of preferred Lewis acids include: zinc chloride, tin tetrachloride, boron trichloride, boron trifluoride and boron tribromide. Of these, we prefer the inorganic acids (particularly sulfuric acid).

After completion of the reaction, the product may be recovered from the reaction mixture by conventional means. For example, one suitable recovery procedure comprises: filtering off insoluble materials; distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product may be further purified by a variety of chromatographic techniques or by recrystallization.

Step 80

In this step, a compound of formula (LXVIII) is prepared by reacting a compound of formula (LXV) with a tri-substituted silyl halide of formula $R^F X$ (in which $R^F$ and X are as defined above), preferably in the presence of an inert solvent, and in the presence of a base.

Suitable solvents which may be employed in this reaction include mixtures of water with one or more ethers, such as diethyl ether, tetrahydrofuran or dioxane.

There is no particular limitation upon the nature of the base employed, and any base used in a conventional reaction of this type may equally be used here. Examples of preferred inorganic bases include: alkali metal carbonates, for example sodium carbonate, potassium carbonate or lithium carbonate; and alkali metal hydroxides, for example sodium hydroxide, potassium hydroxide, barium hydroxide or lithium hydroxide. Examples of preferred organic bases include: triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane and 1,8-diazabicyclo[5.4.0] undec-7-ene. Of these, we prefer the alkali metal hydroxides and organic bases (particularly, pyridine, N-methylmorpholine or 1,8-diazabicyclo[5.4.0]undec-7-ene).

After completion of the reaction, the product may be recovered from the reaction mixture by conventional means. For example, one suitable recovery procedure comprises: filtering off insoluble materials; distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product may be further purified by a variety of chromatographic techniques or by recrystallization.

Step 81

In this step, a compound of formula (LXIX) is prepared by reacting a compound of formula (LXVII) with a oxidizing agent, preferably in an inert solvent.

Preferred solvents which may be employed in this reaction include ketones, such as acetone or methyl ethyl ketone, and mixtures of water with one or more of these ketones.

There is no particular limitation upon the nature of the oxidizing agent employed in this reaction, and any such agent commonly used in conventional oxidation reactions may equally be used here. Examples of preferred inorganic metal oxidizing agents include: manganese oxides and derivatives thereof, such as potassium permanganate or manganese dioxide; ruthenium oxides, such as ruthenium tetraoxide; selenium oxides, such as selenium dioxide; iron compounds, such as ferric chloride; osmium compounds, such as osmium tetraoxide; silver compounds, such as silver oxide; mercury compounds, such as mercury acetate; lead oxide compounds, such as lead oxide or lead tetraoxide; chromic acid compounds, such as potassium chromate, chromic acid and sulfuric acid complex, or chromic acid and pyridine complex; and cerium compounds, such as cerium ammonium nitrate. Examples of preferred inorganic halogen-containing oxidizing agents include: halogen molecules, such as chlorine, bromine or iodine molecule. Examples of other preferred inorganic oxidizing agents include: periodates, such as sodium periodate; ozone; aqueous hydrogen peroxide; nitrites, such as nitrous acid; chlorous acid compounds, such as potassium chlorite or sodium chlorite; and persulfuric acid compounds, such as potassium persulfate or sodium persulfate. Examples of preferred organic oxidizing agents include: organic oxidizing agents used in dimethyl sulfoxide oxidation, such as dicyclohexylcarbodiimide, oxalyl chloride, acetic anhydride or phosphorus pentoxide complex, or pyridine and anhydrous sulfuric acid complex; peroxides, such as t-butyl peroxide; stable cations, such as triphenylmethyl cation; succinimides, such as N-bromosuccinimide; hypochlorite compounds, such as t-butyl hydrochlorite; azodicarboxylic acid compounds, such as azodicarboxylate; a mixture of triphenylphosphine and disulfides, such as dimethyl disulfide, diphenyl disulfide or dipyridyl disulfide; nitrites, such as methyl nitrite; tetrahalogen compounds, such as carbon tetrabromide; and quinone compounds, such as 2,3-dichloro-5,6-dicyano-p-benzoquinone.

After completion of the reaction, the product may be recovered from the reaction mixture by conventional means. For example, one suitable recovery procedure comprises: filtering off insoluble materials; distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product may be further purified by a variety of chromatographic techniques or by recrystallization.

Step 82

In this step, a compound of formula (LXX) is preapred by reacting a compound of formula (LXVII) with an alkyl, aryl or aralkyl halide of formula $R^E X$ (in which $R^E$ and X are as defined above), preferably in the presence of an inert solvent, and in the presence of a base.

Examples of the solvents which may be employed in this reaction include: aliphatic hydrocarbons, such as hexane, heptane, ligroin or petroleum ether; aromatic hydrocarbons, such as benzene, toluene or xylene; ethers, such as diethyl ether, diisopropyl ether, tetrahydrofuran, dioxane, dimethoxyethane and diethylene glycol dimethyl ether; ketones, such as acetone, methyl ethyl ketone, methyl isobutyl ketone, isophorone or cyclohexanone; nitro compounds, such as nitroethane or nitrobenzene; and nitriles, such as acetonitrile or isobutyronitrile.

Examples of the bases which may be employed in this reaction include: inorganic bases, especially alkali metal carbonates (such as sodium carbonate, potassium carbonate or lithium carbonate) and alkali metal hydoxides (such as sodium hydroxide, potassium hydroxide, barium hydroxide or lithium hydroxide); and organic bases, such as triethylamine, tributylamine, diisopropylethylamine, N-methylmorpholine, pyridine, 4-(N,N-dimethylamino) pyridine, N,N-dimethylaniline, N,N-diethylaniline, 1,5-diazabicyclo[4.3.0]non-5-ene, 1,4-diazabicyclo[2.2.2] octane and 1,8-diazabicyclo[5.4.0]undec-7-ene. Of these, we prefer the alkali metal hydroxides and the organic bases (particularly, pyridine, N-methylmorpholine and 1,8-diazabicyclo[5.4.0]undec-7-ene).

After completion of the reaction, the product may be recovered from the reaction mixture by conventional means. For example, one suitable recovery procedure comprises: filtering off insoluble materials; distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product may be further purified by a variety of chromatographic techniques or by recrystallization.

Step 83

In this step, a compound of formula (LXXII) is prepared by reacting a compound of formula (LXVII) with a halogenating agent or a sulfonyl halide, preferably in the presence of an inert solvent and in the presence of a base.

Examples of preferred solvents which may be employed in this reaction include: aliphatic hydrocarbons, such as hexane, heptane, ligroin or petroleum ether; aromatic hydrocarbons, such as benzene, toluene or xylene; ethers, such as diethyl ether, diisopropyl ether, tetrahydrofuran, dioxane, dimethoxyethane, diethylene glycol dimethyl ether; ketones, such as acetone, methyl ethyl ketone, methyl isobutyl ketone, isophorone or cyclohexanone; nitro compounds, such as nitroethane or nitrobenzene; and nitriles, such as acetonitrile or isobutyronitrile.

Preferred halogenating agents which may be used include thionyl chloride and oxalyl chloride.

Preferred sulfonyl halides which may be used include methanesulfonyl chloride, p-toluenesulfonyl chloride and trifluoromethanesulfonyl chloride.

After completion of the reaction, the product may be recovered from the reaction mixture by conventional means. For example, one suitable recovery procedure comprises: filtering off insoluble materials; distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product may be further purified by a variety of chromatographic techniques or by recrystallization.

Step 84

In this step, a compound of formula (LXXI) is prepared by hydrolysis of a compound of formula (LXX), which may have been prepared as described in Step 82, preferably in the presence of an inert solvent, and in the presence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin or petroleum ether; aromatic hydrocarbons, such as benzene, toluene or xylene; ethers, such as diethyl ether, diisopropyl ether, tetrahydrofuran, dioxane, dimethoxyethane or diethylene glycol dimethyl ether; and mixtures of water with any one or more of these ethers.

Examples of preferred bases which may be employed in this reaction include: inorganic bases, especially alkali metal carbonates (such as sodium carbonate, potassium carbonate or lithium carbonate) and alkali metal hydroxides (such as sodium hydroxide, potassium hydroxide, barium hydroxide or lithium hydroxide); and organic bases, such as triethylamine, tributylamine, diisopropylethylamine, N-methylmorpholine, pyridine, 4-(N,N-dimethylamino) pyridine, N,N-dimethylaniline, N,N-diethylaniline, 1,5-diazabicyclo[4.3.0]non-5-ene, 1,4-diazabicyclo[2.2.2]octane and 1,8-diazabicyclo[5.4.0]undec-7-ene. Of these, we prefer the alkali metal hydroxides and the organic bases (particularly, pyridine, N-methylmorpholine and 1,8-diazabicyclo[5.4.0]undec-7-ene).

After completion of the reaction, the product may be recovered from the reaction mixture by conventional means. For example, one suitable recovery procedure comprises: filtering off insoluble materials; distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product may be further purified by a variety of chromatographic techniques or by recrystallization.

Step 85

In this step, a compound of formula (LXXIV) is prepared by reacting a compound of formula (LXXII) with an azidating agent, preferably in the presence of an inert solvent.

Preferred solvents which may be employed in this reaction include amides, such as dimethylformamide or dimethylacetamide.

Preferred azidating agents which may be employed in this reaction include alkali metal azides, such as lithium azide or sodium azide.

After completion of the reaction, the product may be recovered from the reaction mixture by conventional means. For example, one suitable recovery procedure comprises: filtering off insoluble materials; distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product may be further purified by a variety of chromatographic techniques or by recrystallization.

Step 86

In this step, a compound of formula (LXXIX) is prepared by the hydrolysis of a compound of formula (LXXIV), preferably in the presence of an inert solvent, and in the presence of a base. The reaction is essentially the same as that of, and may be carried out in the same manner as described in, Step 84.

Step 87

In this step, a compound of formula (LXXV) is prepared by contacting a compound of formula (LXXIV), which may have been prepared as described in Step 86, with a reducing agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin or petroleum ether; aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; alcohols, such as methanol, ethanol, propanol, isopropanol, butanol, isobutanol, t-butanol, isoamyl alcohol, diethylene glycol, glycerine, octanol, cyclohexanol or ethylene glycol monomethyl ether; ketones, such as acetone, methyl ethyl ketone, isophorone or cyclohexanone; nitro compounds, such as nitroethane or nitrobenzene; nitriles, such as acetonitrile or isobutyronitrile; amides, such as formamide, dimethylformamide, dimethylacetamide or hexamethylphosphoric triamide; and sulfoxides, such as dimethyl sulfoxide or sulfolane.

The reduction in this step may be carried out, by conventional means, using any suitable reducing agent as follows:

(1) a reaction using zinc in aqueous methanol containing aluminum chloride or in aqueous acetone containing hydrochloric acid;

(2) a reaction using an alkali metal borohydride, such as sodium borohydride or lithium borohydride; an aluminum hydride, such as lithium aluminum hydride or lithium triethoxyaluminum hydride; a hydride reagent, such as sodium tellurium hydride, in an alcohol, such as methanol or ethanol, an ether, such as tetrahydrofuran, or in a mixture of two or more of these solvents;

(3) a catalytic reduction reaction using a catalyst, such as palladium on charcoal, platinum or Raney nickel at ambient temperature in a solvent, for example an alcohol, such as methanol or ethanol, an ether, such as tetrahydrofuran or dioxane, a fatty acid, such as acetic acid, or in a mixture of water and one or more of these organic solvents;

(4) a reaction using a silicon hydride, such as triethylsilyl hydride or triphenylsilyl hydride with a Lewis acid, such as aluminum chloride, tin tetrachloride or titanium tetrachloride;

(5) a reaction using a radical reducing agent, such as tributyltin hydride, triphenyltin hydride or dibutyltin hydride in the presence of a radical initiator, for example azobisisobutyronitrile or triphenylboron as a catalyst.

After completion of the reaction, the product may be recovered from the reaction mixture by conventional means. For example, one suitable recovery procedure comprises: filtering off insoluble materials; distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product may be further purified by a variety of chromatographic techniques or by recrystallization.

Step 88

In this step, a compound of formula (LXXVI) is prepared by the hydrolysis of a compound of formula (LXXV), preferably in the presence of an inert solvent, and in the presence of a base. The reaction is essentially the same as that of, and may be carried out in the same manner as described in, Step 84.

Step 89

In this step, a compound of formula (LXXVII) is prepared by reacting a compound of formula (LXXVI) with an acylating agent, for example a compound of formula $R^DCOX$, $R^DCO.O.COR^D$, $R^DCO.O.COOMe$ or $R^DCO.O.COOEt$ (in which $R^D$, Me, Et and X are as defined above), preferably in the presence of an inert solvent and in the presence of a base. The reaction is essentially the same as that of, and may be carried out in the same manner as described in, Step 80.

Step 90

In this step, a compound of formula (LXXVIII) is prepared by reacting a compound of formula (LXXVI) with an oxycarbonyl halide, preferably in the presence of an inert solvent, and in the presence of a base. The reaction is essentially the same as that of, and may be carried out in the same manner as described in, Step 78.

After completion of the reaction, the product may be recovered from the reaction mixture by conventional means. For example, one suitable recovery procedure comprises: filtering off insoluble materials; distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product may be further purified by a variety of chromatographic techniques or by recrystallization.

Step 91

In the step, a compound of formula (LXXX) is prepared by reacting a compound of formula (LXXII) with a thiocarboxylic acid compound of formula $R^CCOSH$ (in which $R^C$ is as defined above), preferably in the presence of an inert solvent, and in the presence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin or petroleum ether; aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; alcohols, such as methanol, ethanol, propanol, isopropanol, butanol, isobutanol, t-butanol, isoamyl alcohol, diethylene glycol, glycerine, octanol, cyclohexanol or ethylene glycol monomethyl ether; ketones, such as acetone, methyl ethyl ketone, isophorone or cyclohexanone; nitro compounds, such as nitroethane or nitrobenzene; nitriles, such as acetonitrile or isobutyronitrile; amides, such as formamide, dimethylformamide, dimethylacetamide or hexamethylphosphoric triamide; and sulfoxides, such as dimethyl sulfoxide or sulfolane.

Examples of preferred bases which may be employed in this reaction include: inorganic bases, especially alkali metal carbonates (such as sodium carbonate, potassium carbonate or lithium carbonate) and alkali metal hydroxides (such as sodium hydroxide, potassium hydroxide, barium hydroxide or lithium hydroxide); and organic bases, such as triethylamine, tributylamine, diisopropylethylamine, N-methylmorpholine, pyridine, 4-(N,N-dimethylamino) pyridine, N,N-dimethylaniline, N,N-diethylaniline, 1,5-diazabicyclo[4.3.0]non-5-ene, 1,4-diazabicyclo[2.2.2] octane and 1,8-diazabicyclo[5.4.0]undec-7-ene. Of these, we prefer the alkali metal hydroxides and the organic bases (particularly, pyridine, N-methylmorpholine or 1,8-diazabicyclo[5.4.0]undec-7-ene).

After completion of the reaction, the product may be recovered from the reaction mixture by conventional means. For example, one suitable recovery procedure comprises: filtering off insoluble materials; distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product may be further purified by a wide variety of chromatographic techniques or by recrystallization.

Step 92

In this step, a compound of formula (LXXXI) can be prepared by reacting a compound of formula (LXXX), which may have been prepared as described in Step 91, with an alcohol, preferably in the presence of an inert solvent, and in the presence of an acid.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin or petroleum ether; aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; alcohols, such as methanol, ethanol, propanol, isopropanol, butanol, isobutanol, t-butanol, isoamyl alcohol, diethylene glycol, glycerine, octanol, cyclohexanol or ethylene glycol monomethyl ether; ketones, such as acetone, methyl ethyl ketone, isophorone or cyclohexanone; nitro compounds, such as nitroethane or nitrobenzene; nitriles, such as acetonitrile or isobutyronitrile; amides, such as formamide, dimethylformamide, dimethylacetamide or hexamethylphosphoric triamide; and sulfoxides, such as dimethyl sulfoxide or sulfolane.

There is likewise no particular limitation upon the nature of the acid employed, and any acid capable of being used in conventional reactions as an acid catalyst may equally be used here. Preferred acids include: inorganic acids, such as hydrochloric acid, hydrobromic acid, sulfuric acid, perchloric acid or phosphoric acid; organic Bronsted acids, such as acetic acid, formic acid, oxalic acid, methanesulfonic acid, p-toluenesulfonic acid, trifluoroacetic acid and trifluoromethanesulfonic acid; and Lewis acids, such as zinc chloride, tin tetrachloride, boron trichloride, boron trifluoride and boron tribromide. Of these, we prefer the inorganic acids (particularly hydrochloric acid).

Methanol is the preferred alcohol.

After completion of the reaction, the product may be recovered from the reaction mixture by conventional means. For example, one suitable recovery procedure comprises: filtering off insoluble materials; distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product may be further purified by a wide variety of chromatographic techniques or by recrystallization.

Step 93

In this step, a compound of formula (LXXXII) is prepared by reacting a compound of formula (LXXXI), which may have been prepared as described in Step 92, with a silver salt.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin or petroleum ether; aromatic hydrocarbons, such as benzene, toluene or xylene; esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; alcohols, such as methanol, ethanol, propanol, isopropanol, butanol, isobutanol, t-butanol, isoamyl alcohol, diethylene glycol, glycerine, octanol, cyclohexanol or ethylene glycol monomethyl ether; ketones, such as acetone, methyl ethyl ketone, isophorone or cyclohexanone; nitro compounds, such as nitroethane or nitrobenzene; nitriles, such as acetonitrile or isobutyronitrile; amides, such as formamide, dimethylformamide, dimethylacetamide or hexamethylphosphoric triamide; and sulfoxides, such as dimethyl sulfoxide or sulfolane.

Silver acetate is the preferred silver salt.

After completion of the reaction, the product may be recovered from the reaction mixture by conventional means. For example, one suitable recovery procedure comprises: filtering off insoluble materials; distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product may be further purified by a wide variety of chromatographic techniques or by recrystallization.

Step 94

In this step, a compound of formula (LXXXIII) is prepared by reacting a compound of formula (LXXXII), which may have been prepared as described in Step 93, with a disulfidating agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin or petroleum ether; aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; alcohols, such as methanol, ethanol, propanol, isopropanol, butanol, isobutanol, t-butanol, isoamyl alcohol, diethylene glycol, glycerine, ocatanol, cyclohexanol or ethylene glycol monomethyl ether; ketones, such as acetone, methyl ethyl ketone, isophorone or cyclohexanone; nitro compounds, such as nitroethane or nitrobenzene; nitriles, such as acetonitrile or isobutyronitrile; amides, such as formamide, dimethylformamide, dimethylacetamide or hexamethylphosphoric triamide; and sulfoxides, such as dimethyl sulfoxide or sulfolane.

Preferred disulfidating agents include a combination of the alkylmercaptan whose alkylthio group it is desired to introduce and a 2,4-dinitrophenylsulfenyl halide, particularly, 2,4-dinitrophenylsulfenyl chloride.

After completion of the reaction, the product may be recovered from the reaction mixture by conventional means. For example, one suitable recovery procedure comprises: filtering off insoluble materials; distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product may be further purified by a wide variety of chromatographic techniques or by recrystallization.

Step 95

In this step, a compound of formula (LXXXIV) is prepared by the hydrolysis of a compound of formula (LXXXIII), preferably in the presence of an inert solvent, and in the presence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin or petroleum ether; aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; alcohols, such as methanol, ethanol, propanol, isopropanol, butanol, isobutanol, t-butanol, isoamyl alcohol, diethylene glycol, glycerine, octanol, cyclohexanol or ethylene glycol monomethyl ether; ketones, such as acetone, methyl ethyl ketone, isophorone or cyclohexanone; nitro compounds, such as nitroethane or nitrobenzene; nitriles, such as acetonitrile or isobutyronitrile; amides such as formamide, dimethylformamide, dimethylacetamide or hexamethylphosphoric triamide; and sulfoxides, such as dimethyl sulfoxide or sulfolane.

Examples of preferred bases which may be employed in this reaction include: inorganic bases, especially alkali metal carbonates (such as sodium carbonate, potassium carbonate or lithium carbonate) and alkali metal hydroxides (such as sodium hydroxide, potassium hydroxide, barium hydroxide or lithium hydroxide); and organic bases, such as triethylamine, tributylamine, diisopropylethylamine, N-methylmorpholine, pyridine, 4-(N,N-dimethylamino) pyridine, N,N-dimethylaniline, N,N-diethylaniline, 1,5-diazabicyclo[4.3.0]non-5-ene, 1,4-diazabicyclo[2.2.2]octane and 1,8-diazabicyclo[5.4.0]undec-7-ene. Of these, we prefer the alkali metal hydroxides and the organic bases (particularly, pyridine, N-methylmorpholine or 1,8-diazabicyclo[5.4.0]undec-7-ene).

After completion of the reaction, the product may be recovered from the reaction mixture by conventional means. For example, one suitable recovery procedure comprises: filtering off insoluble materials; distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product may be further purified by a wide variety of chromatographic techniques or by recrystallization.

Step 96

In this step, a compound of formula (LXXXV) is prepared by reacting a compound of formula (LXXII) with a thiol compound of formula $R^B SH$ (in which $R^B$ is as defined above), preferably in the presence of an inert solvent, and in the presence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin or petroleum ether; aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; alcohols, such as methanol, ethanol, propanol, isopropanol, butanol, isobutanol, t-butanol, isoamyl alcohol, diethylene glycol, glycerine, octanol, cyclohexanol or ethylene glycol monomethyl ether; ketones, such as acetone, methyl ethyl ketone, isophorone or cyclohexanone; nitro compounds, such as nitroethane or nitrobenzene; nitriles, such as acetonitrile or isobutyronitrile; amides, such as formamide, dimethylformamide, dimethylacetamide or hexamethylphosphoric triamide; and sulfoxides, such as dimethyl sulfoxide or sulfolane.

Examples of preferred bases which may be employed in this reaction include: inorganic bases, especially alkali metal carbonates (such as sodium carbonate, potassium carbonate or lithium carbonate) and alkali metal hydroxides (such as sodium hydroxide, potassium hydroxide, barium hydroxide or lithium hydroxide); and organic bases, such as triethylamine, tributylamine, diisopropylethylamine, N-methylmorpholine, pyridine, 4-(N,N-dimethylamino) pyridine, N,N-dimethylaniline, N,N-diethylaniline, 1,5-diazabicyclo[4.3.0]non-5-ene, 1,4-diazabicyclo[2.2.2]octane and 1,8-diazabicyclo[5.4.0]undec-7-ene. Of these, we prefer the alkali metal hydroxides and the organic bases (particularly, pyridine, N-methylmorpholine or 1,8-diazabicyclo[5.4.0]undec-7-ene).

After completion of the reaction, the product may be recovered from the reaction mixture by conventional means. For example, one suitable recovery procedure comprises: filtering off insoluble materials; distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product may be further purified by a wide variety of chromatographic techniques or by recrystallization.

Step 97

In this step, a compound of formula (LXXXVI) is prepared by hydrolysis of a compound of formula (LXXXV), which may have been prepared as described in Step 96, preferably in the presence of an inert solvent, and in the presence of a base. The reaction is essentially the same as that of, and may be carried out in the same manner as described in, Step 84.

Step 98

In this step, a compound of formula (LXXXVII) is prepared by the hydrolysis of a compound of formula (LXXXI), which may have been prepared as described in Step 92, preferably in the presence of an inert solvent, and in the presence of a base. The reaction is essentially the same as that of, and may be carried out in the same manner as described in, Step 84.

Step 99

In this step, a compound of formula (LXXIII) is prepared by reacting a compound of formula (LXV) with a tri-substituted silyl halide, preferably in the presence of an inert solvent, and in the presence of a base. The reaction is essentially the same as that of, and may be carried out in the same manner as described in, Step 47.

Step 100

In this step, a compound of formula (LXXXVIII) is prepared by reacting a compound of formula (LXXII) with an cyanating agent, preferably in the presence of an inert solvent.

Preferred solvents which may be employed in this reaction include amides, such as dimethylformamide or dimethylacetamide.

Preferred cyanating agents which may be employed in this reaction include alkali metal cyanides, such as potassium cyanide or sodium cyanide.

After completion of the reaction, the product may be recovered from the reaction mixture by conventional means. For example, one suitable recovery procedure comprises: filtering off insoluble materials; distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. In general, the product can be used as a starting material for the next step without any further purification. However, if desired, the product may be further purified by a variety of chromatographic techniques or by recrystallization.

Step 101

In this step, a compound of formula (LXXXIX) is prepared by the hydrolysis of a compound of formula (LXXXVIII), which may have been prepared as described in Step 100, preferably in the presence of an inert solvent, and in the presence of a base. The reaction is essentially the same as that of, and may be carried out in the same manner as described in, Step 84.

Step 102

In this step, a compound of formula (IIIb), which may be one of the starting materials used for the preparation of the compounds of the present invention, is prepared by isomerization of a compound of formula (IIIa), preferably in the presence of an inert solvent, and in the presence of a base.

Preferred solvents which may be employed in this reaction include water alone or a mixture of water and an organic solvent, for example: an ether, such as tetrahydrofuran, dioxane, or diethyl ether; a ketone, such as acetone or methyl ethyl ketone; or an aromatic hydrocarbon, such as benzene or toluene.

Preferred isomerizing agents which may be employed in this reaction include: inorganic bases, especially alkali metal carbonates (such as sodium carbonate, potassium carbonate or lithium carbonate), alkali metal hydroxides (such as sodium hydroxide, potassium hydroxide, barium hydroxide or lithium hydroxide) and dialkali metal hydrogenphosphates (such as disodium hydrogenphosphate or dipotassium hydrogen phosphate); and organic bases, such as triethylamine, tributylamine, diisopropylethylamine, N-methylmorpholine, pyridine, 4-(N,N-dimethylamino) pyridine, N,N-dimethylaniline, N,N-diethylaniline, 1,5-diazabicyclo[4.3.0]non-5-ene, 1,4-diazabicyclo[2.2.2] octane and 1,8-diazabicyclo[5.4.0]undec-7-ene. Of these, we prefer the dialkali metal hydrogenphosphates (particularly disodium hydrogenphosphate).

After completion of the reaction, the product may be recovered from the reaction mixture by conventional means. For example, one suitable recovery procedure comprises: adjusting the pH to a value of about 2.0; and then separating and purifying the desired compound by a variety of chromatographic techniques or by recrystallization.

Step 103

In this step, a compound of formula (Ib) is prepared by isomerization of a compound of formula (Ia), preferably in the presence of an inert solvent, and in the presence of a base.

Preferred solvents which may be employed in this reaction include water alone or a mixture of water and an organic solvent, for example: an ether, such as tetrahydrofuran, dioxane, or diethyl ether; a ketone, such as acetone or methyl ethyl ketone; or an aromatic hydrocarbon, such as benzene or toluene.

Preferred isomerizing agents which may be employed in this reaction include: inorganic bases, especially alkali metal carbonates (such as sodium carbonate, potassium carbonate or lithium carbonate), alkali metal hydroxides (such as sodium hydroxide, potassium hydroxide, barium hydroxide or lithium hydroxide) and dialkali metal hydrogenphosphates (such as disodium hydrogenphosphate or dipotassium hydrogen phosphate); and organic bases, such as triethylamine, tributylamine, diisopropylethylamine, N-methylmorpholine, pyridine, 4-(N,N-dimethylamino) pyridine, N,N-dimethylaniline, N,N-diethylaniline, 1,5-diazabicyclo[4.3.0]non-5-ene, 1,4-diazabicyclo[2.2.2] octane and 1,8-diazabicyclo[5.4.0]undec-7-ene. Of these, we prefer the dialkali metal hydrogenphosphates (particularly disodium hydrogenphosphate).

After completion of the reaction, the product may be recovered from the reaction mixture by conventional means. For example, one suitable recovery procedure comprises: adjusting the pH to a value of about 2.0; filtering off insoluble materials; distilling off the solvent; pouring the reaction mixture into water; acidifying the mixture with an inorganic acid, such as hydrochloric acid or sulfuric acid; extracting the mixture with a water-immiscible solvent, such as benzene, diethyl ether or ethyl acetate; and distilling off the solvent from the extract. If the resulting compound is to be used as an intermediate in the preparation of other compounds, then, in general, it can be used without any further purification. However, since the product may be the required final product, it may, if desired, be further purified by a variety of chromatographic techniques, notably column chromatography or preparative thin layer chromatography, or by recrystallization.

Where a compound of formula (LXXXVII) is used as a starting compound in place of the compound of formula (LXV), the corresponding thio compounds can be prepared by similar procedures to those described in Step 78 through 82 and Step 84.

The acid halides used for preparing the compounds of the present invention are commercially available or may be prepared by using a conventional halogenating agent (such as thionyl chloride or oxalyl chloride).

The compounds of the present invention exhibit potent anti-tumor activities against P388 cells inoculated into mice and against a wide variety of human cancers. They showed good oral absorbability and a low toxicity, and are free from harmful side effects. Therefore, they can be used for the treatment or prevention of tumorigenic diseases as a new pyrimidine nucleoside anti-tumor drug. The compounds of the invention are also useful as intermediates for preparing other excellent anti-tumor drugs. The pyrimidine nucleoside derivatives of the invention can be administered to homeothermal animals, including human beings. For this purpose, they can be administered parenterally by intravenous injection, hypodermic injection, intramuscular injection or suppository, or orally in the form of tablets, capsules, powders, granules or other well known formulations.

The dose will vary depending upon the condition of the patient as well as upon the route, frequency and period of administration but, in general, the compounds of the present invention may be administered in a daily dose of from 0.05 to 5 g for an adult human patient, either as a single dose or as divided doses.

The compounds can, if desired, be used in association with other anti-tumor drugs, for example, a nitrosourea drug such as 5Fu, AraC, ACNU or BCNU, Cisplatin, Daunomycin, Adriamycin, Mitomycin C, Eposide and the like. Pharmaceutical preparations containing the pyrimidine nucleoside derivatives of the present invention can be produced for administration according to conventional means.

Compositions for injection can be offered in the form of an unit-dosage ampule or a vial for multi-dosages. It can optionally comprise conventional additives, such as suspension aids, stabilizers or dispersants. In general, it may be offered in the form of a powder, which is redissolved before use in an appropriate solvent, for example, a sterile aqueous pyrogen-free medium. Such a pharmaceutical preparation can be prepared, for example, by dissolving the pyrimidine nucleoside derivative in acetone, pipetting the solution into a vial, adding water, and lyophilizing. Compositions for oral administration may be offered in the form of tablets, capsules, powders, granules or syrups, each of which comprises an suitable amount of the pyrimidine nucleoside derivative of the present invention in admixture with appropriate carriers, diluents or adjuvants.

BIOLOGICAL ACTIVITY

The biological activity of the compounds of the present invention is demonstrated by the following tests.

1) Anti-tumor activity against p-388 leukemia

The test animals employed were female mice, 8 weeks of age, of the $CDF_1$ strain, each weighing 21–25 g. The mice were divided into groups. each of 5 mice, and all mice within the group were treated identically. Into each mouse was implanted intraperitoneally $1 \times 10^6$ cells of the leukemia p-388.

The test compounds 1-9, 1-11, 1-15, 1-31 and 1-62 were dissolved in 0.2 ml of N,N-dimethylacetamide and the solution was mixed with 10% Emulphor (trade mark)-physiological saline on an agate mortar. Test compounds 1-34 and 1-41 were dissolved in a small amount of Tween 80 (registered trade mark) and immediately thereafter physiological saline was added to the solution form a suspension. The suspension was administered intraperitoneally on the first, fifth and ninth days following implantation of the leukemia cells. The period for which the mice survived was determined. A control group was treated identically, except that no active compound was administered.

The anti-tumor effect is shown in the following Table 3 as the increase in life span [ILS (%)], calculated from the following equation [R. I. Geran et al, Cancer Chemother. Rept., 3 (1972)]:

$$ILS\ (\%) = (Dt/Dc - 1) \times 100$$

where

Dt=average number of days survival by the test group; and

Dc=average number of days survival by the control group. In this test Dc was 9–10 days.

The compounds of the invention are identified in the following Table by the numbers assigned to them in the foregoing list, given in Table 1.

TABLE 3

| Ex. No. | Cpd No. | dose (mg/kg) | ILS (%) | 30 days survivors |
|---|---|---|---|---|
| 1 | 1-11 | 50 | 189 | 2/5 |
| 17 | 1-9 | 200 | >200 | 4/5 |
| 19 | 1-15 | 100 | 202 | 0/5 |
| 21 | 1-31 | 200 | 152 | 0/5 |
| 23 | 1-62 | 200 | 159 | 0/5 |
| 25 | 1-41 | 100 | 159 | 2/5 |
| 26 | 1-34 | 100 | >195 | 3/5 |

As is shown in the above Table 3, all of the compounds tested exhibited higher anti-tumor activities in the liquid type tumor model (p-388 leukemia ip implanted) in terms of increase in life span.

2) Anti-tumor activity against M5076 fibrosarcoma

The test animals used were female mice, 8–10 weeks old, of the $BDF_1$ strain, weighing 20–25 g. The mice were purchased from Charles River Japan Inc., Kanagawa Japan. The mice were divided into experimental groups, each group containing 6 mice, and all mice within each group were treated identically. Each mouse was inoculated subcutaneously with $1 \times 10^6$ viable cells (the number of cells was measured by a dye exclusion method under microscopy) of the mouse fibrosarcoma M5076.

The test compounds listed in the following Table were dissolved in 0.2 ml of N,N-dimethylacetamide and the solution was mixed with 10% Emulphor (trade mark)-physiological saline on an agate mortar. The final concentration of N,N-dimethylacetamide was 5% v/v. The solution was administered orally on the first, fourth, seventh, tenth, thirteenth and sixteenth days following inoculation of the fibrosarcoma cells. The period for which the mice survived and the % inhibition of tumor growth were determined. A control group was not treated.

The anti-tumor effect is shown in the following Table 4 as the percent growth inhibition [GI (%)], calculated from the following equations [R. I. Geran et al., Cancer Chemother. Rept., 3 (1972)]:

$$GI\ (\%) = (1 - TDt/TDc) \times 100$$

where

TDt=average value of tumor sizes on the twentieth day in the treated group; and

TDc=average value of tumor sizes on the twentieth day in the control group;

tumor size=(tumor length+tumor width)/2.

The compounds of the invention are identified in the following Table by the numbers assigned to them in the foregoing list, given in Table 1.

TABLE 4

| Ex. No. | Cpd No. | growth inhibition (%) optimal dose | growth inhibition (%) optimal dose/4 | 60 day survivors optimal dose |
|---|---|---|---|---|
| 1 | 1-11 | 99.2 | 90.2 | 5/6 |
| 9 | 1-1 | 97.7 | 61.1 | 4/6 |
| 10 | 1-5 | 93.0 | 70.4 | 3/6 |
| 12 | 1-13 | 98.1 | 88.9 | 4/6 |

TABLE 4-continued

| Ex. No. | Cpd No. | growth inhibition (%) optimal dose | growth inhibition (%) optimal dose/4 | 60 day survivors optimal dose |
|---|---|---|---|---|
| 17 | 1-9 | 97.3 | 79.1 | 5/6 |
| 19 | 1-15 | 96.5 | 88.7 | 5/6 |
| 23 | 1-62 | 99.0 | 83.3 | 6/6 |
| 25 | 1-41 | 99.2 | 76.2 | 5/6 |
| 26 | 1-34 | 96.0 | 87.2 | 5/6 |

As is shown in the above Table 4, all of the compounds tested exhibited higher anti-tumor activities in the solid type tumor model (M5076 fibrosarcoma sc implanted) in terms of tumor growth inhibition.

Both of the tests given above are accepted in this field as providing a model for the efficacy of anti-tumor drugs in humans.

The invention is further illustrated by the following Examples, which demonstrate the preparation of various of the compounds of the present invention. In these Examples, all mesh sizes use the Tyler standard.

EXAMPLE 1

2'-Cyano-2'-deoxy-$N^4$-palmitoyl-1-$\beta$-D-arabinofuranosylcytosine

1(a) 2'-Cyano-2'-deoxy-1-$\beta$-D-arabinofuranosylcytosine

A solution of 8.66 g (30 mmole) of 2'-cyano-2'-deoxy-1-$\beta$-D-arabinofuranosylcytosine monohydrochloride dissolved in 50 ml of water was passed through a column packed with 90 ml of Dowex 1x2 (trade name) ion-exchange resin ($CH_3COO^-$ type), and the column was washed with 300 ml of water. The effluent and the washings were combined and lyophilized, to give 7.23 g (yield 95.5%) of the title compound as a colorless powder.

Nuclear Magnetic Resonance Spectrum (hexadeuterated dimethyl sulfoxide, 270 MHz) $\delta$ ppm:

7.28 (1H, broad singlet);
7.23 (1H, broad singlet);
7.83 (1H, doublet, J=7.8 Hz);
6.17 (1H, doublet, J=7.3 Hz);
6.17 (1H, doublet, J=5.9 Hz);
5.77 (1H, doublet, J=7.3 Hz);
5.12–5.16 (1H, multiplet);
4.36–4.44 (1H, multiplet);
3.56–3.80 (4H, multiplet).

1(b) 2'-Cyano-2'-deoxy-3',5'-O-(1,1,3,3-tetraisopropyldisiloxane-1,3-diyl)-1-$\beta$-D-arabinofuranosylcytosine 5.045 g (20 mmole) of 2'-cyano-2'-deoxy-1-$\beta$-D-arabinofuranosylcytosine [prepared as described in step (a) above] were dried three times by azeotropic distillation with pyridine, and the residue was suspended in 200 ml of pyridine. 6.7 ml (21 mmole) of 1,3-dichloro-1,1,3,3-tetraisopropyldisiloxane were added to the suspension, and the resulting mixture was stirred at room temperature for 1 hour in an atmosphere of nitrogen. The solution was concentrated to about one half of its original volume by distillation under reduced pressure, and the concentrate was diluted with 200 ml of ethyl acetate. The diluted solution was washed twice, each time with 200 ml of a saturated aqueous solution of sodium hydrogencarbonate. It was then dried over anhydrous magnesium sulfate. The solvent was removed by distillation under reduced pressure, and the resulting residue was mixed with a mixture of toluene and methanol. The mixture was subjected to azeotropic distillation, to give 11.21 g of a residue. This was purified by column chromatography through 300 g of silica gel (230–400 mesh), using methylene chloride containing 5% by volume methanol as the eluent, to give 8.67 g (yield 87%) of the title compound as a foam.

Nuclear Magnetic Resonance Spectrum ($CDCl_3$, 270 MHz) $\delta$ ppm:

7.69 (1H, doublet, J=7.26 Hz);
6.31 (1H, doublet, J=7.26 Hz);
5.74 (1H, doublet, J=7.26 Hz);
4.64 (1H, doublet of doublets, J=7.26 & 7.26 Hz);
4.15–4.04 (2H, multiplet);
3.84 (1H, doublet of triplets, J=7.26 & 3.30 Hz);
3.67 (1H, doublet of doublets, J=7.26 & 7.26 Hz);
1.15–0.93 (28H, multiplet).

1(c) 2'-Cyano-2'-deoxy-$N^4$-palmitoyl-3',5'-O-(1,1,3,3-tetraisopropyldisiloxane-1,3-diyl)-1-$\beta$-D-arabinofuranosylcytosine A mixture of 1.48 g (3 mmole) of 2'-cyano-2'-deoxy-3',5'-O-(1,1,3,3-tetraisopropyldisiloxane-1,3-diyl)-1-$\beta$-D-arabinofuranosylcytosine [prepared as described in step (b) above] and 3.07 g (12 mmole) of palmitic acid was dried by azeotropic distillation using 50 ml of benzene, and the residue was dissolved in 30 ml of tetrahydrofuran. 2.47 g (12 mmole) of dicyclohexylcarbodiimide and 120 mg (0.9 mmole) of 4-(N,N-dimethylamino)pyridine were added to the solution, and the resulting mixture was stirred at 50° C. for 2.5 hours in an atmosphere of nitrogen. At the end of this time, the insoluble materials were removed by filtration, and the filtrate was freed from the solvent by distillation under reduced pressure. The residue was partitioned between 100 ml of ethyl acetate and 50 ml of a 5% w/v aqueous solution of sodium hydrogencarbonate. The organic layer was washed with 50 ml of a saturated aqueous solution of sodium chloride and dried over anhydrous magnesium sulfate. The solvent was distilled off under reduced pressure, and the residue was purified by column chromatography through silica gel, using methylene chloride containing 1% v/v methanol as the eluent, to give 1.85 g of the title compound as a caramel-like solid.

Nuclear Magnetic Resonance Spectrum (hexadeuterated dimethyl sulfoxide, 270 MHz) $\delta$ ppm:

10.94 (1H, singlet);
8.02 (1H, doublet, J=7.82 Hz);
7.30 (1H, doublet, J=7.32 Hz);
6.21 (1H, doublet, J=7.83 Hz);
4.69 (1H, singlet);
4.22 (2H, multiplet);
3.98 (1H, doublet, J=2.45 Hz);
3.42 (1H, doublet, J=3.92 Hz);
2.40 (2H, triplet, J=7.32 Hz);
1.53 (2H, singlet);
0.82–1.23 (55H).

1(d) 2'-Cyano-2'-deoxy-$N^4$-palmitoyl-1-$\beta$-D-arabinofuranosylcytosine 0.31 ml (5.45 mmole) of acetic acid and 2.84 g (10.9 mmole) of tetrabutylammonium fluoride were added, whilst ice-cooling and stirring, to a solution of 4.0 g (5.45 mmole) of 2'-cyano-2'-deoxy-$N^4$-palmitoyl-3',5'-O-(1,1,3,3-tetraisopropyldisiloxane-1,3-diyl)-1-$\beta$-D-arabinofuranosylcytosine [prepared as described in step (c)

above] in 60 ml of tetrahydrofuran (which had previously been dried over molecular sieve 3A), and the resulting mixture was stirred for 40 minutes in an atmosphere of nitrogen. The reaction mixture was then concentrated to dryness by evaporation under reduced pressure, and the residue was partitioned between 100 ml of methylene chloride and 50 ml of a saturated aqueous solution of sodium chloride. The organic layer was washed with 50 ml of a saturated aqueous solution of sodium chloride and dried over anhydrous magnesium sulfate. The solvent was then removed by distillation under reduced pressure, and the residual caramel-like solid was purified by column chromatography through silica gel, using methylene chloride containing 4% v/v methanol as the eluent, to give 2.25 g of the title compound as a colorless powder.

Nuclear Magnetic Resonance Spectrum (hexadeuterated dimethyl sulfoxide, 270 MHz) δ ppm:

10.91 (1H, singlet);

8.36 (1H, doublet, J=7.8 Hz);

7.29 (1H, doublet, J=7.8 Hz);

6.25 (1H, doublet, J=5.4 Hz);

6.21 (1H, doublet, J=7.3 Hz);

5.22 (1H, broad singlet);

4.43 (1H, multiplet);

3.61–3.93 (4H, multiplet);

2.40 (2H, triplet, J=7.3 Hz);

1.54 (2H, triplet, J=6.8 Hz);

1.24 (24H, singlet);

0.83–0.88 (3H, multiplet).

EXAMPLE 2

2'-Cyano-2'-deoxy-$N^4$-palmitoyl-1-β-D-arabinofuranosylcytosine

A mixture of 12.9 g (51.1 mmole) of 2'-cyano-2'-deoxy-1-β-D-arabinofuranosylcytosine [prepared as described in Example 1(a) above] and 38.1 g (76.7 mmole) of palmitic anhydride was placed in a 1 liter round-bottomed flask, and 51 ml of dimethylformamide were added thereto. The resulting mixture was stirred in an oil bath kept at 100° C. for 20 minutes, whilst taking care to protect it from moisture. The disappearance of the starting compound was confirmed by thin layer chromatography (using methylene chloride containing 5% v/v methanol as the developing solvent). When the starting compound had disappeared, 513 ml of diisopropyl ether were added, whilst stirring, to the reaction mixture, and the mixture was allowed to stand for 1 hour, whilst ice-cooling. At the end of this time, insoluble materials were collected by filtration. The insoluble materials were completely dissolved in 513 ml of propanol by heating with stirring, and the solution was allowed to stand overnight in a refrigerator, to give 18.0 g of the title compound as a colorless powder, having the same physico-chemical properties as the product of Example 1.

EXAMPLE 3

2'-Cyano-2'-deoxy-$N^4$-palmitoyl-1-β-D-arabinofuranosylcytosine

A solution of 290 mg (1 mmole) of 2'-cyano-2'-deoxy-1-β-D-arabinofuranosylcytosine monohydrochloride in pyridine was azeotropically distilled three times, and the residue was dissolved again in pyridine. 0.65 ml (5 mmole) of trimethylsilyl chloride were then added to the solution, whilst ice-cooling, and the mixture was stirred for 30 minutes, whilst still ice-cooling. 1.53 g (5 mmole) of palmitoyl chloride were then added to the mixture, which was then stirred at room temperature for 5 hours. At the end of this time, 2 ml of water were added to the reaction mixture, whilst ice-cooling, and the mixture was stirred at room temperature for 2 hours. The solvent was then removed by distillation under reduced pressure, and the residue was mixed with a 1:2:2 by volume mixture of water, pyridine and methylene chloride. The organic layer was separated, washed with water and dried over anhydrous magnesium sulfate, after which the solvent was removed by distillation under reduced pressure. The residue was dissolved in a 96:4 by volume mixture of methylene chloride and methanol, and placed on a column packed with silica gel. The column was eluted with the same mixture of methylene chloride and methanol as described above, to give 0.44 g of the title compound, having the same physico-chemical properties as the product of Example 1.

EXAMPLE 4

2'-Cyano-2'-deoxy-$N^4$-palmitoyl-1-β-D-arabinofuranosylcytosine

4(a) $N^4$-palmitoylcytidine

A mixture of 24.3 g (100 mmole) of cytidine and 54.34 g (110 mmole) of palmitic anhydride was placed in a round-bottomed flask, and 60 ml of dimethylformamide were added to the mixture. The resulting mixture was stirred in an oil bath kept at 100° C. for 4 hours and then cooled to room temperature, after which 500 ml of diisopropyl ether were added, with stirring. The crystals thus obtained were collected by filtration and recrystallized from 500 ml of propanol. The resulting crystals were again collected by filtration and dried in a desiccator, to give 44.85 g of the title compound as a colorless powder.

Nuclear Magnetic Resonance Spectrum (hexadeuterated dimethyl sulfoxide, 270 MHz) δ ppm:

10.81 (1H, singlet);

8.40 (1H, doublet, J=7.32 Hz);

7.20 (1H, doublet, J=7.33 Hz);

5.76 (1H, doublet, J=2.44 Hz);

5.45 (1H, singlet);

5.08 (2H, doublet, J=29.78 Hz);

3.90 (1H, singlet);

3.95 (2H, triplet, J=4.88 Hz);

3.66 (2H, doublet of doublets, J=12.21 & 40.00 Hz).

4(b) 3',5'-O-(1,1,3,3-Tetraisopropyldisiloxane-1,3-diyl)-$N^4$-palmitoyl-1-β-D-ribofuranosylcytosine 6.71 ml (21 mmole) of 1,3-dichloro-1,1,3,3-tetraisopropyldisiloxane were added to a solution of 10.11 g (21 mmole) of $N^4$-palmitoylcytidine [prepared as described in step (a) above] in 105 ml of pyridine, and the resulting mixture was stirred at room temperature for 21 hours. At the end of this time, 2.225 g (21 mmole) of sodium carbonate, 1.76 g (21 mmole) of sodium hydrogencarbonate and 10 ml of methanol were added to the reaction mixture, and the mixture thus obtained was concentrated to dryness by evaporation under reduced pressure. The resulting residue was mixed with ethanol and again concentrated by evaporation under reduced pressure. This operation was repeated once again. The residue was then mixed with toluene and again concentrated three times by evaporation under reduced pressure. The residue was diluted with 100 ml of ethyl acetate, and the resulting dilute solution was placed on a microwave vibrator and then allowed to stand in a refrigerator. Insoluble materials were filtered off, and the filtrate was concentrated to dryness by evaporation under reduced pressure, to give 17 g of a crude product. This crude product was purified by column chromatography through silica gel, using methylene chloride containing 1% v/v methanol as the eluent. Those fractions containing the desired compound were collected and concentrated to dryness by evaporation under reduced pressure, to give 14.5 g of the title compound as a colorless caramel-like solid.

Nuclear Magnetic Resonance Spectrum (hexadeuterated dimethyl sulfoxide, 270 MHz) δ ppm:

10.84 (1H, multiplet);
8.12 (1H, doublet, J=7.33 Hz);
7.22 (1H, doublet, J=7.33 Hz);
5.59 (1H, singlet);
4.24 (1H, singlet);
4.19 (1H, singlet);
4.05 (2H, quartet, J=6.35 & 7.32 Hz);
3.95 (1H, singlet);
2.37 (2H, triplet, J=7.3 Hz);
1.52 (2H, singlet);
0.82–1.23 (55H).

4(c) 1-[3,5-O-(1,1,3,3-tetraisopropyldisiloxane-1,3-diyl)-β-D-erythropentofuran-2-urosyl]-N$^4$-palmitoylcytosine 7.41 g (19.71 mmole) of pyridinium dichromate, 6 g of molecular sieve 3A and 1.86 ml (19.71 mmole) of acetic anhydride were added to 50 ml of dry methylene chloride, and the resulting mixture was stirred for 30 minutes. A solution of 4.76 g (6.57 mmole) of 3',5'-O-(1,1,3,3-tetraisopropyldisiloxane-1,3-diyl)-N$^4$-palmitoyl-1-β-D-ribofuranosylcytosine [prepared as described in step (b) above] dissolved in 30 ml of methylene chloride was then added to the mixture. The reaction mixture was then stirred at room temperature for 7 hours, after which 100 ml of ethyl acetate were added, and insoluble materials were filtered off. The filtrate was washed with 50 ml each of 0.5N aqueous hydrochloric acid, a saturated aqueous solution of sodium chloride, a saturated aqueous solution of sodium hydrogencarbonate (twice) and again a saturated aqueous solution of sodium chloride, in that order, and dried over anhydrous magnesium sulfate. It was then concentrated to dryness by evaporation under reduced pressure, to give 4.19 g of the title compound as a crude product.

Nuclear Magnetic Resonance Spectrum (hexadeuterated dimethyl sulfoxide, 270 MHz) δ ppm:

10.9 (1H, doublet, J=18.07 Hz);
8.14 (1H, doublet, J=7.32 Hz);
7.26 (1H, doublet, J=7.33 Hz);
6.09 (1H, doublet, J=7.32 Hz);
5.06 (1H, doublet, J=8.3 Hz);
3.93–4.03 (6H, multiplet);
2.39 (2H, multiplet);
1.51 (2H, doublet, J=5.86 Hz);
0.82–1.23 (55H).

4(d) 2'-Cyano-3',5'-O-(1,1,3,3-tetraisopropyldisiloxane-1,3-diyl)-N$^4$-palmitoyl-1-β-D-ribofuranosylcytosine 121 ml of a 1M aqueous solution of sodium dihydrogenphosphate dihydrate and 4.47 g of sodium cyanide were added, with stirring, to a solution of 33.83 g (46.84 mmole) of 1-[3,5-O-(1,1,3,3-tetraisopropyldisiloxane-1,3-diyl)-β-D-erythropentofuran-2-urosyl]-N$^4$-palmitoylcytosine [prepared as described in step (c) above] in 243 ml of ethyl acetate, and the resulting mixture was stirred vigorously at room temperature for 4.5 hours. At the end of this time, the organic layer was separated and washed three times, each time with 100 ml of a saturated aqueous solution of sodium chloride. The solution was dried over anhydrous magnesium sulfate, the drying agent was filtered off and the filtrate was concentrated to dryness by evaporation under reduced pressure, to give 35.57 g of the title compound as a crude product.

Nuclear Magnetic Resonance Spectrum (hexadeuterated dimethyl sulfoxide, 270 MHz) δ ppm:

10.97 (1H, doublet, J=9.76 Hz);
7.82 (1H, doublet, J=7.32 Hz);
7.68 (1H, singlet);
7.23–7.32 (1H, multiplet);
6.33 (1H, singlet);
4.24 (1H, triplet, J=7.32 Hz);
3.92–4.13 (6H, multiplet);
2.37–2.42 (2H, multiplet);
1.53 (2H, triplet, J=5.61 Hz);
0.82–1.23 (55H).

4(e) 2'-Cyano-3',5'-O-(1,1,3,3-tetraisopropyldisiloxane-1,3-diyl)-N$^4$-palmitoyl-2'-phenoxythiocarbonyloxy-β-D-ribofuranosylcytosine 123 mg (1.01 mole) of 4-(N,N-dimethylamino)pyridine, 8.74 ml (63.21 mole) of phenoxythiocarbonyl chloride and 8.81 ml (63.21 mole) of triethylamine were added to a solution of 31.57 g (4 mole) of 2'-cyano-3',5'-O-(1,1,3,3-tetraisopropyldisiloxane-1,3-diyl)-N$^4$-palmitoyl-1-β-D-ribofuranosylcytosine [prepared as described in step (d) above] in 250 ml of methylene chloride, under a stream of nitrogen, and the resulting mixture was stirred for 6 hours. At the end of this time, the reaction mixture was washed three times, each time with 100 ml of a saturated aqueous solution of sodium chloride, and was then dried over anhydrous magnesium sulfate. The drying agent was removed by filtration, and the filtrate was concentrated to dryness by evaporation under reduced pressure, to give 39.37 g of the title compound as a crude product.

Nuclear Magnetic Resonance Spectrum (hexadeuterated dimethyl sulfoxide, 270 MHz) δ ppm:

11.08 (1H, singlet);
7.98 (1H, doublet, J=7.32 Hz);
7.29 (5H, multiplet);
6.97 (1H, doublet, J=7.32 Hz);
6.81 (1H, singlet);
4.03–4.21 (12H, multiplet);
2.41–2.48 (2H, multiplet);
1.54 (2H, doublet, J=6.35 Hz);
0.82–1.22 (55H).

4(f) 2'-Cyano-2'-deoxy-N$^4$-palmitoyl-3',5'-O-(1,1,3,3-tetraisopropyldisiloxane-1,3-diyl)-β-D-arabinofuranosylcytosine 1.029 g (6.268 mmole) of azobisisobutyronitrile and 16.88 ml (62.68 mmole) of tributyltin hydride were added, under a stream of nitrogen, to a solution of 37 g (41.79 mmole) of 2'-cyano-3',5'-O-(1,1,3,3-tetraisopropyldisiloxane-1,3-diyl)-N$^4$-palmitoyl-2'-phenoxythiocarbonyloxy-β-D-ribofuranosylcytosine [prepared as described in step (e) above] in 210 ml of toluene, and the resulting mixture was heated under reflux in an oil bath kept at 100° C. for 3.5 hours. At the end of this time, the reaction mixture was concentrated to dryness by evaporation under reduced pressure. The residue was dissolved in methylene chloride and purified by column chromatography through silica gel, using methylene chloride containing 2% v/v methanol as the eluent, to give 16.33 g of the title compound as a caramel-like solid.

4(g) 2'-Cyano-2'-deoxy-$N^4$-palmitoyl-β-D-arabinofuranosylcytosine

Following a procedure similar to that described in Example 1(d), the title compound, having the same physico-chemical properties as the product of Example 1, was obtained in a yield of 67%.

EXAMPLE 5

2'-Cyano-2'-deoxy-5'-O-palmitoyl-1-β-D-arabinofuranosylcytosine

5(a) $N^4$-Benzyloxycarbonyl-2'-cyano-2'-deoxy-1-β-D-arabinofuranosylcytosine

A solution of 2.89 g (10 mmole) of 2'-cyano-2'-deoxy-1-β-D-arabinofuranosylcytosine [prepared as described in Example 1(a)] in pyridine was distilled azeotropically, and the residue was dissolved in 50 ml of pyridine. 6.32 ml (50 mmole) of trimethylsilyl chloride were gradually added to the resulting solution, whilst ice-cooling, and the resulting mixture was stirred at room temperature for 1 hour. 24.4 ml (50 mmole) of a 30–35% solution of carbobenzoxy chloride in toluene were then added dropwise, whilst ice-cooling. The reaction mixture was stirred at room temperature and then allowed to stand overnight. At the end of this time, 20 ml of water were added to the mixture, whilst ice-cooling, and the mixture was stirred at room temperature for 2 hours, after which methylene chloride was added. The organic layer was separated, washed three times, each time with a saturated aqueous solution of sodium chloride, and dried over anhydrous magnesium sulfate. The solvent was then removed by distillation under reduced pressure, and the residue was purified by column chromatography through silica gel, using a 96:4 by volume mixture of methylene chloride and methanol as the eluent, to give 1.72 g of the title compound as fine white needles.

Nuclear Magnetic Resonance Spectrum (hexadeuterated dimethyl sulfoxide, 270 MHz) δ ppm:

10.92 (1H, singlet);
8.36 (1H, doublet, J=7.3 Hz);
7.34–7.44 (5H, multiplet);
7.11 (1H, doublet, J=7.3 Hz);
6.25 (1H, doublet, J=5.4 Hz);
6.21 (1H, doublet, J=6.8 Hz);
5.24 (1H, doublet, J=5.4 Hz);
5.20 (2H, singlet);
4.40–4.47 (1H, multiplet);
3.63–3.93 (4H, multiplet).

5(b) $N^4$-Benzyloxycarbonyl-2'-cyano-2'-deoxy-5'-O-dimethoxytrityl-1-β-D-arabinofuranosylcytosine A solution of 1.70 g (4.40 mmole) of $N^4$-benzyloxycarbonyl-2'-cyano-2'-deoxy-1-β-D-arabinofuranosylcytosine [prepared as described in step (a) above] in pyridine was distilled azeotropically, and the resulting residue was dissolved in 50 ml of pyridine. 2.16 g (6.60 mmole) of dimethoxytrityl chloride were added to the solution, and the resulting mixture was stirred at room temperature for 6 hours in a stream of nitrogen. The reaction mixture was allowed to stand overnight, and then 0.72 g (2.20 mmole) of dimethoxytrityl chloride was added. The mixture was then stirred for 1 hour. At the end of this time, the solvent was removed by distillation under reduced pressure, and the residue was dissolved in ethyl acetate. The resulting solution was washed with a saturated aqueous solution of sodium chloride and dried over anhydrous magnesium sulfate. The solvent was then removed by distillation under reduced pressure, and the residue was purified by column chromatography through silica gel, using a 98:2 by volume mixture of methylene chloride and methanol as the eluent, to give 2.37 g of the title compound as a foam.

Nuclear Magnetic Resonance Spectrum (hexadeuterated dimethyl sulfoxide, 270 MHz) δ ppm:

10.95 (1H, singlet);
8.24 (1H, doublet, J=7.3 Hz);
7.25–7.43 (9H, multiplet);
6.90–6.96 (5H, multiplet);
6.38 (1H, doublet, J=5.9 Hz);
6.27 (1H, doublet, J=7.3 Hz);
5.20 (2H, singlet);
4.57–4.62 (1H, multiplet);
3.94–3.98 (2H, multiplet);
3.75 (6H, singlet);
3.42 (2H, doublet of doublets, J=4.4 & 11.0 Hz).

5(c) $N^4$-Benzyloxycarbonyl-3'-O-t-butyldimethylsilyl-2'-cyano-2'-deoxy-1-β-D-arabinofuranosylcytosine 6.41 g (42.52 mmole) of t-butyldimethylsilyl chloride and 3.29 g (48.3 mmole) of imidazole were added to a solution of 3.27 g (4.75 mmole) of $N^4$-benzyloxycarbonyl-2'-cyano-2'-deoxy-5'-O-dimethoxytrityl-1-β-D-arabinofuranosylcytosine [prepared as described in step (b) above] in 150 ml of dimethylformamide, and the resulting mixture was stirred at room temperature for 4 hours in a stream of nitrogen, after which it was allowed to stand overnight at the same temperature. The solvent was then removed by distillation under reduced pressure, and the resulting residue was dissolved in ethyl acetate. The solution was washed with a saturated aqueous solution of sodium chloride and dried over anhydrous magnesium sulfate. The solvent was then removed by distillation under reduced pressure, and the residue was mixed with 50 ml of methylene chloride. Insoluble materials were filtered off, and 50 ml of methylene chloride containing 5% v/v trifluoroacetic acid were added dropwise, whilst ice-cooling, to the filtrate. The mixture was then stirred for 2 hours, whilst ice-cooling. At the end of this time, 150 ml of a saturated aqueous solution of sodium hydrogencarbonate were added to the reaction mixture, and the mixture was stirred for 15 minutes. The organic layer was then separated and washed with a saturated aqueous solution of sodium hydrogencarbonate and a saturated aqueous solution of sodium chloride, in that order. The mixture was then dried over anhydrous magnesium sulfate, and the solvent was removed by distillation under reduced pressure. The resulting residue was purified by column chromatography through silica gel, using a 98:2 by volume mixture of methylene chloride and methanol as the eluent, to give 1.77 g of the title compound as a foam.

Nuclear Magnetic Resonance Spectrum (hexadeuterated dimethyl sulfoxide, 270 MHz) δ ppm:

10.94 (1H, singlet);
8.33 (1H, doublet, J=7.8 Hz);
7.13 (1H, doublet, J=7.8 Hz);
6.23 (1H, doublet, J=7.3 Hz);
4.61 (1H, triplet, J=7.3 Hz);
3.99–4.04 (1H, multiplet);
3.56–3.89 (3H, multiplet);
0.88 (9H, singlet);

0.14–0.15 (6H, multiplet).

5(d) $N^4$-Benzyloxycarbonyl-3'-O-t-butyldimethylsilyl-2'-cyano-2'-deoxy-5'-O-palmitoyl-1-β-D-arabinofuranosylcytosine A mixture of 1.75 g (3.58 mmole) of $N^4$-benzyloxycarbonyl-3'-O-t-butyldimethylsilyl-2'-cyano-2'-deoxy-1-β-D-arabinofuranosylcytosine [prepared as described in step (c) above] and pyridine was distilled azeotropically, and the residue was dissolved in 50 ml of pyridine. 0.96 ml of palmitoyl chloride and 87 mg (0.72 mmole) of dimethylaminopyridine were added to the solution, and the resulting mixture was stirred at room temperature for 6 hours, after which 0.96 ml of palmitoyl chloride were added to the mixture. The mixture was allowed to stand overnight at room temperature, and then the solvent was removed by distillation under reduced pressure. The resulting residue was dissolved in ethyl acetate, and the solution was washed with 0.1N aqueous hydrochloric acid, with a saturated aqueous solution of sodium hydrogencarbonate and with an aqueous solution of sodium chloride, in that order. The mixture was dried over anhydrous magnesium sulfate, and then the solvent was removed by distillation under reduced pressure. The resulting residue was purified by column chromatography through silica gel, using a 98.4:1.6 by volume mixture of methylene chloride and methanol as the eluent, to give 1.71 g of the title compound as a foam.

Nuclear Magnetic Resonance Spectrum (hexadeuterated dimethyl sulfoxide, 270 MHz) δ ppm:

10.98 (1H, singlet);
8.07 (1H, doublet, J=7.8 Hz);
7.34–7.43 (5H, multiplet);
7.15 (1H, doublet, J=7.8 Hz);
6.27 (1H, doublet, J=7.8 Hz);
5.20 (2H, singlet);
4.68 (1H, triplet, J=7.3 Hz);
4.02–4.38 (4H, multiplet);
2.35–2.40 (2H, multiplet);
1.51–1.56 (2H, multiplet);
1.22 (24H, singlet);
0.82–0.88 (12H, multiplet);
0.13–0.16 (6H, multiplet).

5(e) $N^4$-Benzyloxycarbonyl-2'-cyano-2'-deoxy-5'-O-palmitoyl-1-β-D-arabinofuranosylcytosine 0.13 ml (2.29 mole) of acetic acid and 1.22 g (4.65 mole) of tetrabutylammonium fluoride were added to a solution of 1.69 g (2.29 mole) of $N^4$-benzyloxycarbonyl-3'-O-t-butyldimethylsilyl-2'-cyano-2'-deoxy-5'-O-palmitoyl-1-β-D-arabinofuranosylcytosine [prepared as described in step (d) above] in 35 ml of tetrahydrofuran, in a stream of nitrogen and whilst ice-cooling. The resulting mixture was then stirred for 2 hours, also whilst ice-cooling. At the end of this time, the solvent was removed by distillation under reduced pressure, and the resulting residue was subjected to column chromatography through silica gel, using a 97:3 by volume mixture of methylene chloride and methanol as the eluent, to give 1.06 g of the title compound as fine white needles.

Nuclear Magnetic Resonance Spectrum (hexadeuterated dimethyl sulfoxide, 270 MHz) δ ppm:

10.97 (1H, singlet);
8.07 (1H, doublet, J=7.8 Hz);
7.32–7.43 (5H, multiplet);
7.14 (1H, doublet, J=7.3 Hz);
6.39 (1H, doublet, J=4.9 Hz);
6.22 (1H, doublet, J=7.3 Hz);
5.20 (2H, singlet);
3.92–4.48 (5H, multiplet);
2.35 (2H, triplet, J=7.3 Hz);
1.50–1.55 (2H, multiplet);
1.22 (24H, broad singlet);
0.82–0.87 (3H, multiplet).

5(f) 2'-Cyano-2'-deoxy-5'-O-palmitoyl-1-β-D-arabinofuranosylcytosine

A solution of 1.00 g (1.60 mmole) of $N^4$-benzyloxycarbonyl-2'-cyano-2'-deoxy-5'-O-palmitoyl-1-β-D-arabinofuranosylcytosine [prepared as described in step (e) above] dissolved in 50 ml of acetic acid was stirred at room temperature for 3 hours in the presence of 100 mg of 10% w/w palladium-on-charcoal and in an atmosphere of hydrogen. At the end of this time, the catalyst was removed by filtration, and the filtrate was freed from the solvent by distillation under reduced pressure. The residue was mixed with ethanol, and the mixture was subjected to azeotropic distillation. The residue was dissolved in a mixture of methylene chloride and ethanol, and the resulting solution was filtered through a membrane filter. The filtrate was freed from the solvent by distillation under reduced pressure, and the residue was lyophilized from benzene, to give 563 mg of the title compound as a colorless powder.

EXAMPLE 6

$N^4$-Acetyl-2'-cyano-2'-deoxy-5'-O-palmitoyl-1-β-D-arabinofuranosylcytosine

6(a) $N^4$-Acetyl-2'-cyano-2'-deoxy-5'-O-dimethoxytrityl-1-β-D-arabinofuranosylcytosine 1.73 g (5.097 mmole) of dimethoxytrityl chloride were added to a solution of 1.0 g (3.398 mmole) of $N^4$-acetyl-2,-cyano-2'-deoxy-1-β-D-arabinofuranosylcytosine in 25 ml of pyridine, and the resulting mixture was stirred at room temperature and then allowed to stand overnight at the same temperature. At the end of this time, the solvent was removed by distillation under reduced pressure, and the residue was mixed with ethyl acetate and water. The organic layer was separated, washed with a saturated aqueous solution of sodium chloride and dried over anhydrous magnesium sulfate. The solvent was distilled off under reduced pressure, and the residue was purified by column chromatography through silica gel, using a 95:5 by volume mixture of methylene chloride and methanol as the eluent, to give 1.90 g of a fraction mainly consisting of the title compound.

Nuclear Magnetic Resonance Spectrum (hexadeuterated dimethyl sulfoxide, 270 MHz) δ ppm:

10.96 (1H, singlet);
8.23 (1H, doublet, J=7.8 Hz);
7.24–7.41 (10H, multiplet);
7.11 (1H, doublet, J=7.8 Hz);
6.88–6.92 (5H, multiplet);
6.37 (1H, doublet, J=5.9 Hz);
6.28 (1H, doublet, J=7.3 Hz);
4.57–4.62 (1H, multiplet);
3.93–3.99 (2H, multiplet);
3.75 (6H, singlet);
3.31–3.41 (2H, multiplet);
2.11 (3H, singlet).

6(b) $N^4$-Acetyl-3'-O-t-butyldimethylsilyl-2'-cyano-2'-deoxy-1-β-D-arabinofuranosylcytosine 4.22 g (28 mmole) of t-butyldimethylsilyl chloride and 2.17 g (31.84 mmole) of imidazole were added to a solution of 1.90 g (3.18 mmole) of $N^4$-acetyl-2'-cyano-2'-deoxy-5'-O-dimethoxytrityl-1-β-D-arabinofuranosylcytosine [prepared as described in step (a) above] in 150 ml of dimethylformamide, and the resulting mixture was stirred at room temperature for 7 hours and then allowed to stand overnight at the same temperature. At the end of this time, the solvent was removed by distillation under reduced pressure, and the resulting residue was mixed with water containing 80% by volume acetic acid. The mixture was then heated under reflux for 15 minutes, after which the solvent was distilled off under reduced pressure, and the residue was dissolved in ethyl acetate. The resulting solution was washed with a saturated aqueous solution of sodium hydrogencarbonate and with a saturated aqueous solution of sodium chloride, in that order. The solution was dried over anhydrous magnesium sulfate, and then the solvent was distilled off under reduced pressure. The residue was purified by column chromatography through silica gel, using a 99:1 by volume mixture of methylene chloride and methanol as the eluent, to give 0.89 g of the title compound as a foam.

Nuclear Magnetic Resonance Spectrum (hexadeuterated dimethyl sulfoxide, 270 MHz) δ ppm:

10.96 (1H, singlet);
8.33 (1H, doublet, J=7.8 Hz);
7.27 (1H, doublet, J=7.8 Hz);
6.24 (1H, doublet, J=7.3 Hz);
5.26–5.30 (1H, multiplet);
4.61 (1H, triplet, J=7.3 Hz);
4.01 (1H, triplet, J=7.3 Hz);
3.56–3.89 (3H, multiplet);
2.11 (3H, singlet);
0.89 (9H, singlet);
0.12–0.15 (6H, multiplet).

6(c) $N^4$-Acetyl-3'-O-t-butyldimethylsilyl-2'-cyano-2'-deoxy-5'-O-palmitoyl-1-β-D-arabinofuranosylcytosine 0.90 ml (2.94 mmole) of palmitoyl chloride were added, whilst ice-cooling, to a solution of 0.60 g (1.47 mmole) of $N^4$-acetyl-3'-O-t-butyldimethylsilyl-2'-cyano-2'-deoxy-1-β-D-arabinofuranosylcytosine [prepared as described in step (b) above] in 30 ml of pyridine, and the resulting mixture was stirred at room temperature for 3.5 hours. At the end of this time, the solvent was removed by distillation under reduced pressure, and the residue was mixed with a mixture of ethyl acetate and water. The organic layer was separated, washed with 0.1N aqueous hydrochloric acid, with a saturated aqueous solution of sodium hydrogencarbonate and with a saturated aqueous solution of sodium chloride, in that order, and dried over anhydrous magnesium sulfate. The solvent was removed by distillation under reduced pressure, and the residue was purified by column chromatography through silica gel, using a 97:3 by volume mixture of methylene chloride and methanol as the eluent, to give 0.35 g of the title compound as a foam.

Nuclear Magnetic Resonance Spectrum (hexadeuterated dimethyl sulfoxide, 270 MHz) δ ppm:

10.99 (1H, singlet);
8.08 (1H, doublet, J=7.8 Hz);
7.30 (1H, doublet, J=7.8 Hz);
6.27 (1H, doublet, J=7.8 Hz);
4.69 (1H, triplet, J=7.3 Hz);
4.22–4.38 (2H, multiplet);
4.02–4.09 (2H, multiplet);
2.37 (2H, triplet, J=7.3 Hz);
2.12 (3H, singlet);
1.51–1.56 (2H, multiplet);
1.23 (24H, singlet);
0.83–0.88 (12H, multiplet);
0.14 (6H, doublet, J=8.3 Hz).

6(d) $N^4$-Acetyl-2'-cyano-2'-deoxy-5'-O-palmitoyl-1-β-D-arabinofuranosylcytosine 0.02 ml (0.356 mmole) of acetic acid and 186 mg (0.711 mmole) of tetrabutylammonium fluoride were added, whilst ice-cooling and under a stream of nitrogen, to a solution of 0.23 g (0.356 mmole) of $N^4$-acetyl-3'-O-t-butyldimethylsilyl-2'-deoxy-5'-O-palmitoyl-1-β-D-arabinofuranosylcytosine [prepared as described in step (c) above] in 5 ml of tetrahydrofuran, and the resulting mixture was stirred for 2 hours, whilst still ice-cooling. The solvent was then removed by distillation under reduced pressure, and the residue was purified by column chromatography through silica gel, using a 97:3 by volume mixture of methylene chloride and methanol as the eluent. The crude product thus obtained was recrystallized from benzene to give 176 mg of the title compound as fine white needles.

Nuclear Magnetic Resonance Spectrum (hexadeuterated dimethyl sulfoxide, 270 MHz) δ ppm:

10.98 (1H, singlet);
8.07 (1H, doublet, J=7.8 Hz);
7.29 (1H, doublet, J=7.3 Hz);
6.38 (1H, doublet, J=5.9 Hz);
6.23 (1H, doublet, J=7.3 Hz);
3.92–4.51 (5H, multiplet);
2.35 (2H, triplet, J=7.3 Hz);
2.11 (3H, singlet);
1.50–1.55 (2H, multiplet);
1.22 (24H, singlet);
0.83–0.88 (3H, multiplet).

EXAMPLE 7

2'-Cyano-2'-deoxy-3'-O-palmitoyl-1-β-D-arabinofuranosylcytosine

7(a) 2'-Cyano-2'-deoxy-$N^4$,5'-O-bis(dimethoxytrityl)-1-β-D-arabinofuranosylcytosine A mixture of 2.0 g (6.93 mmole) of 2'-cyano-2'-deoxy-1-β-D-arabinofuranosylcytosine monohydrochloride and pyridine was distilled azeotropically, and the resulting residue was dissolved in 50 ml of pyridine. 3.52 g (10.4 mmole) of dimethoxytrityl chloride were added to the solution, and the resulting mixture was stirred at room temperature for 2 hours in an atmosphere of nitrogen. At the end of this time, the solvent was removed by distillation under reduced pressure, and the residue was dissolved in ethyl acetate. This solution was washed with a saturated aqueous solution of sodium chloride and dried over anhydrous magnesium sulfate. The solvent was then removed by distillation under reduced pressure, and the residue was purified by column chromatography through silica gel, using a 95:5 by volume mixture of methylene chloride and methanol as the eluent, to give 2.5 g of the title compound as a foam.

Nuclear Magnetic Resonance Spectrum (hexadeuterated dimethyl sulfoxide, 270 MHz) δ ppm:

8.50 (1H, broad singlet);
7.65 (1H, doublet, J=7.3 Hz);
7.10–7.37 (17H, multiplet);

6.81–6.91 (10H, multiplet);

6.23 (1H, doublet, J=6.8 Hz);

6.15 (1H, doublet, J=7.3 Hz);

4.47–4.49 (1H, multiplet);

3.81–3.84 (2H, multiplet);

3.28 (2H, broad singlet);

3.72–3.74 (12H, multiplet).

7(b) 2'-Cyano-2'-deoxy-3'-O-palmitoyl-1-β-D-arabinofuranosylcytosine 1.90 ml (6.18 mmole) of palmitoyl chloride and 60 mg (0.49 mmole) of dimethylaminopyridine were added to a solution of 2.12 g (2.47 mmole) of 2'-cyano-2'-deoxy-$N^4$, 5'-O-bis(dimethoxytrityl)-1-β-D-arabinofuranosylcytosine [prepared as described in step (a) above] in 100 ml of pyridine, and the resulting mixture was stirred at room temperature for 4 hours. At the end of this time, 0.38 mg (1.24 mmole) of palmitoyl chloride and 20 mg (0.07 mmole) of dimethylaminopyridine were added. The reaction mixture was then stirred at room temperature for 2.5 hours, after which the solvent was removed by distillation under reduced pressure. The residue was dissolved in ethyl acetate, and the resulting solution was washed with a saturated aqueous solution of sodium chloride. It was then dried over anhydrous magnesium sulfate, the solvent was removed by distillation under reduced pressure, and the residue was mixed with 140 ml of water containing 90% by volume acetic acid. The mixture was heated at 60° C. for 1 hour, and then the solvent was removed by distillation under reduced pressure. The residue was purified by column chromatography through silica gel, using a 90:10 by volume mixture of methylene chloride and methanol as the eluent. Those fractions containing the title compound were collected and concentrated by evaporation under reduced pressure, to give 0.85 g of a residue, which was recrystallized from 6 ml of methanol to give 270 mg of the title compound as fine white needles.

Nuclear Magnetic Resonance Spectrum (hexadeuterated dimethyl sulfoxide, 270 MHz) δ ppm:

7.82 (1H, doublet, J=7.3 Hz);

7.32 (1H, broad singlet);

7.27 (1H, broad singlet);

6.12 (1H, doublet, J=6.8 Hz);

5.79 (1H, doublet, J=7.3 Hz);

5.40–5.44 (1H, multiplet);

5.18–5.22 (1H, multiplet);

4.03–4.12 (2H, multiplet);

3.57–3.75 (2H, multiplet);

2.34–2.39 (2H, triplet, J=7.3 Hz);

1.51–1.56 (2H, triplet, J=6.8 Hz);

1.24 (24H, singlet);

0.83–0.89 (3H, multiplet).

EXAMPLE 8

2'-Cyano-2'-deoxy-3',5'-di-O-palmitoyl-1-β-D-arabinofuranosylcytosine

8(a) 2'-Cyano-2'-deoxy-$N^4$-(2,2,2-trichloroethyloxycarbonyl)-1-β-D-arabinofuranosylcytosine 4.42 ml of chlorotrimethylsilane were added, at 0° C. and in an atmosphere of nitrogen, to a solution of 2.00 g of 2'-cyano-2'-deoxy-1-β-D-arabinofuranosylcytosine monohydrochloride in 35 ml of pyridine, and the resulting mixture was stirred for 2 hours, after which 4.65 ml of 2,2,2-trichloroethyl chloroformate were added. The reaction mixture was stirred overnight at room temperature, after which it was mixed with 15 ml of water, stirred for 2 hours and extracted with methylene chloride. The extract was dried over anhydrous magnesium sulfate, and the solvent was removed by distillation under reduced pressure. The residue was purified by column chromatography through silica gel, using a 95:5 by volume mixture of methylene chloride and methanol as the eluent, to give 2.35 g of the title compound as fine white needles.

Nuclear Magnetic Resonance Spectrum (CD$_3$OD+CDCl$_3$, 270 MHz) δ ppm:

8.48 (1H, doublet, J=8 Hz);

7.37 (1H, doublet, J=8 Hz);

6.27 (1H, doublet, J=7 Hz);

4.92 (2H, singlet);

4.61 (1H, triplet, J=7 Hz);

3.70–4.10 (12H, multiplet).

8(b) 2'-Cyano-2'-deoxy-3',5'-di-O-palmitoyl-$N^4$-(2,2,2-trichloroethoxycarbonyl)-1-β-D-arabinofuranosylcytosine 7 mg of 4-dimethylaminopyridine, 575 mg of dicyclohexylcarbodiimide and 716 mg of palmitic acid were added to a solution of 542 mg of 2'-cyano-2'-deoxy-$N^4$-(2,2,2-trichloroethyloxycarbonyl)-1-β-D-arabinofuranosylcytosine [prepared as described in step (a) above] in 16 ml of tetrahydrofuran, and the resulting mixture was stirred at room temperature for 7.5 hours in an atmosphere of nitrogen. 366 mg of palmitic acid and 263 mg of dicyclohexylcarbodiimide were then added to the mixture, which was then stirred overnight at room temperature. At the end of this time, 163 mg of palmitic acid and 132 mg of dicyclohexylcarbodiimide were added to the reaction mixture, and the mixture was stirred for a further 4 hours. The resulting precipitate was filtered off, and the filtrate was freed from the solvent by distillation under reduced pressure. The residue was dissolved in tetrahydrofuran, and the resulting precipitate was removed by filtration. The filtrate was concentrated by evaporation under reduced pressure, and the residue was dissolved in ethyl acetate. The resulting precipitate was again removed by filtration. The filtrate was washed with 0.1N aqueous hydrochloric acid and with a saturated aqueous solution of sodium chloride, in that order, and dried over anhydrous magnesium sulfate. The solvent was removed by distillation under reduced pressure, and the residue was purified by column chromatography through silica gel, using a 3:1 by volume mixture of cyclohexane and ethyl acetate as the eluent, to give 700 mg of the title compound.

Nuclear Magnetic Resonance Spectrum (CDCl$_3$, 270 MHz) δ ppm:

8.03 (1H, doublet, J=7 Hz);

7.35 (1H, doublet, J=7 Hz);

6.15 (1H, doublet, J=5 Hz);

5.43 (1H, doublet, J=2 Hz);

4.85 (2H, singlet);

4.60 (1H, doublet of doublets, J=13 & 3 Hz);

4.42 (1H, doublet of doublets, J=13 & 3 Hz);

4.33 (1H, multiplet);

4.03 (1H, doublet, J=5 Hz);

2.43 (2H, triplet, J=7 Hz);

2.38 (2H, triplet, J=7 Hz);

1.50–1.60 (4H, multiplet);

1.10–1.40 (48H, multiplet);

0.88 (6H, triplet, J=7 Hz).

8(c) 2'-Cyano-2'-deoxy-3',5'-di-O-palmitoyl-1-β-D-arabinofuranosylcytosine 16.3 ml of a 1M aqueous solution of sodium dihydrogenphosphate and 358 mg of zinc dust were added to a solution of 355 mg of 2'-cyano-2'-deoxy-3',5'-di-O-palmitoyl-N$^4$-(2,2,2-trichloroethoxycarbonyl)-1-β-D-arabinofuranosylcytosine [prepared as described in step (b) above] in 16.5 ml of tetrahydrofuran, and the resulting mixture was stirred at room temperature for 2 hours, after which it was allowed to stand overnight in a refrigerator. At the end of this time, the solvent was removed by distillation under reduced pressure, and the resulting residue was extracted with a 2:1 by volume mixture of methylene chloride and methanol, with heating. Precipitated materials were removed by filtration, and the filtrate was freed from the solvent by distillation under reduced pressure. The residue was dissolved in methylene chloride, and the resulting solution was washed with a saturated aqueous solution of sodium chloride. The organic layer was dried over anhydrous magnesium sulfate and concentrated by evaporation under reduced pressure, to give colorless crystals, which were recrystallized from ethanol to give 170 mg of the title compound. The mother liquor was concentrated by evaporation under reduced pressure, and the residue was purified by column chromatography through silica gel, using a 95:5 by volume mixture of methylene chloride and methanol as the eluent, to give 51 mg of the title compound as white needles.

Nuclear Magnetic Resonance Spectrum (CDCl$_3$, 270 MHz) δ ppm:

7.70 (1H, doublet, J=7 Hz);
5.78 (1H, doublet, J=7 Hz);
6.17 (1H, doublet, J=5 Hz);
5.40 (1H, doublet, J=3 Hz);
4.59 (1H, doublet of doublets, J=12 & 3 Hz);
4.40 (1H, doublet of doublets, J=12 & 4 Hz);
4.26 (1H, multiplet);
3.93 (1H, doublet, J=5 Hz);
2.43 (2H, triplet, J=7 Hz);
2.37 (2H, triplet, J=7 Hz);
1.50–1.70 (4H, multiplet);
1.10–1.40 (48H, multiplet);
0.88 (6H, triplet, J=7 Hz).

EXAMPLE 9

2'-Cyano-2'-deoxy-N$^4$-hexanoyl-1-β-D-arabinofuranosylcytosine 4 ml of dimethylformamide were added to a mixture of 1.00 g (4 mmole) of 2'-cyano-2'-deoxy-1-β-D-arabinofuranosylcytosine [prepared as described in Example 1(a) above] and 1.29 g (6 mmole) of hexanoic anhydride, and the resulting mixture was stirred in an oil bath kept at 100° C. for 30 minutes. At the end of this time, the solvent was removed by distillation under reduced pressure, and the residue was mixed with 100 ml of diisopropyl ether and triturated using an ultrasonic vibrator. Insoluble materials were collected by filtration and dried by evaporation under reduced pressure. They were then dissolved in a small amount of a mixture of methylene chloride and methanol. The solution was purified by column chromatography through silica gel, using a 99:1 by volume mixture of methylene chloride and methanol as the eluent, to give 0.88 g of the title compound as a foam.

Nuclear Magnetic Resonance Spectrum (hexadeuterated dimethyl sulfoxide, 270 MHz) δ ppm:

10.92 (1H, singlet);
8.36 (1H, doublet, J=7.8 Hz);
7.29 (1H, doublet, J=7.3 Hz);
6.26 (1H, doublet, J=5.4 Hz);
6.21 (1H, doublet, J=6.8 Hz);
5.23 (1H, triplet, J=5.4 Hz);
4.43 (1H, quartet, J=7.3 & 13.2 Hz);
3.59–3.93 (4H, multiplet);
2.40 (2H, triplet, J=7.3 Hz);
1.50–1.61 (2H, multiplet);
1.23–1.33 (4H, multiplet);
0.87 (3H, triplet, J=6.8 Hz).

EXAMPLE 10

2'-Cyano-N$^4$-decanoyl-2'-deoxy-1-β-D-arabinofuranosylcytosine 4 ml of dimethylformamide were added to a mixture of 1.00 g (4 mmole) of 2'-cyano-2'-deoxy-1-β-D-arabinofuranosylcytosine [prepared as described in Example 1(a) above] and 1.96 g (6 mmole) of decanoic anhydride, and the resulting mixture was stirred in an oil bath kept at 100° C. for 30 minutes. At the end of this time, the solvent was removed by distillation under reduced pressure, and the resulting residue was mixed with 100 ml of diisopropyl ether and triturated using an ultrasonic vibrator. Insoluble materials were collected by filtration and dried by evaporation under reduced pressure, after which they were dissolved in a small amount of a mixture of methylene chloride and methanol. The solution was purified by column chromatography through silica gel, using a 99:1 by volume mixture of methylene chloride and methanol as the eluent, to give 1.06 g of the title compound as fine white needles.

Nuclear Magnetic Resonance Spectrum (hexadeuterated dimethyl sulfoxide, 270 MHz) δ ppm:

10.91 (1H, singlet);
8.36 (1H, doublet, J=7.3 Hz);
7.29 (1H, doublet, J=7.8 Hz);
6.26 (1H, doublet, J=5.4 Hz);
6.21 (1H, doublet, J=7.3 Hz);
5.24 (1H, triplet, J=5.4 Hz);
4.43 (1H, doublet of doublets, J=7.3 & 12.7 Hz);
3.60–3.93 (4H, multiplet);
2.40 (2H, triplet, J=7.3 Hz);
1.54 (2H, triplet, J=6.8 Hz);
1.25 (12H, broad singlet);
0.83–0.88 (3H, multiplet).

EXAMPLE 11

2'-Cyano-2'-deoxy-N$^4$-lauroyl-1-β-D-arabinofuranosylcytosine 4 ml of dimethylformamide were added to a mixture of 1.00 g (4 mmole) of 2'-cyano-2'-deoxy-1-β-D-arabinofuranosylcytosine [prepared as described in Example 1(a) above] and 2.30 g (6 mmole) of lauric anhydride, and the resulting mixture was stirred in an oil bath kept at 100° C. for 30 minutes. At the end of this time, the solvent was removed by distillation under reduced pressure, and the resulting residue was mixed with 100 ml of diisopropyl ether and triturated using an ultrasonic vibrator. Insoluble materials were collected by filtration and mixed with 100 ml of methanol. The mixture was heated under reflux and then filtered through a membrane filter. The filtrate was allowed to stand overnight in a refrigerator and the crystals which separated were collected by filtration to give 72 mg of first crystals of the title compound. The mother liquor was then freed from the solvent by evaporation under reduced pressure, to give 1.85 g of a residue, which was dissolved in 20 ml of methanol with heating. The solution was allowed to stand in a refrigerator to give a further 663 mg of secondary crystals of the title compound. The mother liquor was then concentrated by evaporation under reduced pressure, to give 1.10 g of a residue, which was purified by column chromatography through silica gel, using a 98:2 by volume mixture of methylene chloride and methanol as the eluent, to give a further 0.47 g of the title compound as crystals.

Nuclear Magnetic Resonance Spectrum (hexadeuterated dimethyl sulfoxide, 270 MHz) δ ppm:

10.92 (1H, singlet);

8.36 (1H, doublet, J=7.8 Hz);

7.29 (1H, doublet, J=7.3 Hz);

6.28 (1H, broad singlet);

6.21 (1H, doublet, J=7.3 Hz);

5.25 (1H, broad singlet);

4.44 (1H, triplet, J=6.8 Hz);

3.61–3.94 (4H, multiplet);

2.40 (2H, triplet, J=7.3 Hz);

1.52–1.57 (2H, multiplet);

1.24 (16H, singlet);

0.85 (3H, triplet, J=6.8 Hz).

EXAMPLE 12

2'-Cyano-2'-deoxy-$N^4$-stearoyl-1-β-D-arabinofuranosylcytosine 2.5 ml of dimethylformamide were added to a mixture of 0.63 g (2.5 mmole) of 2'-cyano-2'-deoxy-1-β-D-arabinofuranosylcytosine [prepared as described in Example 1(a) above] and 1.44 g (2.61 mmole) of stearic anhydride, and the resulting mixture was stirred in an oil bath kept at 100° C. for 30 minutes. At the end of this time, the solvent was removed by distillation under reduced pressure, and the resulting residue was mixed with 100 ml of diisopropyl ether and triturated using an ultrasonic vibrator. Insoluble materials were collected by filtration and dried by evaporation under reduced pressure, after which they were mixing with 110 ml of methanol. The mixture was heated under reflux and then allowed to stand overnight in a refrigerator. The crystals which separated were collected by filtration and dried by evaporation under reduced pressure, to give 886 mg of the title compound as fine white needles.

Nuclear Magnetic Resonance Spectrum (hexadeuterated dimethyl sulfoxide, 270 MHz) δ ppm:

10.91 (1H, singlet);

8.36 (1H, doublet, J=7.8 Hz);

7.29 (1H, doublet, J=7.3 Hz);

6.25–6.27 (1H, multiplet);

6.21 (1H, doublet, J=7.3 Hz);

5.22–5.25 (1H, multiplet);

4.40–4.47 (1H, multiplet);

3.60–3.93 (4H, multiplet);

2.40 (2H, triplet, J=7.3 Hz);

1.54 (2H, broad singlet);

1.23 (28H, broad singlet);

0.83–0.88 (3H, multiplet).

EXAMPLE 13

2'-Cyano-2'-deoxy-$N^4$-docosanoyl-1-β-D-arabinofuranosylcytosine 4 ml of dimethylformamide were added to a mixture of 1.00 g (4 mmole) of 2'-cyano-2'-deoxy-1-β-D-arabinofuranosylcytosine [prepared as described in Example 1(a) above] and 3.98 g (6 mmole) of docosanoic anhydride, and the resulting mixture was stirred in an oil bath kept at 100° C. for 30 minutes. At the end of this time, the solvent was removed by distillation under reduced pressure, and the resulting residue was mixed with 100 ml of diisopropyl ether and triturated using an ultrasonic vibrator. Insoluble materials were collected by filtration and dried by evaporation under reduced pressure. The procedure described above was repeated using a further 100 ml of diisopropyl ether. The insoluble materials were dissolved in 40 ml of ethyl acetate with heating and allowed to stand overnight at room temperature. The crystals which separated were collected by filtration. They were then worked up using 80 ml of ethyl acetate and using the same procedure as described above (heating, standing and filtration), to give 1.575 g of the title compound as crystals.

Nuclear Magnetic Resonance Spectrum (hexadeuterated dimethyl sulfoxide, 270 MHz) δ ppm:

10.91 (1H, singlet);

8.36 (1H, doublet, J=8.3 Hz);

7.29 (1H, doublet, J=7.8 Hz);

6.26–6.28 (1H, multiplet);

6.21 (1H, doublet, J=6.8 Hz);

5.23 (1H, broad singlet);

4.41–4.46 (1H, multiplet);

3.62–3.93 (4H, multiplet);

2.40 (2H, triplet, J=6.8 Hz);

1.41–1.53 (2H, multiplet);

1.12–1.23 (36H, multiplet);

0.83–0.85 (3H, multiplet).

EXAMPLE 14

$N^4$-(12-Aminododecanoyl)-2'-cyano-2'-deoxy-1-β-D-arabinofuranosylcytosine monohydrochloride 14(a) $N^4$-t-Butoxycarbonylaminododecanoyl-2'-cyano-2'-deoxy-3',5'-O-(1,1,3,3-tetraisopropyldisiloxane-1,3-diyl)-1-β-D-arabinofuranosylcytosine A mixture of 148.4 mg (0.3 mmole) of 2'-cyano-2'-deoxy-3',5'-O-(1,1,3,3-tetraisopropyldisiloxane-1,3-diyl)-1-β-D-arabinofuranosylcytosine [prepared as described in Example 1(b) above] and 378.5 mg (1.2 mmole) of N-(t-butoxycarbonyl)aminododecanoic acid was mixed with benzene and dried by azeotropic distillation, and the residual mixture was dissolved in 3 ml of tetrahydrofuran. 247.6 mg (1.2 mmole) of dicyclohexylcarbodiimide and 12 mg (0.09 mmole) of dimethylaminopyridine were added to the solution, and the resulting mixture was stirred at 50° C. for a period of 2 hours and 20 minutes in an atmosphere of nitrogen. Insoluble materials were removed by filtration, and the filtrate was concentrated by evaporation under reduced pressure. The residue was mixed with 50 ml of a 5% w/v aqueous solution of sodium hydrogencarbonate and then stirred at room temperature for 30 minutes. At the end of this time, the reaction mixture was extracted with 50 ml of ethyl acetate. The extract was washed once with 50 ml of a 5% w/v aqueous solution of sodium chloride, and dried over anhydrous magnesium sulfate. The solvent was then removed by distillation under reduced pressure, to give 0.69 g of a residue, which was purified by column chromatography through 30 g of silica gel (230–400 mesh), using methylene chloride containing 1 to 3% by volume of methanol as the eluent, to give 193.2 mg (yield 81%) of the title compound as a foam.

Nuclear Magnetic Resonance Spectrum ($CDCl_3$, 270 MHz) δ ppm:

9.97 (1H, broad singlet);

8.03 (1H, doublet, J=7.92 Hz);

7.55 (1H, doublet, J=7.92 Hz);

6.37 (1H, doublet, J=6.60 Hz);

4.64 (1H, doublet of doublets, J=7.92 & 7.92 Hz);

4.55 (1H, broad singlet);

4.21–4.04 (2H, multiplet);

3.90 (1H, doublet of triplets, J=7.92 & 2.85 Hz);

3.77 (1H, doublet of doublets, J=6.60 & 8.58 Hz);

3.14–3.04 (2H, multiplet);

2.64–2.42 (2H, multiplet);

1.72–1.62 (2H, multiplet);

1.45 (9H, singlet);

1.26 (16H, broad singlet);

1.50–0.95 (28H, multiplet).

14(b) $N^4$-t-Butoxycarbonylaminododecanoyl-2'-cyano-2'-deoxy-1-β-D-arabinofuranosylcytosine 13 μl (0.235 mmole) of acetic acid and a solution of 0.47 ml (0.47 mmole) of tetrabutylammonium fluoride in tetrahydrofuran were added to a solution of 186.5 mg (0.235 mmole) of $N^4$-t-butoxycarbonylaminododecanoyl-2'-cyano-2'-deoxy-3',5'-O-(1,1,3,3-tetraisopropyldisiloxane-1,3-diyl)-1-β-D-arabinofuranosylcytosine [prepared as described in step (a) above] in 0.47 ml of tetrahydrofuran, and the resulting mixture was stirred thoroughly for 30 minutes, whilst ice-cooling, in an atmosphere of argon. The solvent was then removed by distillation under reduced pressure, and the resulting residue was dissolved in 20 ml of ethyl acetate. This solution was washed with 20 ml of a saturated aqueous solution of sodium hydrogencarbonate and dried over anhydrous magnesium sulfate, after which the solvent was removed by distillation under reduced pressure. The residue was purified by column chromatography through 10 g of silica gel (230–400 mesh), using methylene chloride containing 3 to 4% by volume of methanol as the eluent, to give 122.4 mg (yield 95%) of the title compound as a foam.

Nuclear Magnetic Resonance Spectrum ($CDCl_3+D_2O$, 270 MHz) δ ppm:

8.26 (1H, doublet, J=7.91 Hz);

7.55 (1H, doublet, J=7.91 Hz);

6.24 (1H, doublet, J=6.60 Hz);

4.75–4.68 (1H, multiplet);

4.10–3.83 (4H, multiplet);

3.12–3.03 (2H, multiplet);

2.48–2.38 (2H, multiplet);

1.70–1.55 (2H, multiplet);

1.44 (9H, singlet);

1.24 (16H, broad singlet).

14(c) $N^4$-(12-Aminododecanoyl)-2'-cyano-2'-deoxy-1-β-D-arabinofuranosylcytosine monohydrochloride 1.5 ml of a 4N dioxane solution of hydrogen chloride were added to a solution of 63.8 mg (0.116 mmole) of $N^4$-t-butoxycarbonylaminododecanoyl-2'-cyano-2'-deoxy-1-β-D-arabinofuranosylcytosine [prepared as described in step (a) above] in 10.5 ml of dioxane, and the resulting mixture was stirred at room temperature for 1 hour, after which 1.5 ml of a 4N dioxane solution of hydrogen chloride were added. The reaction mixture was stirred for 2 hours, and then the solvent was removed by distillation under reduced pressure. The resulting residue was purified by column chromatography through a Lobar column (Gro βe B), using water containing 20% by volume of acetonitrile as the eluent, to give 15.7 mg (yield 28%) of the title compound as a white powder.

EXAMPLE 15

2'-Cyano-2'-deoxy-$N^4$-heptadecanoyl-1-β-D-arabinofuranosylcytosine

290 μl of chlorotrimethylsilane were added, at 0° C. and in an atmosphere of nitrogen, to a solution of 116 mg of 2'-cyano-2'-deoxy-1-β-D-arabinofuranosylcytosine [prepared as described in Example 1(a) above] in pyridine, and the resulting mixture was stirred for 2 hours, after which 755 μl of heptadecanoyl chloride were added. The reaction mixture was stirred overnight at room temperature, after which it was diluted with water and extracted with methylene chloride. The extract was dried over anhydrous magnesium sulfate, and then the solvent was removed by distillation under reduced pressure. The residue was purified by column chromatography through silica gel, using a 1:4 by volume mixture of cyclohexane and ethyl acetate and as the eluent. The resulting crude product was recrystallized from ethyl acetate, to give 94 mg of the title compound as crystals.

Nuclear Magnetic Resonance Spectrum ($CD_3OD+CDCl_3$, 270 MHz) δ ppm:

8.42 (1H, doublet, J=8 Hz);

7.56 (1H, doublet, J=8 Hz);

6.27 (1H, doublet, J=7 Hz);

4.61 (1H, triplet, J=6 Hz);

3.70–4.10 (12H, multiplet);

2.45 (2H, triplet, J=7 Hz);

1.70 (2H, quintet, J=7 Hz);

1.20–1.50 (26H, multiplet);

0.89 (3H, triplet, J=7 Hz).

EXAMPLE 16

2'-Cyano-2'-deoxy-$N^4$-octanoyl-1-β-D-arabinofuranosylcytosine

Following a procedure similar to that described in Example 9, but using an equivalent amount of octanoic anhydride in place of the hexanoic anhydride, 0.95 g of the title compound was obtained as fine white needles.

Nuclear Magnetic Resonance Spectrum (hexadeuterated dimethyl sulfoxide, 270 MHz) δ ppm:

10.91 (1H, broad singlet);

8.36 (1H, doublet, J=7.3 Hz);

7.29 (1H, doublet, J=7.3 Hz);

6.25 (1H, doublet, J=5 Hz);

6.22 (1H, doublet, J=7 Hz);

5.23 (1H, doublet, J=5 Hz);
4.44 (1H, doublet of triplets, J=5 & 7 Hz);
3.91 (1H, triplet, J=7 Hz);
3.60–3.90 (3H, multiplet);
2.40 (2H, triplet, J=7 Hz);
1.45–1.65 (2H, multiplet);
1.10–1.40 (8H, multiplet);
0.86 (3H, triplet, J=7 Hz).

EXAMPLE 17

2'-Cyano-2'-deoxy-$N^4$-tetradecanoyl-1-β-D-arabinofuranosylcytosine

Following a procedure similar to that described in Example 9, but using an equivalent amount of tetradecanoic anhydride in place of the hexanoic anhydride, 1.05 g of the title compound were obtained as fine white needles.

Nuclear Magnetic Resonance Spectrum (hexadeuterated dimethyl sulfoxide, 270 MHz) δ ppm:
10.90 (1H, broad singlet);
8.36 (1H, doublet, J=7.5 Hz);
7.29 (1H, doublet, J=7.5 Hz);
6.25 (1H, doublet, J=6 Hz);
6.21 (1H, doublet, J=7 Hz);
5.22 (1H, broad triplet, J=5 Hz);
4.43 (1H, doublet of triplets, J=6 & 7 Hz);
3.90 (1H, triplet, J=7 Hz);
3.59–3.86 (3H, multiplet);
2.39 (2H, triplet, J=7 Hz);
1.45–1.65 (2H, multiplet);
1.10–1.40 (20H, multiplet);
0.85 (3H, triplet, J=7 Hz).

EXAMPLE 18

2'-Cyano-2'-deoxy-$N^4$-pentadecanoyl-1-β-D-arabinofuranosylcytosine

Following a procedure similar to that described in Example 9, but using an equivalent amount of pentadecanoic anhydride in place of the hexanoic anhydride, 0.96 g of the title compound was obtained as fine white needles.

Nuclear Magnetic Resonance Spectrum (hexadeuterated dimethyl sulfoxide, 270 MHz) δ ppm:
10.90 (1H, broad singlet);
8.36 (1H, doublet, J=7 Hz);
7.29 (1H, doublet, J=7 Hz);
6.25 (1H, doublet, J=6 Hz);
6.21 (1H, doublet, J=7 Hz);
5.22 (1H, doublet, J=5 Hz);
4.43 (1H, doublet of triplets, J=5, 7 Hz);
3.91 (1H, triplet, J=7 Hz);
3.81–3.87 (1H, multiplet);
3.76 & 3.62 (each 1H, doubled doublet of doublets, J=12, 5 & 3, & J=12, 5 & 4 Hz);
2.40 (2H, triplet, J=7 Hz);
1.50–1.60 (2H, multiplet);
1.10–1.40 (22H, multiplet);
0.85 (3H, triplet, J=7 Hz).

EXAMPLE 19

2'-Cyano-2'-deoxy-$N^4$-icosanoyl-1-β-D-arabinofuranosylcytosine

Following a procedure similar to that described in Example 9, but using an equivalent amount of icosanoic anhydride in place of the hexanoic anhydride, 0.56 g of the title compound was obtained as white needles.

Nuclear Magnetic Resonance Spectrum (hexadeuterated dimethyl sulfoxide, 270 MHz) δ ppm:
10.91 (1H, broad singlet);
8.36 (1H, doublet, J=7.8 Hz);
7.29 (1H, doublet, J=7.8 Hz);
6.25 (1H, doublet, J=6 Hz);
6.21 (1H, doublet, J=7 Hz);
5.22 (1H, doublet, J=5 Hz);
4.43 (1H, doublet of triplets, J=6 & 7 Hz);
3.91 (1H, triplet, J=7 Hz);
3.60–3.90 (3H, multiplet);
2.39 (2H, triplet, J=7 Hz);
1.50–1.60 (2H, multiplet);
1.10–1.40 (32H, multiplet);
0.85 (3H, triplet, J=7 Hz).

EXAMPLE 20

2'-Cyano-2'-deoxy-$N^4$-(10-methoxyethoxymethoxydecanoyl)-1-β-D-arabinofuranosylcytosine A solution of 1.80 g of ethoxyformic 10-methoxyethoxymethoxydecanoic anhydride in 5 ml of dry tetrahydrofuran was added to a solution of 899 mg of 2'-cyano-2'-deoxy-1-β-D-arabinofuranosylcytosine [prepared as described in Example 1(a) above] in 10 ml of dry dimethylformamide, and the resulting mixture was stirred at 100° C. for 1.5 hours, whilst excluding moisture. At the end of this time, the solvent was removed by distillation under reduced pressure, and the resulting residue was triturated with diisopropyl ether, using a spatula to induce crystallization. The crystalline solid was finely broken up and then allowed to stand overnight in a refrigerator. The resulting crystals were collected by filtration. They were dissolved in methylene chloride and purified by column chromatography through silica gel, using methylene chloride containing 0.5% by volume of methanol as the eluent. Those fractions containing the desired product were pooled and the solvent was removed by distillation under reduced pressure. The resulting residue was recrystallized from a mixture of hexane and ethyl acetate, to afford 964 mg of the title compound as fine white needles.

Nuclear Magnetic Resonance Spectrum (hexadeuterated dimethyl sulfoxide, 270 MHz) δ ppm:
10.91 (1H, broad singlet);
8.34 (1H, doublet, J=7.5 Hz);
7.29 (1H, doublet, J=7.5 Hz);
6.25 (1H, doublet, J=6 Hz);
6.21 (1H, doublet, J=7 Hz);
5.22 (1H, multiplet);
4.59 (2H, singlet);
4.43 (1H, doublet of triplets, J=5 & 7 Hz);
3.91 (1H, triplet, J=7 Hz);
3.59–3.86 (3H, multiplet);
3.55 (2H, multiplet);
3.38–3.48 (4H, multiplet);
3.24 (3H, singlet);
2.40 (2H, triplet, J=7 Hz);
1.41–1.62 (4H, multiplet);

1.12–1.37 (10H, multiplet).

EXAMPLE 21

2'-Cyano-2'-deoxy-$N^4$-(10-methoxymethoxydecanoyl)-1-β-D-arabinofuranosylcytosine Following a procedure similar to that described in Example 20, but using an equivalent amount of ethoxyformic 10-methoxymethoxydecanoic anhydride in place of the ethoxyformic 10-methoxyethoxymethoxydecanoic anhydride, 0.956 g of the title compound was obtained as fine white needles.

Nuclear Magnetic Resonance Spectrum (hexadeuterated dimethyl sulfoxide, 270 MHz) δ ppm:

10.91 (1H, broad singlet);
8.36 (1H, doublet, J=7.5 Hz);
7.29 (1H, doublet, J=7.5 Hz);
6.25 (1H, doublet, J=6 Hz);
6.21 (1H, doublet, J=7 Hz);
5.22 (1H, multiplet);
4.43 (1H, doublet of triplets, J=5 & 5 Hz);
4.59 (2H, singlet);
3.90 (1H, triplet, J=7 Hz);
3.58–3.87 (3H, multiplet);
3.42 (2H, triplet, J=7 Hz);
3.23 (3H, singlet);
2.40 (2H, triplet, J=7 Hz);
1.41–1.62 (4H, multiplet);
1.14–1.38 (10H, multiplet).

EXAMPLE 22

2'-Cyano-2'-deoxy-$N^4$-(11-methoxycarbonylundecanoyl)-1-β-D-arabinofuranosylcytosine Following a procedure similar to that described in Example 20, but using an equivalent amount of ethoxyformic 11-methoxycarbonylundecanoic anhydride in place of the ethoxyformic 10-methoxyethoxymethoxydecanoic anhydride, 0.85 g of the title compound was obtained as fine white needles.

Nuclear Magnetic Resonance Spectrum (hexadeuterated dimethyl sulfoxide, 270 MHz) δ ppm:

10.91 (1H, broad singlet);
8.36 (1H, doublet, J=7.8 Hz);
7.29 (1H, doublet, J=7.8 Hz);
6.25 (1H, doublet, J=6 Hz);
6.21 (1H, doublet, J=7 Hz);
5.22 (1H, doublet, J=5 Hz);
4.43 (1H, doublet of triplets, J=6 & 7 Hz);
3.91 (1H, triplet, J=7 Hz);
3.60–3.90 (3H, multiplet);
3.57 (3H, singlet);
2.40 (2H, triplet, J=7 Hz);
2.28 (2H, triplet, J=7 Hz);
1.45–1.60 (4H, multiplet);
1.15–1.40 (12H, multiplet).

EXAMPLE 23

2'-Cyano-$N^4$-(11-cyanoundecanoyl)-2'-deoxy-1-β-D-arabinofuranosylcytosine

Following a procedure similar to that described in Example 20, but using an equivalent amount of ethoxyformic 11-cyanoundecanoic ethoxyformic anhydride in place of the ethoxyformic 10-methoxyethoxymethoxydecanoic anhydride, 0.95 g of the title compound was obtained as fine white needles.

Nuclear Magnetic Resonance Spectrum (hexadeuterated dimethyl sulfoxide, 270 MHz) δ ppm:

10.91 (1H, broad singlet);
8.35 (1H, doublet, J=7.8 Hz);
7.29 (1H, doublet, J=7.8 Hz);
6.25 (1H, doublet, J=5 Hz);
6.21 (1H, doublet, J=7 Hz);
5.23 (1H, doublet, J=5 Hz);
4.43 (1H, doublet of triplets, J=5 & 7 Hz);
3.91 (1H, triplet, J=7 Hz);
3.60–3.85 (3H, multiplet);
2.46 (2H, triplet, J=7 Hz);
2.40 (2H, triplet, J=7 Hz);
1.44–1.66 (4H, multiplet);
1.16–1.44 (12H, multiplet).

EXAMPLE 24

2'-Cyano-2'-deoxy-$N^4$-(16-hydroxyhexadecanoyl)-1-β-D-arabinofuranosylcytosine

Following a procedure similar to that described in Example 20, but using an equivalent amount of ethoxyformic 16-hydroxyhexadecanoic anhydride in place of the ethoxyformic 10-methoxyethoxymethoxydecanoic anhydride, 0.85 g of the title compound was obtained as fine white needles.

Nuclear Magnetic Resonance Spectrum (hexadeuterated dimethyl sulfoxide, 270 MHz) δ ppm:

10.90 (1H, broad singlet);
8.35 (1H, doublet, J=7 Hz);
7.29 (1H, doublet, J=7 Hz);
6.25 (1H, doublet, J=6 Hz);
6.21 (1H, doublet, J=7 Hz);
5.22 (1H, doublet, J=5 Hz);
4.44 (1H, doublet of triplets, J=6 & 7 Hz);
4.29 (1H, triplet, J=5 Hz);
3.60–3.90 (3H, multiplet);
3.57 (2H, doublet of triplets, J=5 & 7 Hz);
2.4 (2H, triplet, J=7 Hz);
1.10–1.60 (26H, multiplet).

EXAMPLE 25

2'-Cyano-2'-deoxy-$N^4$-(16-methoxyethoxymethoxyhexadecanoyl)-1-β-D-arabinofuranosylcytosine Following a procedure similar to that described in Example 20, but using an equivalent amount of ethoxyformic 16-methoxyethoxymethoxyhexadecanoic anhydride in place of the ethoxyformic 10-methoxyethoxymethoxydecanoic anhydride, 0.95 g of the title compound was obtained as fine white needles.

Nuclear Magnetic Resonance Spectrum (hexadeuterated dimethyl sulfoxide, 270 MHz) δ ppm:

10.91 (1H, broad singlet);
8.36 (1H, doublet, J=7.5 Hz);
7.29 (1H, doublet, J=7.5 Hz);

6.25 (1H, doublet, J=5 Hz);
6.21 (1H, doublet, J=7 Hz);
5.22 (1H, doublet, J=5 Hz);
4.59 (2H, singlet);
4.43 (1H, doublet of triplets, J=5 & 7 Hz);
3.90 (1H, triplet, J=7 Hz);
3.59–3.86 (3H, multiplet);
3.52–3.58 (2H, multiplet);
3.24 (3H, singlet);
3.40 (2H, triplet, J=7 Hz);
1.41–1.61 (4H, multiplet);
1.12–1.37 (22H, multiplet).

EXAMPLE 26

2'-Cyano-2'-deoxy-$N^4$-(16-methoxymethoxyhexadecanoyl)-1-β-D-arabinofuranosylcytosine Following a procedure similar to that described in Example 20, but using an equivalent amount of ethoxyformic 16-methoxymethoxyhexadecanoic anhydride in place of the ethoxyformic 10-methoxyethoxymethoxydecanoic anhydride, 0.86 g of the title compound was obtained as fine white needles.

Nuclear Magnetic Resonance Spectrum (hexadeuterated dimethyl sulfoxide, 270 MHz) δ ppm:

10.90 (1H, broad singlet);
8.37 (1H, doublet, J=7.3 Hz);
7.31 (1H, doublet, J=7.3 Hz);
6.30 (1H, doublet, J=5 Hz);
6.21 (1H, doublet, J=6.6 Hz);
5.28 (1H, triplet, J=5.31 Hz);
4.53 (2H, singlet);
4.42 (1H, doublet of triplets, J=5.0 & 7.3 Hz);
3.90 (1H, triplet, J=7.3 Hz);
3.85–3.65 (3H, multiplet);
3.23 (3H, singlet);
2.40 (2H, multiplet);
1.39–1.62 (4H, multiplet);
1.24 (22H, broad singlet).

EXAMPLE 27

$N^4$-(16-Acetoxyhexadecanoyl)-2'-cyano-2'-deoxy-1-β-D-arabinofuranosylcytosine

Following a procedure similar to that described in Example 20, but using an equivalent amount of 16-acetoxyhexadecanoic ethoxyformic anhydride in place of the ethoxyformic 10-methoxyethoxymethoxydecanoic anhydride, 0.95 g of the title compound was obtained as fine white needles.

Nuclear Magnetic Resonance Spectrum (hexadeuterated dimethyl sulfoxide, 270 MHz) δ ppm:

10.91 (1H, broad singlet);
8.35 (1H, doublet, J=7.5 Hz);
7.29 (1H, doublet, J=7.5 Hz);
6.25 (1H, doublet, J=6 Hz);
6.21 (1H, doublet, J=7 Hz);
5.23 (1H, doublet, J=5 Hz);
4.43 (1H, doublet of triplets, J=6 & 7 Hz);
3.97 (2H, triplet, J=7 Hz);
3.90 (1H, triplet, J=7 Hz);
3.59–3.86 (3H, multiplet);
2.39 (2H, triplet, J=7 Hz);
1.98 (3H, singlet);
1.43–1.63 (4H, multiplet);
1.17–1.38 (22H, multiplet).

EXAMPLE 28

$N^4$-(16-Carbamoyloxyhexadecanoyl)-2'-cyano-2'-deoxy-1-β-D-arabinofuranosylcytosine Following a procedure similar to that described in Example 20, but using an equivalent amount of 16-carbamoyloxyhexadecanoic ethoxyformic anhydride in place of the ethoxyformic 10-methoxyethoxymethoxydecanoic anhydride, 0.56 g of the title compound was obtained as fine white needles.

Nuclear Magnetic Resonance Spectrum (hexadeuterated dimethyl sulfoxide, 270 MHz) δ ppm:

10.91 (1H, broad singlet);
8.37 (1H, doublet, J=7.5 Hz);
7.30 (1H, doublet, J=7.5 Hz);
6.39 (2H, broad singlet);
6.25 (1H, doublet, J=5.3 Hz);
6.21 (1H, doublet, J=7 Hz);
5.24 (1H, triplet, J=5.3 Hz);
4.44 (1H, doublet of triplets, J=5 & 7 Hz);
3.90 (1H, triplet, J=7 Hz);
3.59–3.97 (5H, multiplet);
2.40 (2H, triplet, J=7.3 Hz);
1.40–1.65 (4H, multiplet);
1.10–1.39 (22H, multiplet).

EXAMPLE 29

$N^4$-(16-Acetylthiohexadecanoyl)-2'-cyano-2'-deoxy-1-β-D-arabinofuranosylcytosine Following a procedure similar to that described in Example 20, but using an equivalent amount of 16-acetylthiohexadecanoic ethoxyformic anhydride in place of the ethoxyformic 10-methoxyethoxymethoxydecanoic anhydride, 0.86 g of the title compound was obtained as fine white needles.

Nuclear Magnetic Resonance Spectrum (hexadeuterated dimethyl sulfoxide, 270 MHz) δ ppm:

10.91 (1H, broad singlet);
8.36 (1H, doublet, J=7 Hz);
7.29 (1H, doublet, J=7 Hz);
6.25 (1H, doublet, J=6 Hz);
6.21 (1H, doublet, J=7 Hz);
5.23 (1H, multiplet);
4.43 (1H, doublet of triplets, J=6 & 7 Hz);
3.91 (1H, triplet, J=7 Hz);
3.60–3.90 (3H, multiplet);
2.81 (2H, triplet, J=7 Hz);
2.40 (2H, triplet, J=7 Hz);
2.31 (3H, singlet);
1.40–1.70 (4H, multiplet);
1.10–1.40 (22H, multiplet).

EXAMPLE 30

N⁴-(16-Benzyloxycarbonylaminohexadecanoyl)-2'-cyano-2'-deoxy-1-β-D-arabinofuranosylcytosine Following a procedure similar to that described in Example 20, but using an equivalent amount of 16-benzyloxycarbonylaminohexadecanoic ethoxyformic anhydride in place of the ethoxyformic 10-methoxyethoxymethoxydecanoic anhydride, 1.15 g of the title compound were obtained as fine white needles.

Nuclear Magnetic Resonance Spectrum (hexadeuterated dimethyl sulfoxide, 270 MHz) δ ppm:

10.91 (1H, broad singlet);
8.36 (1H, doublet, J=7 Hz);
7.29 (1H, doublet, J=7 Hz);
7.25–7.45 (5H, multiplet);
7.20 (1H, broad triplet, J=6 Hz);
6.25 (1H, doublet, J=6 Hz);
6.21 (1H, doublet, J=7 Hz);
5.23 (1H, doublet, J=5 Hz);
5.00 (2H, singlet);
4.43 (1H, doublet of triplets, J=6 & 7 Hz);
3.91 (1H, triplet, J=7 Hz);
3.60–3.90 (3H, multiplet);
2.97 (2H, triplet, J=6 Hz);
2.40 (2H, triplet, J=7 Hz);
1.10–1.60 (26H, multiplet).

EXAMPLE 31

N⁴-(16-Azidohexadecanoyl)-2'-cyano-2'-deoxy-1-β-D-arabinofuranosylcytosine

Following a procedure similar to that described in Example 20, but using an equivalent amount of 16-azidohexadecanoic ethoxyformic anhydride in place of the ethoxyformic 10-methoxyethoxymethoxydecanoic anhydride, 0.88 g of the title compound was obtained as fine white needles.

Nuclear Magnetic Resonance Spectrum (hexadeuterated dimethyl sulfoxide, 270 MHz) δ ppm:

10.91 (1H, broad singlet);
8.36 (1H, doublet, J=7.3 Hz);
7.29 (1H, doublet, J=7.3 Hz);
6.25 (1H, doublet, J=6 Hz);
6.21 (1H, doublet, J=7 Hz);
5.23 (1H, triplet, J=5 Hz);
4.43 (1H, doublet of triplets, J=6 & 7 Hz);
3.91 (1H, triplet, J=7 Hz);
3.60–3.90 (3H, multiplet);
3.30 (2H, triplet, J=7 Hz);
2.40 (2H, triplet, J=7 Hz);
1.40–1.70 (4H, multiplet);
1.10–1.40 (26H, multiplet).

EXAMPLE 32

2'-Cyano-2'-deoxy-N⁴-(16-methylsulfonyloxyhexadecanoyl)-1-β-D-arabinofuranosylcytosine Following a procedure similar to that described in Example 20, but using an equivalent amount of ethoxyformic 16-methylsulfonyloxyhexadecanoic anhydride in place of the ethoxyformic 10-methoxyethoxymethoxydecanoic anhydride, 0.87 g of the title compound was obtained as fine white needles.

Nuclear Magnetic Resonance Spectrum (hexadeuterated dimethyl sulfoxide, 270 MHz) δ ppm:

10.91 (1H, broad singlet);
8.36 (1H, doublet, J=7.8 Hz);
7.29 (1H, doublet, J=7.8 Hz);
6.25 (1H, doublet, J=6 Hz);
6.23 (1H, doublet, J=7 Hz);
5.00–5.40 (1H, multiplet);
4.37–4.48 (1H, multiplet);
4.17 (2H, triplet, J=6.5 Hz);
3.90 (1H, triplet, J=7 Hz);
3.80–3.90 (3H, multiplet);
3.14 (3H, singlet);
2.4 (2H, triplet, J=7 Hz);
1.45–1.75 (4H, multiplet);
1.15–1.45 (22H, multiplet).

EXAMPLE 33

2'-Cyano-2'-deoxy-N⁴-(16-methylthiomethoxyhexadecanoyl)-1-β-D-arabinofuranosylcytosine Following a procedure similar to that described in Example 20, but using an equivalent amount of ethoxyformic 16-methylthiomethoxyhexadecanoic anhydride in place of the ethoxyformic 10-methoxyethoxymethoxydecanoic anhydride, 0.45 g of the title compound was obtained as fine white needles.

Nuclear Magnetic Resonance Spectrum (hexadeuterated dimethyl sulfoxide, 270 MHz) δ ppm:

10.90 (1H, broad singlet);
8.36 (1H, doublet, J=7.3 Hz);
7.29 (1H, doublet, J=7.3 Hz);
6.25 (1H, doublet, J=5.9 Hz);
6.21 (1H, doublet, J=6.8 Hz);
5.23 (1H, triplet, J=5.4 Hz);
4.43 (1H, doublet of triplets, J=5.9 & 7.3 Hz);
3.90 (1H, doublet of doublets, J=6.8 & 7.3 Hz);
3.83, 3.76 & 3.62 (each 1H, together multiplet);
3.43 (2H, triplet, J=6.4 Hz);
2.40 (2H, triplet, J=7.3 Hz);
2.07 (3H, singlet);
1.38–1.61 (4H, multiplet);
1.12–1.37 (22H, multiplet).

EXAMPLE 34

N⁴-(11-Carbamoylundecanoyl)-2'-cyano-2'-deoxy-1-β-D-arabinofuranosylcytosine

Following a procedure similar to that described in Example 20, but using an equivalent amount of 11-carbamoylundecanoic ethoxyformic anhydride in place of the ethoxyformic 10-methoxyethoxymethoxydecanoic anhydride, 0.55 g of the title compound was obtained as fine white needles.

Nuclear Magnetic Resonance Spectrum (hexadeuterated dimethyl sulfoxide, 270 MHz) δ ppm:

10.91 (1H, broad singlet);
8.36 (1H, doublet, J=7.8 Hz);
7.29 (1H, doublet, J=7.8 Hz);
7.19 (1H, broad singlet);
6.65 (1H, broad singlet);
6.26 (1H, doublet, J=5 Hz);
6.21 (1H, doublet, J=7 Hz);
5.23 (1H, triplet, J=5 Hz);
4.44 (1H, doublet of triplets, J=4 & 7 Hz);
3.91 (1H, triplet, J=7 Hz);
3.60–3.90 (3H, multiplet);
2.40 (2H, triplet, J=7 Hz);
2.01 (2H, triplet, J=7 Hz);
1.35–1.65 (4H, multiplet);
1.10–1.35 (12H, multiplet).

EXAMPLE 35

$N^4$-(6-Bromohexanoyl)-2'-cyano-2'-deoxy-1-β-D-arabinofuranosylcytosine

Following a procedure similar to that described in Example 20, but using an equivalent amount of 6-bromohexanoic ethoxyformic anhydride in place of the ethoxyformic 10-methoxyethoxymethoxydecanoic anhydride, 0.78 g of the title compound was obtained as a white powder.

Nuclear Magnetic Resonance Spectrum (hexadeuterated dimethyl sulfoxide, 270 MHz) δ ppm:

10.93 (1H, broad singlet);
8.36 (1H, doublet, J=7.8 Hz);
7.29 (1H, doublet, J=7.8 Hz);
6.27 (1H, doublet, J=6 Hz);
6.21 (1H, doublet, J=7 Hz);
5.22 (1H, doublet, J=5 Hz);
4.44 (1H, doublet of triplets, J=6 & 7 Hz);
3.91 (1H, triplet, J=7 Hz);
3.60–3.90 (3H, multiplet);
3.53 (2H, triplet, J=7 Hz);
2.42 (2H, triplet, J=7 Hz);
1.81 (2H, quartet, J=7 Hz);
1.58 (2H, quartet, J=7 Hz);
1.30–1.45 (2H, multiplet).

EXAMPLE 36

$N^4$-(3-Benzyldithiopropionyl)-2'-cyano-2'-deoxy-1-β-D-arabinofuranosylcytosine Following a procedure similar to that described in Example 20, but using an equivalent amount of 3-benzyldithiopropionic ethoxyformic anhydride in place of the ethoxyformic 10-methoxyethoxymethoxydecanoic anhydride, 0.21 g of the title compound was obtained as a white powder.

Nuclear Magnetic Resonance Spectrum (hexadeuterated dimethyl sulfoxide, 270 MHz) δ ppm:

11.05 (1H, broad singlet);
8.38 (1H, doublet, J=7.5 Hz);
7.23–7.33 (6H, multiplet);
6.25 (1H, doublet, J=5 Hz);
6.21 (1H, doublet, J=7 Hz);
5.23 (1H, triplet, J=5 Hz);
4.44 (1H, doublet of triplets, J=5 & 7 Hz);
3.99 (2H, singlet);
3.91 (1H, triplet, J=7 Hz);
3.59–3.85 (3H, multiplet);
2.81 (4H, broad singlet).

EXAMPLE 37

2'-Cyano-2'-deoxy-$N^4$-palmitoylcytidine

37(a) 2'-Cyano-2'-deoxycytidine

A solution of 1.0 g of 2'-cyano-2'-deoxy-1-β-D-arabinofuranosylcytosine [prepared as described in Example 1(a) above] dissolved in 40 ml of 0.2M aqueous disodium hydrogenphosphate (having a pH value of 9.00) was allowed to stand at room temperature for 16 hours, after which its pH was adjusted to a value of 2.16 by the addition of 15 ml of 1N aqueous hydrochloric acid. The reaction mixture was then purified by chromatography through a preparative high performance liquid chromatography column (Inertsil PREP-ODS, 20.0×250 mm, SHI7502), using water containing 2.5% by volume of methanol as the eluent. Unreacted 2'-cyano-2'-deoxy-1-β-D-arabinofuranosylcytosine was eluted first. After this had been eluted, the subsequent eluents from each column were pooled and the solvent was removed by distillation under reduced pressure. The residue was lyophilized, to afford 500 mg of the title compound as a white powder.

Nuclear Magnetic Resonance Spectrum (hexadeuterated dimethyl sulfoxide, 270 MHz) δ ppm:

7.79 (1H, doublet, J=7.3 Hz);
7.48–7.67 (2H, broad doublet, J=51.7 Hz);
6.30 (1H, doublet, J=7.8 Hz);
6.26 (1H, doublet, J=5.8 Hz);
5.82 (1H, doublet, J=7.3 Hz);
5.13 (1H, singlet);
4.34–4.39 (1H, multiplet);
3.90–3.94 (1H, multiplet);
3.56–3.67 (3H, multiplet).

37(b) 2'-Cyano-2'-deoxy-$N^4$-palmitoylcytidine 1.47 g (2.97 mole) of palmitic anhydride was added to a solution of 500 mg of 2'-cyano-2'-deoxycytidine [prepared as described in step (a) above] in 10 ml of dimethylformamide, and the resulting mixture was stirred in an oil-bath kept at 95° C. for 30 minutes. At the end of this time, the reaction mixture was concentrated to dryness by evaporation under reduced pressure, and the residue was recrystallized from methanol, to afford 860.9 mg of the title compound as fine white needles.

Nuclear Magnetic Resonance Spectrum (hexadeuterated dimethyl sulfoxide, 270 MHz) δ ppm:

10.92 (1H, singlet);
8.25 (1H, doublet, J=7.8 Hz);
7.25 (1H, doublet, J=7.3 Hz);
6.28 (2H, triplet, J=5.8 Hz);
4.38 (1H, singlet);
3.97–4.00 (1H, doublet of doublets, J=6.3 & 7.3 Hz);
3.75 (2H, triplet, J=6.3 Hz);
3.57–3.65 (1H, multiplet);
2.39 (2H, triplet, J=7.3 Hz);
1.48–1.55 (2H, doublet of doublets, J=13.1 & 14.6 Hz);
1.23 (24H, singlet);

EXAMPLE 38

2'-Cyano-2'-deoxy-N⁴-(9-palmitoleyl)-1-β-D-arabinofuranosylcytosine 0.115 ml (1.2 mmole) of ethyl chlorocarbonate and 0.167 ml (1.2 mmole) of triethylamine were added, whilst ice-cooling and stirring in an atmosphere of nitrogen, to a solution of 0.14 ml (0.8 mmole) of 9-palmitoleic acid in 4 ml of tetrahydrofuran, and the resulting mixture was stirred for 2 hours at 0° C. and then for a further 5.5 hours at room temperature. The white material which precipitated was removed by filtration, and the filtrate was freed from the solvent by distillation under reduced pressure. The residue was dissolved in 0.5 ml of dimethylformamide, and 101 mg (0.4 mmole) of 2'-cyano-2'-deoxy-1-β-D-arabinofuranosylcytosine [prepared as described in Example 1(a) above] were added to the solution. The resulting mixture was stirred at 100° C. for 40 minutes, after which the solvent was removed by distillation under reduced pressure, and the resulting residue was mixed with 5 ml of diisopropyl ether and triturated using an ultrasonic vibrator. Insoluble materials were collected by centrifugation and were purified by column chromatography through silica gel (230–400 mesh), using methylene chloride containing 4% by volume of methanol as the eluent, to give 108 mg of the title compound as a white powder after lyophilization from benzene.

Nuclear Magnetic Resonance Spectrum (hexadeuterated dimethyl sulfoxide, 270 MHz) δ ppm:

10.91 (1H, singlet);
8.36 (1H, doublet, J=7.8 Hz);
7.29 (1H, doublet, J=7.8 Hz);
6.25 (1H, doublet, J=5.9 Hz);
6.21 (1H, doublet, J=7.3 Hz);
5.31–5.34 (2H, multiplet);
5.23 (1H, triplet, J=5.4 Hz);
4.40–4.47 (1H, multiplet);
3.60–3.93 (4H, multiplet);
2.40 (2H, triplet, J=7.3 Hz);
1.95–1.99 (4H, multiplet);
1.51–1.54 (2H, multiplet);
1.26 (16H, singlet);
0.82–0.87 (3H, multiplet).

EXAMPLE 39

2'-Cyano-2'-deoxy-N⁴-(9,12,15-octadecatrienyl)-1-β-D-arabinofuranosylcytosine 0.105 ml (1.1 mole) of ethyl chlorocarbonate and 0.153 ml (1.1 mole) of triethylamine were added, whilst ice-cooling and stirring in an atmosphere of nitrogen, to a solution of 0.22 ml (0.735 mmole) of 9,12,15-octadecatrienoic acid in 4 ml of tetrahydrofuran, and the resulting mixture was stirred for 2 hours at 0° C. and then for a further 3.5 hours at room temperature. The white material which precipitated were removed by filtration, and the filtrate was freed from the solvent by distillation under reduced pressure. The resulting residue was dissolved in 0.5 ml of dimethylformamide, and 80 mg (0.32 mole) of 2'-cyano-2'-deoxy-1-β-D-arabinofuranosylcytosine [prepared as described in Example 1(a) above] were added to the solution. The resulting mixture was stirred at 100° C. for 60 minutes, after which the solvent was removed by distillation under reduced pressure, and the resulting residue was purified by column chromatography through silica gel (230–400 mesh), using methylene chloride containing 5% by volume of methanol as the eluent, to give 77 mg of the title compound as a white powder after lyophilization from benzene.

Nuclear Magnetic Resonance Spectrum (hexadeuterated dimethyl sulfoxide, 270 MHz) δ ppm:

10.91 (1H, singlet);
8.36 (1H, doublet, J=7.8 Hz);
7.29 (1H, doublet, J=7.8 Hz);
6.25 (1H, doublet, J=5.9 Hz);
6.21 (1H, doublet, J=7.3 Hz);
5.22–5.41 (6H, multiplet);
4.40–4.47 (1H, multiplet);
3.57–3.93 (4H, multiplet);
2.75–2.79 (4H, multiplet);
2.40 (2H, triplet, J=7.3 Hz);
1.98–2.09 (4H, multiplet);
1.51–1.56 (2H, multiplet);
1.27 (8H, singlet);
0.89–0.95 (3H, multiplet).

We claim:

1. A compound of formula (I):

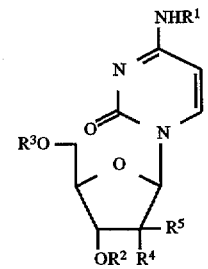

wherein:
R¹ is an unsubstituted alkanoyl group having 14–20 carbon atoms;
R²=R³=hydrogen; and
one of R⁴ and R⁵ represents a hydrogen atom and the other represents a cyano group.

2. The compound of claim 1, selected from the group consisting of 2'-cyano-2'-deoxy-N⁴-tetradecanoyl-1-β-D-arabinofuranosylcytosine and pharmaceutically acceptable salts thereof.

3. The compound of claim 1, selected from the group consisting of 2'-cyano-2'-deoxy-N⁴-pentadecanoyl-1-β-D-arabinofuranosylcytosine and pharmaceutically acceptable salts thereof.

4. The compound of claim 1, selected from the group consisting of 2'-cyano-2'-deoxy-N⁴-palmitoyl-1-β-D-arabinofuranosylcytosine and pharmaceutically acceptable salts thereof.

5. The compound of claim 1, selected from the group consisting of 2'-cyano-2'-deoxy-N⁴-heptadecanoyl-1-β-D-arabinofuranosylcytosine and pharmaceutically acceptable salts thereof.

6. The compound of claim 1, wherein R¹ is unsubstituted C14 to C18 alkanoyl group.

7. A pharmaceutical composition for the treatment of tumors, which comprises an effective amount of an active compound in admixture with a pharmaceutically acceptable carrier or diluent, wherein said active compound is selected from the group consisting of compounds of formula (I) and salts and esters thereof, as defined in claim 1.

8. A method for the treatment of tumors, which comprises administering to an animal an effective amount of an active compound, wherein said active compound is selected from the group consisting of compounds of formula (I) and salts and esters thereof, as claimed in claim 1.

9. The compound of claim 1 wherein $R^1$ is an unsubstituted alkanoyl group having 14 to 16 carbon atoms.

10. A pharmaceutical composition for the treatment of tumors, which comprises a pharmaceutically effective amount of an active compound in admixture with a pharmaceutically acceptable carrier or diluent, wherein said active compound is selected from the group consisting of compounds of formula (I) and salts and esters thereof, as defined in claim 9.

11. A method for the treatment of tumors, which comprises administering to an animal a pharmaceutically effective amount of an active compound, wherein said active compound is selected from the group consisting of compounds of formula (I) and salts and esters thereof, as claimed in claim 9.

* * * * *

UNITED STATES PATENT AND TRADEMARK OFFICE
CERTIFICATE OF CORRECTION

PATENT NO. : 5,691,319
DATED : November 25, 1997
INVENTOR(S) : Kaneko et al

It is certified that error appears in the above-identified patent and that said Letters Patent is hereby corrected as shown below:

Column 19, line 47: replace "$C_1 14C_6$" with --$C_1-C_6$--.

Signed and Sealed this

Fifteenth Day of May, 2001

Attest:

NICHOLAS P. GODICI

*Attesting Officer*  *Acting Director of the United States Patent and Trademark Office*